United States Patent
Irazoqui et al.

(10) Patent No.: US 11,191,961 B2
(45) Date of Patent: Dec. 7, 2021

(54) WIRELESS GLAUCOMA THERAPY

(71) Applicant: Purdue Research Foundation, West Lafayette, IN (US)

(72) Inventors: Pedro Irazoqui, Lafayette, IN (US); Gabriel Simon, West Lafayette, IN (US); Gabriel Omar Albors, West Lafayette, IN (US); Jack Williams, Lafayette, IN (US); Zhi Wang, West Lafayette, IN (US); Quan Yuan, West Lafayette, IN (US); Curtis Slaubaugh, West Lafayette, IN (US); Hansraj Singh Bhamra, San Jose, CA (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/312,720

(22) PCT Filed: Jun. 22, 2017

(86) PCT No.: PCT/US2017/038879
§ 371 (c)(1),
(2) Date: Dec. 21, 2018

(87) PCT Pub. No.: WO2017/223387
PCT Pub. Date: Dec. 28, 2017

(65) Prior Publication Data
US 2019/0344076 A1 Nov. 14, 2019

Related U.S. Application Data

(60) Provisional application No. 62/513,749, filed on Jun. 1, 2017, provisional application No. 62/509,002, filed on May 19, 2017, provisional application No. 62/467,816, filed on Mar. 6, 2017, provisional application No. 62/433,006, filed on Dec. 12, 2016, provisional application No. 62/353,481, filed on Jun. 22, 2016.

(51) Int. Cl.
*A61N 1/36* (2006.01)
*A61N 2/00* (2006.01)
(Continued)

(52) U.S. Cl.
CPC ....... *A61N 1/36046* (2013.01); *A61N 1/0526* (2013.01); *A61N 1/40* (2013.01);
(Continued)

(58) Field of Classification Search
CPC .......... A61N 2/00; A61N 2/002; A61N 2/004; A61N 2/006; A61N 2/008; A61N 2/02;
(Continued)

(56) References Cited

U.S. PATENT DOCUMENTS

| 4,603,697 A | 8/1986 | William |
| 4,614,193 A | 9/1986 | Saul et al. |

(Continued)

FOREIGN PATENT DOCUMENTS

| JP | 2009-541005 A | 11/2009 |
| WO | WO 2009/150688 | 12/2009 |
| WO | WO 2015/157725 | 10/2015 |

OTHER PUBLICATIONS

EP Supplementary Partial European Search Report in European Appln. No. 17816256, dated Jun. 14, 2019, 16 pages.
(Continued)

*Primary Examiner* — Carrie R Dorna
(74) *Attorney, Agent, or Firm* — Fish & Richardson P.C.

(57) ABSTRACT

Systems and methods for wireless glaucoma therapy involving the administration of energy to an eye of a mammalian subject in a therapeutically effective amount sufficient to (1) decrease the inflow of aqueous humor into the anterior segment of the eye and/or (2) increase the outflow of aqueous humor from the anterior segment of the eye. Systems and methods involve the use of wireless power transfer (WPT) and optional stimulus coils adapted to be positioned on and/or within the eye. A Fresnel lens is also disclosed for vision correction, which may be used alone or in combination with the system for wireless glaucoma therapy.

18 Claims, 77 Drawing Sheets

(51) Int. Cl.
*A61N 2/02* (2006.01)
*A61F 9/00* (2006.01)
*A61N 1/05* (2006.01)
*A61N 1/40* (2006.01)
*G02C 7/04* (2006.01)

(52) U.S. Cl.
CPC ............... *A61N 2/004* (2013.01); *A61N 2/02* (2013.01); *G02C 7/04* (2013.01); *A61F 9/00* (2013.01)

(58) Field of Classification Search
CPC ............... A61N 1/36046; A61F 9/0017; A61F 9/00781
See application file for complete search history.

(56) References Cited

U.S. PATENT DOCUMENTS

| | | | |
|---|---|---|---|
| 2002/0013545 A1 | 1/2002 | Soltanpour et al. | |
| 2003/0195438 A1* | 10/2003 | Petillo | A61H 23/0263 601/15 |
| 2006/0224215 A1 | 10/2006 | Pattern et al. | |
| 2007/0282405 A1 | 12/2007 | Wong et al. | |
| 2007/0284205 A1 | 12/2007 | Wong et al. | |
| 2008/0058793 A1* | 3/2008 | Pilla | A61N 1/32 606/33 |
| 2011/0022118 A1* | 1/2011 | Rickard | A61N 1/36046 607/53 |
| 2011/0238133 A1* | 9/2011 | Gross | A61N 1/0526 607/53 |
| 2013/0006326 A1* | 1/2013 | Ackermann | A61N 1/36046 607/53 |
| 2014/0213843 A1 | 7/2014 | Pilla et al. | |
| 2017/0007834 A1 | 1/2017 | Pedro et al. | |

OTHER PUBLICATIONS

PCT International Search Report and Written Opinion in International Appln. No. PCT/US2017/038879, dated Sep. 27, 2017, 15 pages.

* cited by examiner

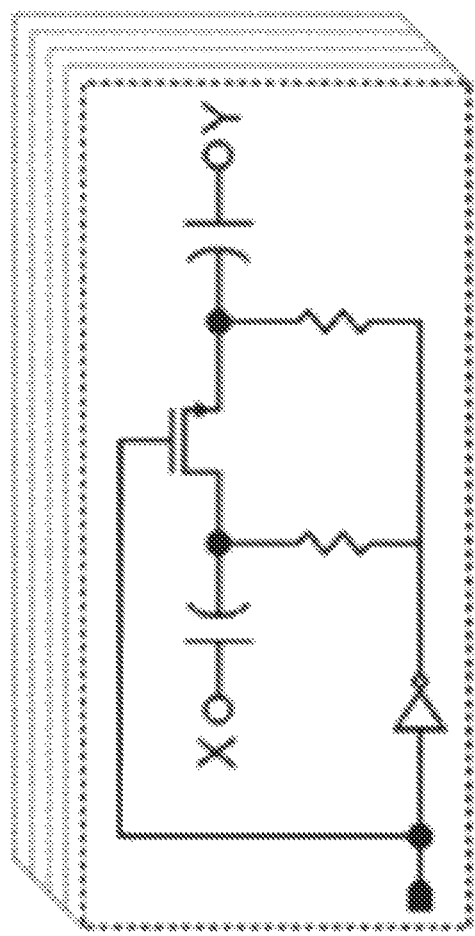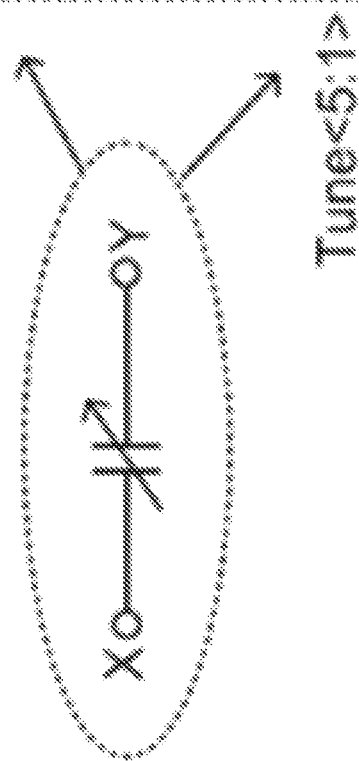
FIG. 57

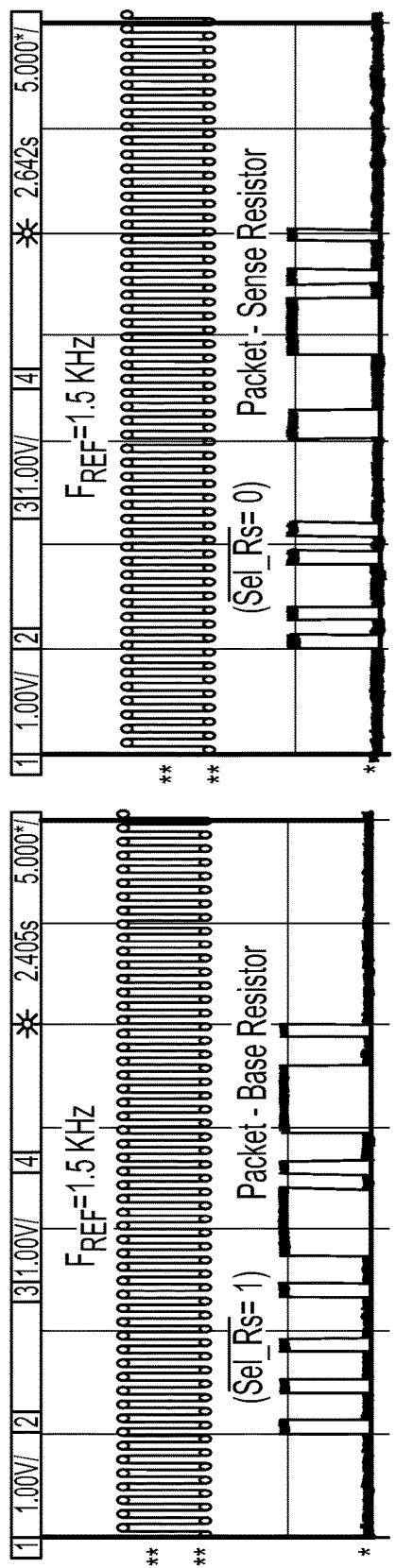
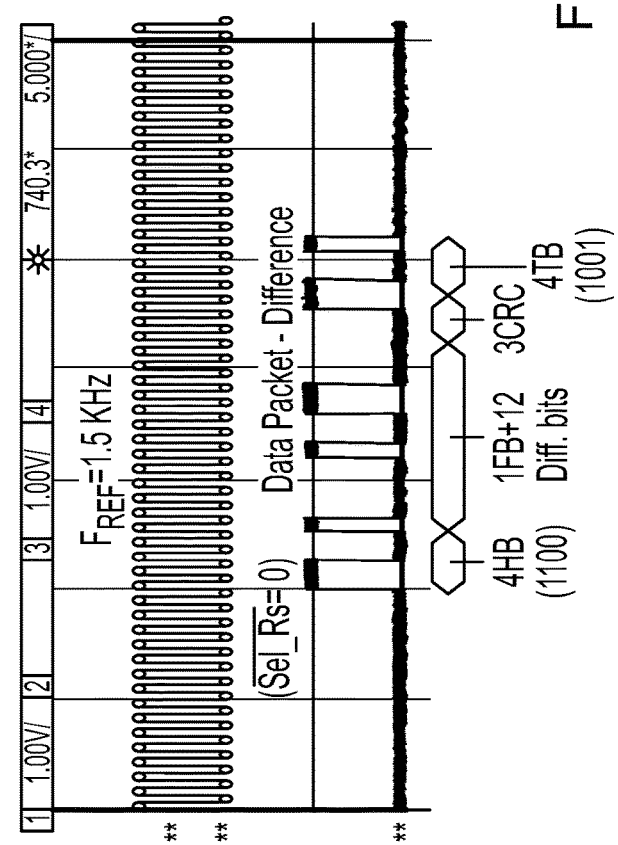
FIG. 64A
FIG. 64B
FIG. 64C

WIRELESS GLAUCOMA THERAPY

CROSS-REFERENCE TO RELATED APPLICATIONS

This application is a National Stage application under 35 U.S.C. § 371 of International Application No. PCT/US2017/038879, filed Jun. 22, 2017, which claims the benefit under 35 U.S.C. § 119(e) of U.S. Patent Application No. 62/353,481 entitled "WIRELESS GLAUCOMA THERAPY SYSTEM AND RELATED METHODS" (filed Jun. 22, 2016), U.S. Patent Application No. 62/433,006 entitled "CONTACT LENS WITH EMBEDDED COIL FOR WIRELESS GLAUCOMA THERAPY" (filed Dec. 12, 2016), U.S. Patent Application No. 62/467,816, entitled "OPTICAL FRAME SYSTEM FOR WIRELESS GLAUCOMA THERAPY" (filed Mar. 6, 2017), U.S. Patent Application No. 62/509,002 entitled "SYSTEMS AND METHODS FOR WIRELESS GLAUCOMA THERAPY" (filed May 19, 2017), and U.S. Patent Application No. 62/513,749 entitled "IMPLANTABLE INTRAOCULAR LENS FOR VISION CORRECTION" (filed Jun. 1, 2017), the entire contents of each is incorporated herein by reference.

BACKGROUND

The present invention relates generally to wireless stimulation of biological tissue (e.g. nerves, muscle tissue, etc.) and, in one exemplary implementation, to therapy for glaucoma based on the wireless administration of energy to the eye of a mammalian subject (e.g. human, rodent, etc.) to reduce an elevated intraocular pressure (IOP).

Glaucoma is currently the leading cause of blindness and continues to cause blindness in around 10% of even those patients who receive the most up to date treatment. The primary cause of glaucoma is an excess of intraocular pressure (IOP) which presses on and damages the optic nerve. In a normally functioning mammalian eye, fluid (namely, aqueous humor) is pumped into the anterior segment of the eye to, among other things, maintain a healthy IOP and provide nutrients to the structures in the anterior segment. The fluid is then drained out primarily through the drainage tissues at the junction of the cornea and iris in the region of the eye known as the limbus. In glaucoma, an elevated IOP results from an excess of aqueous humor which may be due to a combination of a) the ciliary body producing too much fluid (increased inflow) and/or b) too much resistance to aqueous humor drainage out of the eye (limited outflow) depending upon the type of glaucoma.

Glaucoma may take many forms. Open-angle glaucoma is where the aqueous humor does not drain as quickly due to abnormal resistance in the trabecular meshwork and Schlemm's canal pathway. The increase in IOP in open-angle glaucoma is usually a slow process and generally does not exhibit any symptoms. When vision starts to decrease, severe damage has already been done to the optic nerve. Closed-angle (sometimes referred to as "Angle-closure glaucoma") is where the aqueous humor does not drain from the eye because of a blockage or resistance in the trabecular network by the iris. This causes a sudden spike in the intraocular pressure and is considered an emergency. Congenital glaucoma is a birth defect caused by abnormal eye development. Secondary glaucoma is caused by external factors such as drugs, disease, or trauma. Open-Angle glaucoma is the most common form of glaucoma and has a clear genetic component. When considered in all forms, the populations of patients with glaucoma or high IOP (pre-glaucoma) are predicted to grow steadily due to, among other reasons, the demographic increase in the aging population.

Existing medical and surgical treatments attempt to reduce IOP to non-damaging levels by targeting either the drainage or production of aqueous humor, but with limited success. The two primary approaches include the use of eye-drops to regulate fluid flow and surgeries to open drainage channels in the eye. The pharmacological (eye-drop) methods for reducing IOP in glaucoma and ocular hypertensive patients provide only acute relief of symptoms for the chronic disease. The surgical approaches have largely focused on implanting a stent or similar structure to wick or facilitate the drainage of aqueous humor. Laser surgical approaches achieve a similar same effect as stents by creating or increasing openings in the drainage region of the eye. Bleb surgeries create an opening out of the anterior chamber to facilitate drainage. Such surgical approaches have enjoyed limited clinical success for a host of reasons, including the increased risk of infection due to the bacterial pathway that exists by virtue of the physical drainage element (e.g. bleb) extending outside the eye during use. The same infection risk is present for the prior art efforts involving the use of electrical stimulation of the eye to reduce IOP, which typically include hard-wired electrodes with leads extending from the eye during use.

There is a need to develop a method to chronically reduce IOP of all patients with glaucoma or ocular hypertension to a safe level without causing unacceptable side effects

SUMMARY

The details of one or more embodiments of the subject matter described in this specification are set forth in the accompanying drawings and the description below. Other features, aspects, and advantages of the invention will become apparent from the description, the drawings, and the claims.

In some implementations, a system for wirelessly reducing elevated intraocular pressure in an eye of a mammalian subject includes a coil constructed from an elongated conductor formed into a plurality of windings. Said coil is adapted to be positioned in proximity to an eye of a mammalian subject. The system also includes a signal generator in electrical communication with said coil. Said signal generator is configured to generate a signal to produce an electromagnetic field transmitted wirelessly from said coil to said eye of said mammalian subject in a therapeutically effective amount to reduce an elevated intraocular pressure within said eye of said mammalian subject.

Such implementations can optionally include one or more of the following features, which can be combined in any possible combination or sub-combination. Said elevated intraocular pressure within said eye of said mammalian subject can be reduced by at least one of (i) decreasing aqueous humor inflow into an anterior segment of said eye and (ii) increasing aqueous humor outflow from said anterior segment of said eye. Said decrease in intraocular fluid inflow into said segment of said eye can occur as a result of said electromagnetic field causing a ciliary epithelium pump within a ciliary body within said eye to reverse or slow the generation of intraocular fluid into said anterior segment of said eye. Said increase in intraocular fluid outflow from said anterior segment of said eye can occur as a result of said electromagnetic field causing at least one fluid pathway out of said anterior segment to open, dilate, or otherwise increase in fluid outflow facility. Said at least one fluid pathway within said eye can include a drainage pathway through at least a portion of the Canal of Schlemm of said eye and a uveoscleral outflow mechanism from the anterior segment of said eye. Said therapeutically effective amount of said electromagnetic field can be in the range of $10^{-6}$ Tesla to $10^{-1}$ Tesla. Said stimulus signal can be a biphasic rectangular waveform with a frequency in the range of 0.1 Hz to 1 KHz, a pulse duration in the range of 0.1 milliseconds to 1000 microseconds, and a pulse amplitude in the range of 0.01 milli-Amps to 100 milli-Amps. Said coil can be part of a pair of glasses to be worn by said mammalian subject. Said coil can be attached to an optical frame to be worn by said mammalian subject. Said coil can be part of a sleep mask adapted to be worn by said mammalian subject such that said coil is positioned adjacent to said eye of said mammalian subject. Said coil can be part of a pillow adapted to be used by said mammalian subject such that said coil is positioned adjacent to said eye of said mammalian subject. The system can further include a passive stimulation electrode assembly adapted to be positioned at least one of on, within and near said eye of said mammalian subject. Said passive stimulation electrode assembly can be adapted to wirelessly receive said electromagnetic field from said coil and stimulate at least one intraocular structure to reduce said elevated intraocular pressure within a mammalian eye. Said stimulation of said at least one intraocular structure by said passive stimulation electrode assembly can reduce said elevated intraocular pressure by at least one of (i) decreasing aqueous humor inflow into said anterior segment of said eye, and (ii) increasing aqueous humor outflow from said anterior segment of said eye. Said decrease in aqueous humor inflow into said anterior segment of said eye by said passive stimulation electrode assembly occurs as a result of said stimulation by said passive stimulation electrode assembly can cause a ciliary epithelium pump within a ciliary body within said eye to reverse or slow the generation of aqueous humor into said anterior segment of said eye. Said increase in aqueous humor outflow from said anterior segment of said eye by said passive stimulation electrode assembly can occur as a result of said stimulation by said passive stimulation electrode assembly causing at least one fluid pathway out of said anterior segment to open, dilate, or otherwise increase in fluid outflow facility. Said at least one fluid pathway within said eye can include a drainage pathway through at least a portion of the Canal of Schlemm of said eye and a uveoscleral outflow mechanism from the anterior segment of said eye. Said passive stimulation electrode assembly can be part of a contact lens adapted to be positioned on said eye of said mammalian subject. Said passive stimulation electrode assembly can be positioned within said contact lens. Said passive stimulation electrode assembly can be positioned on an eye-contacting surface of said contact lens. Said passive stimulation electrode assembly can include at least one serpentine trace to enable said passive stimulation electrode assembly to assume a 3-dimensional shape to facilitate placement over said eye of said mammalian subject as part of said contact lens. Said passive stimulation electrode assembly can be adapted to be implanted within said eye of said mammalian subject. Said passive stimulation electrode assembly can be adapted to be implanted within a sub-conjunctival region of said eye of said mammalian subject. Said passive stimulation electrode assembly can be adapted to be implanted within an intraocular lens of said eye of said mammalian subject. The system can further include a Fresnel lens adapted to be positioned adjacent to or within said eye of said mammalian subject to focus incoming light rays on a retina of said eye of said mammalian subject for vision correction. Said Fresnel lens can include a) a lens substrate having a having an index of refraction, a diameter of 5 mm or less, and a thickness 1 millimeter or less, and b) a plurality of refraction regions on said lens substrate. Said plurality of refraction regions can have an index of refraction different from said index of refraction of said lens substrate. Said refraction regions of said Fresnel lens can be manufactured from metallic traces on said lens substrate. Said Fresnel lens can be adapted to be disposed within a contact lens for application to an exterior of said eye of said mammalian patient. Said Fresnel lens can be adapted to be surgically implanted within said eye of said mammalian subject such that said Fresnel is disposed at least one of over and within said intraocular lens. Said Fresnel lens can be adapted to be surgically implanted within said sub-conjunctival region of said eye of said mammalian subject. Said Fresnel lens can have a diameter in the range of 2 mm to 4 mm and a thickness in the range of 1 micrometer and 2 micrometers. The system can further include a wireless pressure sensor adapted to be disposed within said eye of said mammalian subject to enable closed-loop feedback for the delivery of said stimulation signal.

In some implementations, a device for reducing elevated intraocular pressure in an eye of a mammalian subject includes a stimulation electrode assembly adapted to be positioned at least one of on, within and near said eye of said mammalian subject. Said passive stimulation electrode assembly is adapted to deliver a stimulation signal to at least one intraocular structure in a therapeutically effective amount to reduce said elevated intraocular pressure within a mammalian eye by (i) decreasing aqueous humor inflow into an anterior segment of said eye, and (ii) increasing aqueous humor outflow from said anterior segment of said eye.

Such implementations can optionally include one or more of the following features, which can be combined in any possible combination or sub-combination. Said stimulation electrode assembly can be a passive stimulation electrode adapted to receive an electromagnetic field from a signal generator and transmit said stimulation signal to said at least one intraocular structure to reduce said elevated intraocular pressure of said eye of said mammalian subject. Said decrease in aqueous humor inflow into said anterior segment of said eye by said stimulation electrode assembly can occur as a result of said stimulation by said stimulation electrode assembly causing a ciliary epithelium pump within a ciliary body within said eye to reverse or slow the generation of aqueous humor into said anterior segment of said eye. Said increase in aqueous humor outflow from said anterior segment of said eye by said stimulation electrode assembly can occur as a result of said stimulation by said stimulation electrode assembly causing at least one fluid pathway out of said anterior segment to open, dilate, or otherwise increase in fluid outflow facility. Said at least one fluid drainage pathway within said eye can include a drainage pathway through at least a portion of the Canal of Schlemm of said eye and a uveoscleral outflow mechanism from the anterior segment of said eye. Said stimulation electrode assembly can be part of a contact lens adapted to be positioned on said eye of said mammalian subject. Said stimulation electrode assembly can be positioned within said contact lens. Said stimulation electrode assembly can be positioned on an eye-contacting surface of said contact lens. Said stimulation electrode assembly can include at least one serpentine trace to enable said stimulation electrode assembly to assume a 3-dimensional shape to facilitate placement over said eye of said mammalian subject as part of said contact lens. Said stimulation electrode assembly can be adapted to be implanted within said eye of said mammalian subject. Said stimulation electrode assembly can be adapted to be implanted within a sub-conjunctival region of said eye of said mammalian subject. Said passive stimulation electrode assembly can be adapted to be implanted within an intraocular lens of said eye of said mammalian subject. The device can further include a Fresnel lens adapted to be positioned adjacent to or within said eye of said mammalian subject to focus incoming light rays on a retina of said eye of said mammalian subject for vision correction. Said Fresnel lens can include a) a lens substrate having a having an index of refraction, a diameter of 5 mm or less, and a thickness 1 millimeter or less, and b) a plurality of refraction regions on said lens substrate. Said plurality of refraction regions can have an index of refraction different from said index of refraction of said lens substrate. Said refraction regions of said Fresnel lens can be manufactured from metallic traces on said lens substrate. Said Fresnel lens can be adapted to be disposed within a contact lens containing said stimulation electrode assembly, wherein said contact lens is adapted for application to an exterior of said eye of said mammalian patient. Said Fresnel lens can be formed as part of a structure with said stimulation electrode assembly. Said structure can be adapted to be surgically implanted within said eye of said mammalian subject such that said Fresnel is disposed at least one of over and within said intraocular lens. Said Fresnel lens and said stimulation electrode assembly can be adapted to be surgically implanted within at least one of said sub-conjunctival region and an intraocular lens of said eye of said mammalian subject. Said Fresnel lens can have a diameter in the range of 2 mm to 4 mm and a thickness in the range of 1 micrometer and 2 micrometers. The device can further include a wireless pressure sensor adapted to be disposed within said eye of said mammalian subject to enable closed-loop feedback for the delivery of said stimulation signal.

In some implementations, a device for vision correction for an eye of a mammalian subject includes a Fresnel lens adapted to be positioned adjacent to or within said eye of said mammalian subject to focus incoming light rays on a retina of said eye of said mammalian subject for vision correction.

Such implementations can optionally include one or more of the following features, which can be combined in any possible combination or sub-combination. Said Fresnel lens can include a) a lens substrate having a having an index of refraction, a diameter of 5 mm or less, and a thickness 1 millimeter or less, and b) a plurality of refraction regions on said lens substrate. Said plurality of refraction regions can have an index of refraction different from said index of refraction of said lens substrate. Said refraction regions of said Fresnel lens can be manufactured from metallic traces on said lens substrate. Said Fresnel lens can be adapted to be disposed within a contact lens for application to an exterior of said eye of said mammalian patient. Said Fresnel lens can be adapted to be surgically implanted within said eye of said mammalian subject such that said Fresnel is disposed at least one of over and within said intraocular lens. Said Fresnel lens can be adapted to be surgically implanted within said sub-conjunctival region of said eye of said mammalian subject. Said Fresnel lens can have a diameter of 5 mm or less and a thickness of 1 millimeter or less. Said Fresnel lens can be adapted to be disposed within a contact lens containing a stimulation electrode assembly, wherein said contact lens is adapted for application to an exterior of said eye of said mammalian patient. Said Fresnel lens can be formed as part of a structure with a stimulation electrode assembly. Said structure can be adapted to be surgically implanted within said eye of said mammalian subject such that said Fresnel is disposed at least one of over and within said intraocular lens. Said Fresnel lens and a stimulation electrode assembly can be adapted to be surgically implanted within at least one of said sub-conjunctival region and an intraocular lens of said eye of said mammalian subject. The device can further include a wireless pressure sensor adapted to be disposed within said eye of said mammalian subject to enable closed-loop feedback for the delivery of said stimulation signal.

In some implementations, a method of wirelessly reducing elevated intraocular pressure in an eye of a mammalian subject includes transmitting an electromagnetic field wirelessly from a coil to an eye of a mammalian subject, the electromagnetic field delivered in an amount therapeutically effective to reduce an elevated intraocular pressure within said eye. Said coil can be constructed from an elongated conductor formed into a plurality of windings.

Such implementations can optionally include one or more of the following features, which can be combined in any possible combination or sub-combination. The method can further include positioning the coil in proximity to an eye of said mammalian subject. The method can further include generating a signal to produce said electromagnetic field. Transmitting said electromagnetic field can reduce an elevated intraocular pressure within said eye of said mammalian subject by at least one of (i) decreasing aqueous humor inflow into an anterior segment of said eye, and (ii) increasing aqueous humor outflow from said anterior segment of said eye. Said decrease in intraocular fluid inflow into said segment of said eye can occur as a result of said electromagnetic field causing a ciliary epithelium pump within a ciliary body within said eye to reverse or slow the generation of intraocular fluid into said anterior segment of said eye. Said increase in intraocular fluid outflow from said anterior segment of said eye can occur as a result of said electromagnetic field causing at least one fluid pathway out of said anterior segment to open, dilate, or otherwise increase in fluid outflow facility. Said at least one fluid pathway within said eye can include a drainage pathway through at least a portion of the Canal of Schlemm of said eye and a uveoscleral outflow mechanism from the anterior segment of said eye. Transmitting an electromagnetic field can include transmitting an electromagnetic field in the range of $10^{-6}$ Tesla to $10^{-1}$ Tesla. Said coil can be part of a pair of glasses to be worn by said mammalian subject. Said coil can be attached to an optical frame to be worn by said mammalian subject. Said coil can be part of a sleep mask adapted to be worn by said mammalian subject such that said coil is positioned adjacent to said eye of said mammalian subject. Said coil can be part of a pillow adapted to be used by said mammalian subject such that said coil is positioned adjacent to said eye of said mammalian subject. Transmitting the electromagnetic field wirelessly from said coil to said eye can include transmitting the electromagnetic field from the coil to a passive stimulation electrode assembly adapted to stimulate at least one intraocular structure to reduce an elevated intraocular pressure. Said passive stimulation electrode assembly can be adapted to be positioned near said eye of said mammalian subject. Said passive stimulation electrode assembly can be adapted to be positioned on said eye of said mammalian subject. Said passive stimulation electrode assembly can be adapted to be positioned within said eye of said mammalian subject. Said stimulation of said at least one intraocular structure by said passive stimulation electrode assembly can reduce said elevated intraocular pressure by at least one of (i) decreasing aqueous humor inflow into said anterior segment of said eye, and (ii) increasing aqueous humor outflow from said anterior segment of said eye. Said decrease in aqueous humor inflow into said anterior segment of said eye by said passive stimulation electrode assembly can occur as a result of said stimulation by said passive stimulation electrode assembly causing a ciliary epithelium pump within a ciliary body within said eye to reverse or slow the generation of aqueous humor into said anterior segment of said eye. Said increase in aqueous humor outflow from said anterior segment of said eye by said passive stimulation electrode assembly can occur as a result of said stimulation by said passive stimulation electrode assembly causing at least one fluid pathway out of said anterior segment to open, dilate, or otherwise increase in fluid outflow facility. Said at least one fluid pathway within said eye can include a drainage pathway through at least a portion of the Canal of Schlemm of said eye and a uveoscleral outflow mechanism from the anterior segment of said eye. Said passive stimulation electrode assembly can be part of a contact lens adapted to be positioned on said eye of said mammalian subject. Said passive stimulation electrode assembly can be positioned within said contact lens. Said passive stimulation electrode assembly can be positioned on an eye-contacting surface of said contact lens. Said passive stimulation electrode assembly can include at least one serpentine trace to enable said passive stimulation electrode assembly to assume a 3-dimensional shape. Said passive stimulation electrode assembly can be adapted to be implanted within said eye of said mammalian subject. Said passive stimulation electrode assembly can be adapted to be implanted within a sub-conjunctival region of said eye of said mammalian subject. Said passive stimulation electrode assembly can be adapted to be implanted within an intraocular lens of said eye of said mammalian subject. The method can further include positioning a Fresnel lens adjacent to or within said eye of said mammalian subject, the Fresnel lens adapted to focus incoming light rays on a retina of said eye of said mammalian subject for vision correction. Said Fresnel lens can include a) a lens substrate having a having an index of refraction, a diameter of 5 mm or less, and a thickness 1 millimeter or less, and b) a plurality of refraction regions on said lens substrate. Said plurality of refraction regions can have an index of refraction different from said index of refraction of said lens substrate. Said refraction regions of said Fresnel lens can include metallic traces on said lens substrate. Positioning said Fresnel lens can include positioning a contact lens on an exterior of said eye, the Fresnel lens disposed within the contact lens. Positioning a Fresnel lens adjacent to or within said eye can include surgically implanting the Fresnel lens within said eye of said mammalian. Positioning a Fresnel lens adjacent to or within said eye can include surgically implanting said Fresnel lens at least one of over and within said intraocular lens. Positioning a Fresnel lens adjacent to or within said eye can include surgically implanting said Fresnel lens within said sub-conjunctival region of said eye of said mammalian subject. Said Fresnel lens can have a diameter in the range of 2 mm to 4 mm and a thickness in the range of 1 micrometer and 2 micrometers. The method can further include receiving a pressure signal from a wireless pressure sensor disposed within said eye of said mammalian subject. The amount of electromagnetic field delivered can be based at least in part on closed-loop control using the pressure signal.

In some implementations, a method of reducing elevated intraocular pressure in an eye of a mammalian subject includes transmitting an electromagnetic field to a stimulation electrode assembly positioned near an eye of a mammalian subject. The stimulation electrode assembly is adapted to stimulate at least one intraocular structure to reduce an elevated intraocular pressure within said mammalian eye by (i) decreasing aqueous humor inflow into an anterior segment of said eye, and (ii) increasing aqueous humor outflow from said anterior segment of said eye.

Such implementations can optionally include one or more of the following features, which can be combined in any possible combination or sub-combination. The stimulation electrode assembly can be positioned on said eye. The stimulation electrode assembly can be positioned within said eye. Said stimulation electrode assembly can be a passive stimulation electrode. The method can further include receiving by the stimulation electrode assembly an electromagnetic field from a signal generator and transmitting said stimulation signal to said at least one intraocular structure. Said decrease in aqueous humor inflow into said anterior segment of said eye by said stimulation electrode assembly can occur as a result of said stimulation by said stimulation electrode assembly causing a ciliary epithelium pump within a ciliary body within said eye to reverse or slow the generation of aqueous humor into said anterior segment of said eye. Said increase in aqueous humor outflow from said anterior segment of said eye by said stimulation electrode assembly can occur as a result of said stimulation by said stimulation electrode assembly causing at least one fluid pathway out of said anterior segment to open, dilate, or otherwise increase in fluid outflow facility. Said at least one fluid pathway within said eye can include a drainage pathway through at least a portion of the Canal of Schlemm of said eye and a uveoscleral outflow mechanism from the anterior segment of said eye. Said stimulation electrode assembly can be part of a contact lens adapted to be positioned on said eye of said mammalian subject. Said stimulation electrode assembly can be positioned within said contact lens. Said stimulation electrode assembly can be positioned on an eye-contacting surface of said contact lens. Said passive stimulation electrode assembly can include at least one serpentine trace to enable said passive stimulation electrode assembly to assume a 3-dimensional shape. The method can further include implanting said stimulation electrode assembly within said eye of said mammalian subject. The method can further include implanting said stimulation electrode assembly within a sub-conjunctival region of said eye of said mammalian subject. The method can further include implanting said stimulation electrode assembly within an intraocular lens of said eye of said mammalian subject. The method can further include positioning a Fresnel lens adjacent to or within said eye of said mammalian subject, the Fresnel lens adapted to focus incoming light rays on a retina of said eye of said mammalian subject for vision correction. Said Fresnel lens can include a) a lens substrate having an index of refraction, a diameter of 5 mm or less, and a thickness 1 millimeter or less, and b) a plurality of refraction regions on said lens substrate. Said plurality of refraction regions can have an index of refraction different from said index of refraction of said lens substrate. Said refraction regions of said Fresnel lens can include metallic traces on said lens substrate. Positioning said Fresnel lens can include positioning a contact lens on an exterior of said eye, the Fresnel lens disposed within the contact lens. Positioning a Fresnel lens adjacent to or within said eye can include surgically implanting the Fresnel lens within said eye of said mammalian. Positioning a Fresnel lens adjacent to or within said eye can include surgically implanting said Fresnel lens at least one of over and within said intraocular lens. Positioning a Fresnel lens adjacent to or within said eye can include surgically implanting said Fresnel lens within said sub-conjunctival region of said eye of said mammalian subject. Said Fresnel lens can have a diameter in the range of 2 mm to 4 mm and a thickness in the range of 1 micrometer and 2 micrometers. The method can further include receiving a pressure signal from a wireless pressure sensor disposed within said eye of said mammalian subject. The amount of electromagnetic field delivered can be based at least in part on closed-loop control using the pressure signal.

In some implementations, a method of vision correction in an eye of a mammalian subject includes surgically implanting a Fresnel lens at least one of on or within an eye of a mammalian subject to focus light rays passing through said Fresnel lens on a retina of said eye of said mammalian subject. The Fresnel lens includes a biocompatible construction that includes a lens substrate having a having an index of refraction, a diameter of 5 mm or less, and a thickness 1 millimeter or less, and a plurality of refraction regions on said lens substrate. Said plurality of refraction regions can have an index of refraction different from said index of refraction of said lens substrate.

Such implementations can optionally include one or more of the following features, which can be combined in any possible combination or sub-combination. Said refraction regions of said Fresnel lens can be manufactured from metallic traces on said lens substrate. Surgically implanting said Fresnel lens can include surgically implanting said Fresnel lens at least one of over and within said intraocular lens. Surgically implanting said Fresnel lens can include surgically implanting said Fresnel lens within a sub-conjunctival region of said eye. The method can further include surgically implanting a stimulation electrode assembly. The Fresnel lens can be formed as part of a structure with the stimulation electrode assembly. Surgically implanting said Fresnel lens and said stimulation electrode assembly can include surgically implanting said Fresnel lens and said stimulation electrode assembly within a sub-conjunctival region. Surgically implanting said Fresnel lens and said stimulation electrode assembly can include surgically implanting said Fresnel lens and said stimulation electrode assembly within an intraocular lens of said eye of said mammalian subject. The method can further include receiving a pressure signal from a wireless pressure sensor disposed within said eye of said mammalian subject. The method can further include transmitting an electromagnetic field to said stimulation electrode assembly. The amount of electromagnetic field delivered can be based at least in part on closed-loop control using the pressure signal.

DRAWING DESCRIPTIONS

Figure 10B:
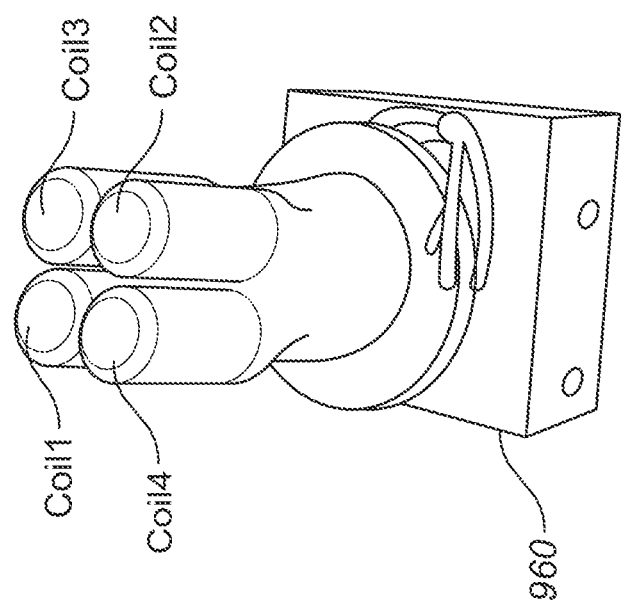
Figure 10A:
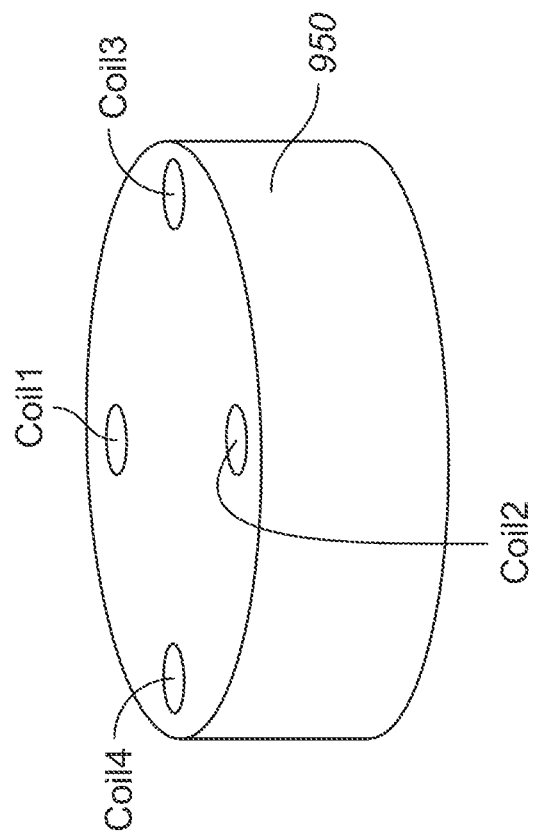

FIGS. 10A-B show an illustration of a coil assembly 1150 for use with the optical frame that can include at least two pairs of electrical coils within each WPT coil.

Figure 11:
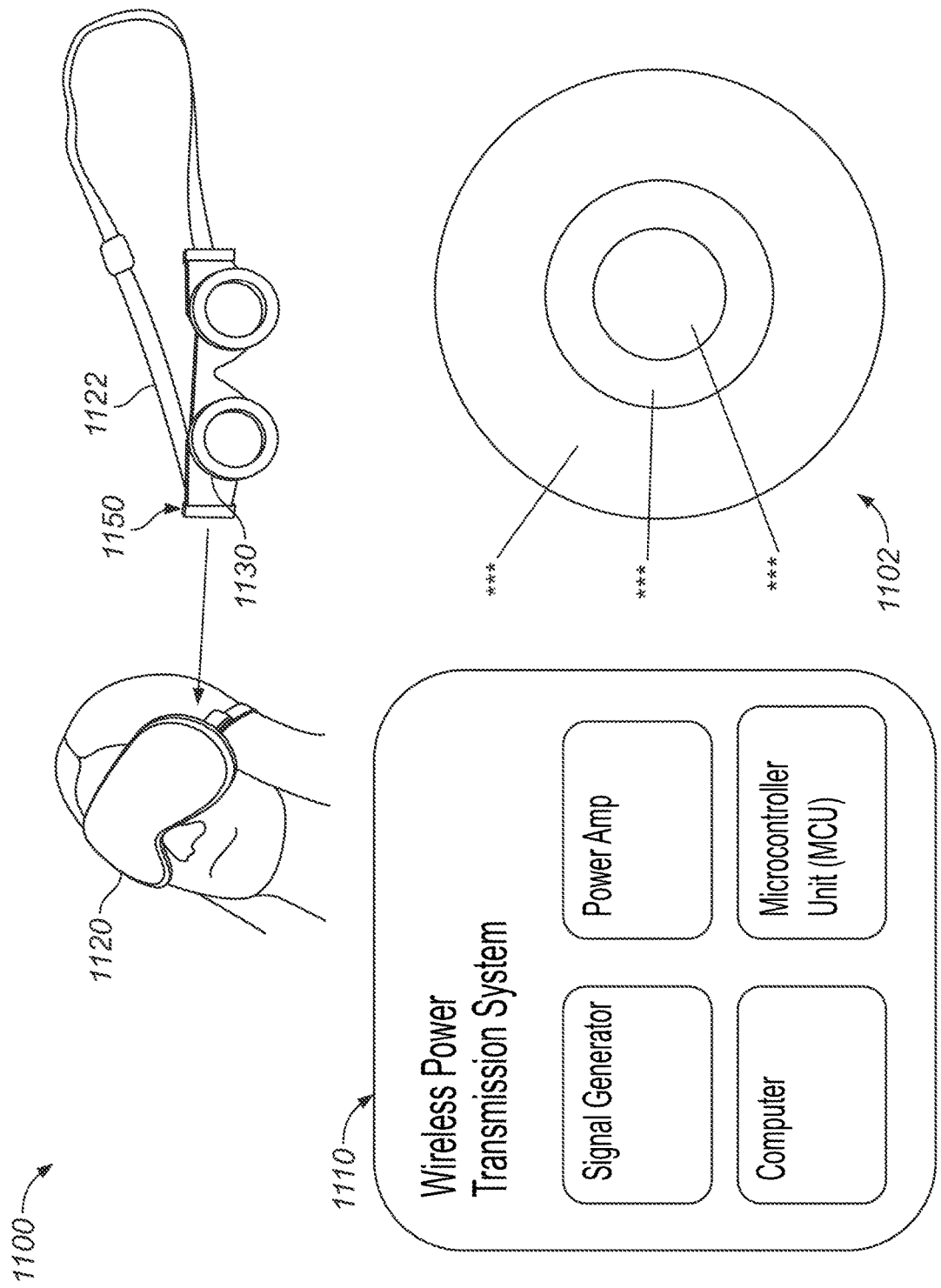

FIG. 11 shows an example wireless glaucoma therapy system involving the use of a wireless power transfer (WPT) coil associated with a sleep mask for implementing the disclosed techniques.

Figure 12:
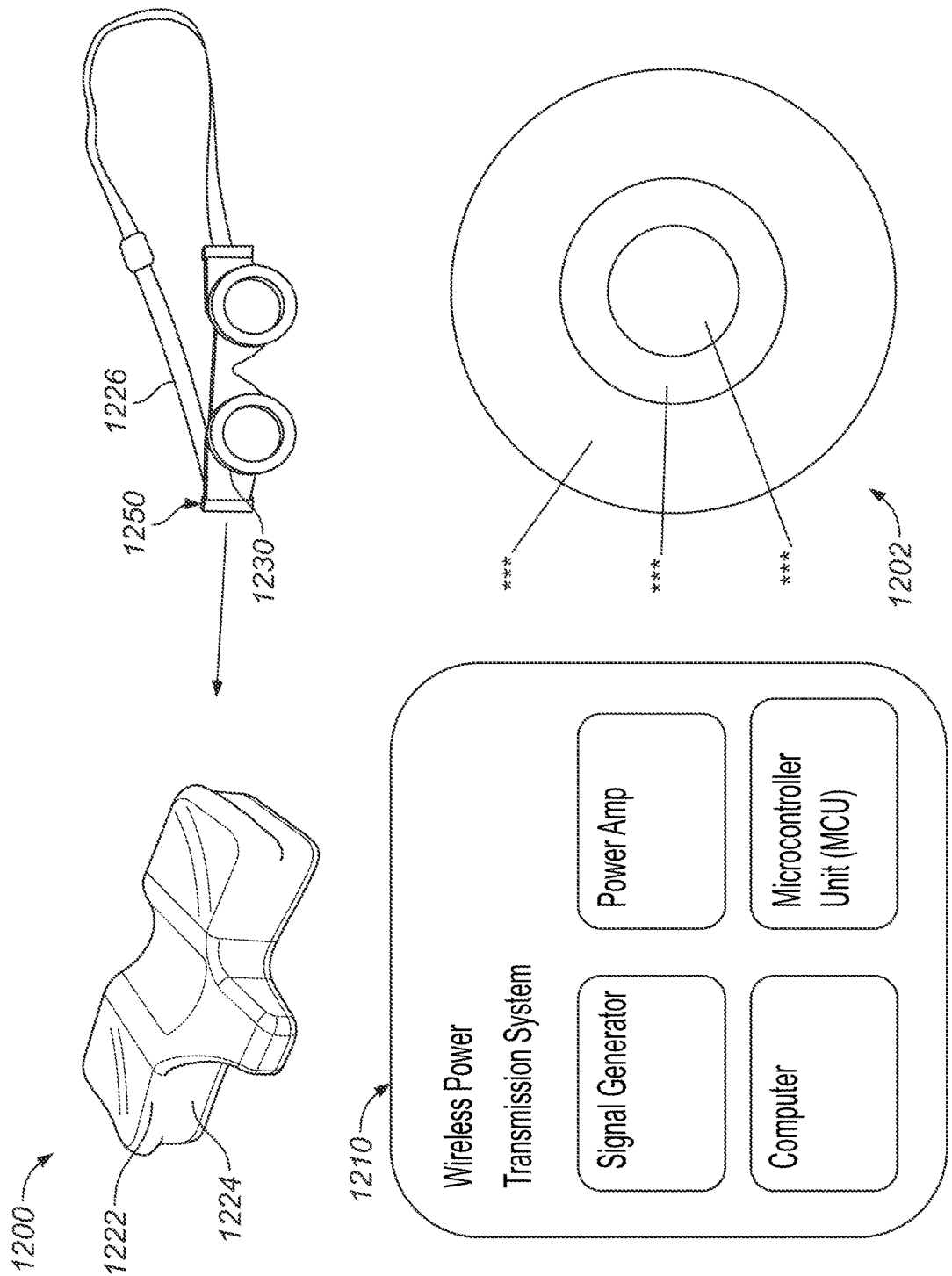

FIG. 12 shows an example wireless glaucoma therapy system involving the use of a wireless power transfer (WPT) coil associated with a pillow for implementing the disclosed techniques.

Figure 13:
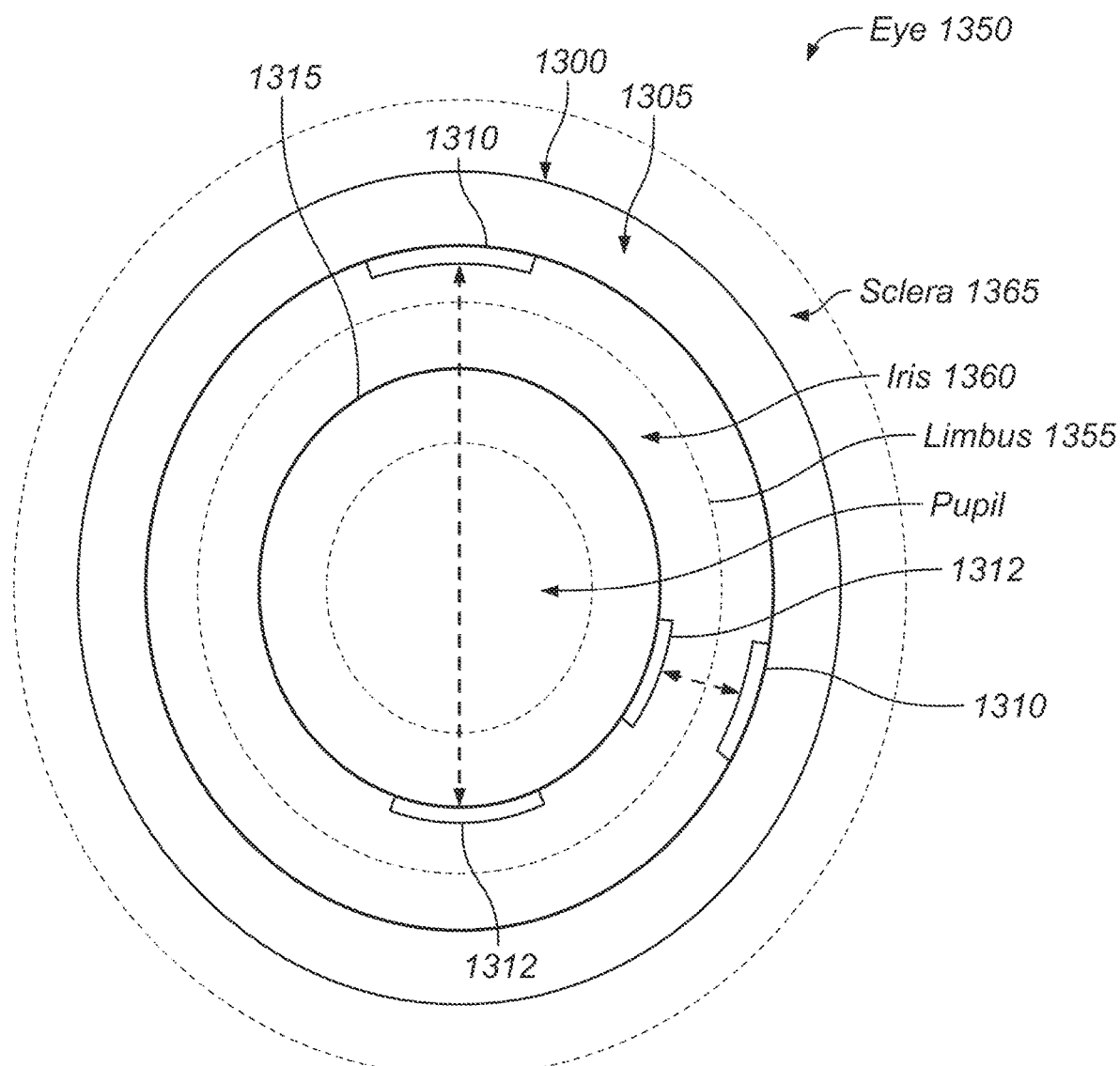

FIG. 13 shows a front view of an eye of a mammalian subject configured with a contact lens equipped with a stimulus coil for implementing the disclosed techniques.

Figure 14:
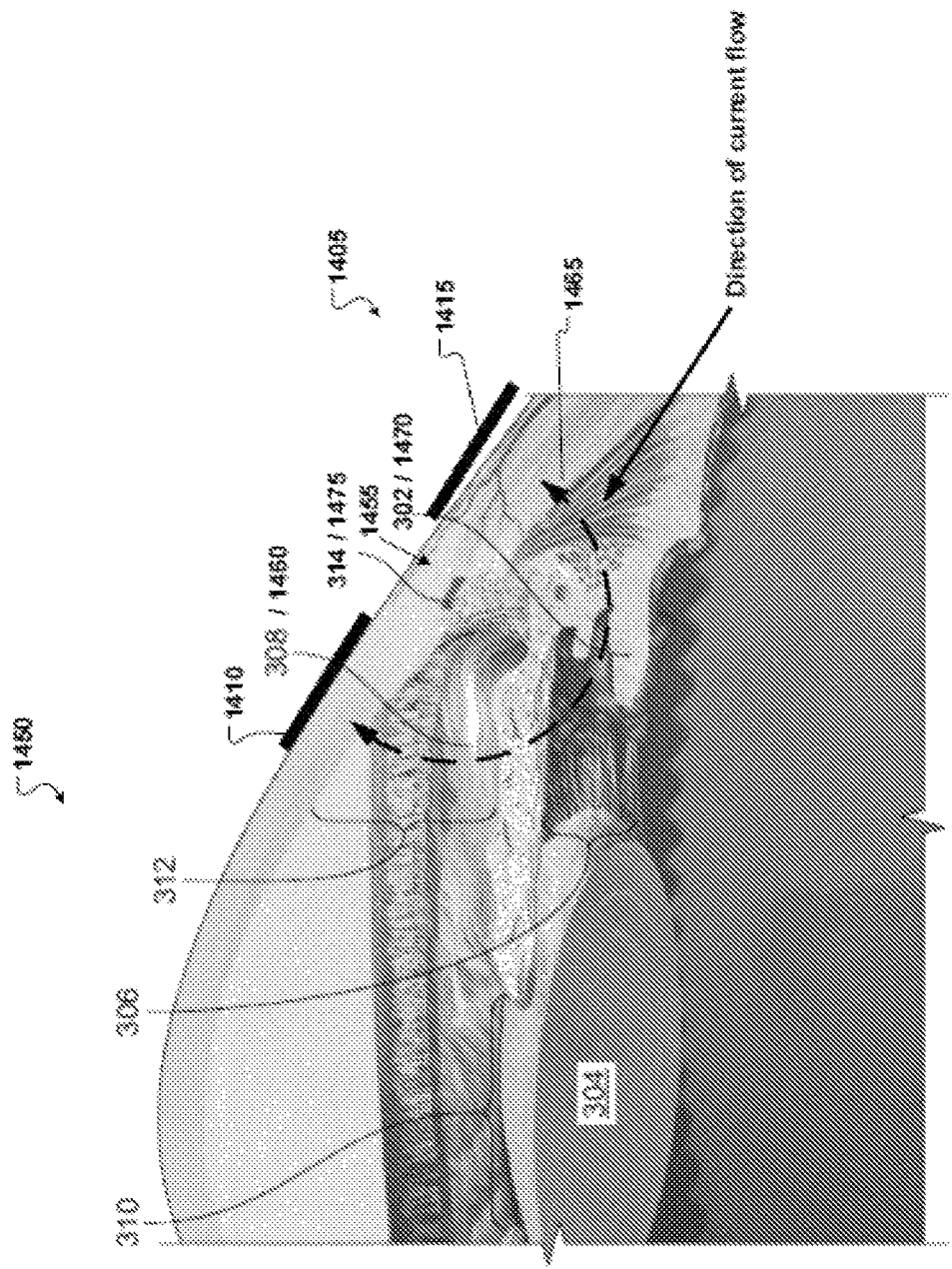

FIG. 14 shows a diagram of the relevant anatomy of a mammalian eye configured with a contact lens equipped with a stimulus coil for implementing the disclosed techniques.

Figure 15:
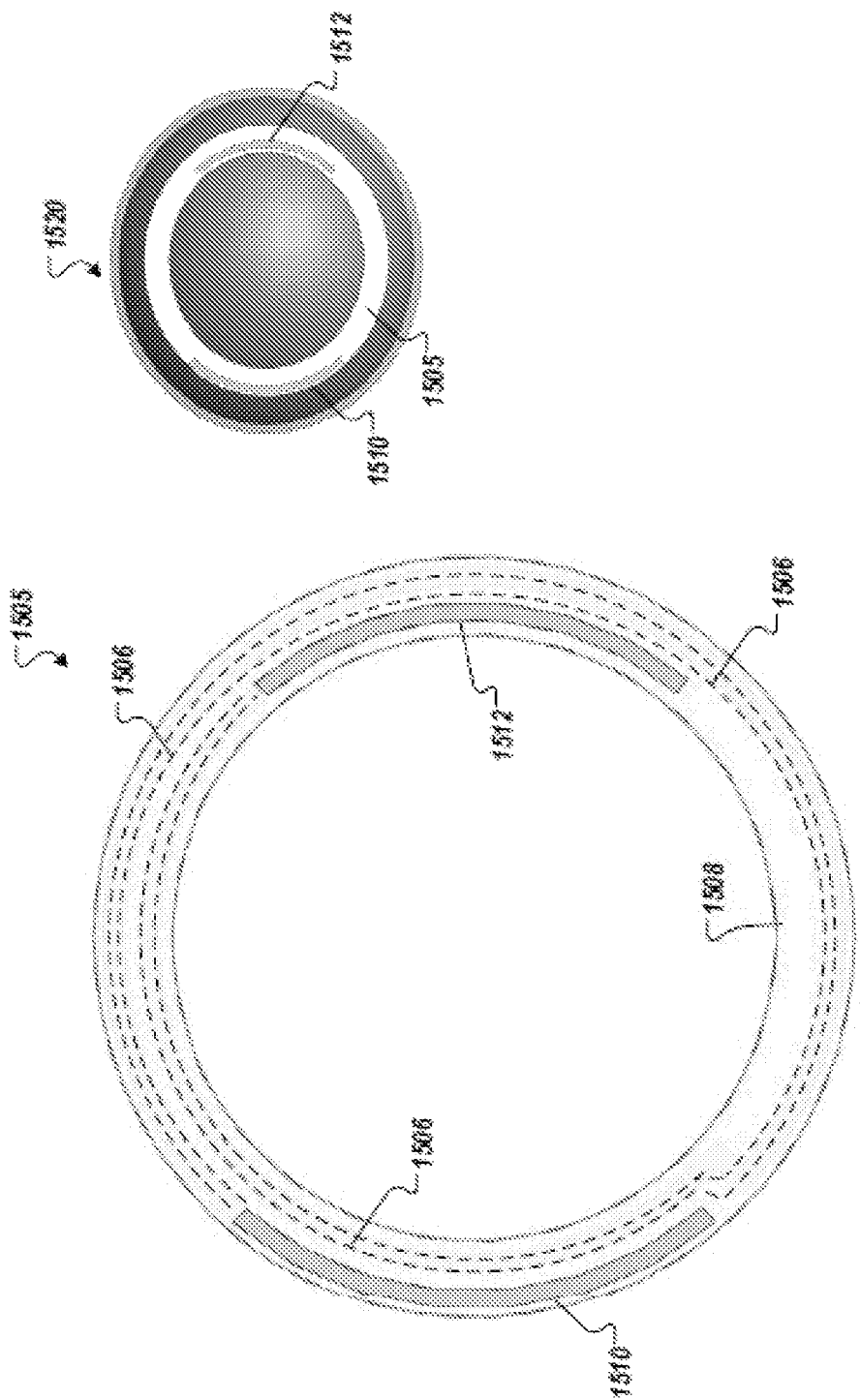

FIG. 15 shows a front view a large round stimulus coil for use with a contact lens on an eye of a mammalian subject for implementing the disclosed techniques.

Figure 16:
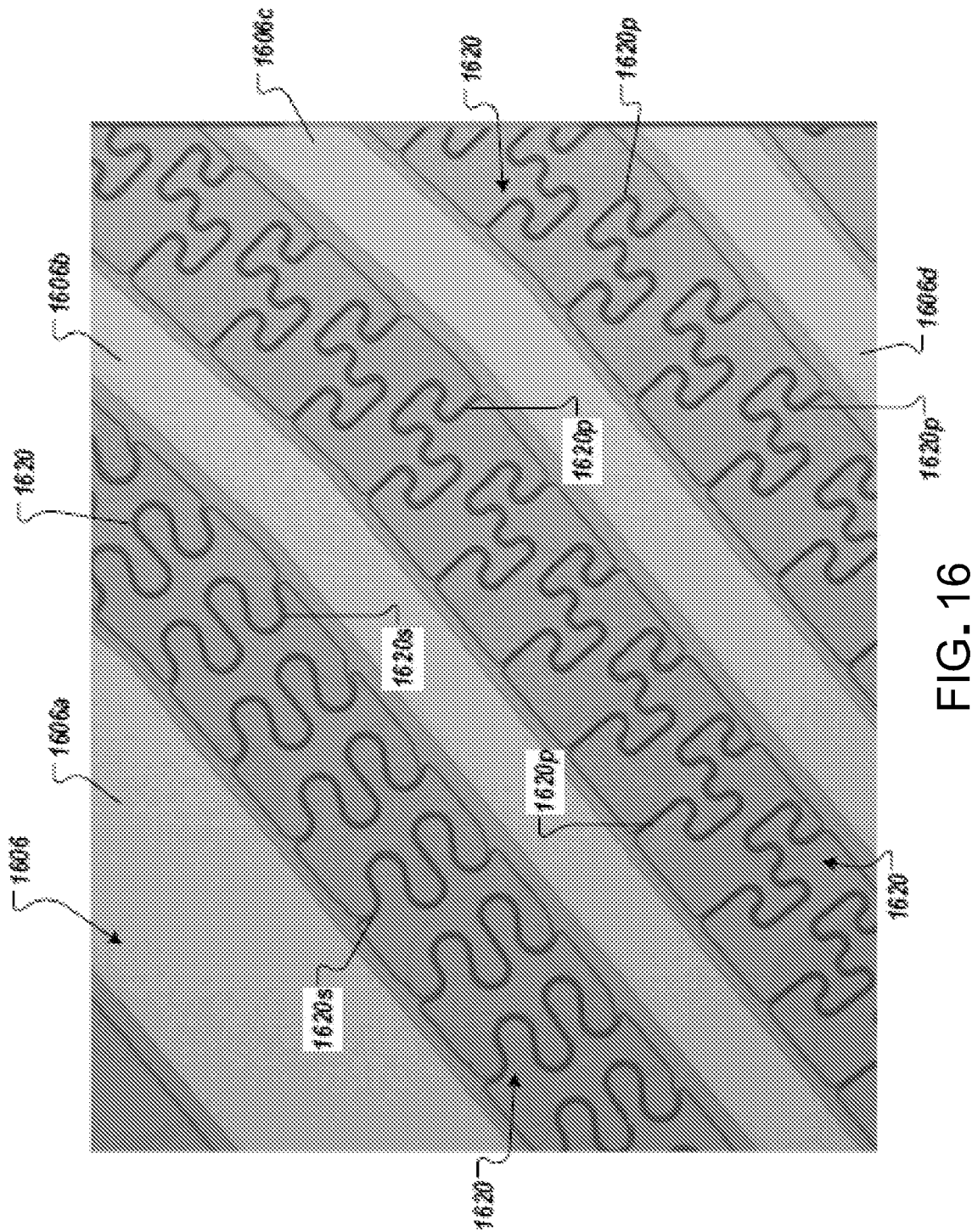

FIG. 16 shows a close-up view of a region of the large round stimulus coil of the type shown in FIG. 15 showing connecting elements that extend between adjacent traces for implementing the disclosed techniques.

Figure 17:
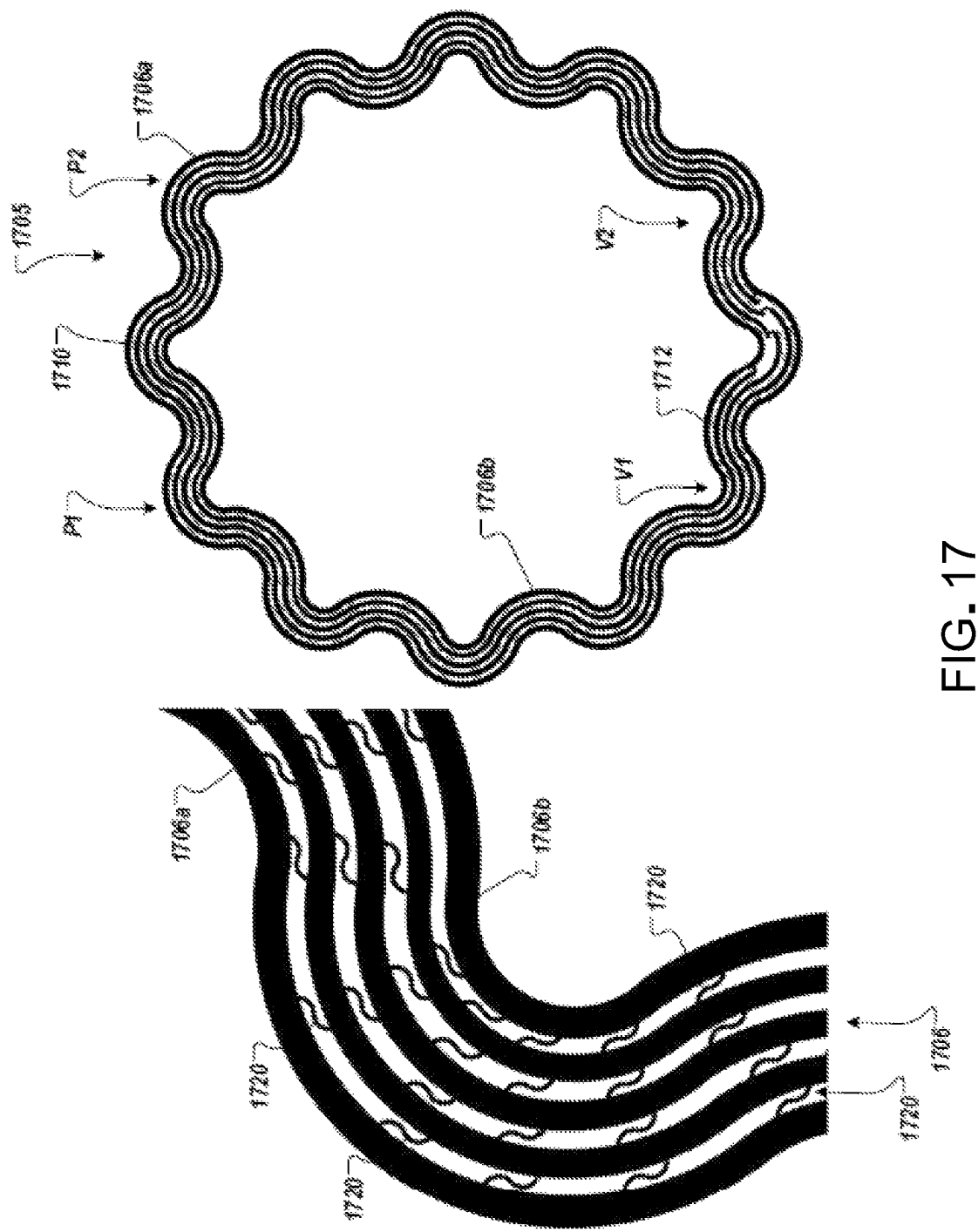

FIG. 17 shows front and exploded sectional views of a first large serpentine stimulus coil for implementing the disclosed techniques.

Figure 18:
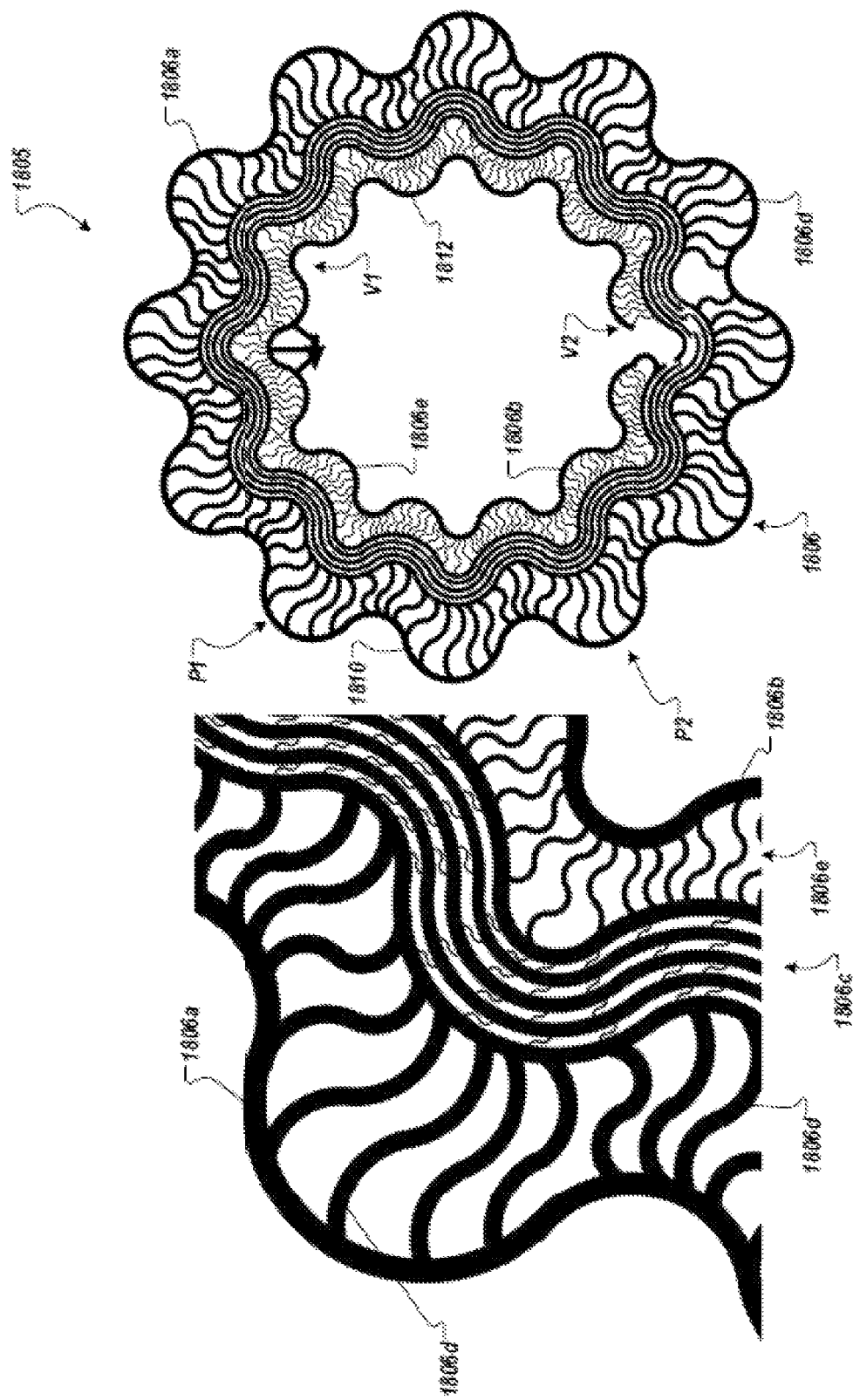

FIG. 18 shows front and exploded sectional views of a second large serpentine stimulus coil for implementing the disclosed techniques.

Figure 19:
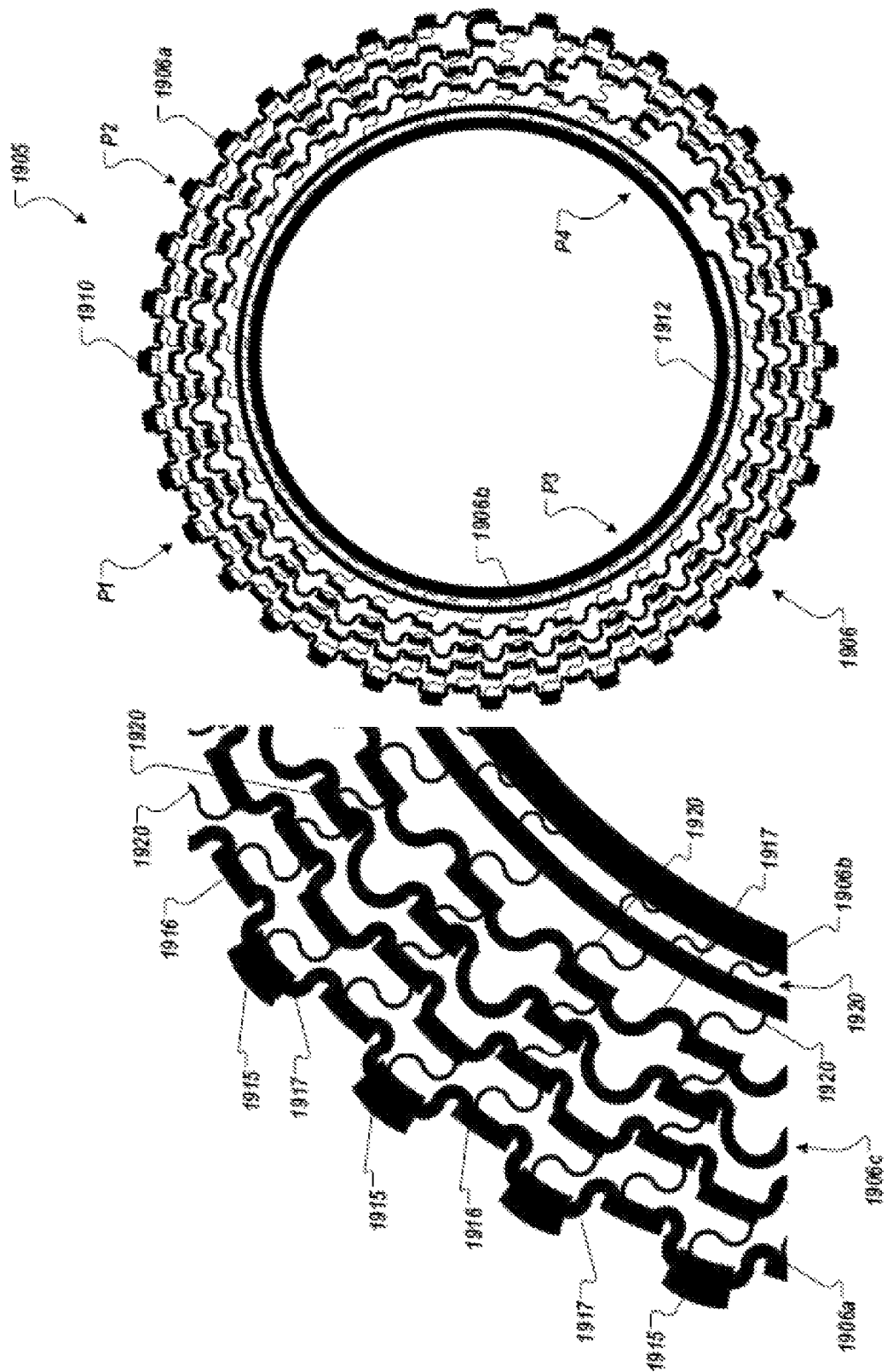

FIG. 19 shows front and exploded sectional views of a large serpentine stimulus coil for implementing the disclosed techniques.

Figure 20:
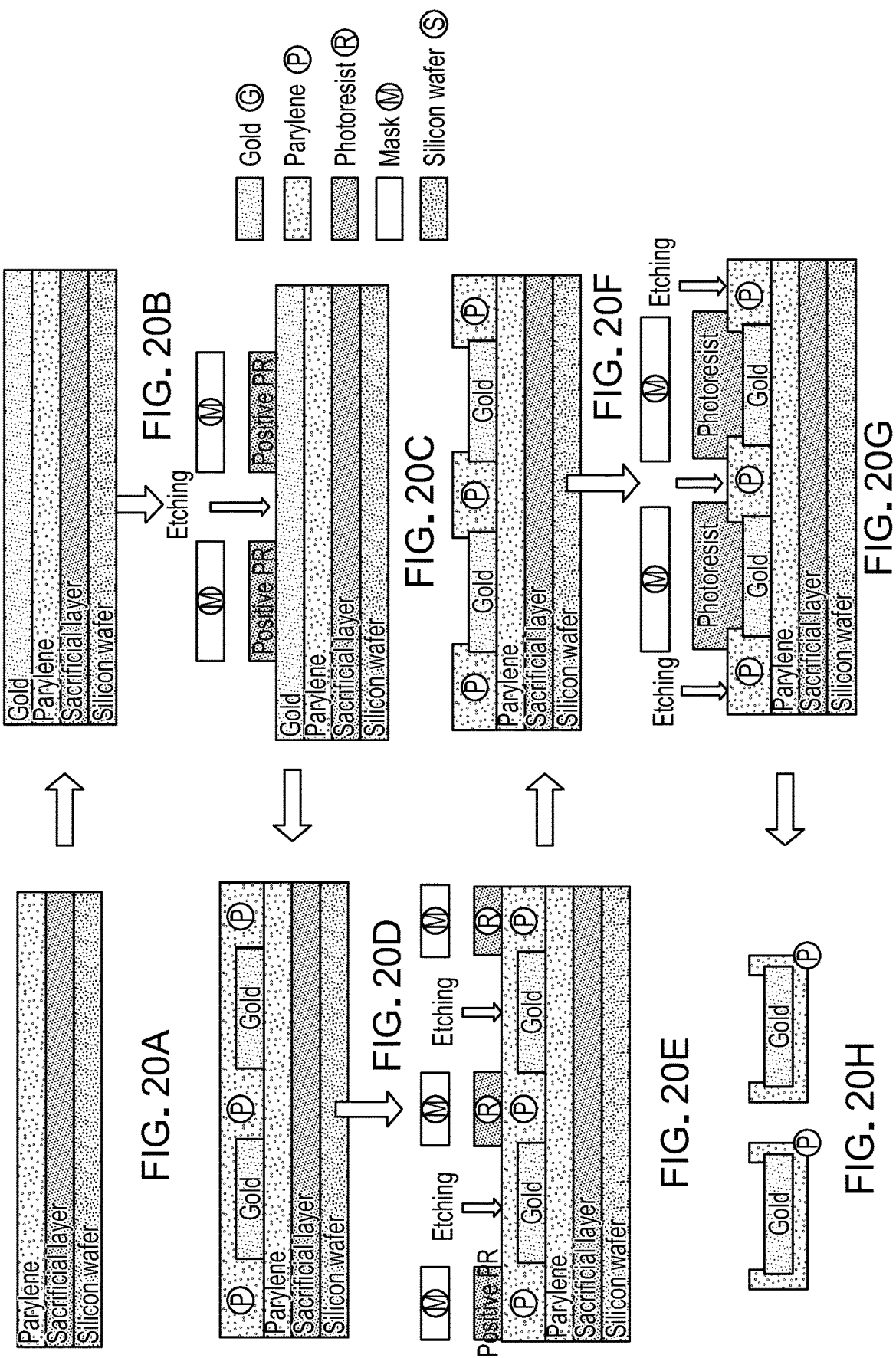

FIG. 20 shows a fabrication method for manufacturing stimulus coils for implantation within an eye of a mammalian subject for implementing the disclosed techniques.

Figure 21:
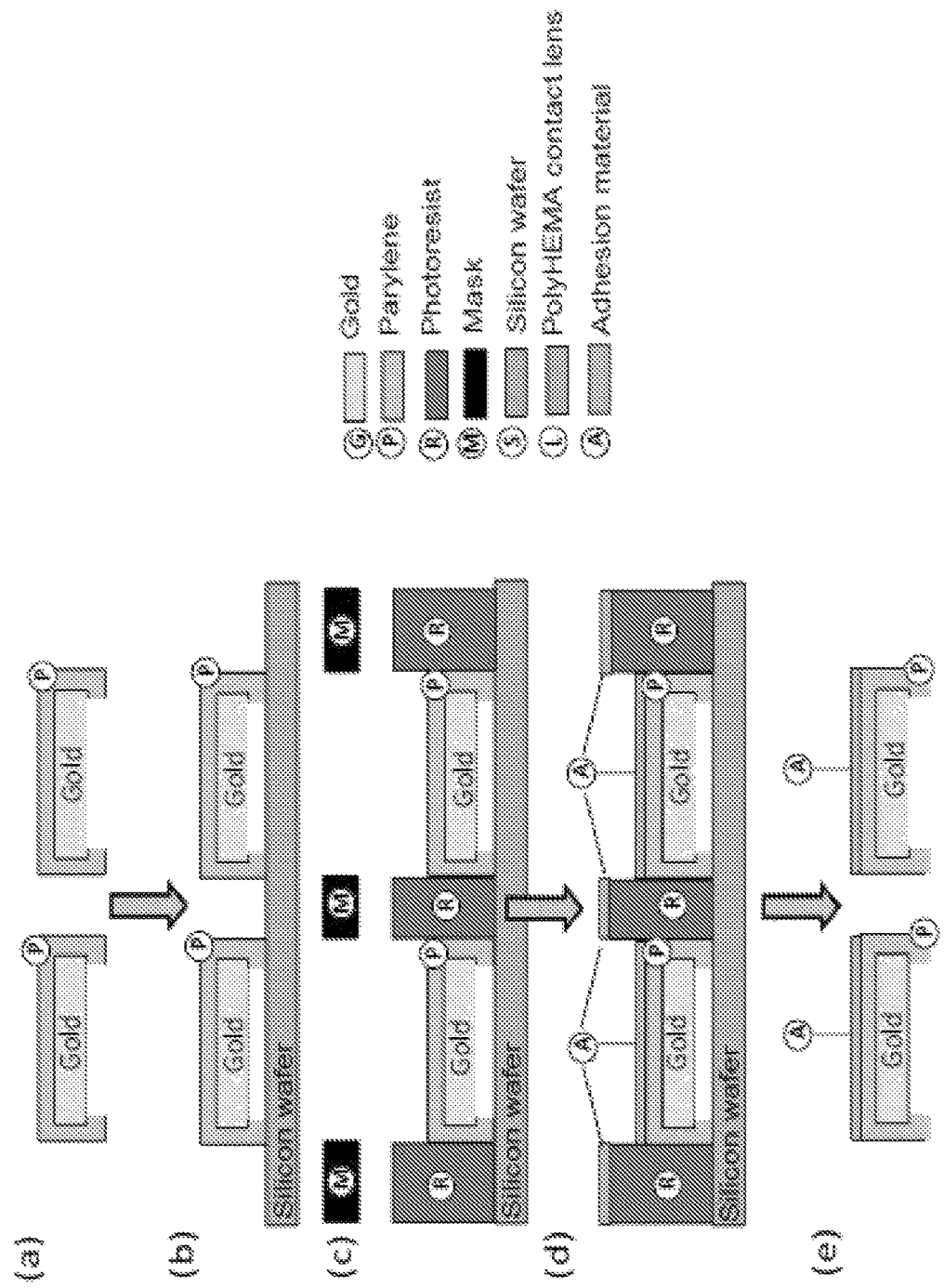

FIG. 21 shows an additional fabrication method for preparing the stimulus coils generated from FIG. 20 for use within or on a substrate lens for implementing the disclosed techniques.

Figure 22:
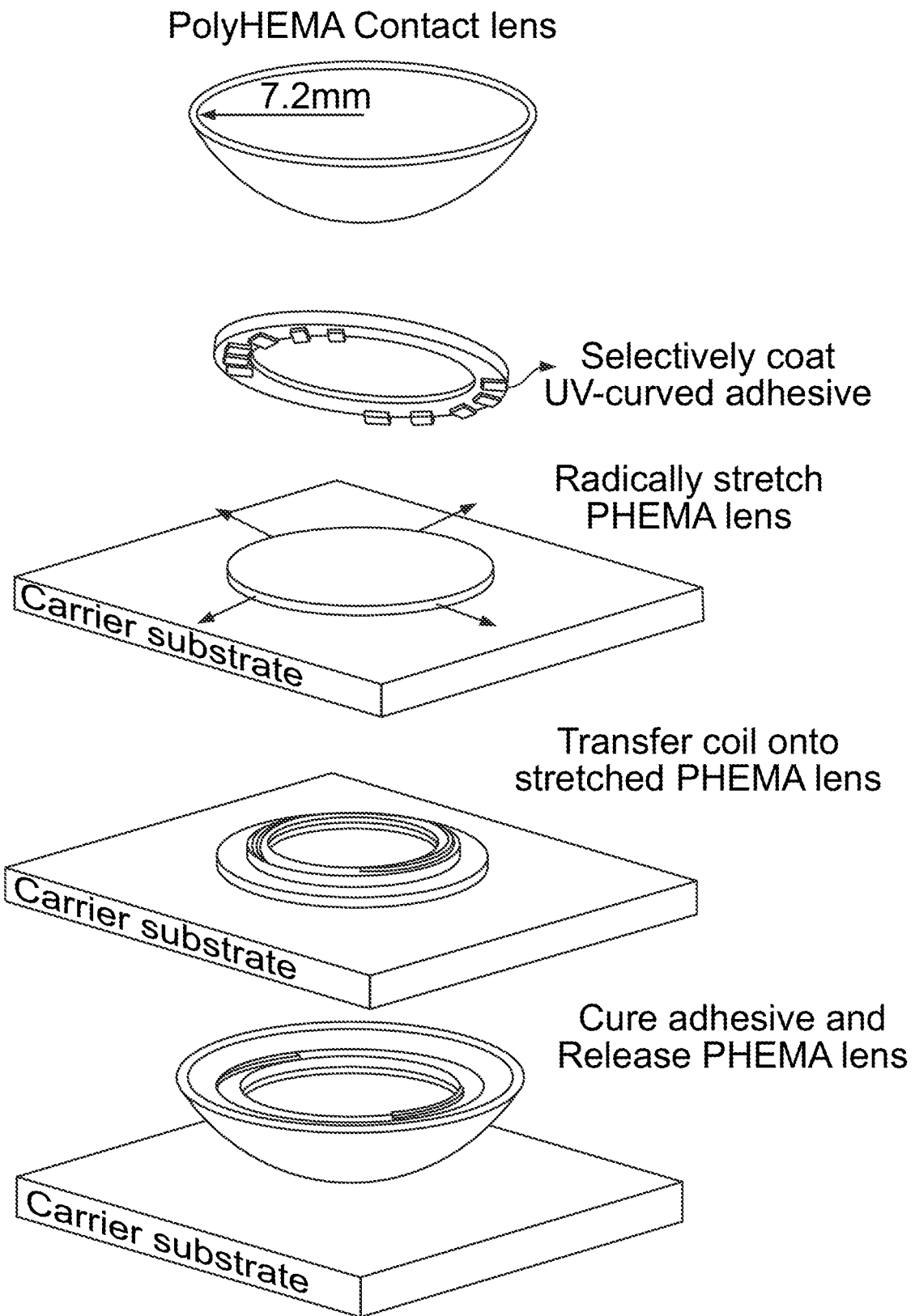
Figure 23:
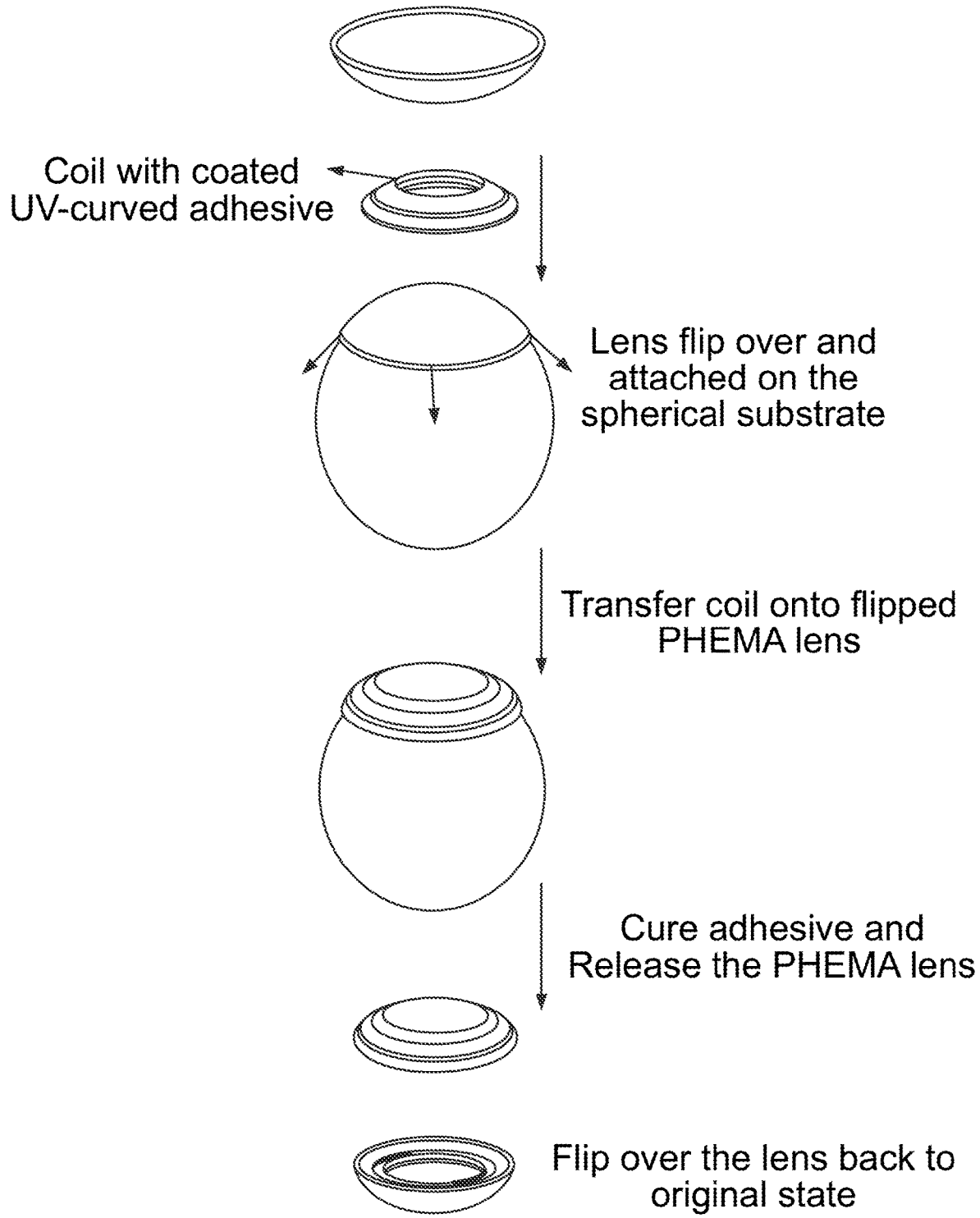

FIGS. 22-23 are strategies for transitioning a stimulus coil from 2D-to-3D to facilitate accommodating the curvature of an eye as part of a contact lens or prosthetic intraocular lens.

Figure 24:
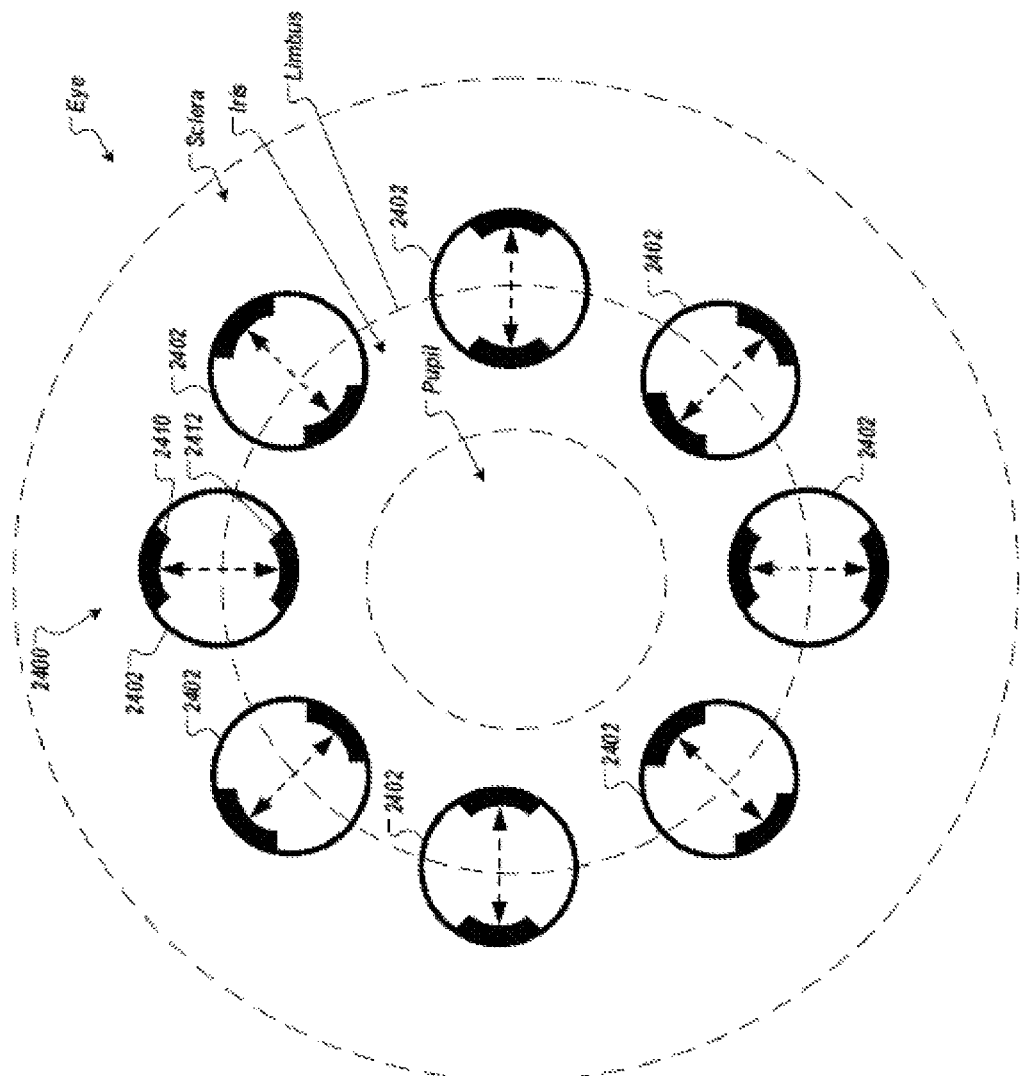
Figure 25:
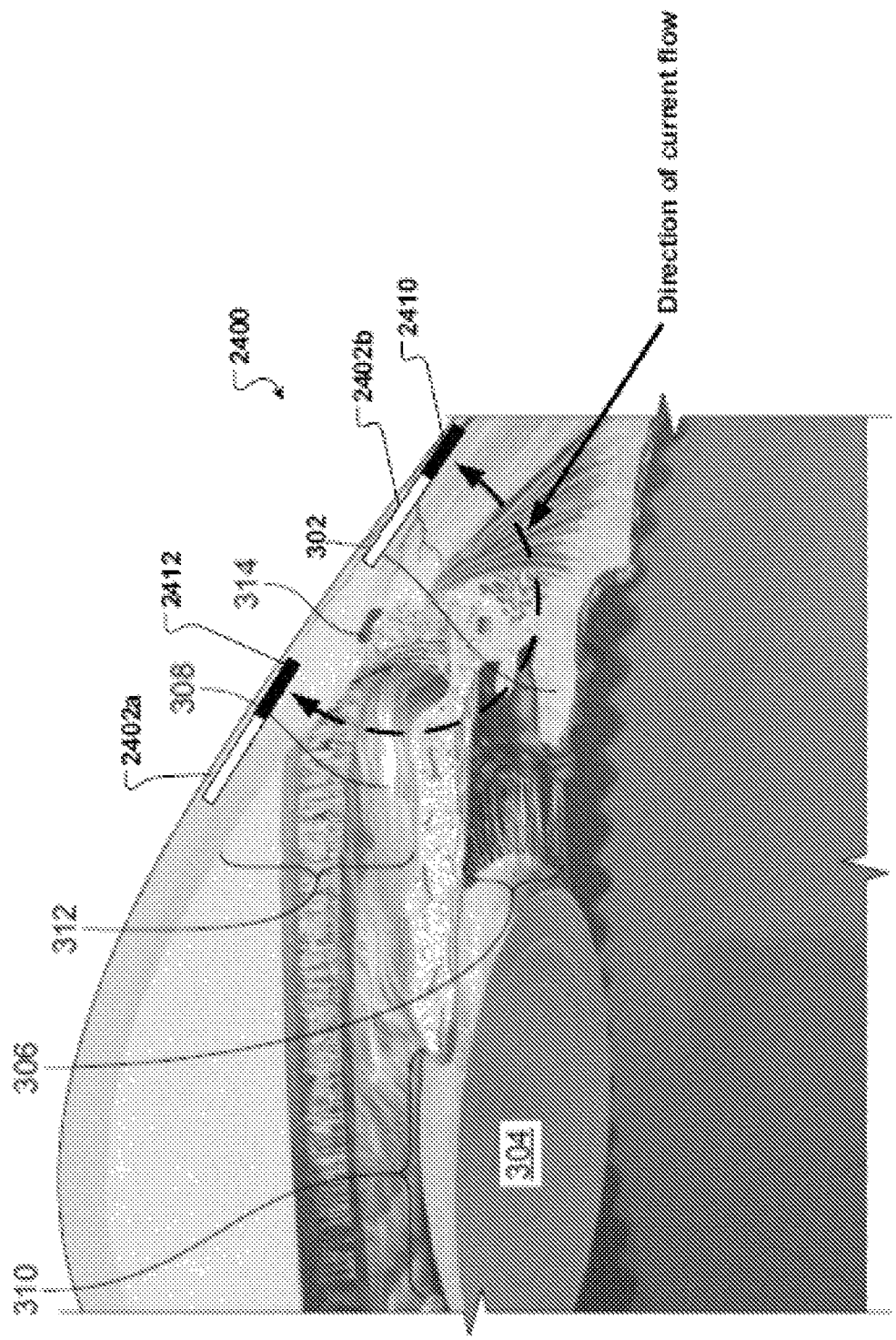

FIGS. 24-25 show front and side diagrammatic view of the relevant anatomy of a mammalian subject configured with a multi-ringed stimulus coil implanted in a sub-conjunctival region for implementing the disclosed techniques.

Figure 26:
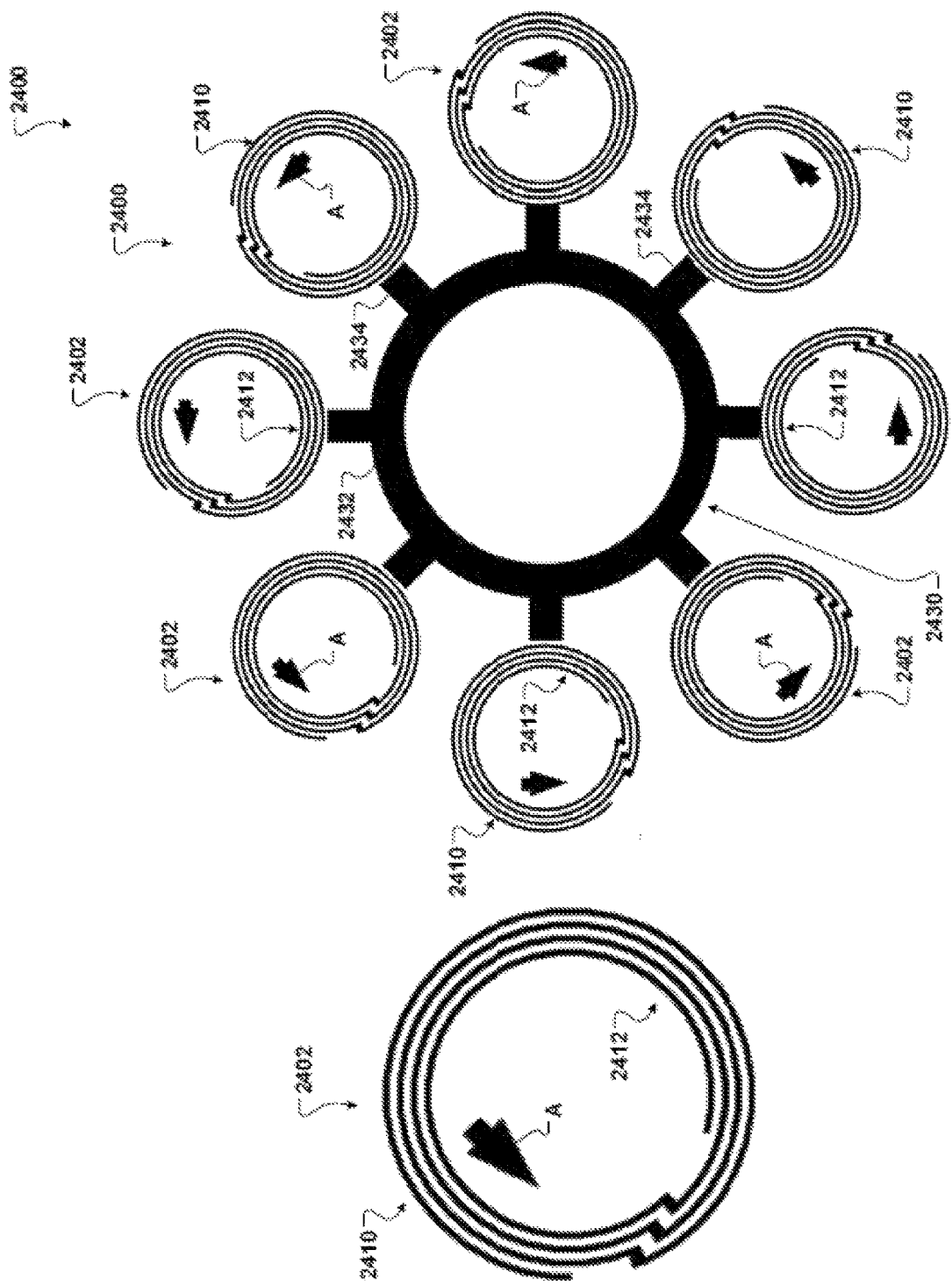

FIG. 26 are front views of the multi-ringed stimulus coil shown in FIGS. 24-25 along with an exploded view of one of the rings for implementing the disclosed techniques.

Figure 27:
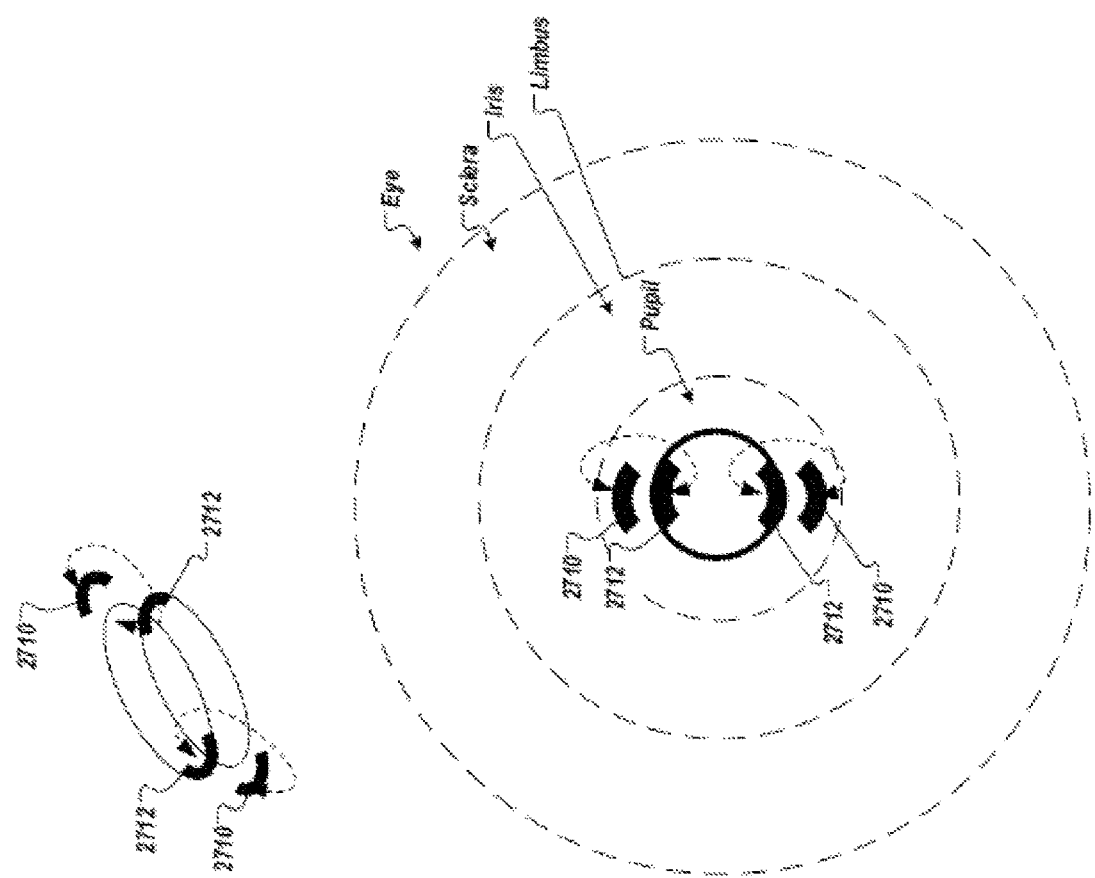
Figure 28:
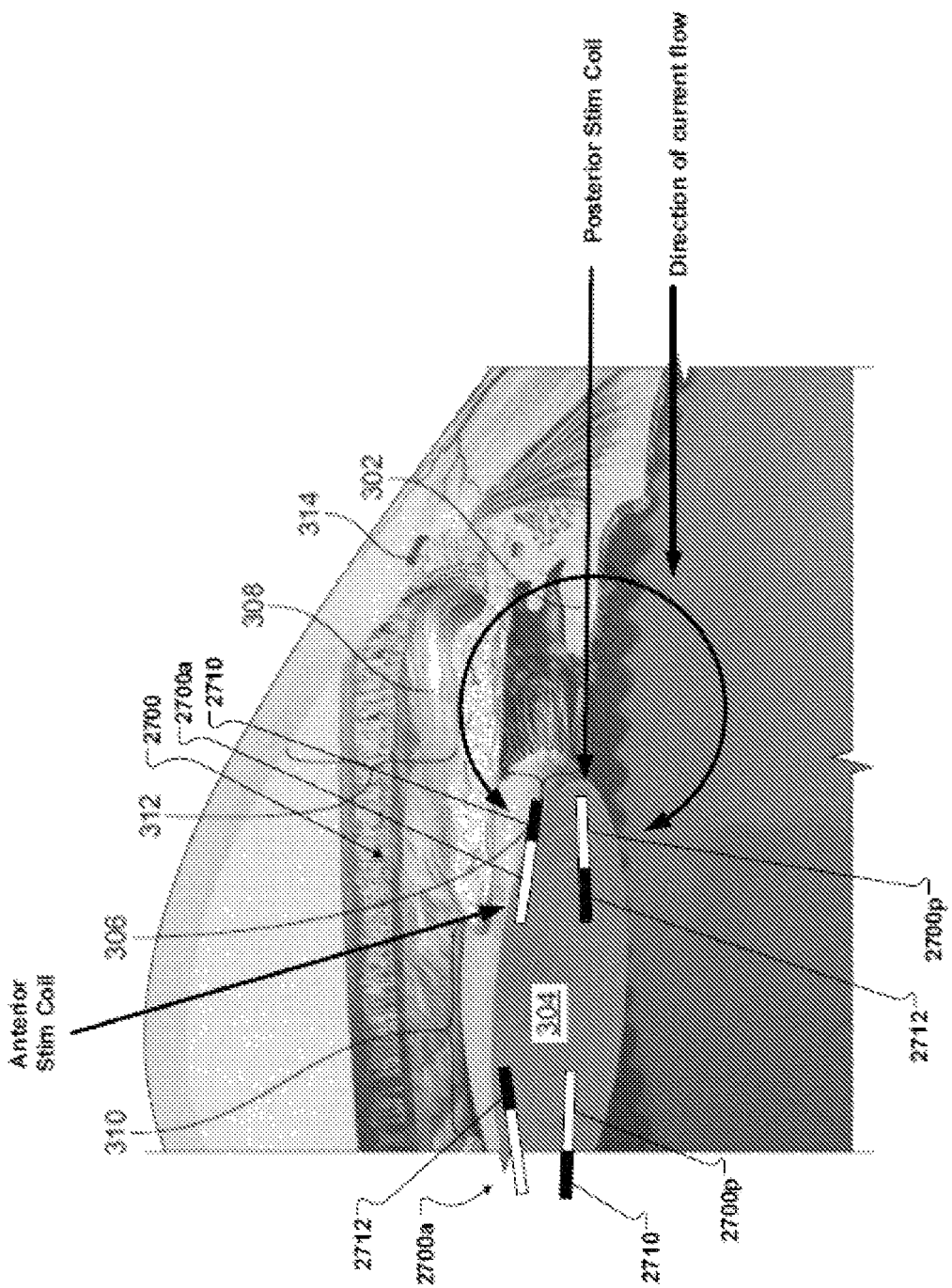

FIG. 27-28 are front and view diagrammatic view of the relevant anatomy of a mammalian eye configured with a stimulus coil implanted within an intraocular lens (IOL) for implementing the disclosed techniques.

Figure 29:
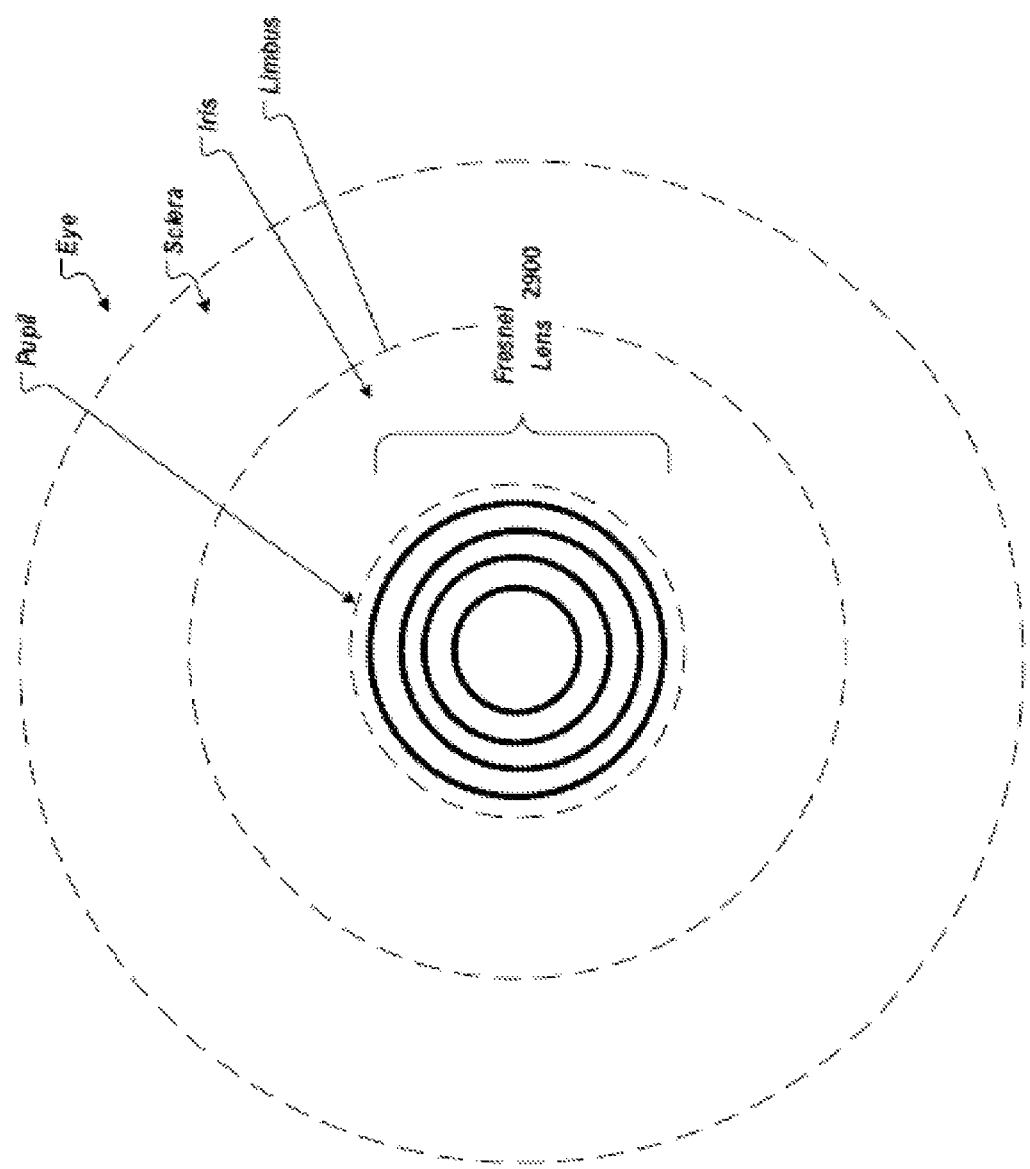
Figure 30:
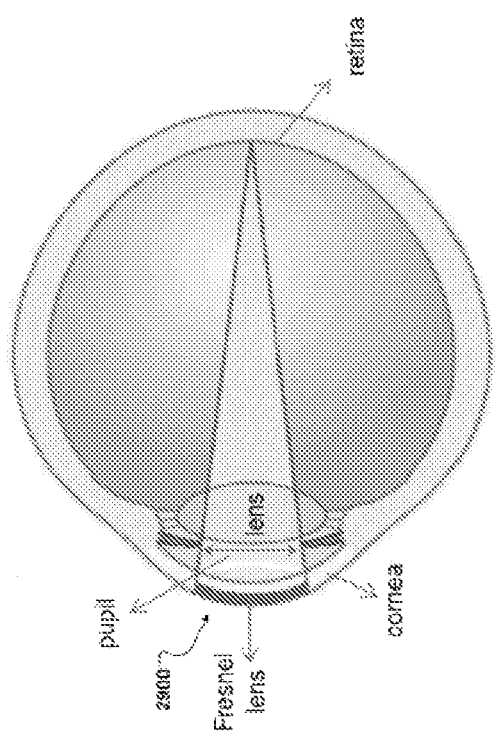

FIGS. 29-30 are front and side diagrammatic views of an eye of a mammalian subject configured with a Fresnel lens for implementing vision correction and optionally the disclosed glaucoma therapy techniques.

Figure 31A:
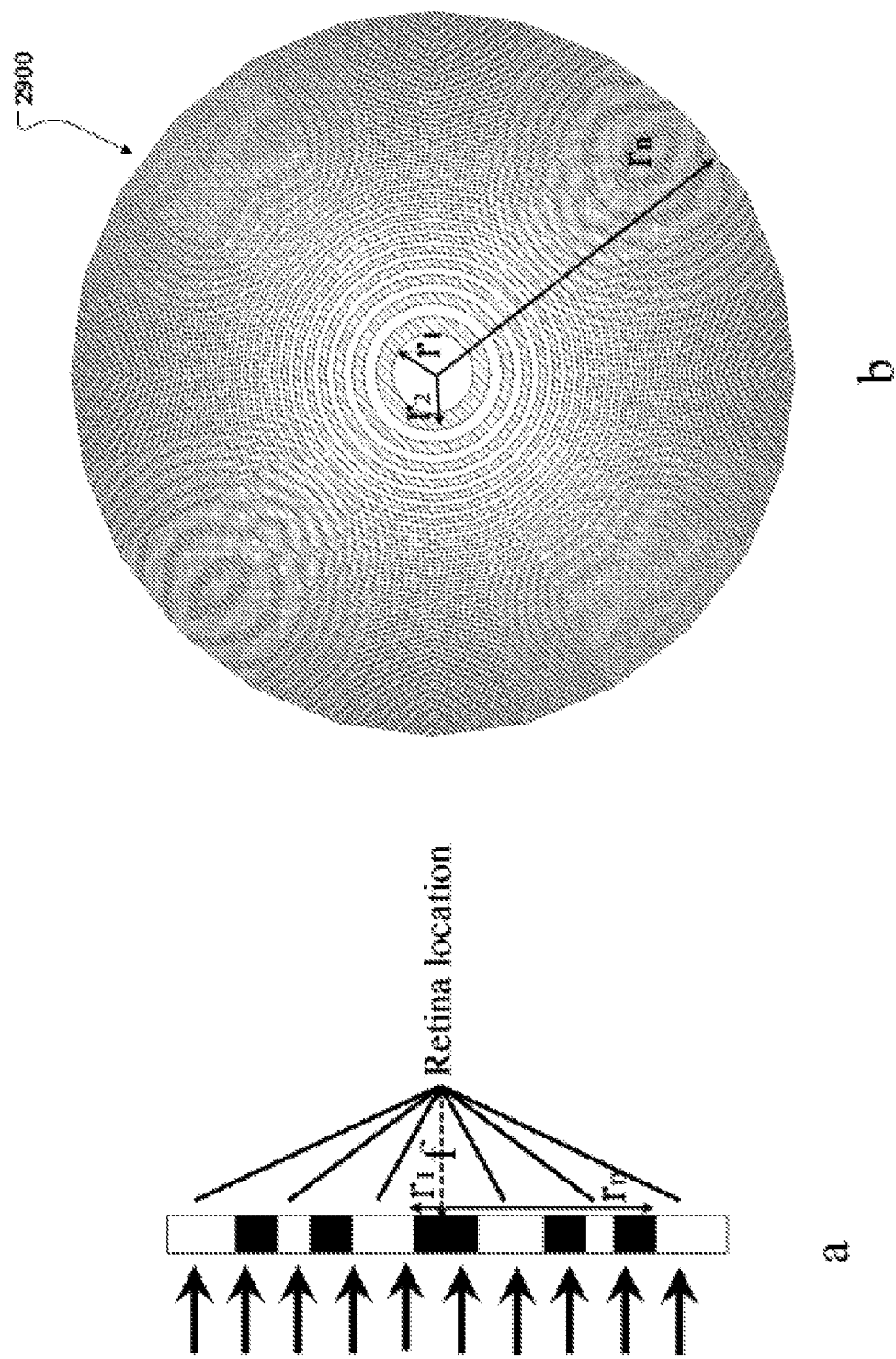
Figure 31B:
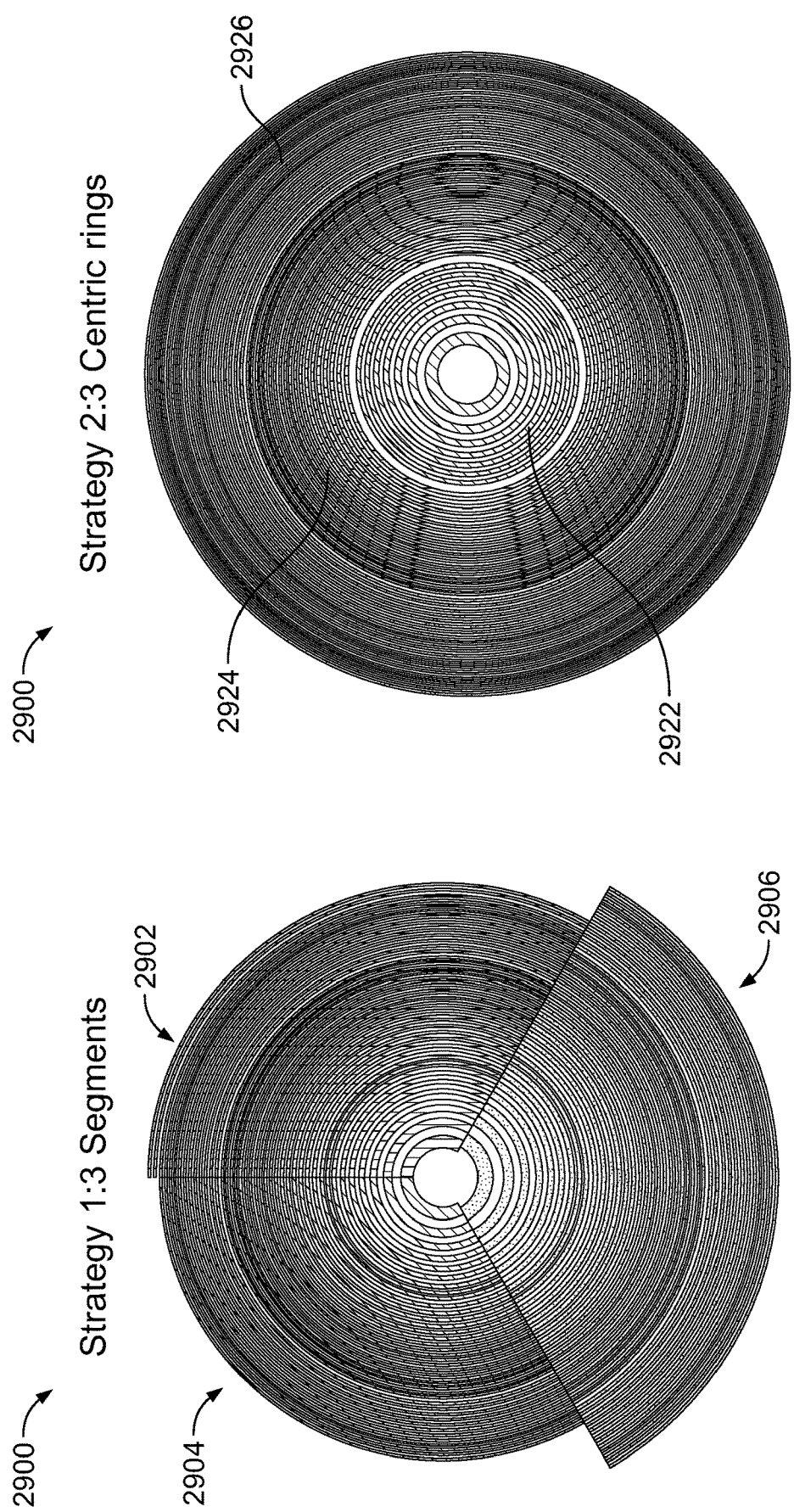

FIGS. 31a-b are views of multiple embodiments of a Fresnel lens for implementing vision correction and optionally the disclosed glaucoma therapy techniques.

FIG. 32 shows a fabrication method for manufacturing a Fresnel lens for vision correction for implementing the disclosed techniques.

Figure 33:
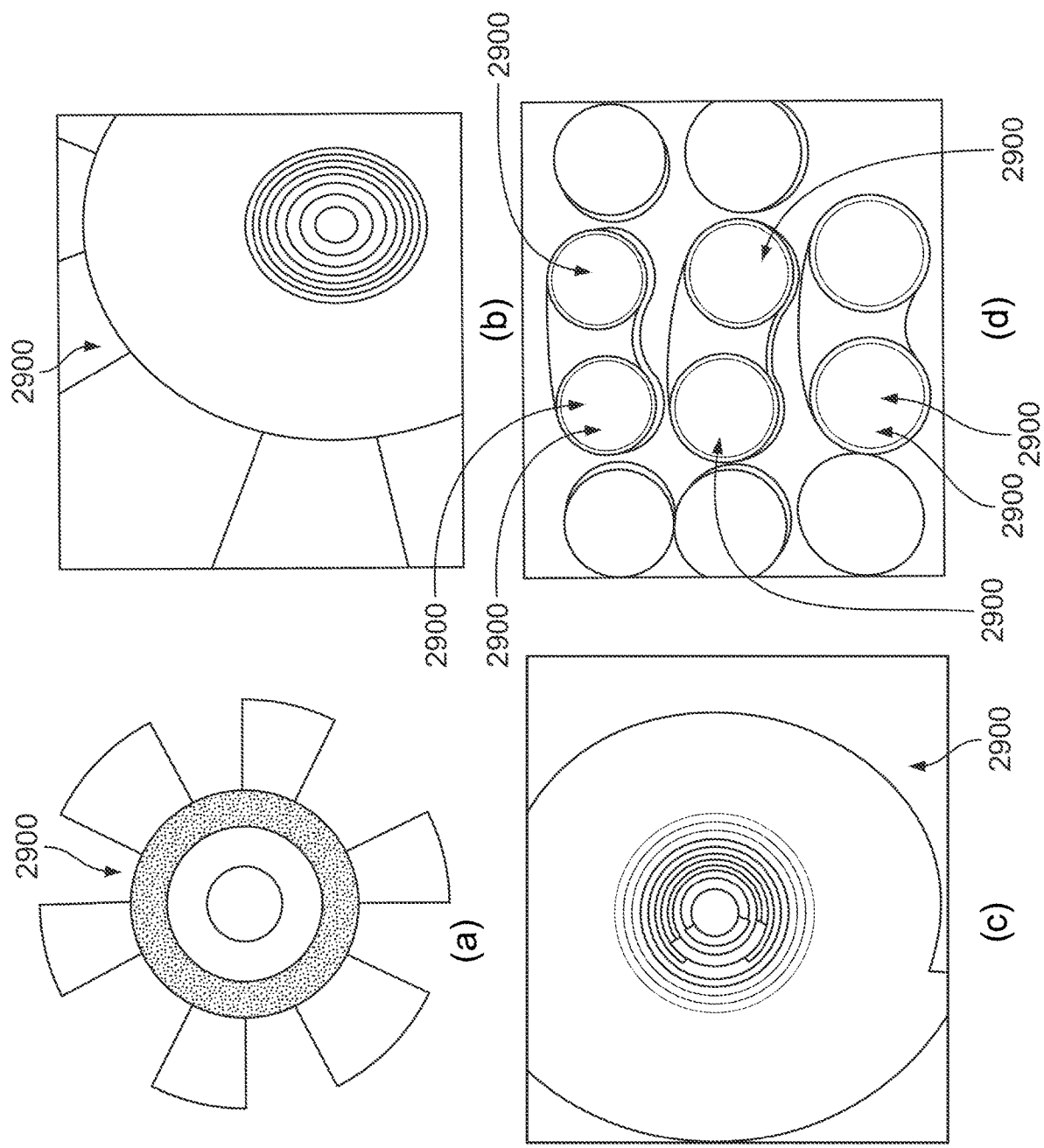

FIG. 33 shows top and diagrammatic views of multiple embodiment of a Fresnel lens for implementing vision correction for implementing the disclosed techniques.

Figure 34:
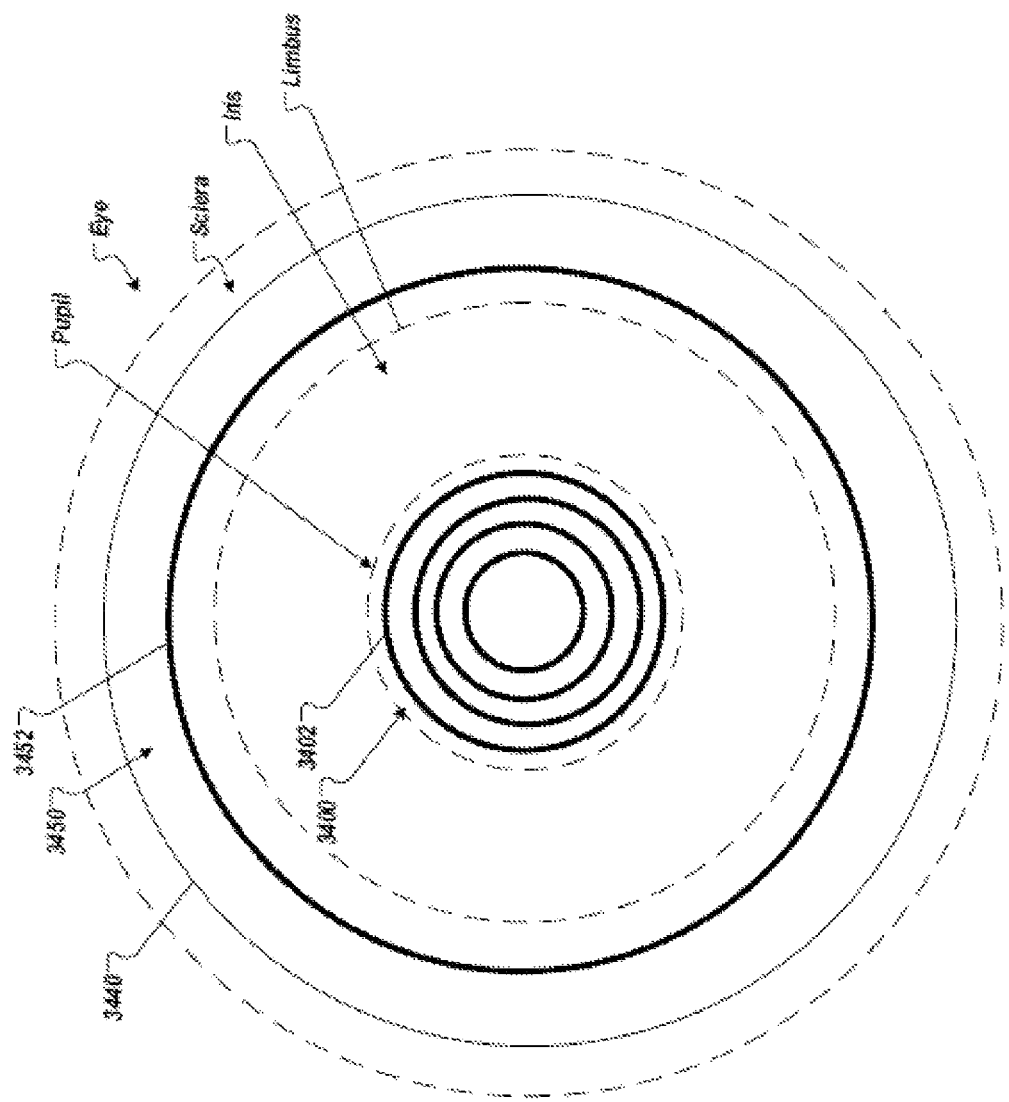
Figure 35:
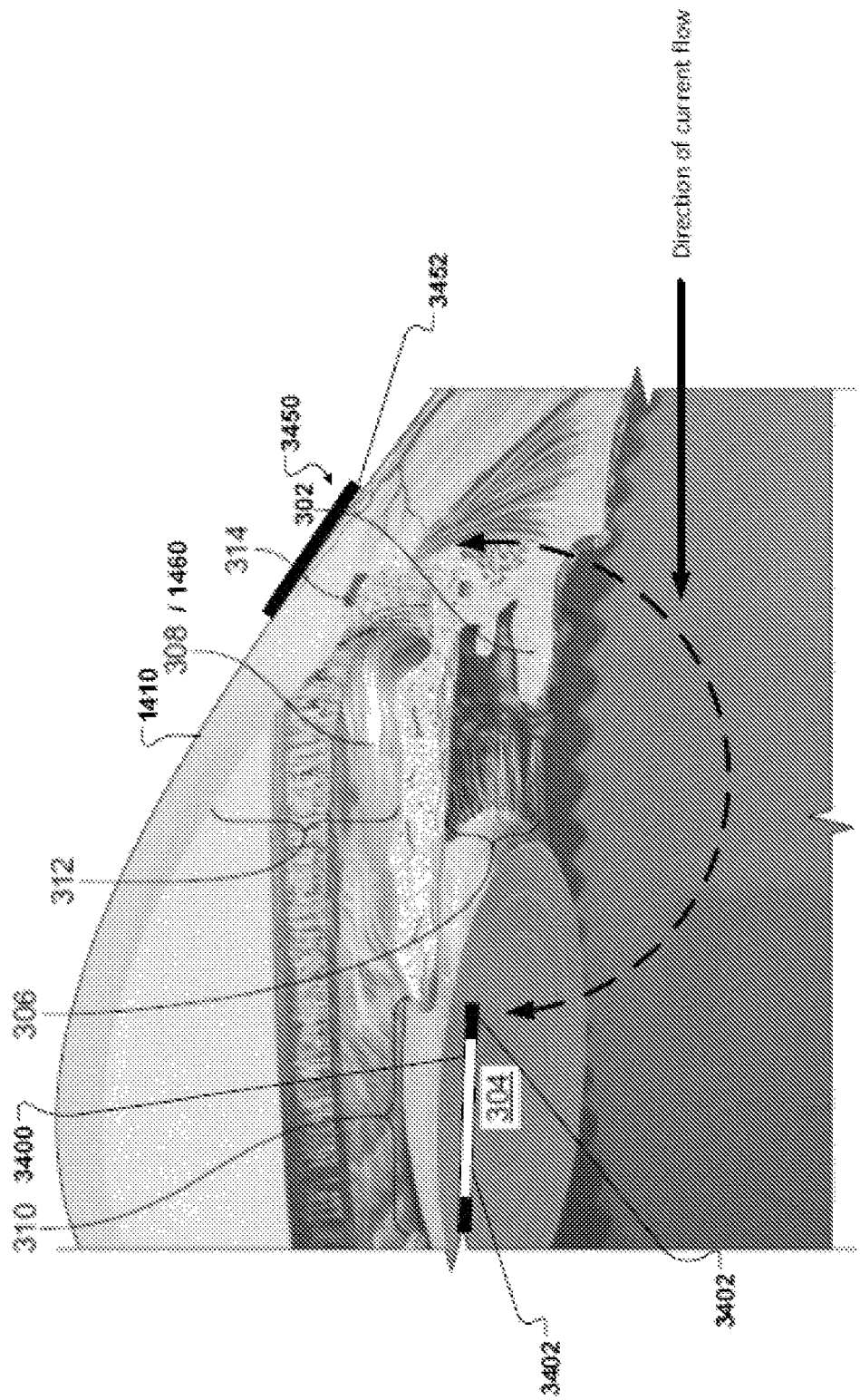

FIG. 34-35 are front and view diagrammatic view of the relevant anatomy of a mammalian eye configured to deliver energy to targeted areas within the eye through the combined use of a) electrode(s) of a Fresnel lens implanted within an intraocular lens, and b) electrode(s) of a stimulus coil within a contact lens applied to the eye for implementing the disclosed techniques.

Figure 36:
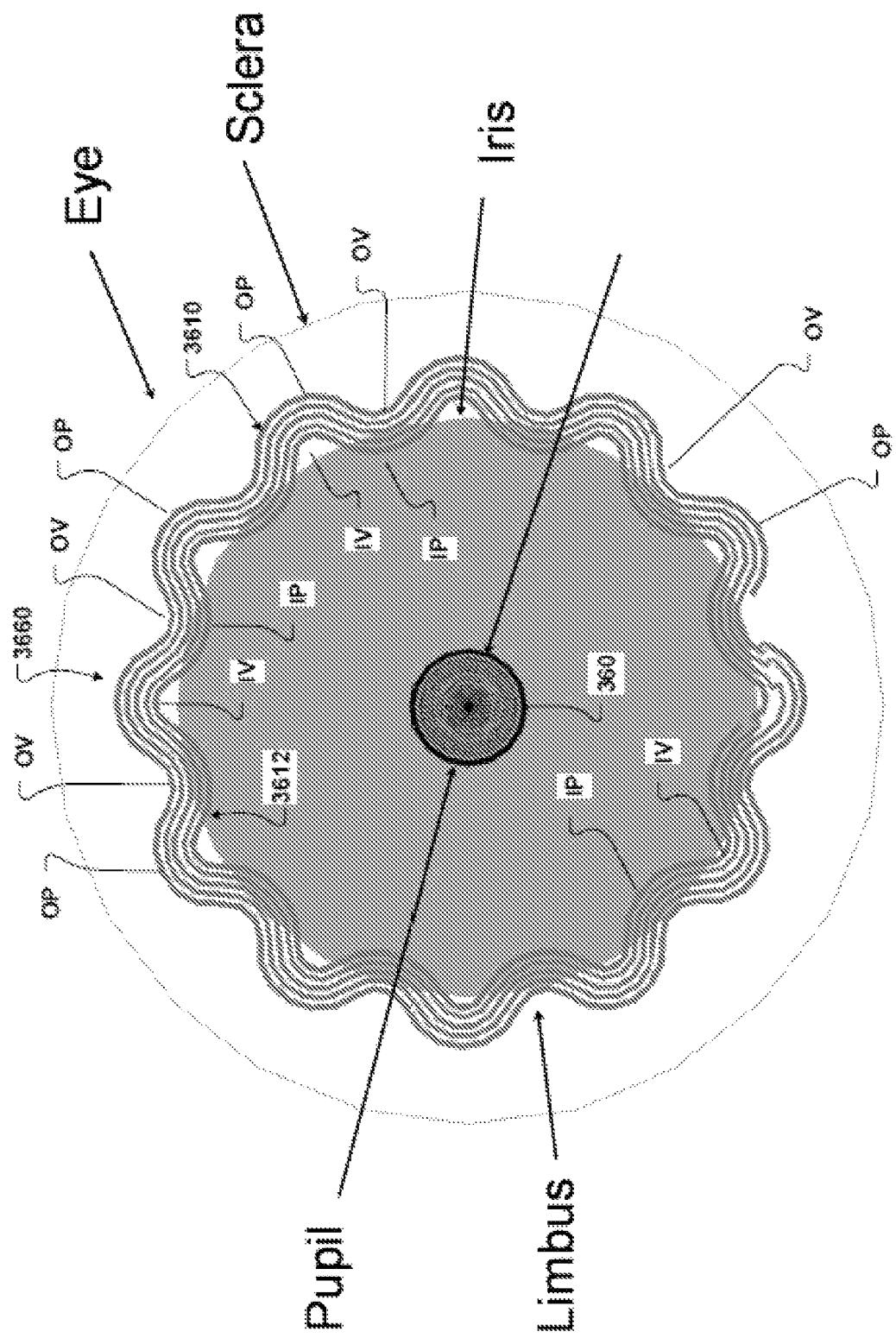

FIG. 36 is a front diagrammatic view of the relevant anatomy of an eye of a mammalian subject with a Fresnel lens and a large stimulus coil (with no direct electrical connection therebetween) for implementing the disclosed techniques.

Figure 37:
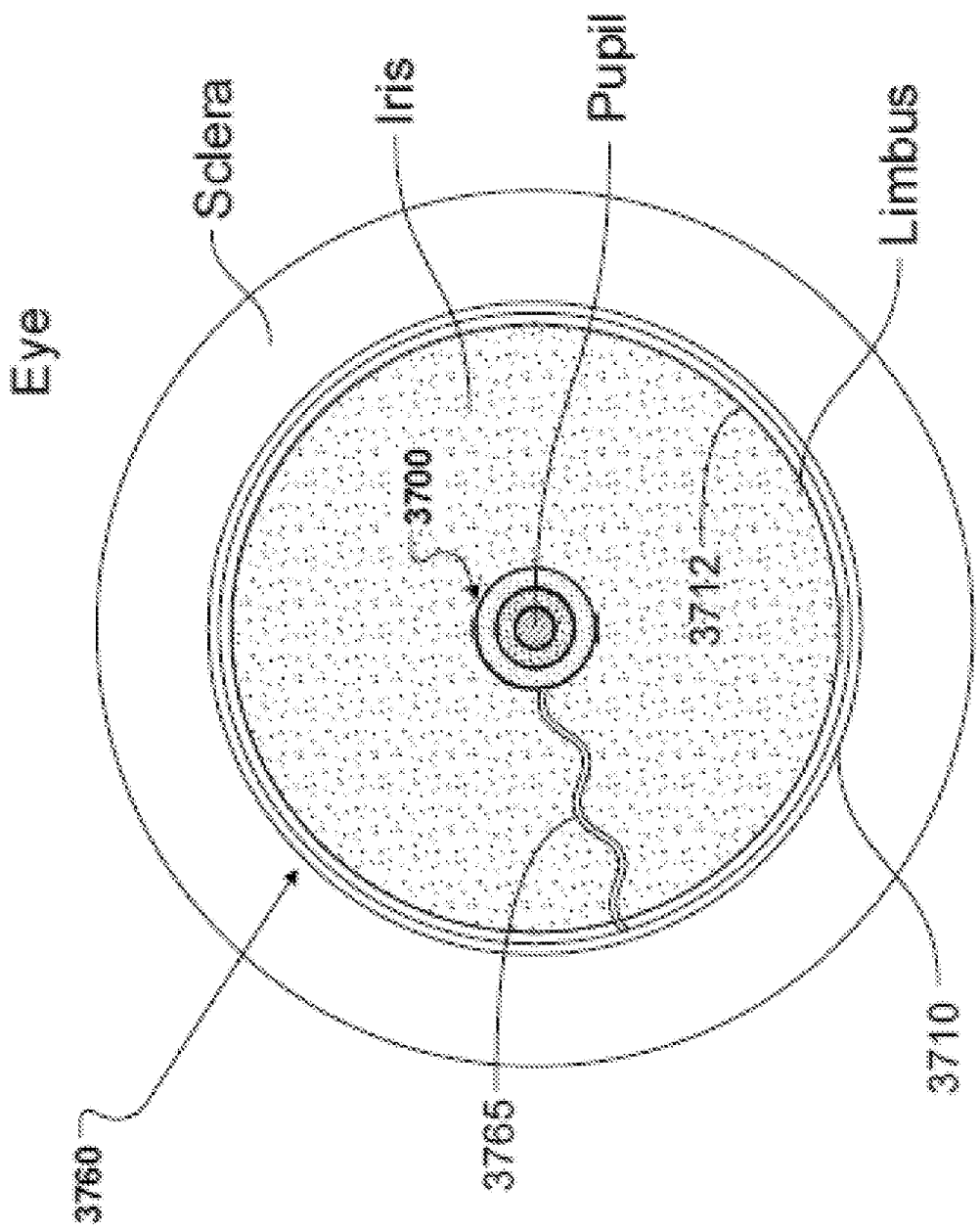

FIG. 37 is a front diagrammatic view of the relevant anatomy of an eye of a mammalian subject with a Fresnel lens and a large stimulus coil (with a direct electrical connection therebetween) for implementing the disclosed techniques.

Figure 38:
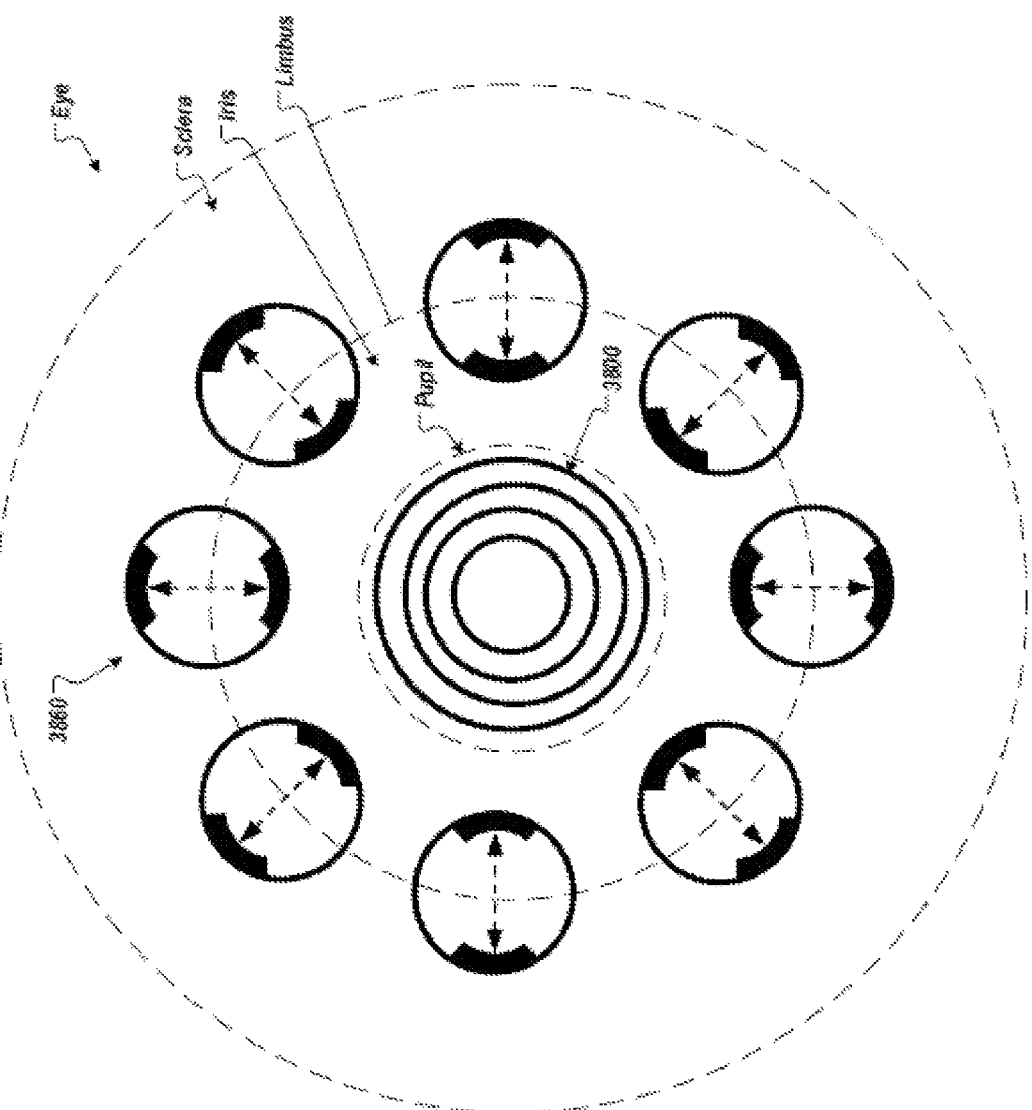
Figure 39:
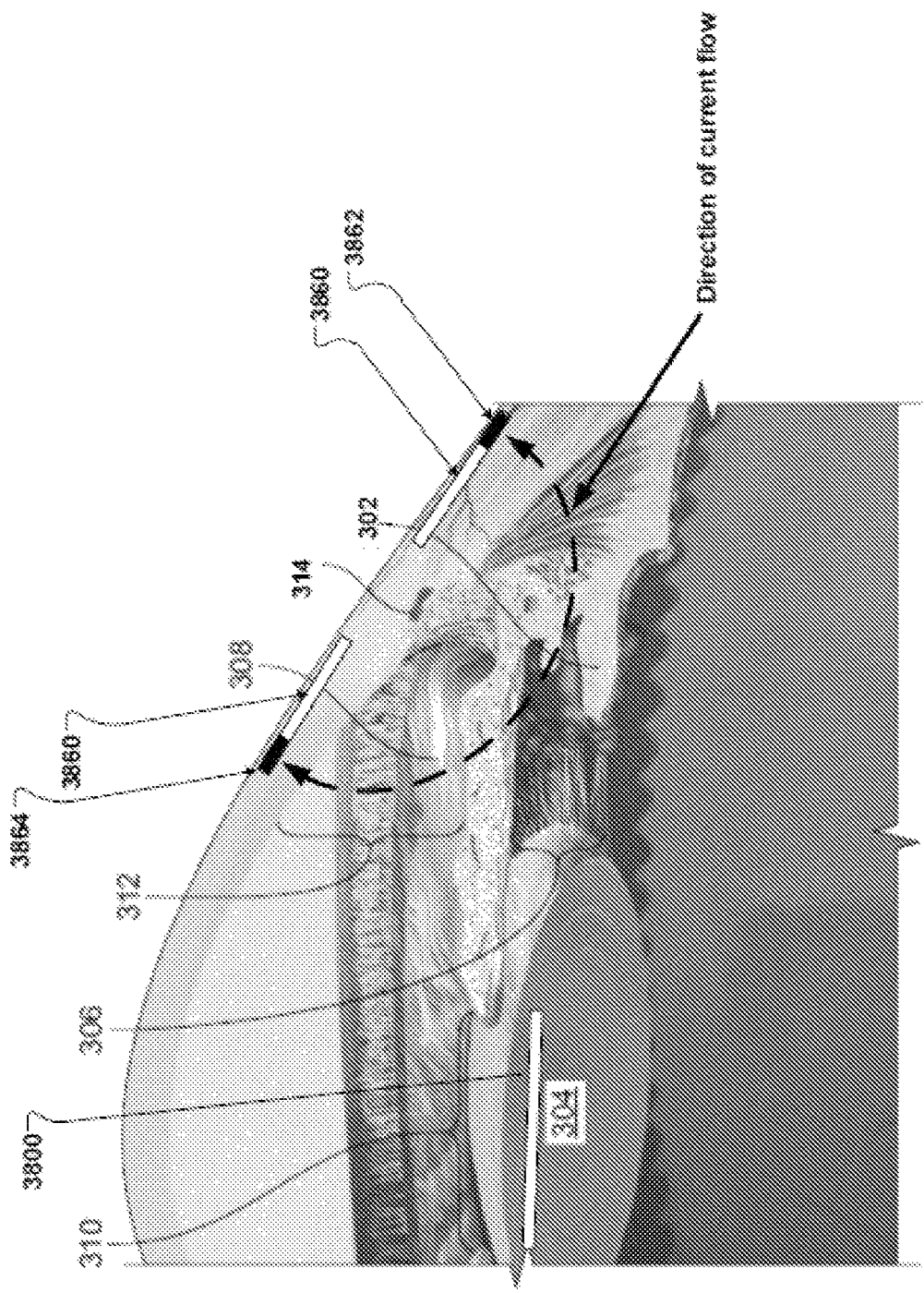

FIG. 38-39 are front and view diagrammatic view of the relevant anatomy of a mammalian eye with a Fresnel lens for vision correction and a multi-ringed stimulation coil assembly for sub-conjunctival implantation for implementing the disclosed techniques.

Figure 40:
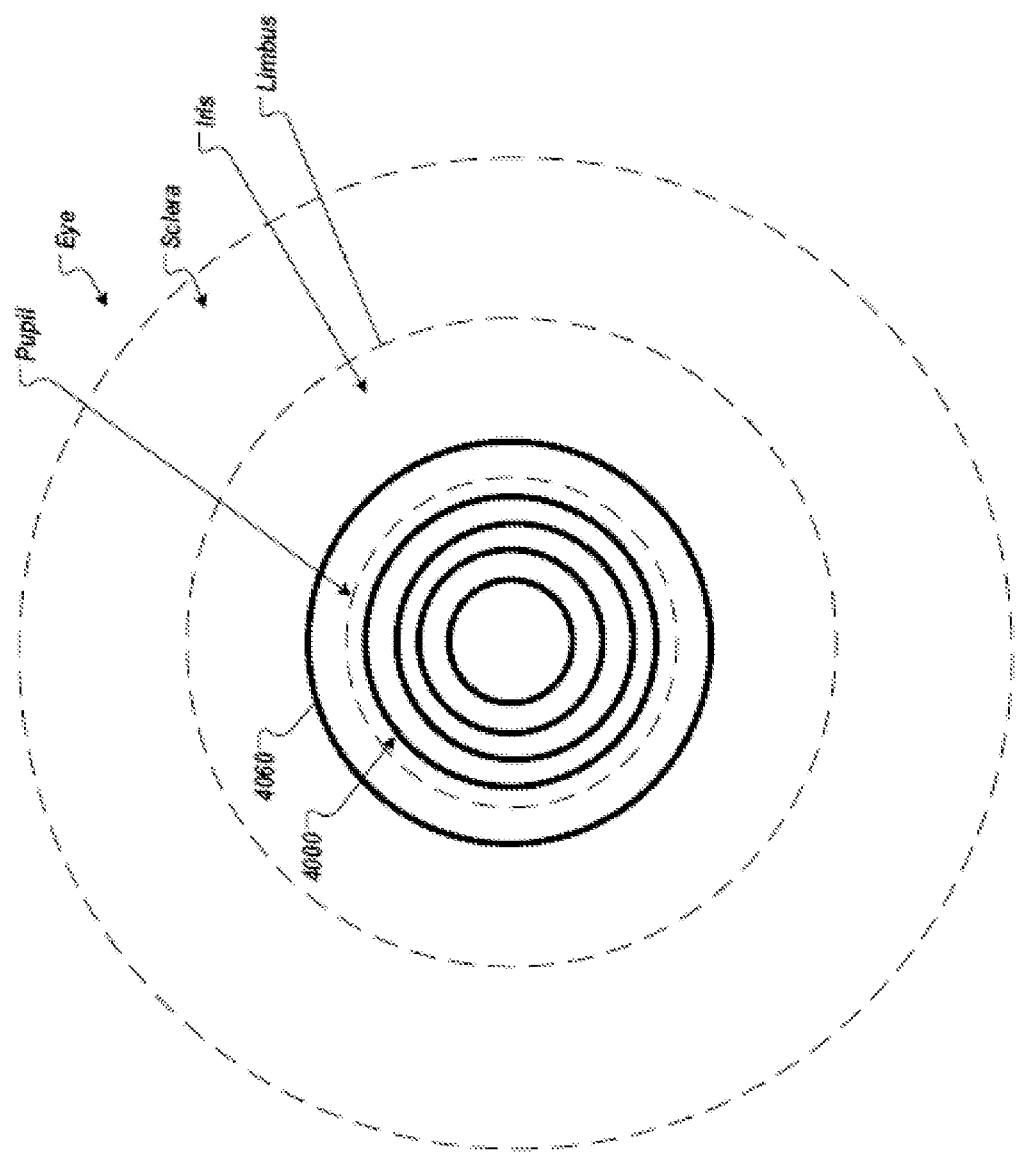
Figure 41:
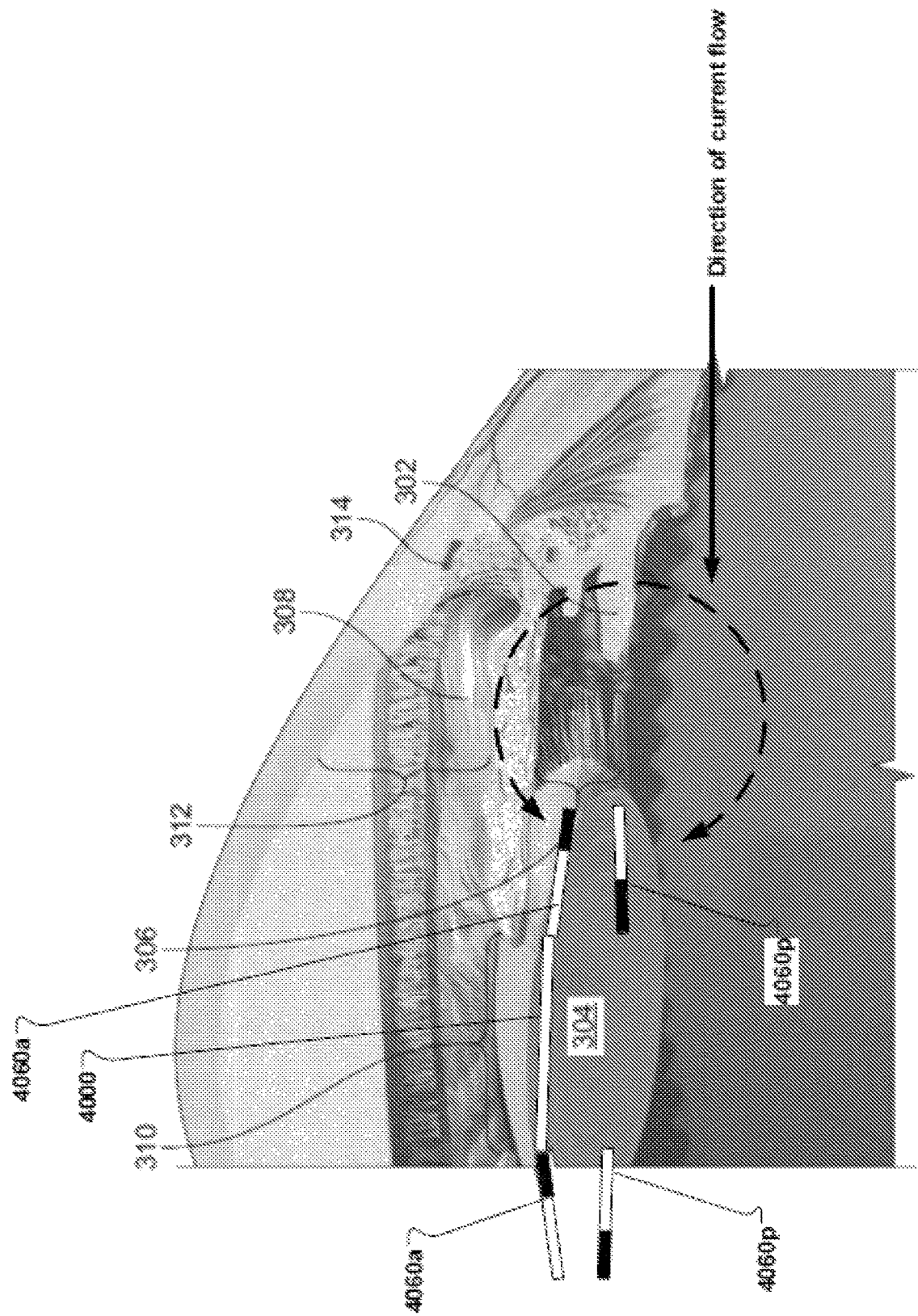

FIG. 40-41 are front and view diagrammatic view of the relevant anatomy of a mammalian eye with a Fresnel lens and two small-round stimulus coils all disposed within an native IOL or a prosthetic IOL for implementing the disclosed techniques.

Figure 42A:
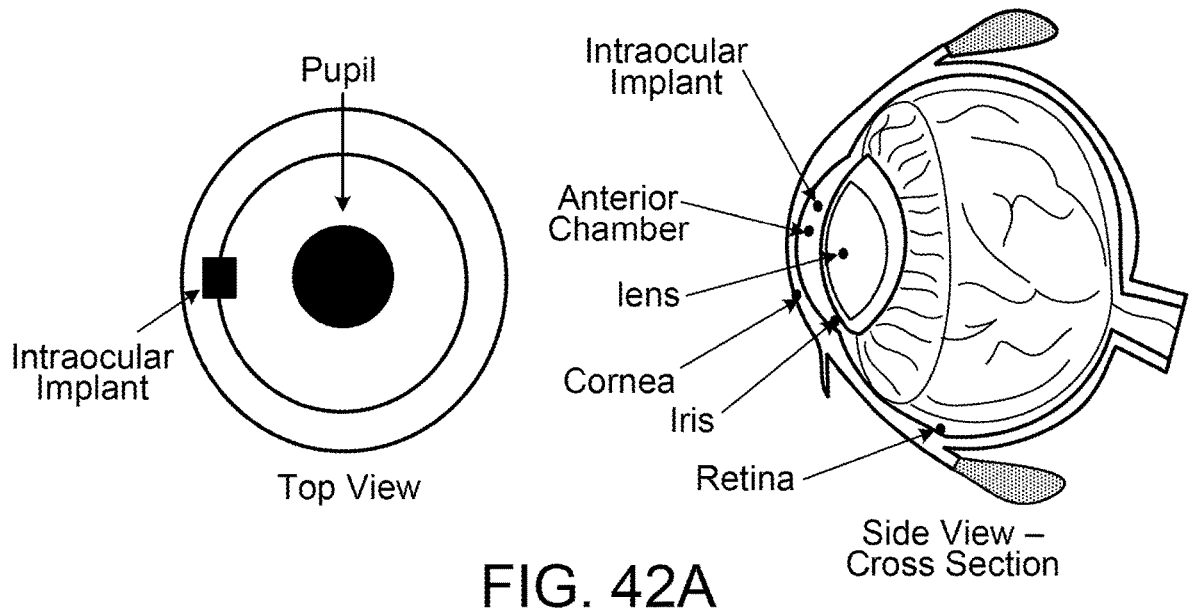
Figure 42B:
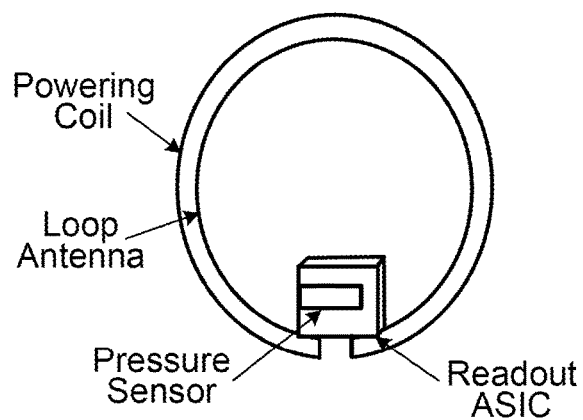

FIG. 42A-B show diagrams of a wireless pressure sensing system for measuring intraocular pressure (IOP) within an eye of a mammalian subject as part of a wireless glaucoma therapy system, including: (A) IOP monitor system and (B) Readout full system implant comprises a readout ASIC, an antenna and a powering coil.

Figure 43:
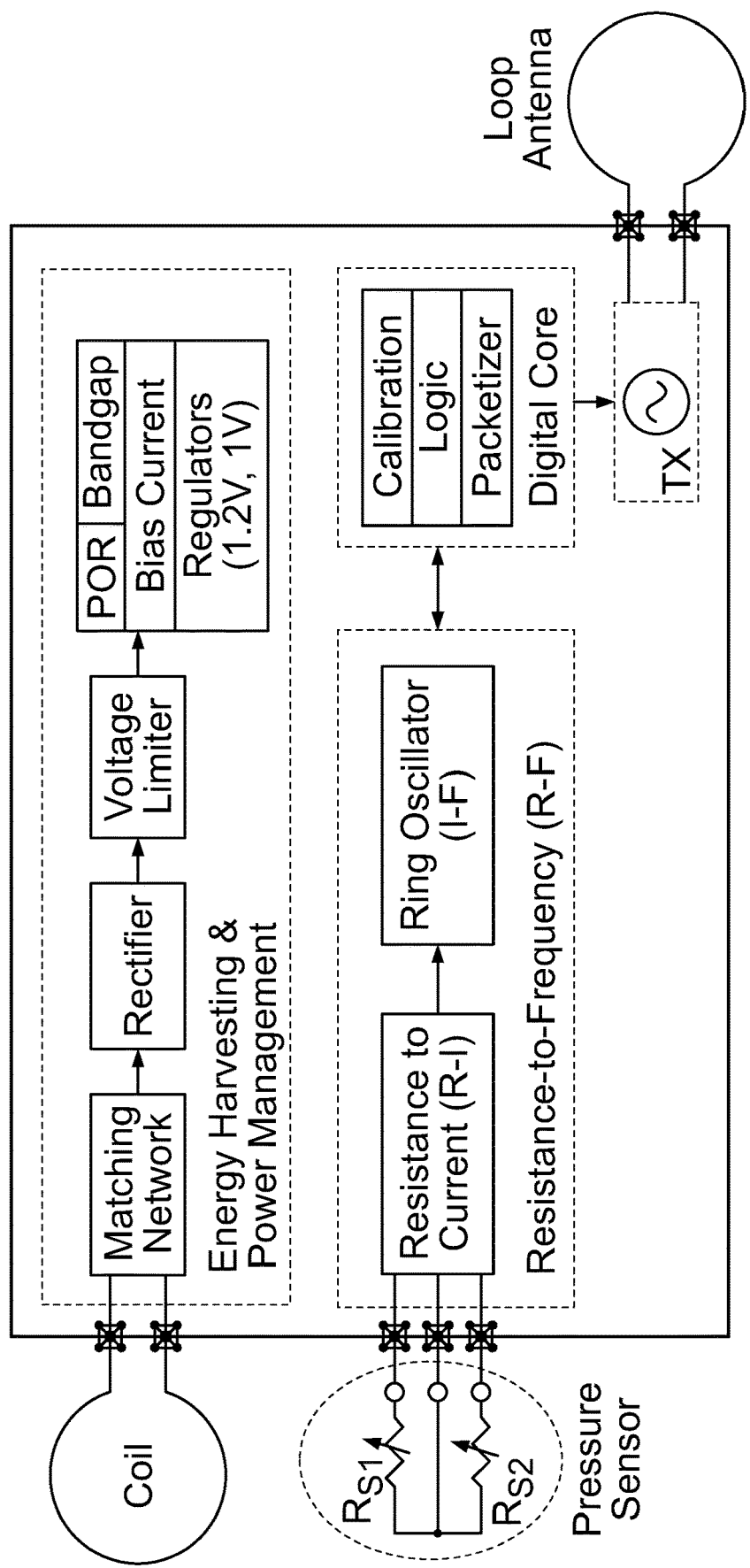

FIG. 43 is a block diagram of a wireless IOP sensing system on a chip (SoC) for implementing the disclosed techniques.

Figure 44:
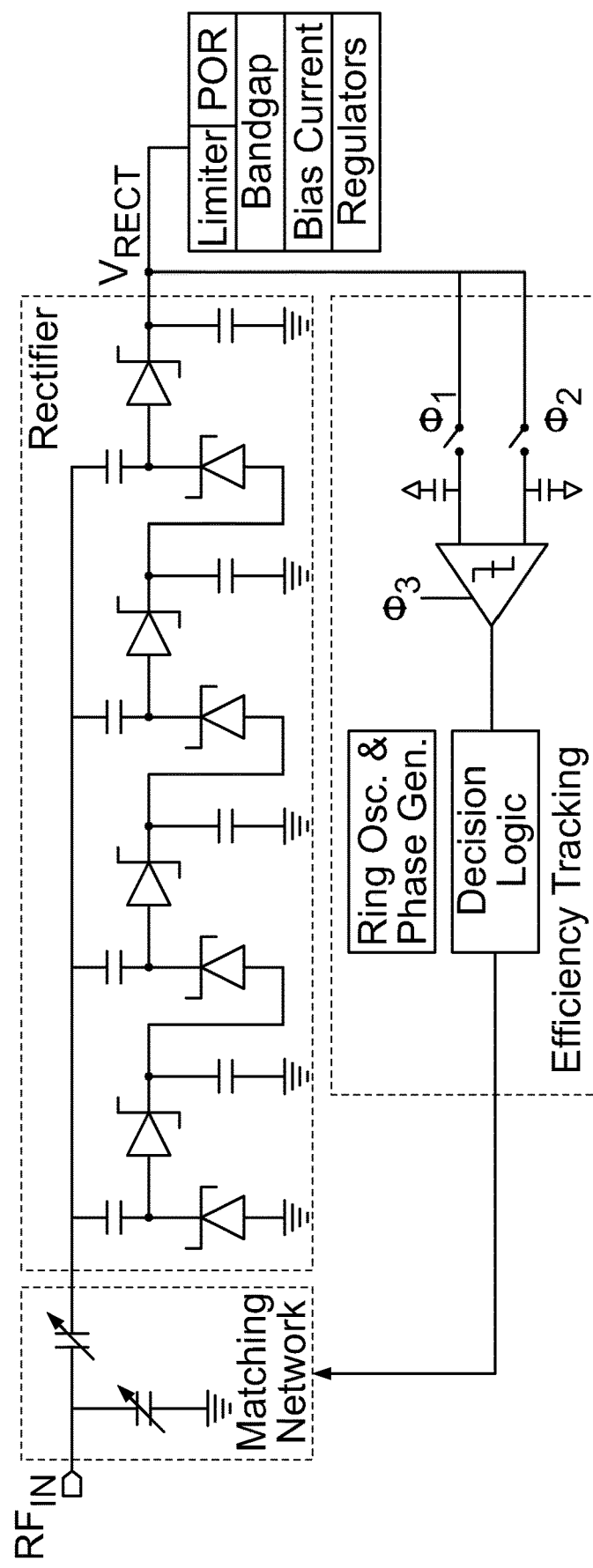

FIG. 44 is a block diagram of energy harvesting (EH) and power management subsystems.

Figure 45:
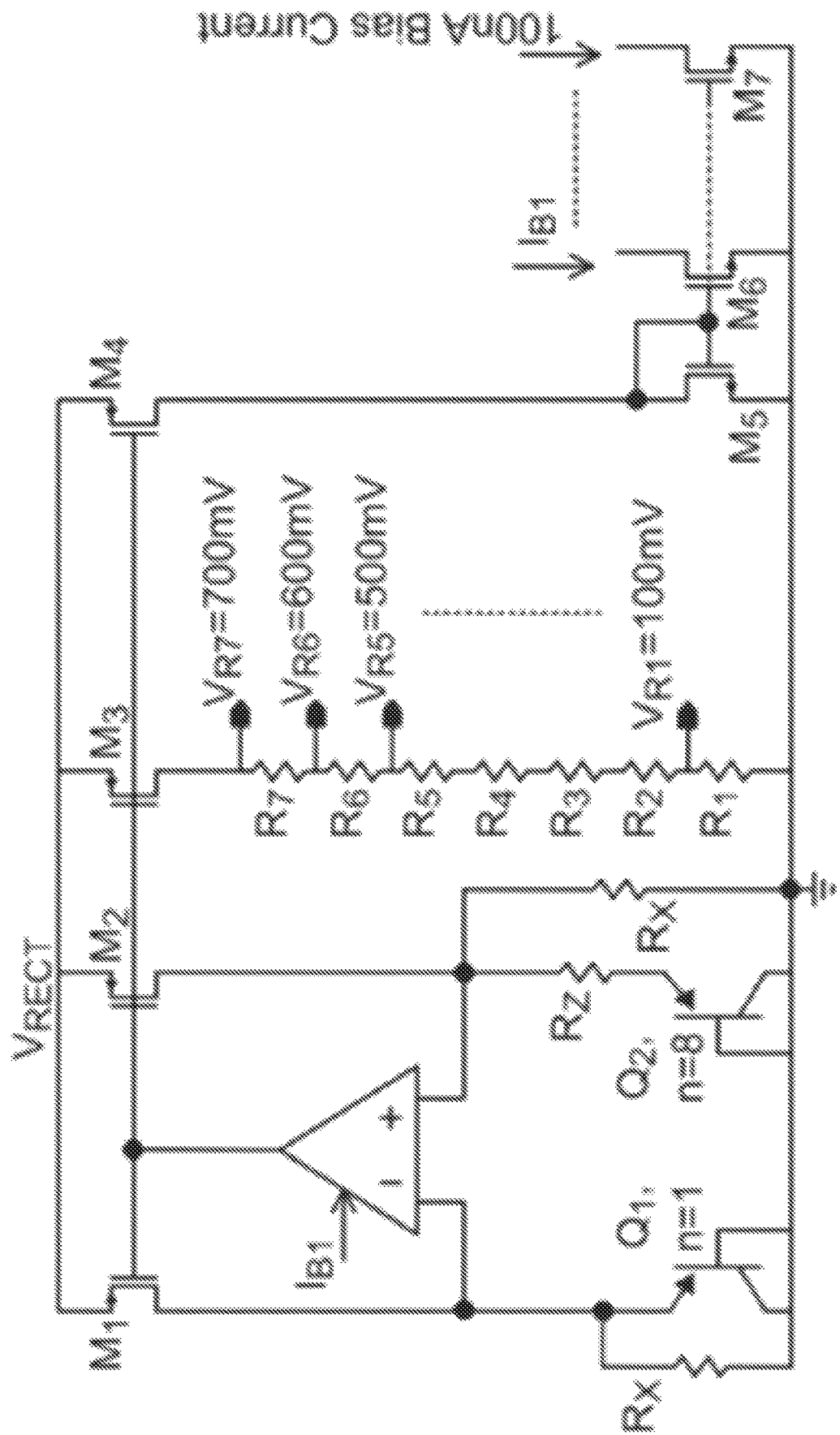

FIG. 45 is a schematic diagram of the bandgap reference to generate pseudo-differential reference voltages and bias currents for the SoC chip.

Figure 46:
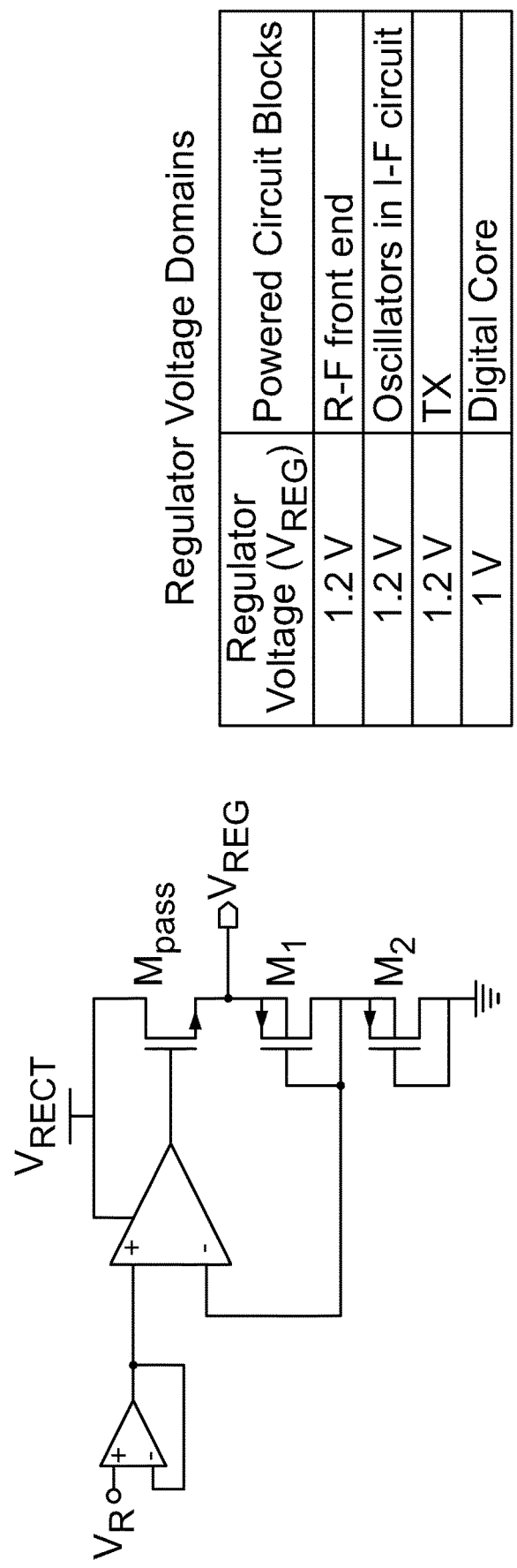

FIG. 46 is a schematic diagram of one of the four voltage regulators and their supply domains.

Figure 47:
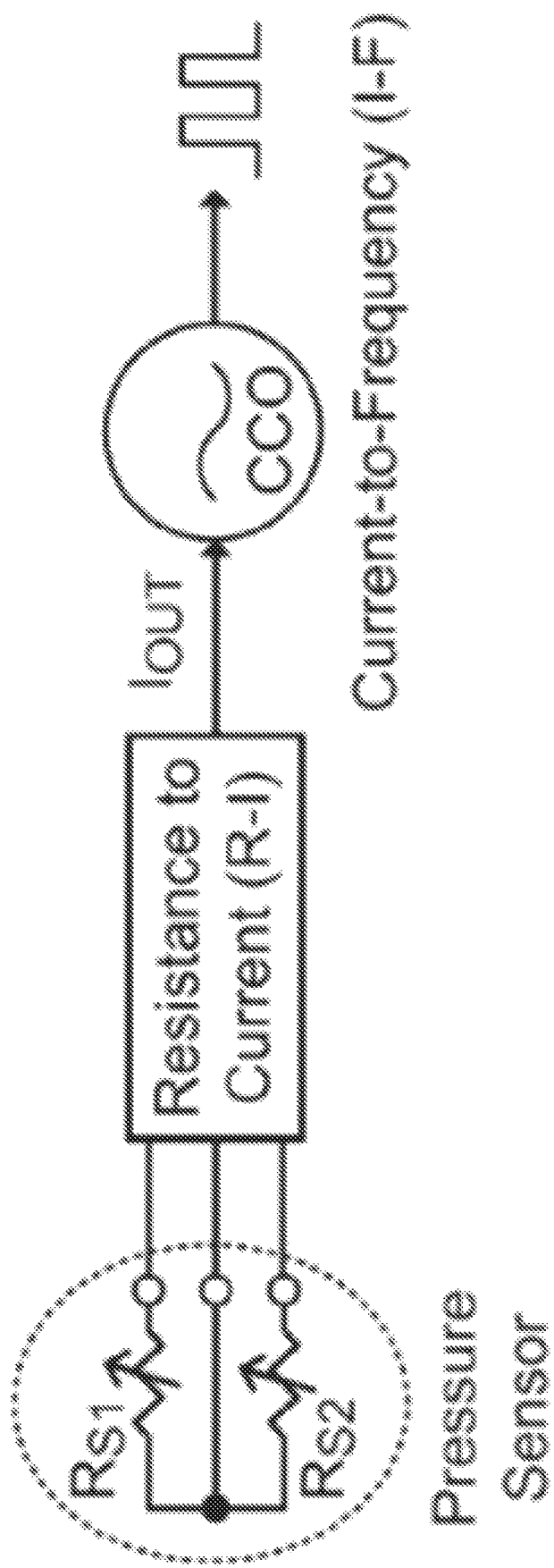

FIG. 47 is a concept diagram of the implemented R-F converter.

Figure 48:
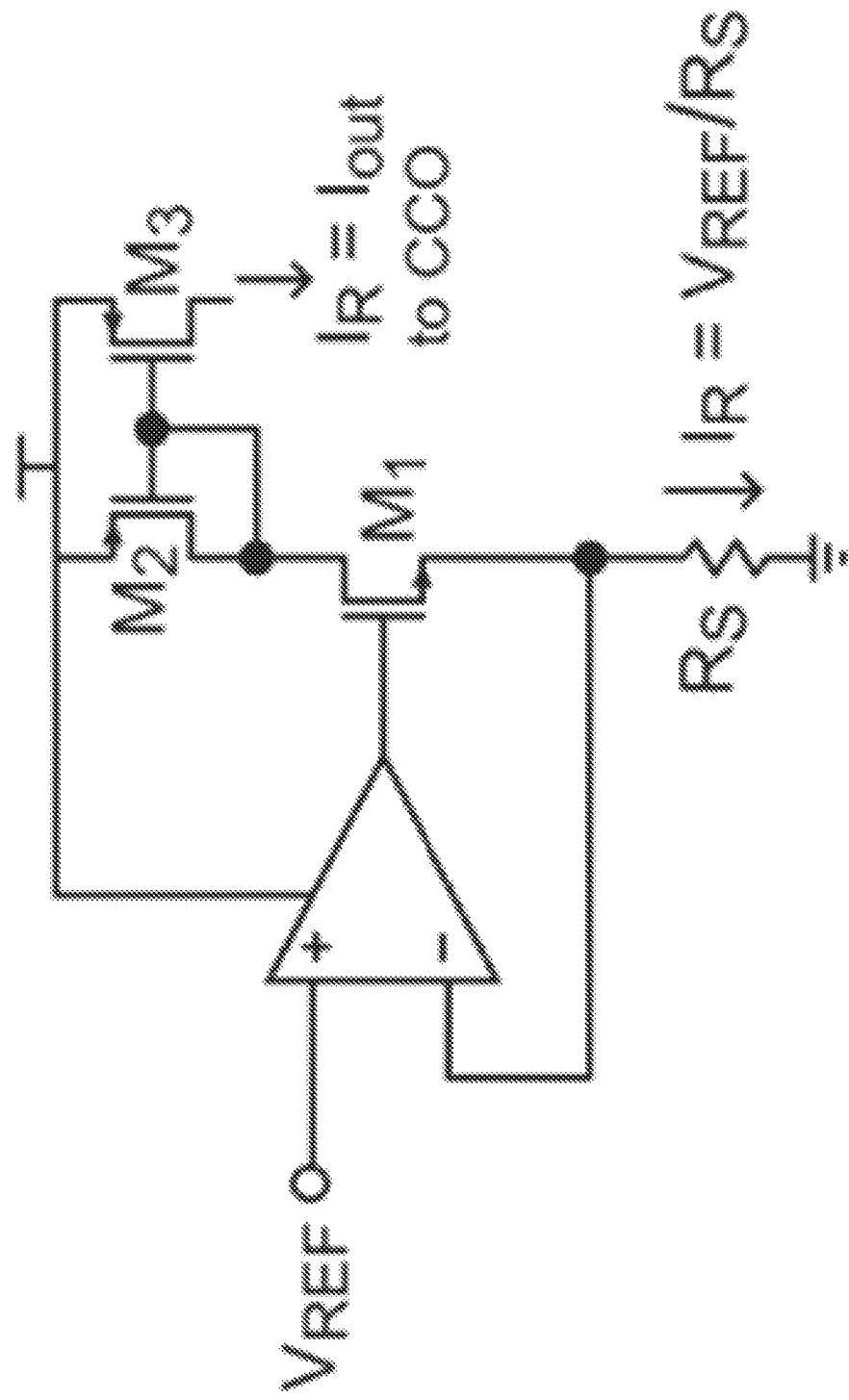

FIG. 48 is a schematic diagram of a conventional R-I converter.

Figure 49:
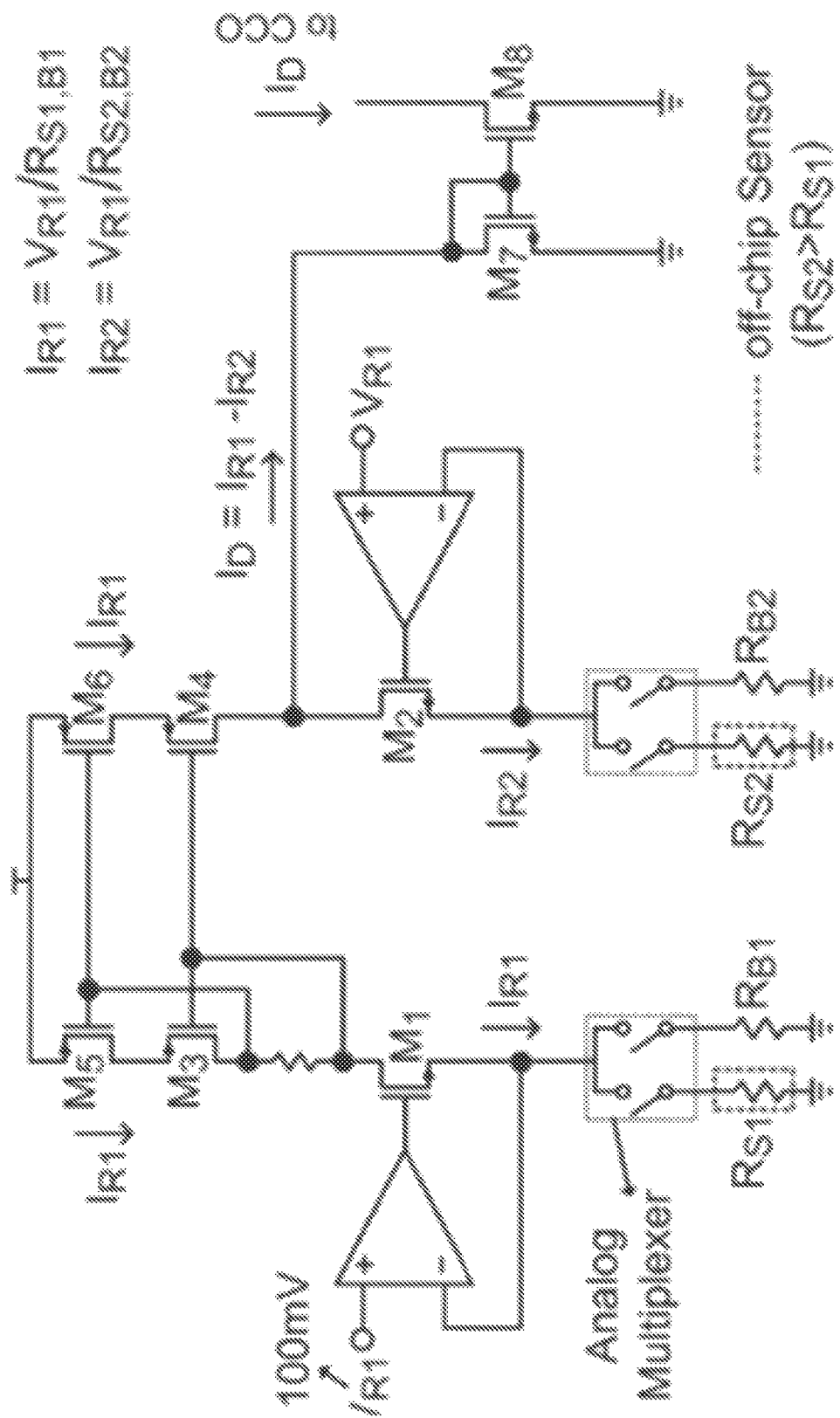

FIG. 49 is a schematic diagram of first differential R-I (R-I1) converter.

Figure 50:
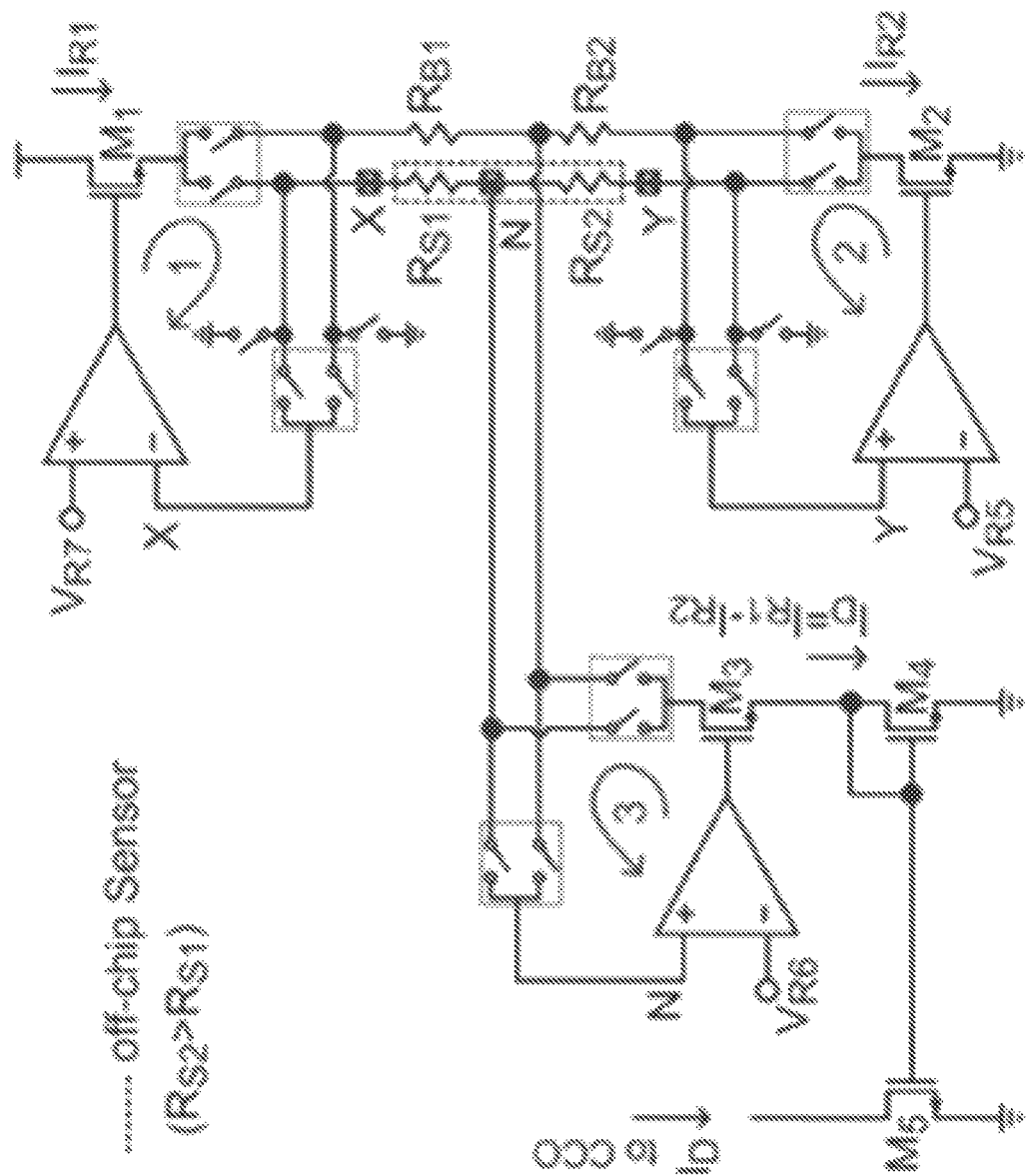

FIG. 50 is a schematic diagram of second differential R-I (R-I2) converter.

Figure 51:
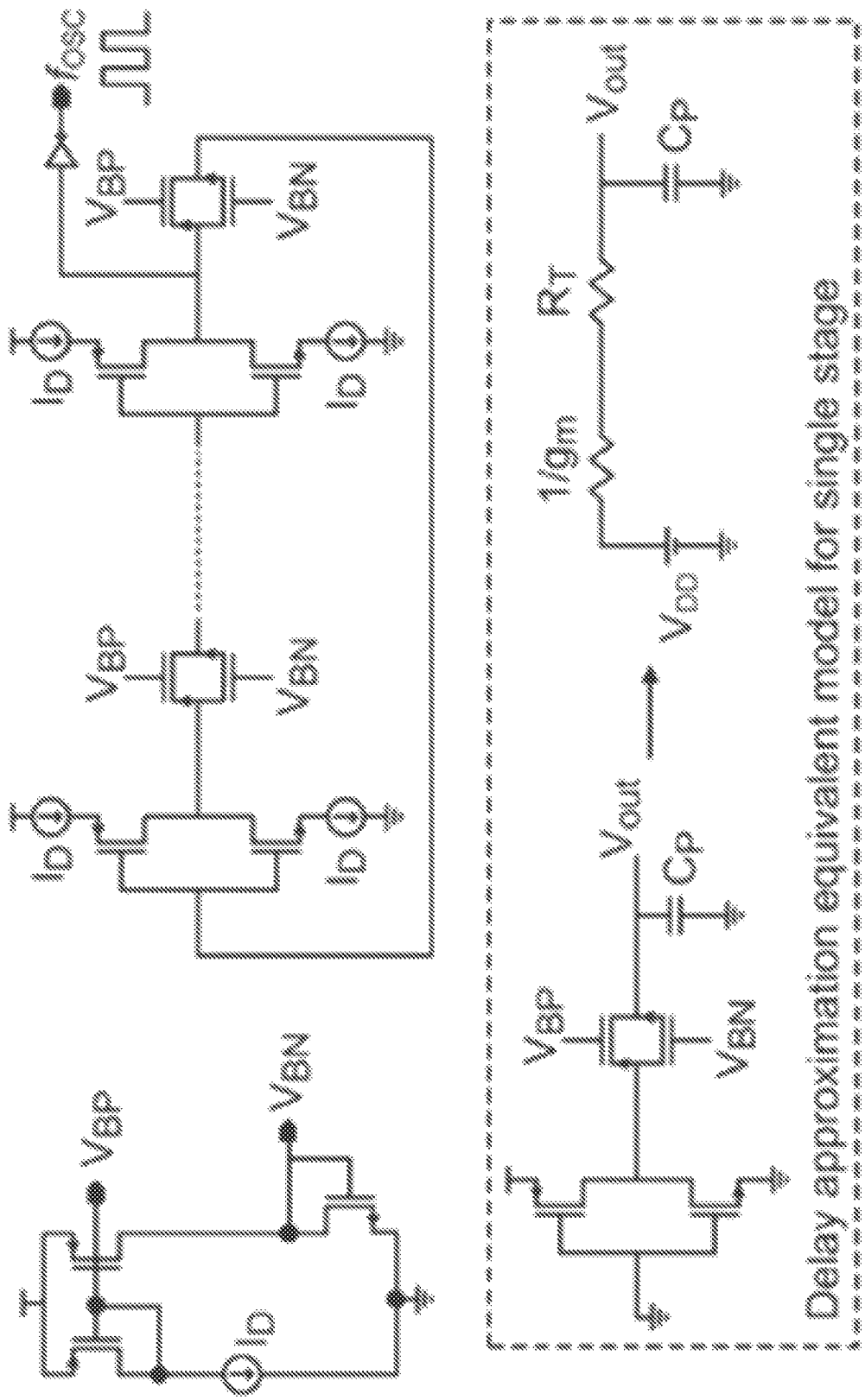

FIG. 51 is a schematic diagram of the ring oscillator, providing I-F conversion.

Figure 52:
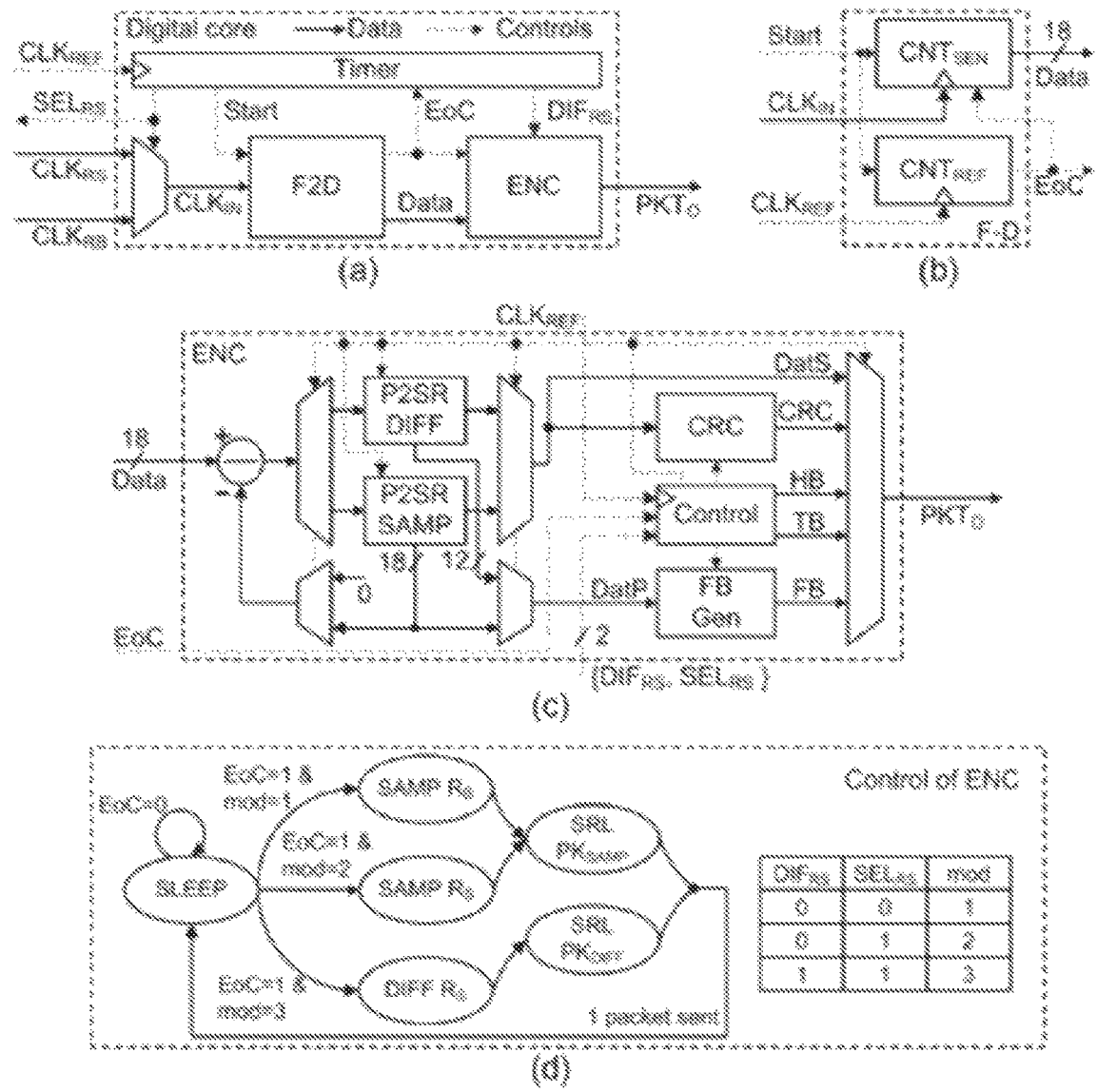

FIG. 52 is a digital Core: (a) Block diagram. (b) F-D converter. (c) Block diagram of encoder (ENC). (d) State diagram of ENC.

Figure 53:
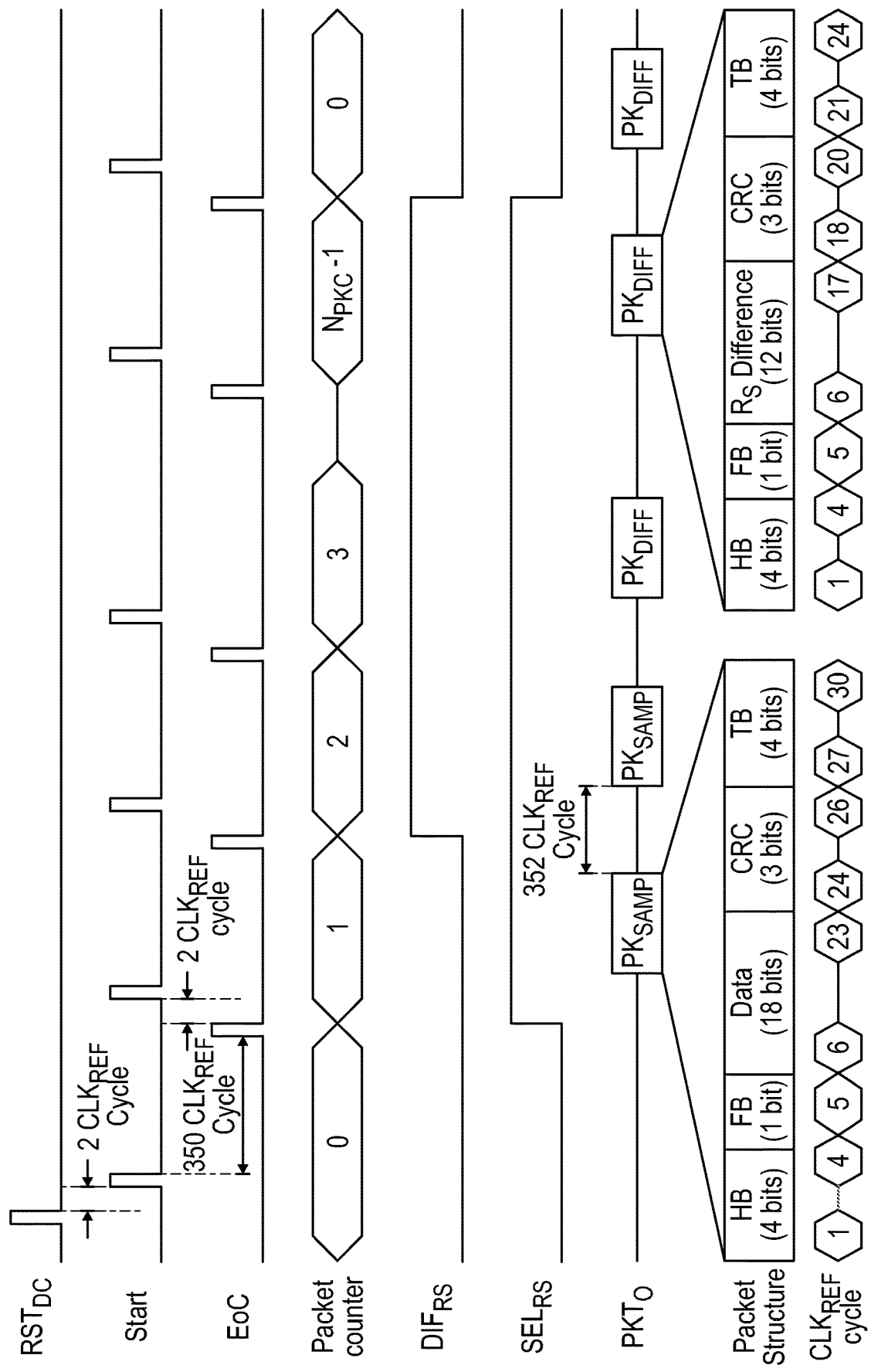

FIG. 53 is a timing diagram of digital core and the packet structure.

Figure 54:
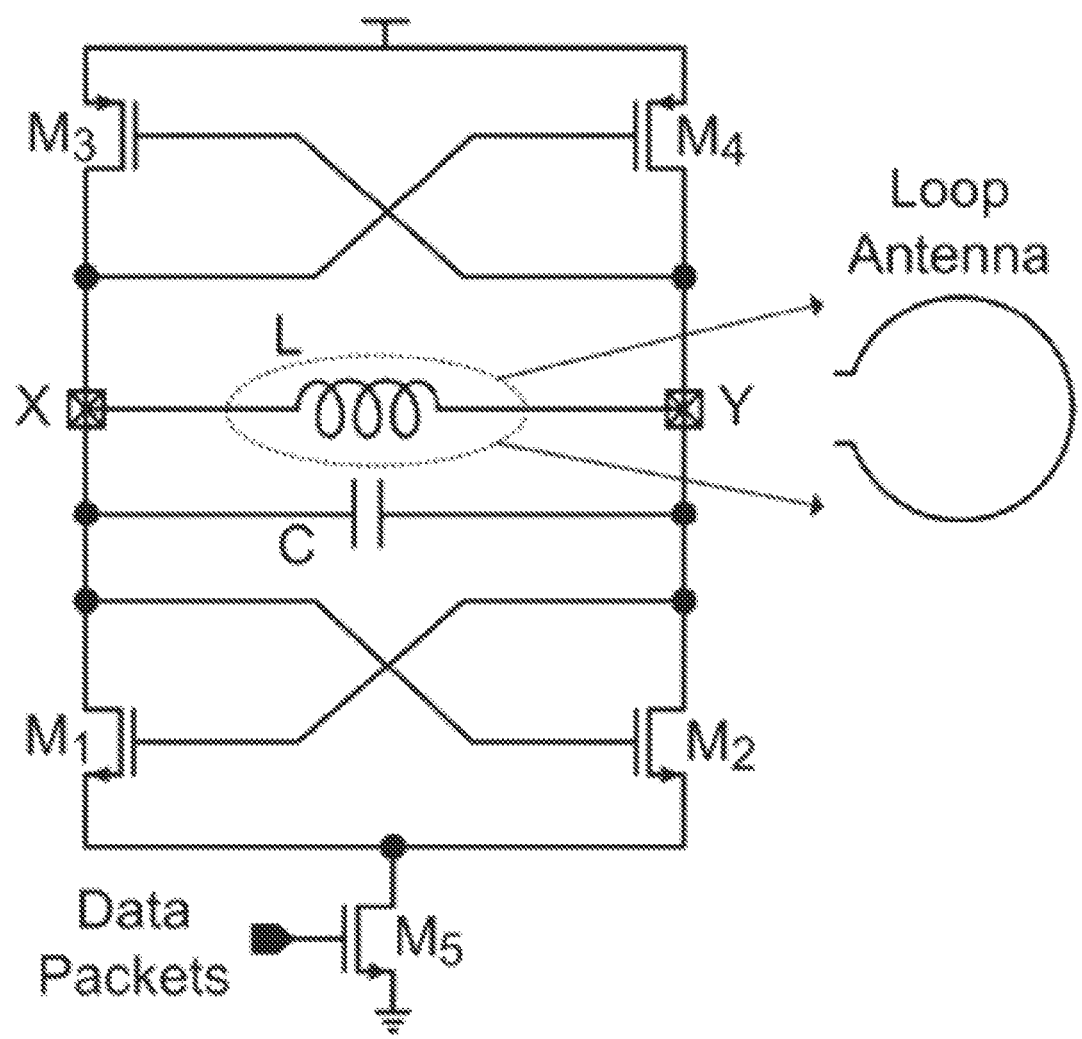

FIG. 54 is a schematic diagram of the 2.45 GHz ISM band transmitter, comprising a voltage-controlled power oscillator (VCPO) and an off-chip loop antenna.

Figure 55:
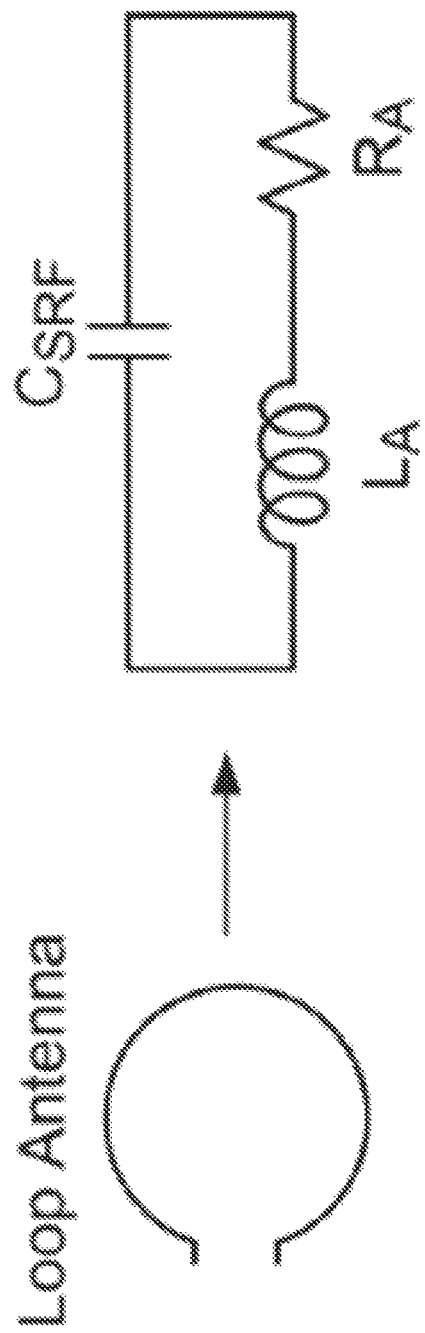

FIG. 55 is an equivalent lumped circuit model of an electrically small loop antenna. The antenna can be modeled as a series combination of an inductor (LA) and a resistor (RA). CSRF models the self-resonance frequency of the loop.

Figure 56B:
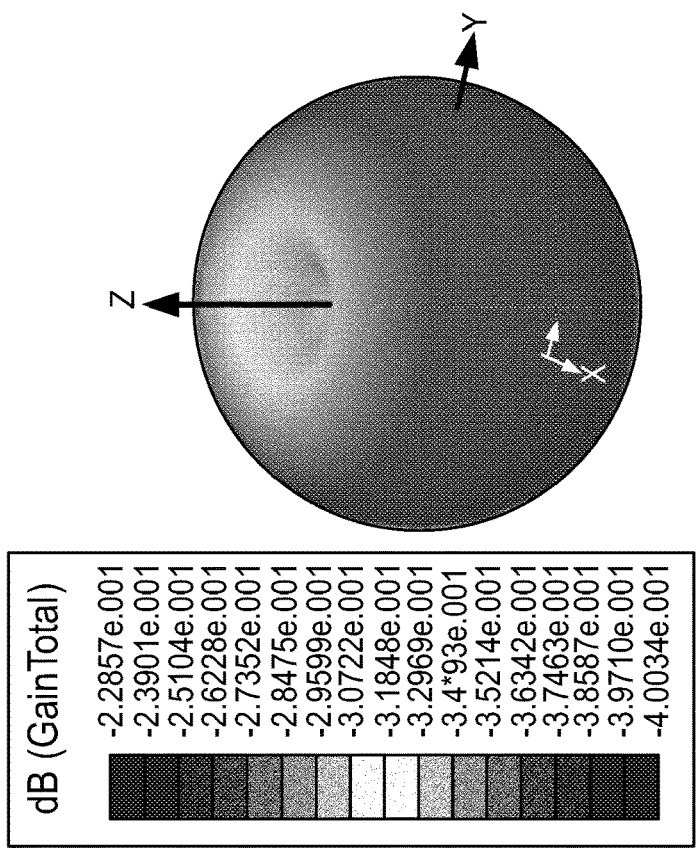
Figure 56A:
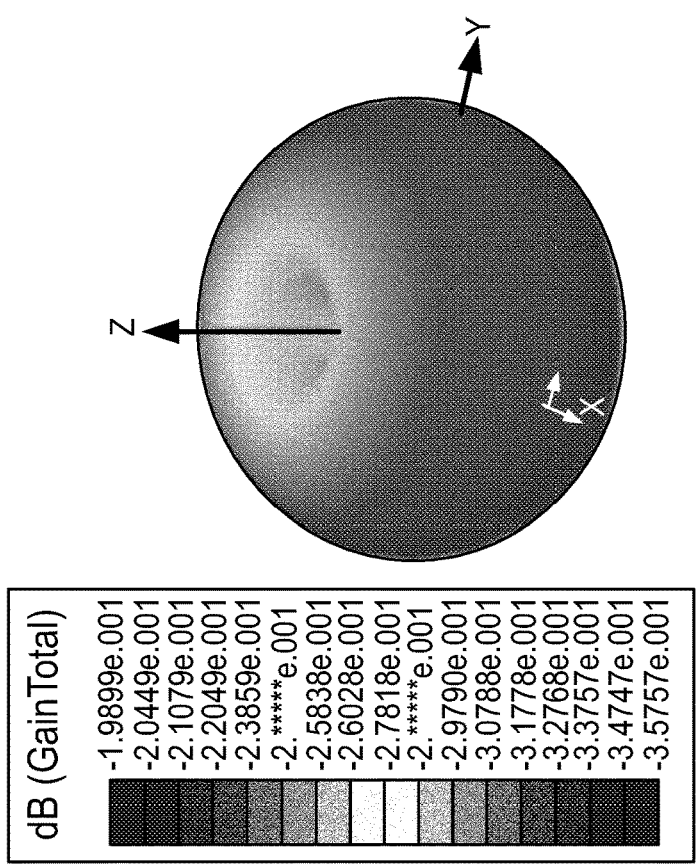

FIG. 56 is a simulated antenna radiation pattern: (a) on a FR-4 board (air). (b) gold trace on a 20 μm thick parylene substrate with a 20 μm parylene coating.

FIG. 57 is a simplified schematic diagram of 5-bit DAC, implemented by MIM capacitors to tune the resonance frequency of the LC tank.

Figure 58:
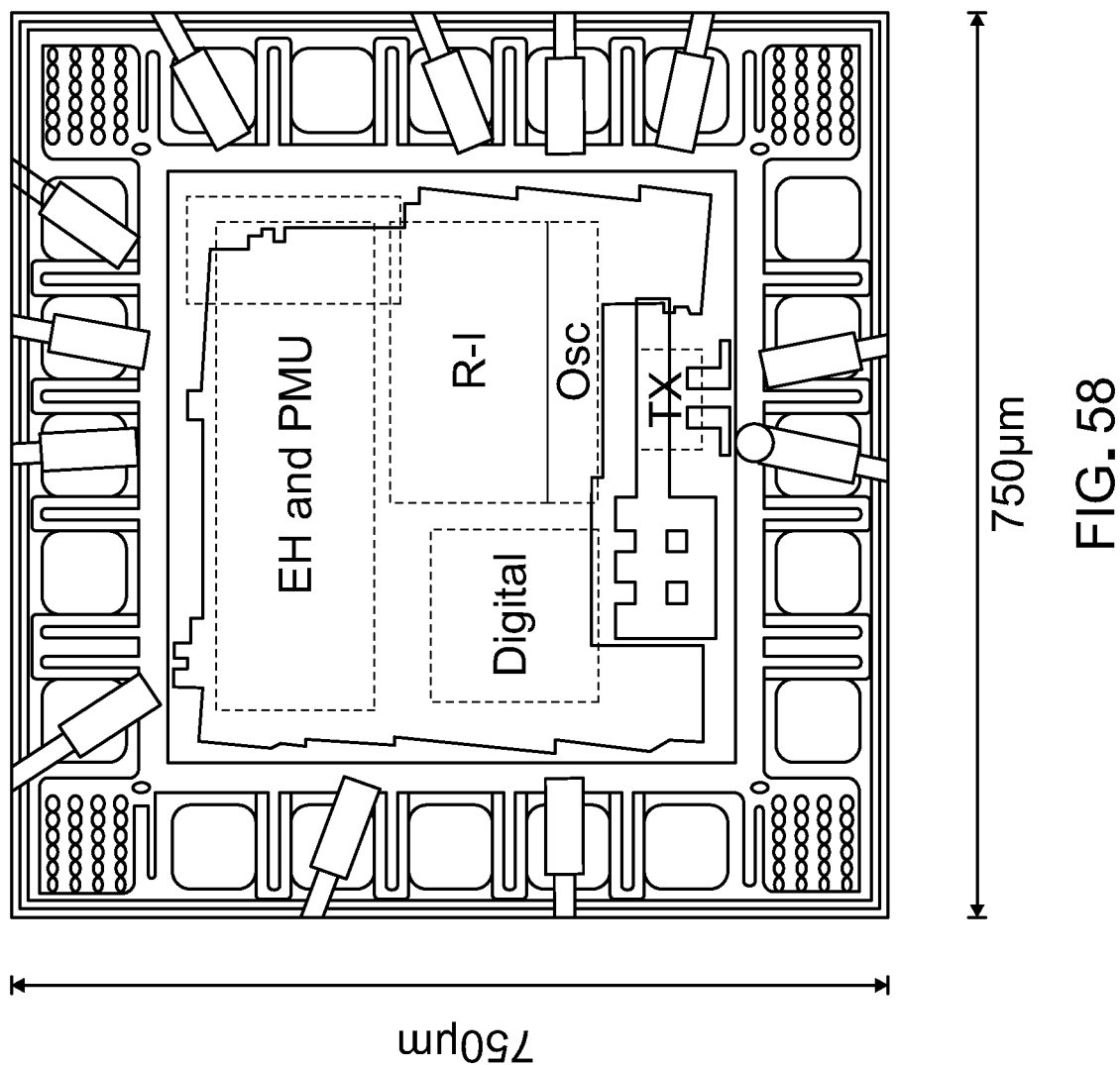

FIG. 58 illustrates a micro-photograph of the implemented chip.

Figure 59:
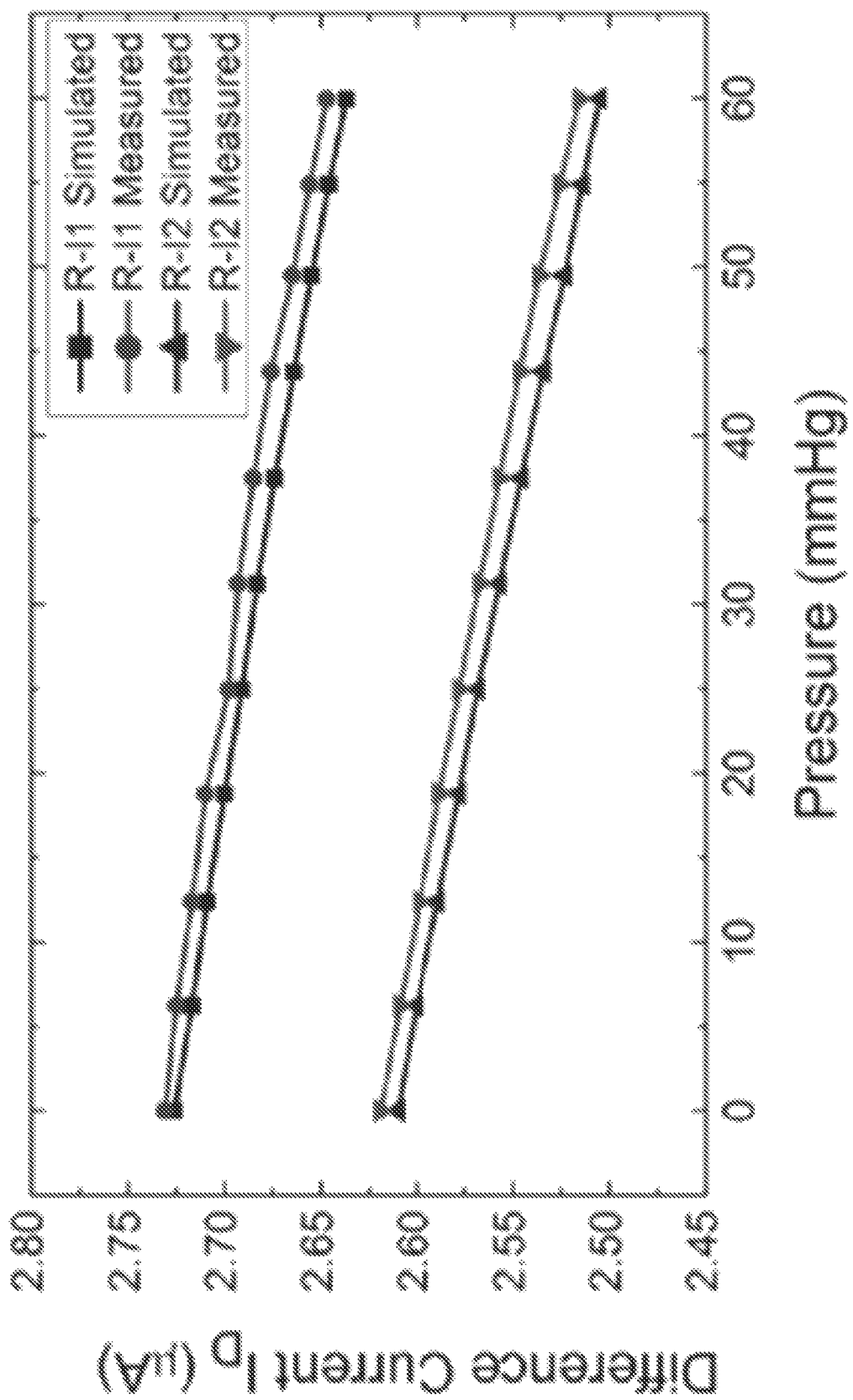

FIG. 59 illustrates a measured and simulated current for the R-I1 Converter.

Figure 60A:
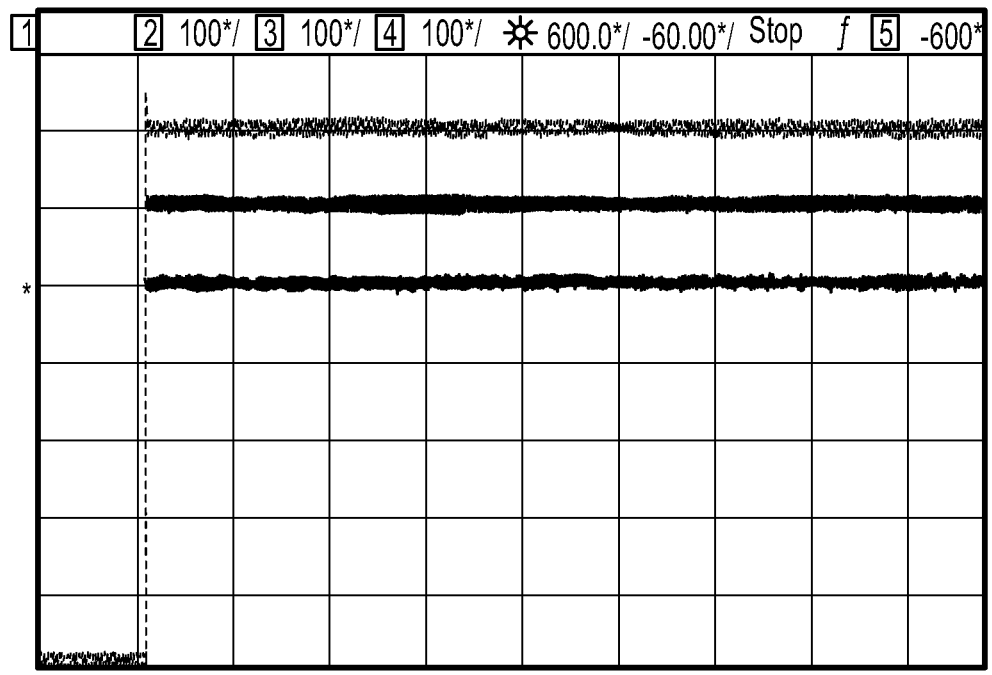
Figure 60B:
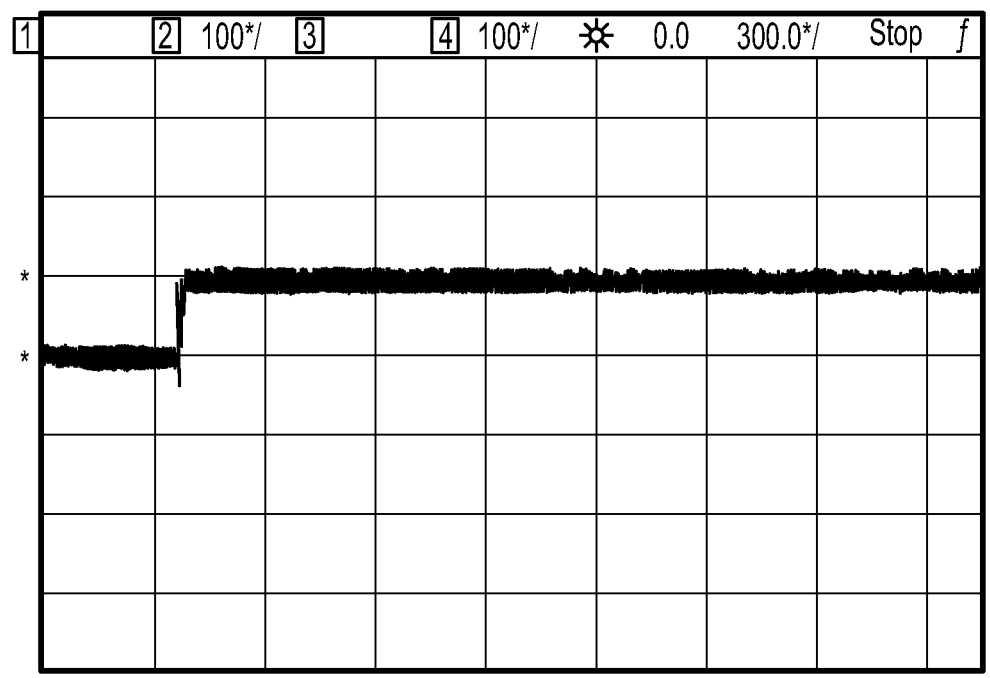

FIG. 60 illustrates a) a Pseudo-differential reference voltage across the sense resistors terminals in R-I2 converter, and (b) 100 mV reference voltage across the sensor resistors in R-I1 converter.

Figure 61:
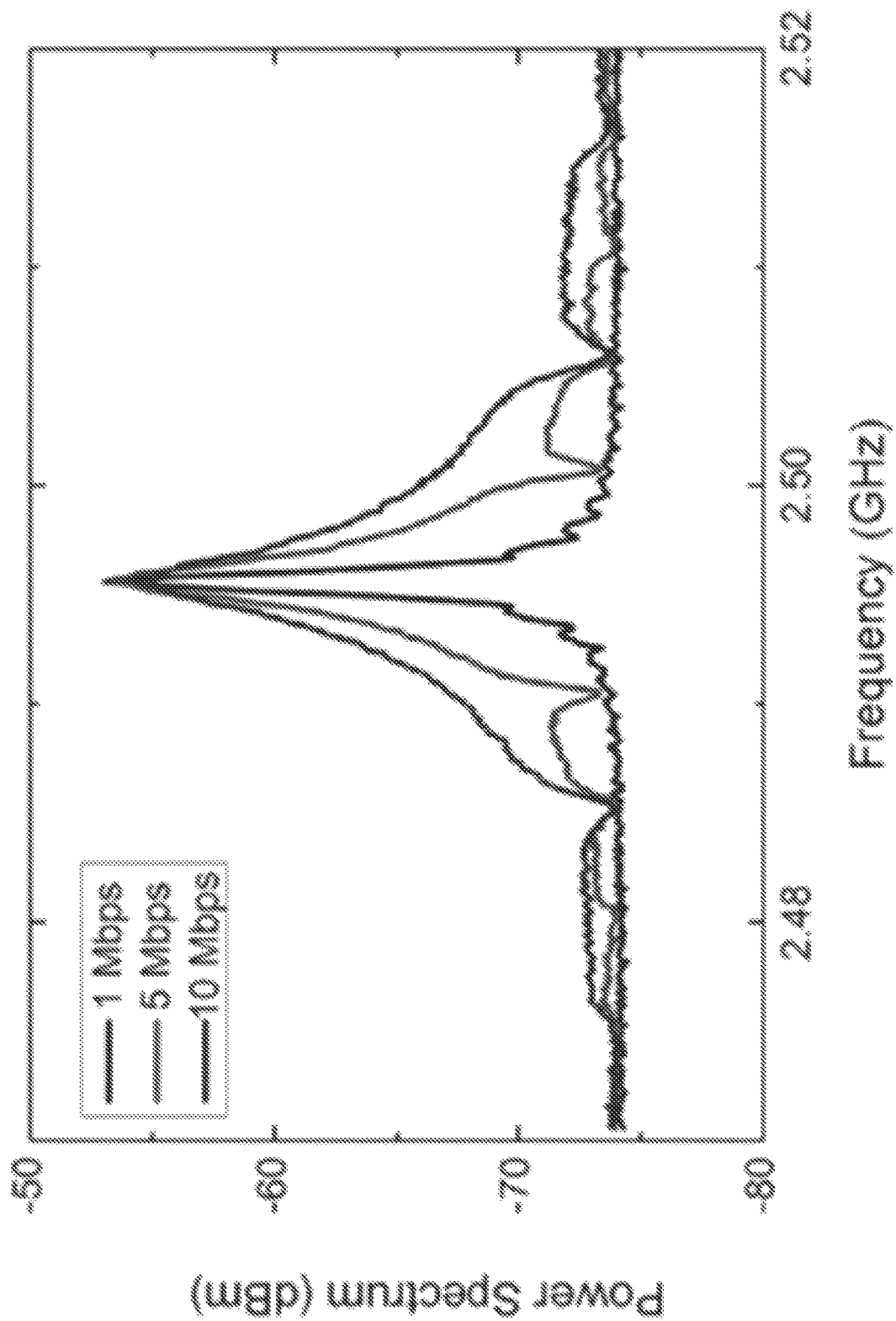

FIG. 61 illustrates a measured TX power spectrum, OOK modulated by the PRBS at various data rates.

Figure 62:
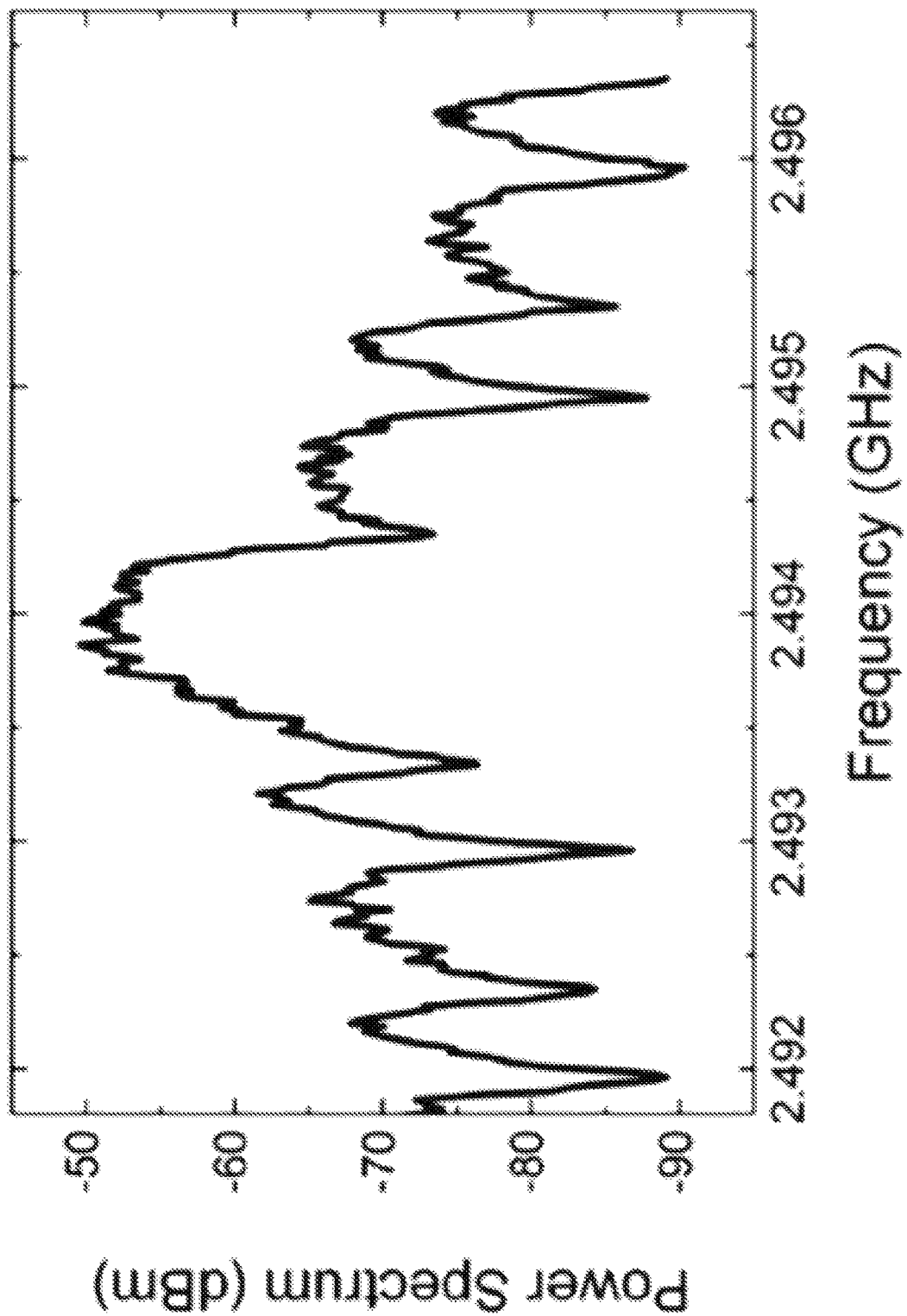

FIG. 62 illustrates a measured TX power spectrum, FSK modulated by 1 Mbps PRBS.

Figure 63:
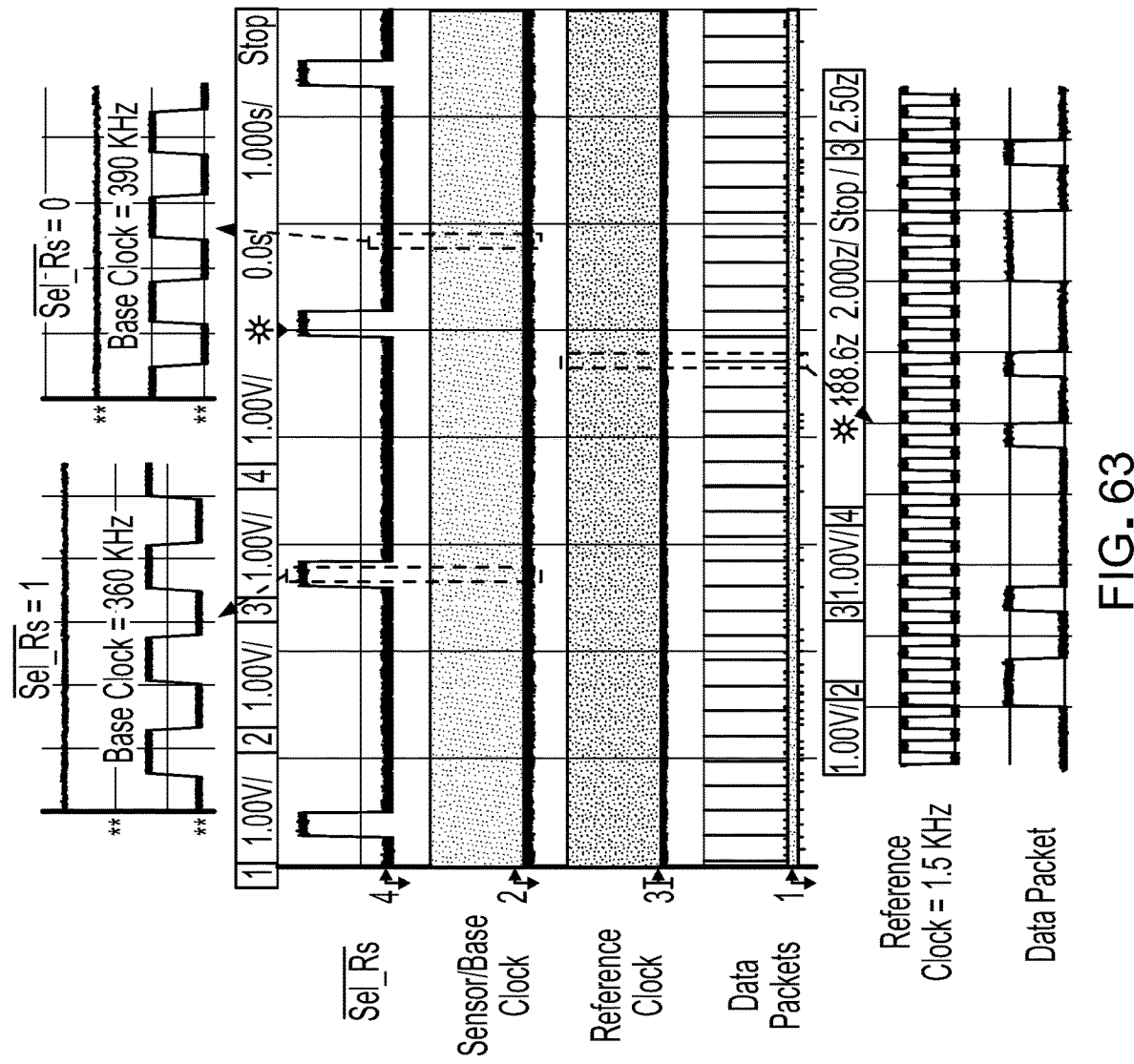

FIG. 63 illustrates a measured waveforms and data packet for the full system.

FIG. 64 illustrates measured data packets that correspond to: a) Base frequency, b) Sensor frequency and c) Difference between two sensor frequencies.

Figure 65:
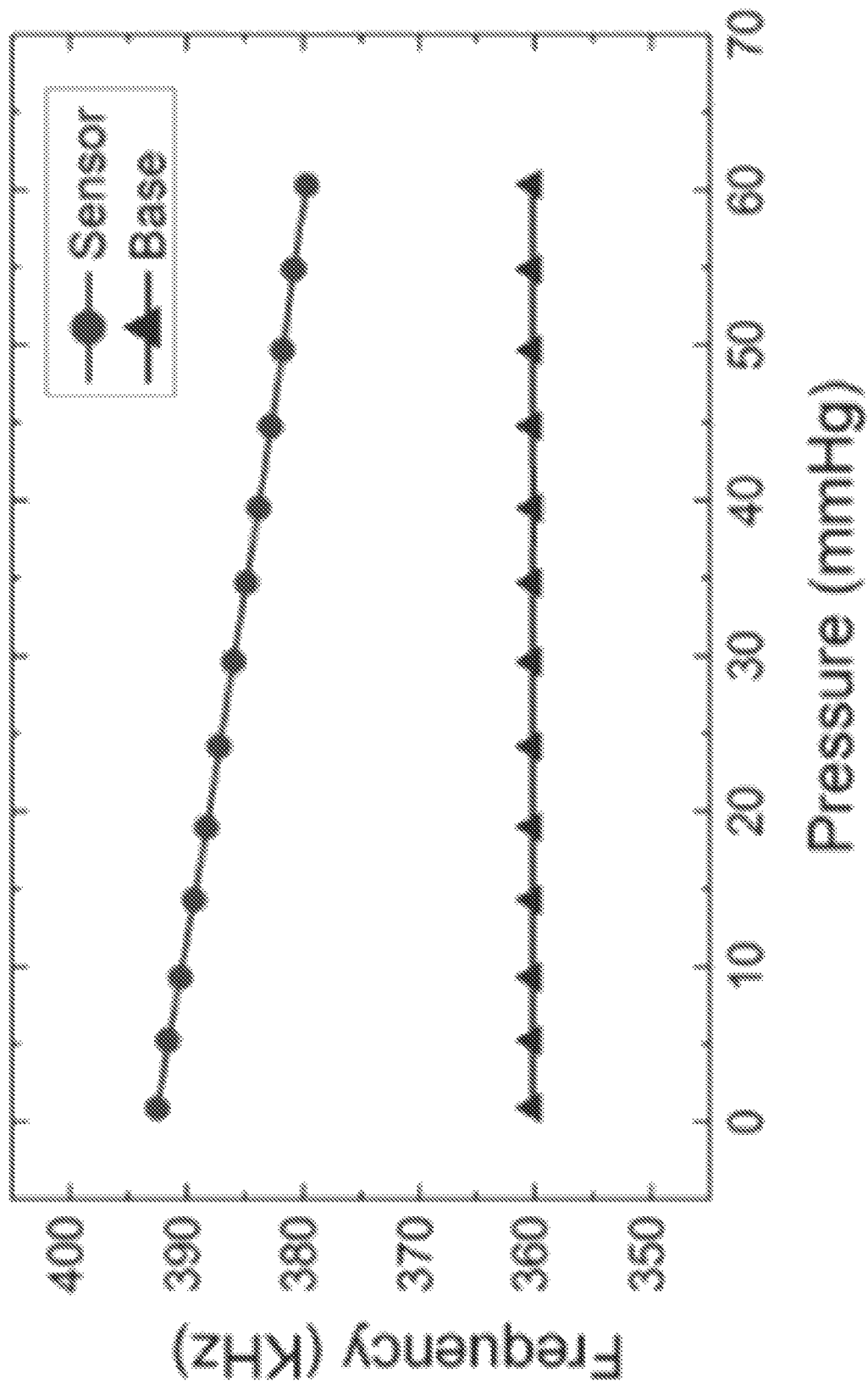

FIG. 65 illustrates measured change in the sensor frequency with pressure, where base frequency remains constant with applied pressure.

Figure 66:
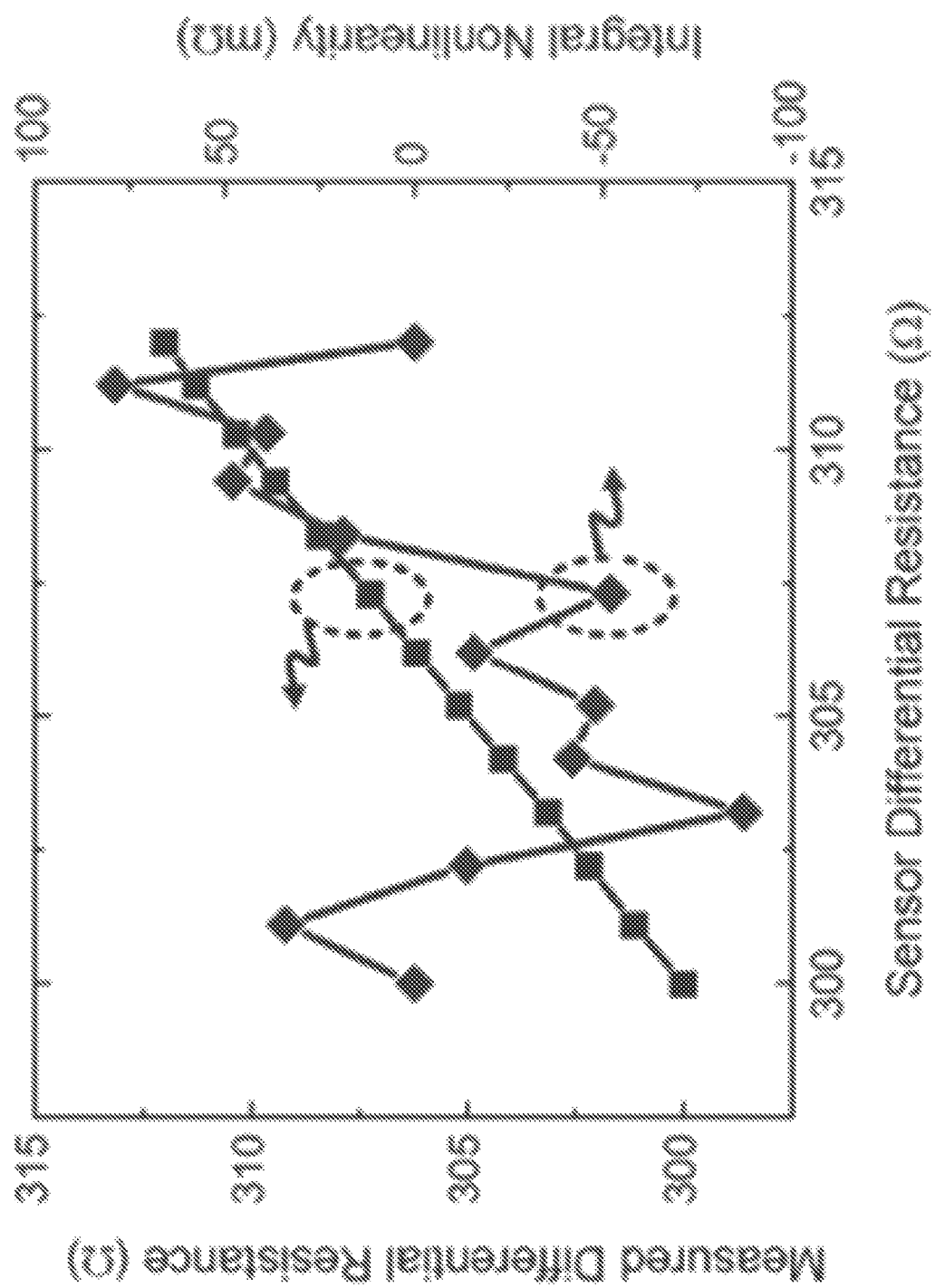

FIG. 66 illustrates measured difference in sensor resistances (RS1–RS2) and integral non-linearity.

Figure 67:
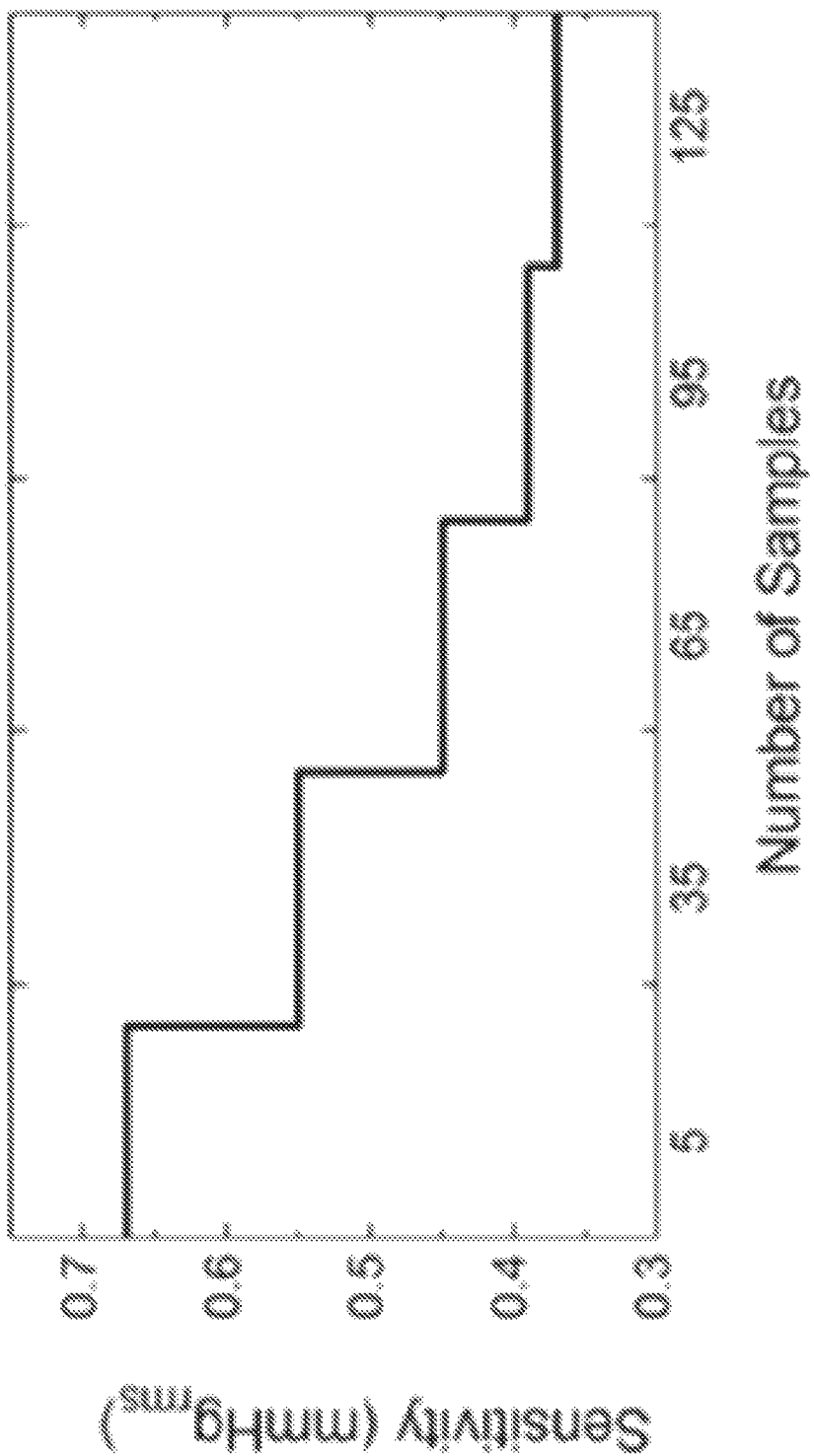

FIG. 67 illustrates measured sensitivity of the chip with number of averaged data samples (or conversion time)

Figure 68:
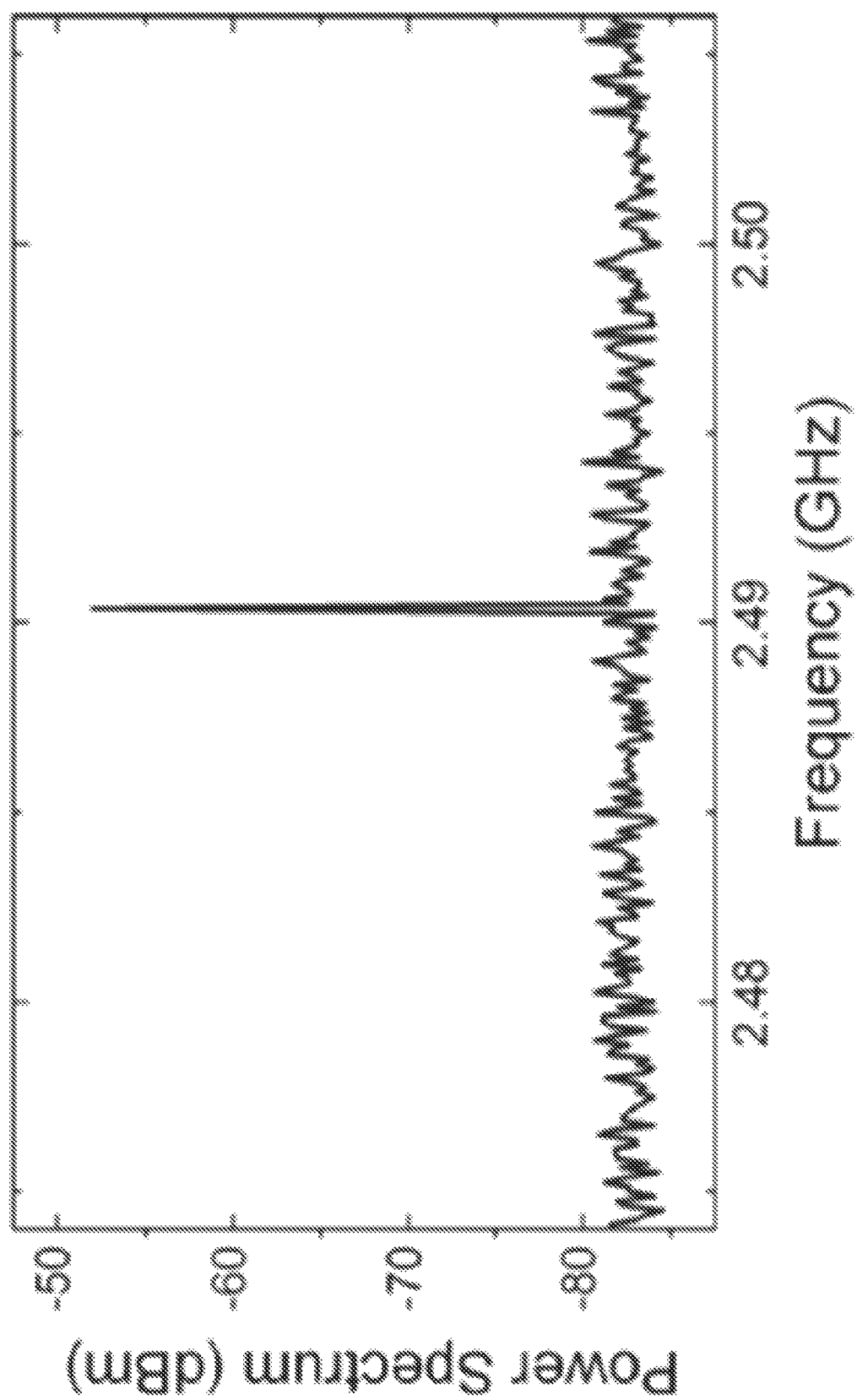

FIG. 68 illustrates measured power spectrum of the received data.

Figure 69:
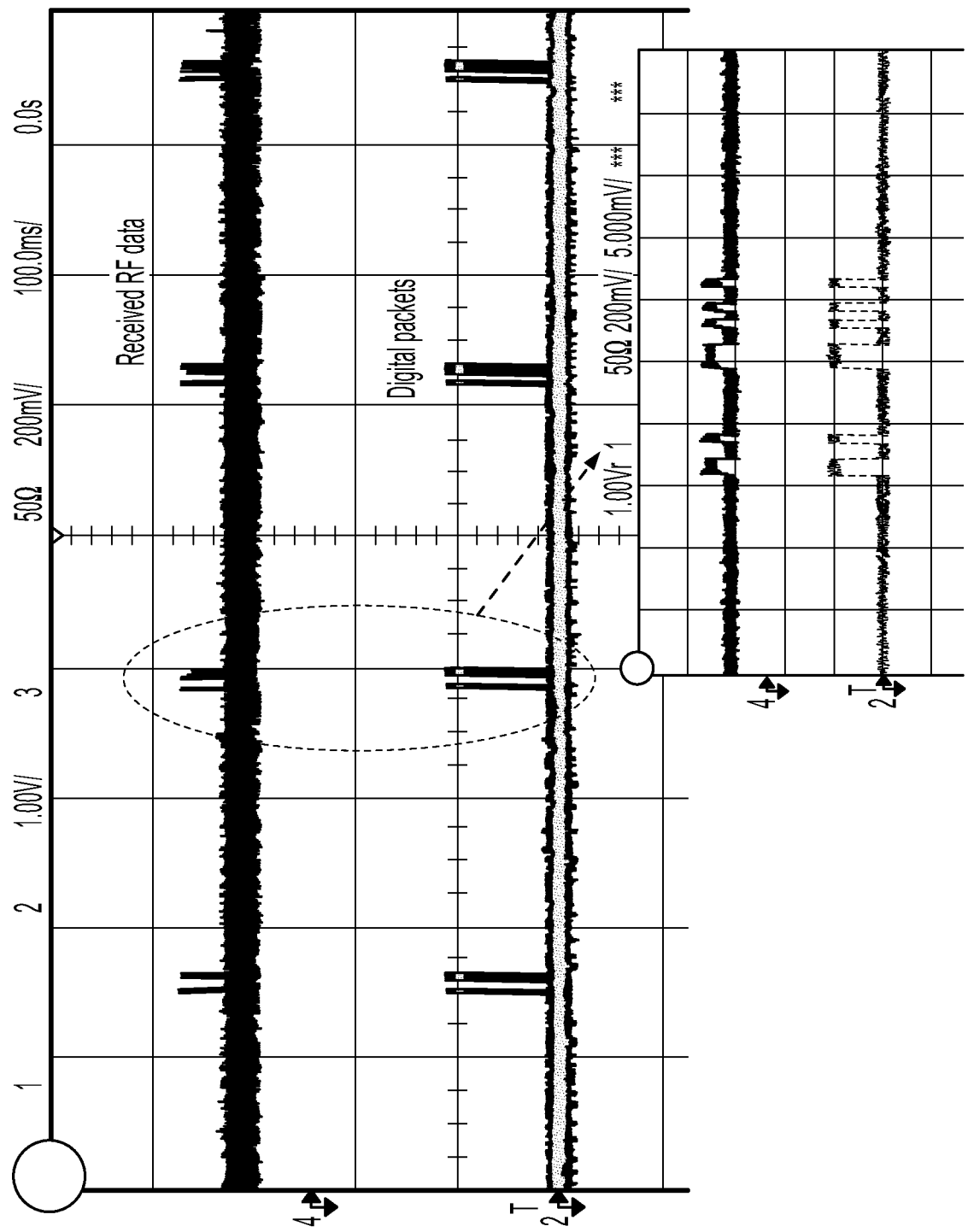

FIG. 69 illustrates received RF data and corresponding digital packets.

Figure 70:
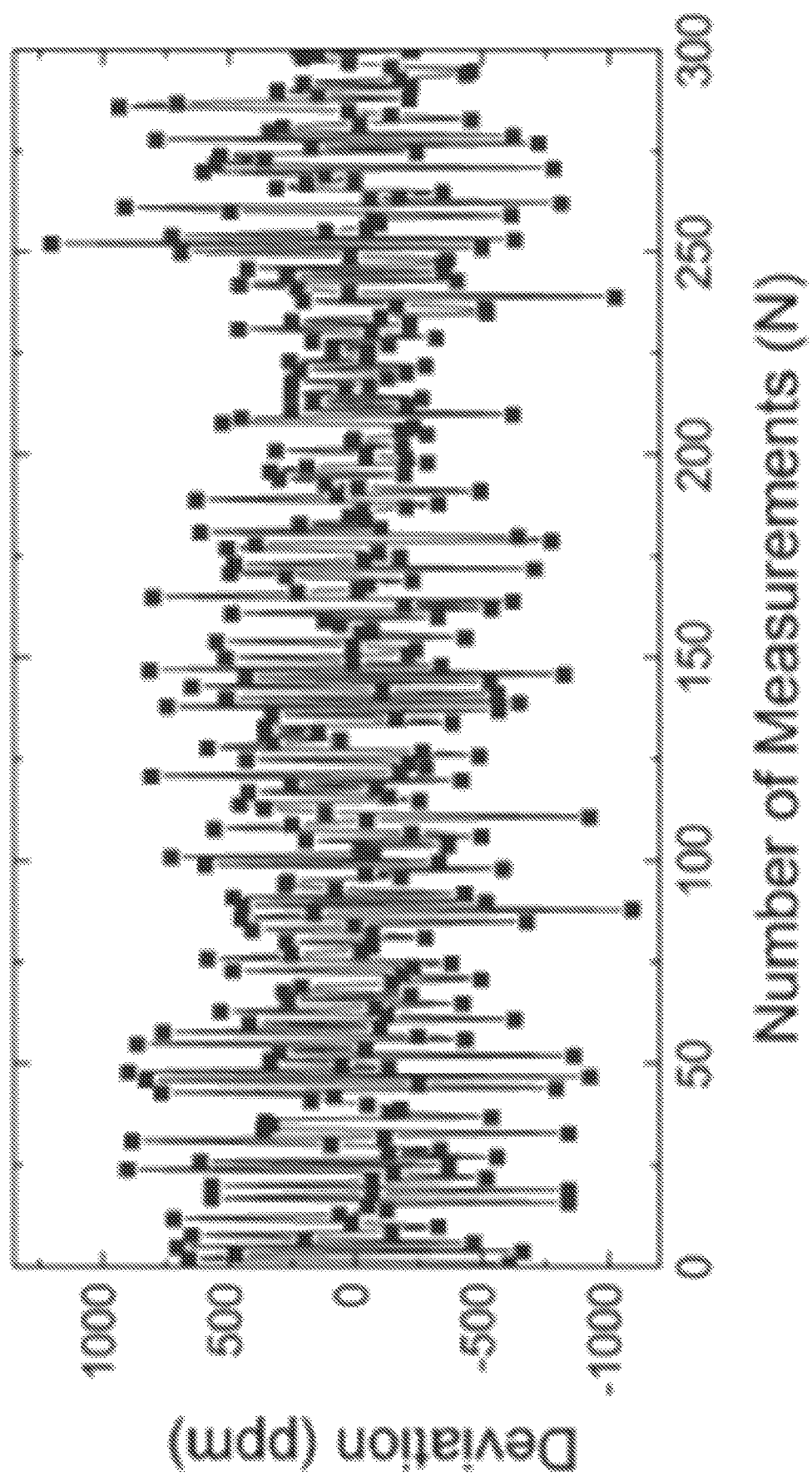

FIG. 70 illustrates a wirelessly measured noise floor for resistance sensing.

Figure 71:
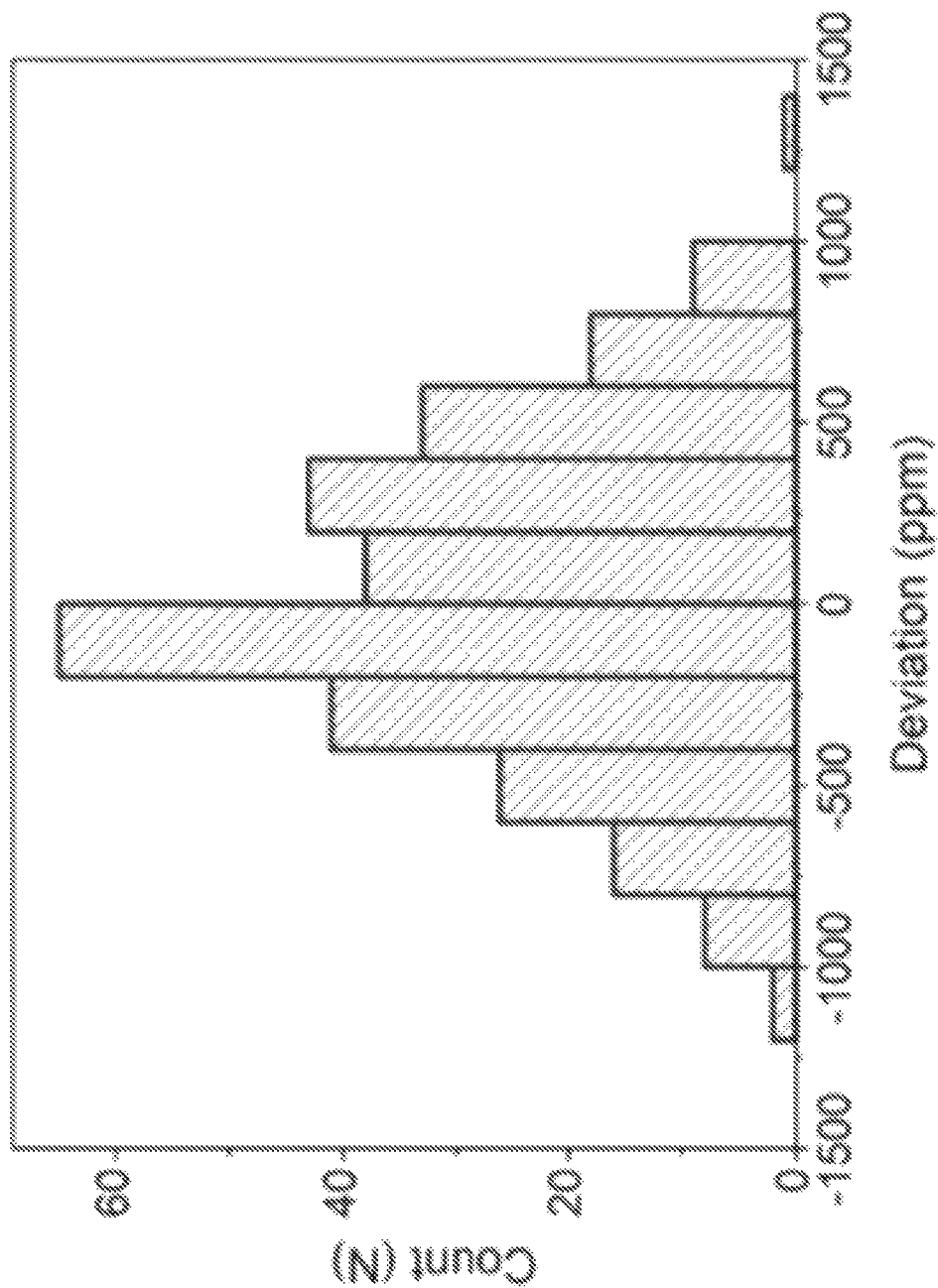

FIG. 71 illustrates a wirelessly measured noise histogram for resistance sensing.

Figure 72:
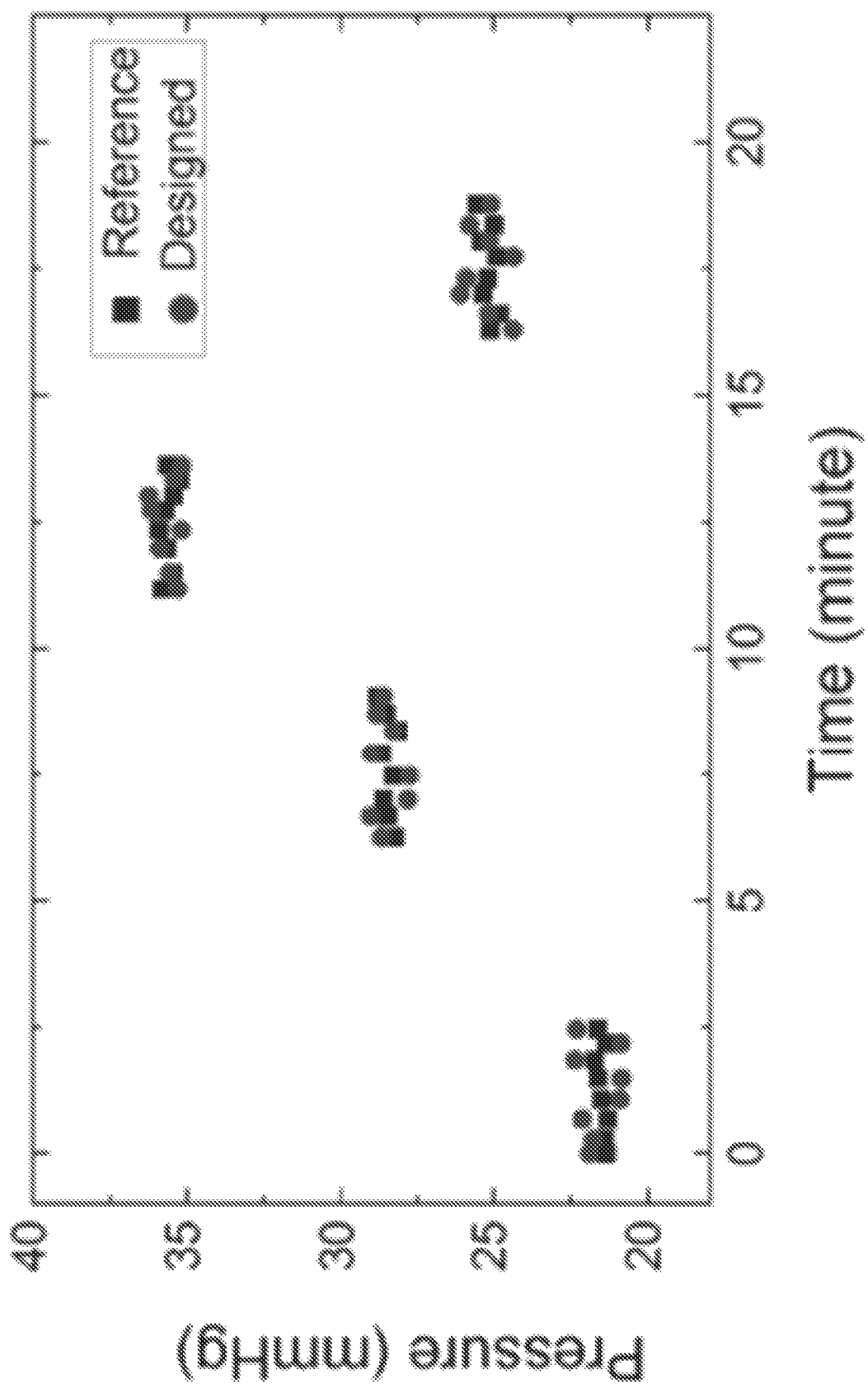

FIG. 72 illustrates a pressure measurement with time.

Figure 73:
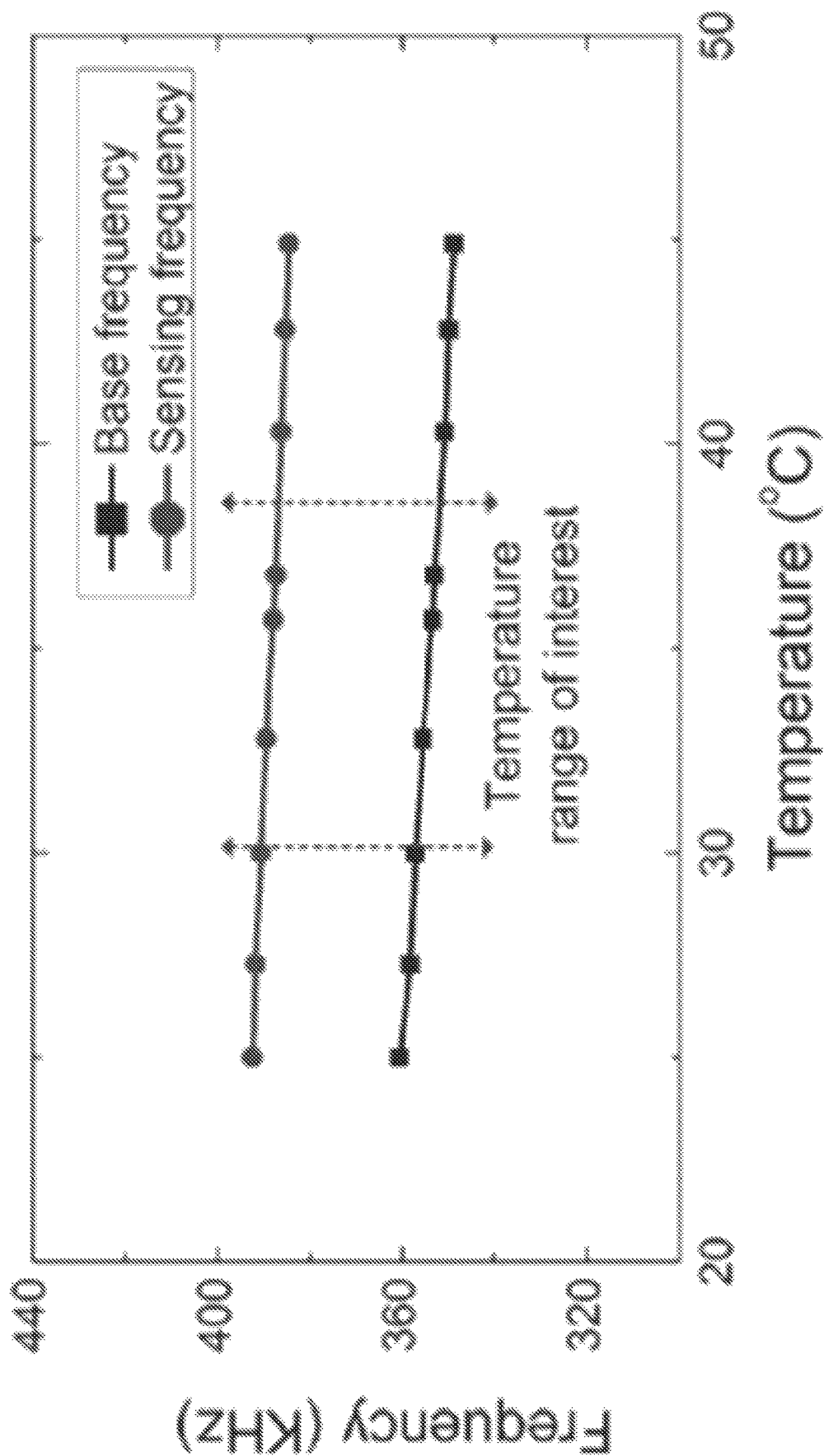

FIG. 73 illustrates measured temperature variation in sensing and base frequencies.

Figure 74B:
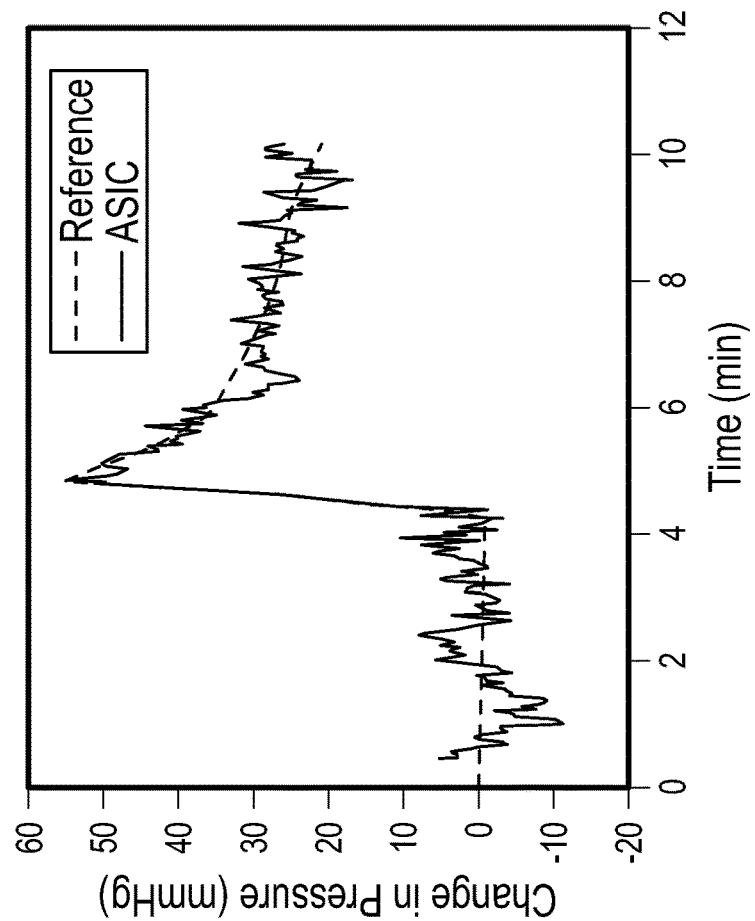
Figure 74A:
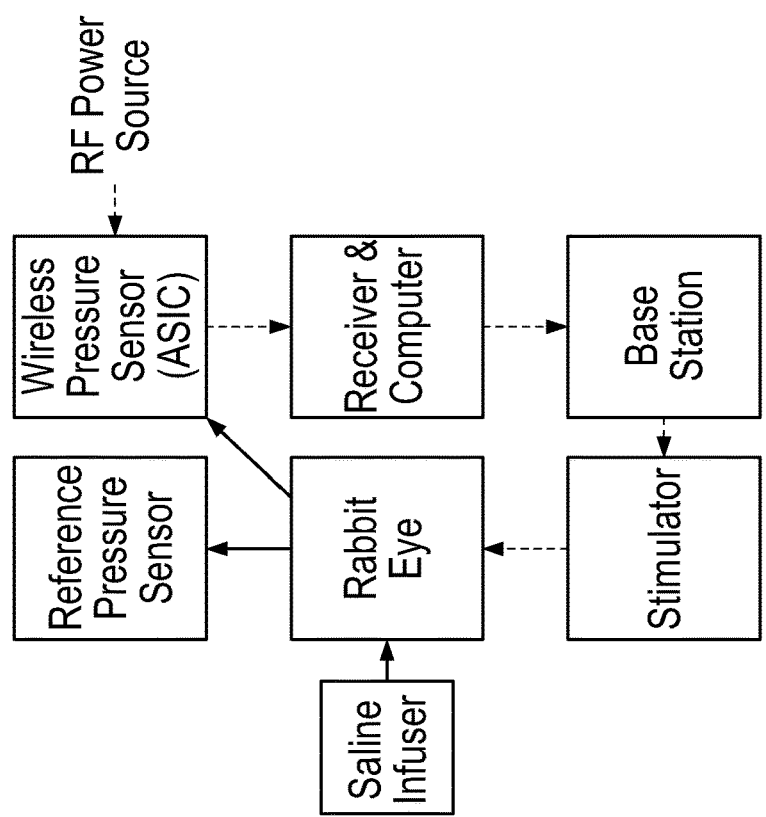

FIG. 74 illustrates in-vivo experiments including: a) Experimental setup, and b) intraocular pressure (IOP) recording.

Like reference, numbers and designations in the various drawings indicate like elements.

DETAILED DESCRIPTION

The present invention enables the wireless administration of energy to an eye of a mammalian subject for the purpose of reducing elevated intraocular pressure (IOP) for those experiencing glaucoma or pre-glaucoma ocular hypertension. This reduction in IOP is based on the delivery of time-varying electromagnetic fields to the eye in a therapeutically effective amount sufficient to (1) decrease the inflow of aqueous humor into the anterior segment of the eye (so-called "fluid inflow decrease") and/or (2) increase the outflow of aqueous humor from the anterior segment of the eye (so-called "fluid outflow increase"). As used herein, the "anterior segment" of the eye is the front third of the eye that includes the structures in front of the vitreous humor: namely the cornea, the iris, the ciliary body, and the intraocular lens. There are two fluid-filled spaces within the anterior segment of the eye: the anterior chamber and the posterior chamber. The anterior chamber of the anterior segment exists between the posterior surface of the cornea (i.e. the corneal epithelium) and the iris. The posterior chamber of the anterior segment extends between the iris and the suspensory ligament of the lens. Aqueous humor fills the spaces of the anterior chamber and posterior chamber to, among other things, provide nutrients to the surrounding structures. The wireless administration of energy to reduce IOP may take multiple forms, as will be described below.

Figure 1:
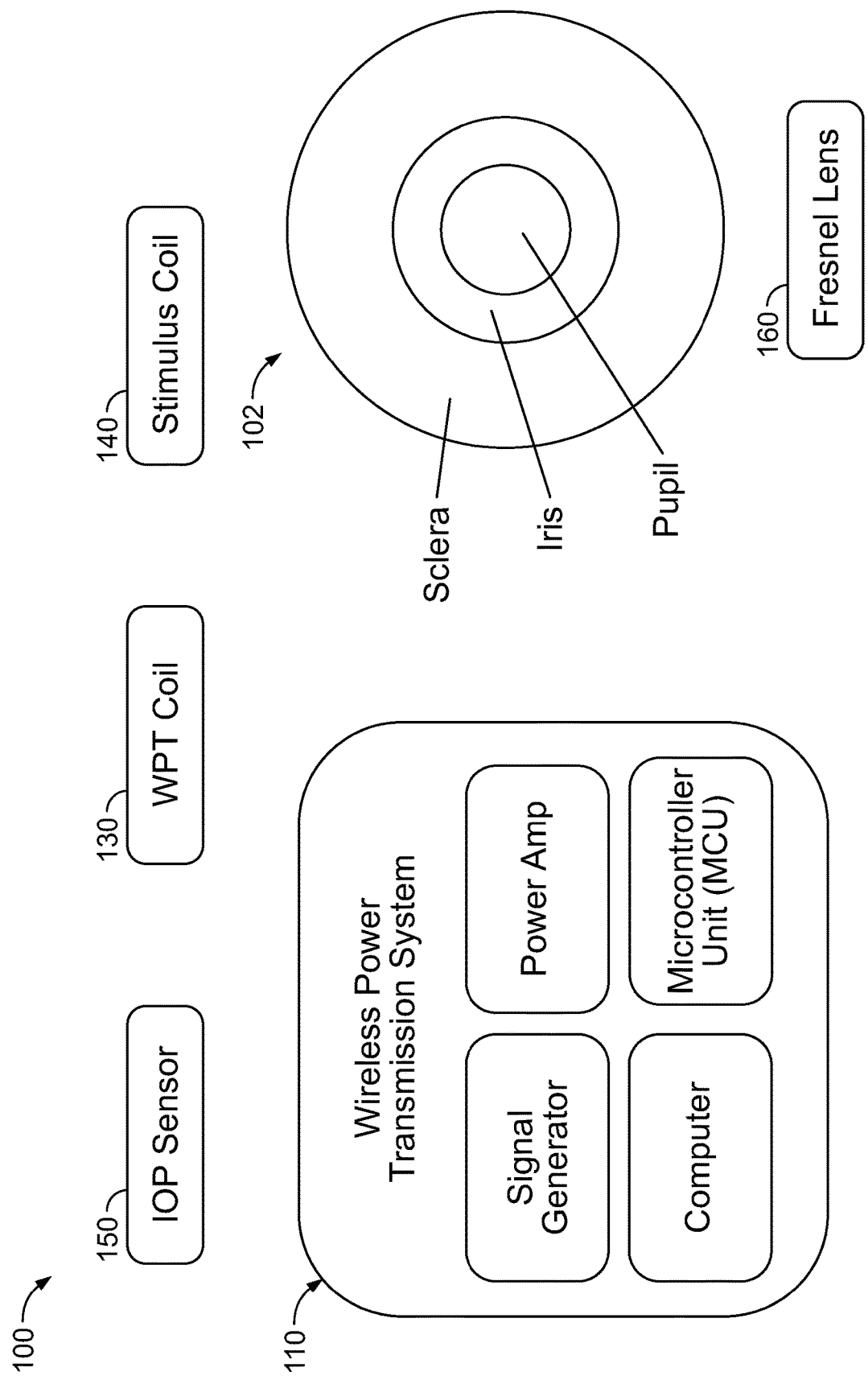
FIG. 1 shows a diagram of an example of a wireless glaucoma therapy system, including a wireless power transfer (WPT) system, a WPT coil, a Stimulus Coil.

FIG. 1 is a block diagram of a wireless glaucoma therapy system 100 for delivering a time-varying electromagnetic field to an eye 102 of a mammalian subject according to the principles and techniques disclosed herein. To do so, the wireless glaucoma therapy system 100 includes a wireless power transfer (WPT) system 110 having suitable control and driving circuitry (e.g. signal generator, power amp, microcontroller unit, computer) for generating a time-varying electromagnetic field from a WPT coil 130 positioned and configured to deliver the time-varying electromagnetic field to the eye 102, either directly or alternatively via stimulus coil 140. The WPT system 110 and the WPT coil 130 may be communicatively linked in any number of suitable manners, including a hard-wired connection (e.g. cable) as well as via wireless communication technologies.

As will be described below, the WPT coil 130 may be positioned near the eye 102 in any number of suitable manners, including but not limited to devices to enable the administration of wireless glaucoma therapy during normal activities of daily living (e.g. WPT coil 130 on eye-glasses), devices to enable the administration of wireless glaucoma therapy in a clinical setting (e.g. WPT coil 130 on an optical frame used by ophthalmologists and/or optometrists), and devices to enable the administration of wireless glaucoma therapy while the subject is sleeping (e.g. WPT 130 as part of a sleep mask, pillow, etc.). In each case, the WPT coil 130 delivers the time-varying electromagnetic field to the eye 102 in a therapeutically effective amount to reduce the IOP within the eye 102 by decreasing the inflow and/or increasing the outflow of aqueous humor into and out of, respectively, the anterior segment of the eye 102.

In another embodiment, the wireless glaucoma therapy system 100 may include a stimulus coil 140 disposed on or within the eye 102. The stimulus coil 140 is configured to receive the electromagnetic field generated by the WPT coil 130 and transmit that energy directly into the eye 102. The physical location of the stimulus coil 140 on or within the eye 102 provides a higher level of energy transmission into the eye 102, which can result in IOP reduction in a shorter time period or to a greater extent than that accomplished by the WPT system 110 and WPT coil 130 alone. As will be explained below, the stimulus coil 140 may be disposed and configured in any number of suitable manners, including (but not necessarily limited to) on or within a contact lens and/or surgically implanted into any suitable area within the eye 102 (e.g. intraocular lens (IOL), sub-conjunctival region, etc.).

In a still further embodiment, the wireless glaucoma therapy system 100 may include a wireless IOP sensor 150 capable of monitoring the intraocular pressure (IOP) within the eye 102. As will be described below, the wireless IOP sensor 150 may be implantable within the eye 102 and communicatively linked with the WPT system 110 to regulate or modify the delivery of therapy in a closed-loop manner based on the values of the monitored IOP. The closed-loop control of the WPT system 110 (including WPT coil 130 and optionally the stimulus coil 140) may be accomplished in any suitable manner, including but not limited to the use of executable software on the computer and/or an "app" on a smartphone, tablet, etc., to modify the delivery of the wireless glaucoma therapy based on the measured IOP in the eye 102.

In yet another embodiment, a Fresnel lens 160 may be employed (used separately or as part of the glaucoma therapy system 100) to focus incoming light rays onto the retina of the eye 102 for the purpose of vision correction. The Fresnel lens 160 may be constructed with a series of metallic traces in order to establish a given optical power to achieve vision correction, namely, by focusing light passing through the Fresnel lens 160 on the retina of the eye 102. The metallic traces of the Fresnel lens 160 may also be capable of receiving the time-varying electromagnetic fields and delivering that energy to the eye for the purpose of glaucoma therapy, especially if the Fresnel lens 160 is electrically coupled to a stimulus coil 140. The Fresnel lens 160 may be employed with the WPT system 110 (including WPT coil 130) in order to deliver glaucoma therapy in addition to vision correction.

Figure 2:
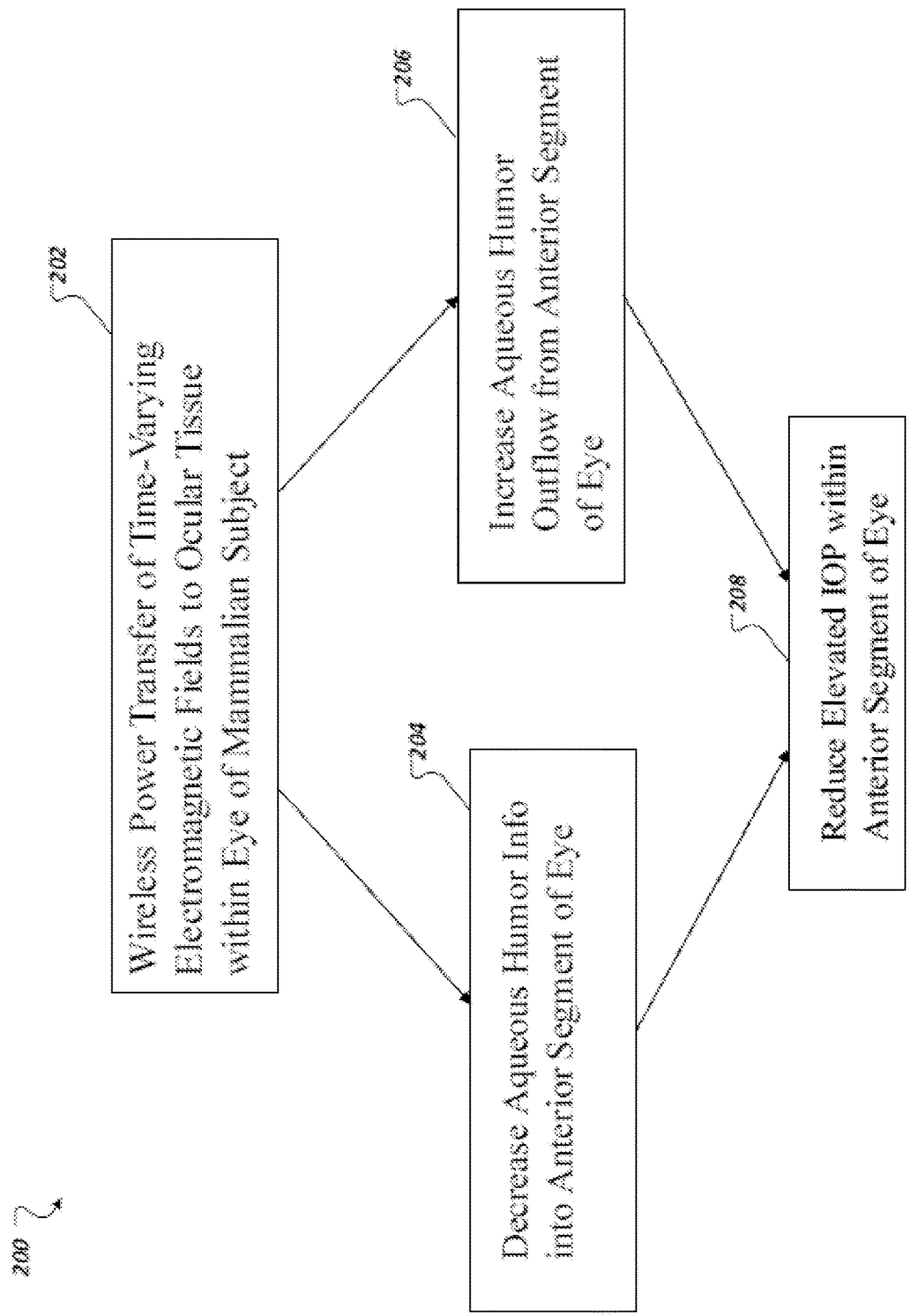
FIG. 2 shows the fundamental methodology of the wireless glaucoma therapy system.

FIG. 2 shows the fundamental methodology 200 of the wireless glaucoma therapy system (e.g., system 100 shown in FIG. 1). Step 202 involves wirelessly transmitting power in the form of time-varying electromagnetic fields to ocular tissue with an eye of a mammalian subject (e.g., eye 102 shown in FIG. 1). Depending upon the manner of wireless power transfer, the wireless transmission of power (step 202) will result in a decrease in aqueous humor inflow into the anterior segment of the eye (step 204) and/or an increase in aqueous humor outflow from the anterior segment of the eye (step 206). More specifically, the wireless transmission of energy via WPT coil (e.g., WPT coil 130 of FIG. 1), with or without a stimulus coil (e.g., stimulus coil 140 of FIG. 1), may provide both a decrease in the aqueous humor into the anterior segment of the eye (step 204) and an increase in the aqueous humor outflow from the anterior chamber of the eye (e.g., eye 102), thus reducing an elevated IOP within the anterior segment of the eye (208).

Figure 3:
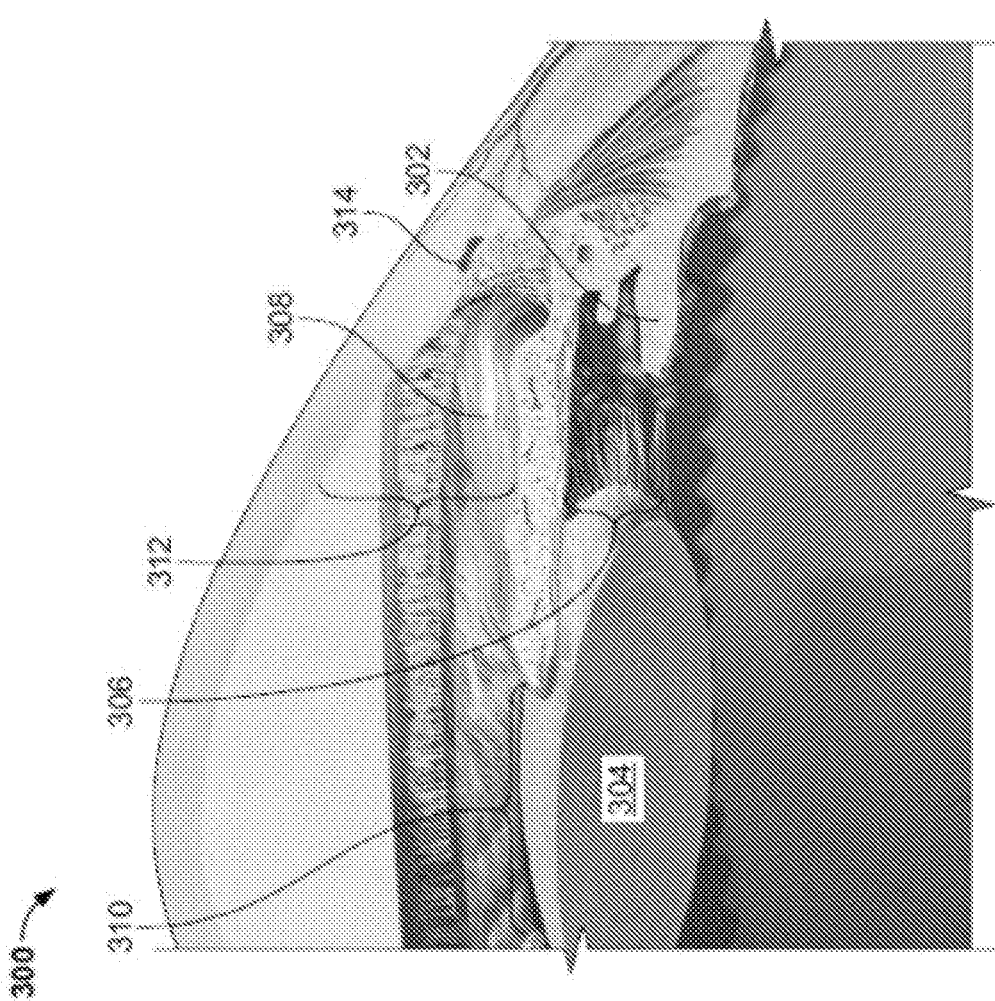
FIG. 3 shows a diagram of the relevant anatomy of an eye of a mammalian subject.

FIG. 3 shows a diagram of the relevant anatomy of an eye 300 of a mammalian subject, specifically in this figure, a human. Within the eye 300, the ciliary body 302 includes a smooth-muscle tissue called the ciliary muscle, which has two different orientations of muscle (circular and longitudinal) with separate functions. The circular muscle tissue of the ciliary body 302 controls the shape of the lens 304 in the eye 300, which changes the focus of the eye 300 so that the image will be clear on the back of the retina. The longitudinal muscle tissue of the ciliary body 302 controls the configuration of the trabecular meshwork. The aqueous humor is secreted by the ciliary body 302.

Aqueous humor is secreted into the posterior chamber 306 of the anterior segment of the eye 300 between the iris 308 and lens 304. It washes over the lens 304 and then moves through the pupil 310 into the anterior chamber 312 of the anterior segment. Ultimately, much of the aqueous humor leaves the eye 300 through two primary pathways, namely a pathway through as least part of the Canal of Schlemm and an uveoscleral pathway through at least part of the ciliary body and choroid. Aqueous humor production, flow and drainage are important for nourishing the front of the eye 300, removing metabolites and normal vision.

In a patient with glaucoma, the aqueous humor builds up in the eye 300. This can be due to the blocking or a slowing of the drainage of the aqueous humor in the trabecular meshwork. As the excess fluid builds in the eye 300, it increases the intraocular pressure. As this pressure increases, it causes the optic nerve to get damaged. If left untreated, the pressure does so much damage to the optic nerve that it can eventually lead to blindness.

Figure 4:
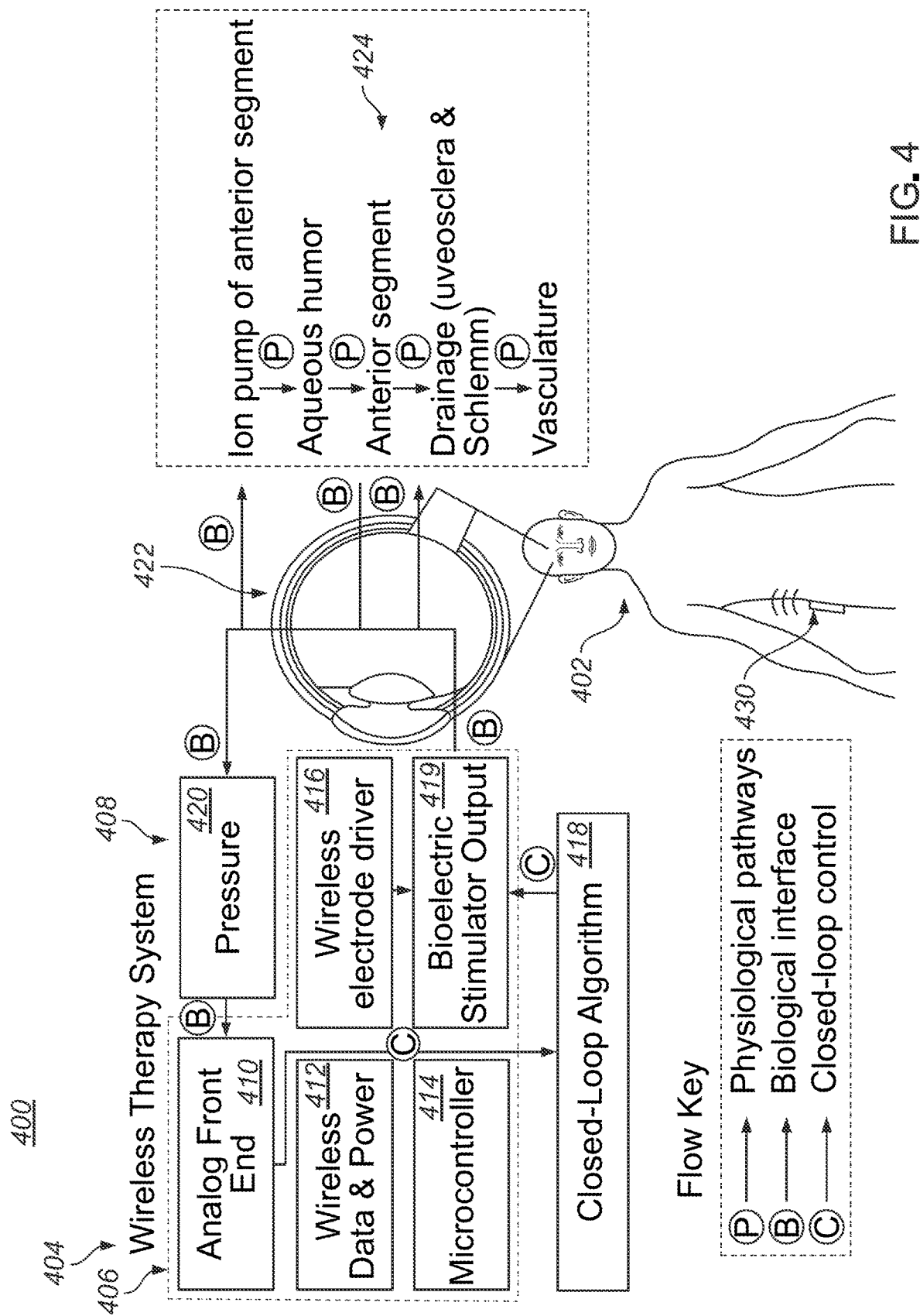
FIG. 4 shows a block diagram of an example of a closed-loop wireless glaucoma therapy system, including various components and the resulting biological effects.

FIG. 4 shows a block diagram of an example of a closed-loop wireless glaucoma therapy system 400, including various components and the resulting biological effects. The wireless glaucoma therapy system 400 includes a controller system 404 (in dashed lines) with various components and circuitry to effectuate a closed-loop algorithm 418 for the monitoring and adjusting the glaucoma therapy based on feedback provided by a wireless pressure sensor 420 (described below) implanted within the eye 422 of the patient.

More specifically, the stimulator output 419, for example, will transmit a given time-varying electromagnetic field into the eye 422 (via WPT coil 130 and optionally stimulus coil 140) depending upon any number of input parameters and/or instructions being acted upon by the microcontroller 414 (e.g., input from the wireless IOP sensor 420 via the analog front end 410). By operating in a closed-loop manner, the wireless glaucoma therapy system 400 can dynamically influence the various physiological pathways 424 to achieve a desired decrease in aqueous humor inflow into and/or increase in aqueous humor outflow from the anterior segment of the eye 422.

In one embodiment, the wireless glaucoma therapy system 400 may be programmed and/or controlled by the patient and/or a physician via a mobile device 430 (e.g. iPhone by Apple, Inc, Galaxy by Samsung, Inc, iWatch by Apple, Inc., etc.) with software capable of wirelessly controlling the function of certain (or all) components of the wireless glaucoma therapy system 400. For example, it is contemplated that the components of the controller system 404 may be disposed on or within the various devices for positioning a WPT coil 130 in proximity to the eye 422 of the subject 402 (e.g. glasses, optical frames, sleep mask, pillow). In this case, the mobile device 430 could be used to wirelessly control the operation of the controller system 404, such as via Bluetooth connectivity between the mobile device 430 and the controller system 404.

The controller system 404 can include components to provide wireless data and power (412) that permits the control device 406 to wirelessly output data to a base station (separate from the mobile device 430) and to be wirelessly powered and/or charged. This output data can include a variety of different patient data, such as a log of conditions detected and therapies delivered, alerts as to currently detected conditions (e.g., elevated IOP), and/or other data. The controller system 404 can transmit this data wirelessly. The controller system 404 can be powered wirelessly (e.g., via RF signals) and can additionally include a local power source (e.g., battery) that can be charge via the wireless signals and that can power the controller system 404 when the wireless signal is unavailable.

The controller system 404 includes an analog front end 410 that receives wireless signals transmitted by the wireless IOP sensor 420. The analog front end 410 provides the received signals to the signal processing subsystem of the microcontroller 414. Signal processing can be performed onboard or offboard, and can involve using a closed-loop algorithm 418, which can be used to identify particular physiological conditions within the patient 402 and can determine, based on the particular detected conditions, whether to modify or alter the bioelectric stimulation at one or more WPT coils located in proximity to the eye 422 and optionally one or more stimulus coils disposed on or within the eye 422.

The closed-loop algorithm 418 can use any of a variety of appropriate techniques to learn the particular physiology of the patient 402 and the patient's particular response to therapy, and can use that information to determine when, how, and under what conditions to provide therapy for the patient 402. For example, the closed-loop algorithm 418 can be initially calibrated for the patient by a physician or other trained technician in a clinical setting, which can involve providing various stimulations and recording the physiological response of the patient 402. After being initially calibrated, the closed-loop algorithm 418 can continue to learn and adapt over time by analyzing data generated by the wireless IOP sensor 420, therapy provided to the patient 402, and the patient's response to the therapy. The closed-loop algorithm 418 can repeatedly monitor patient data and apply stimulation to the ion pump and/or eye muscles (e.g., eye muscles affecting eye drainage) when appropriate until the patient's elevated IOP condition has been reduced and/or dropped below a threshold level. The closed-loop algorithm 418 can be automatically implemented without explicit patient direction.

Figure 5:
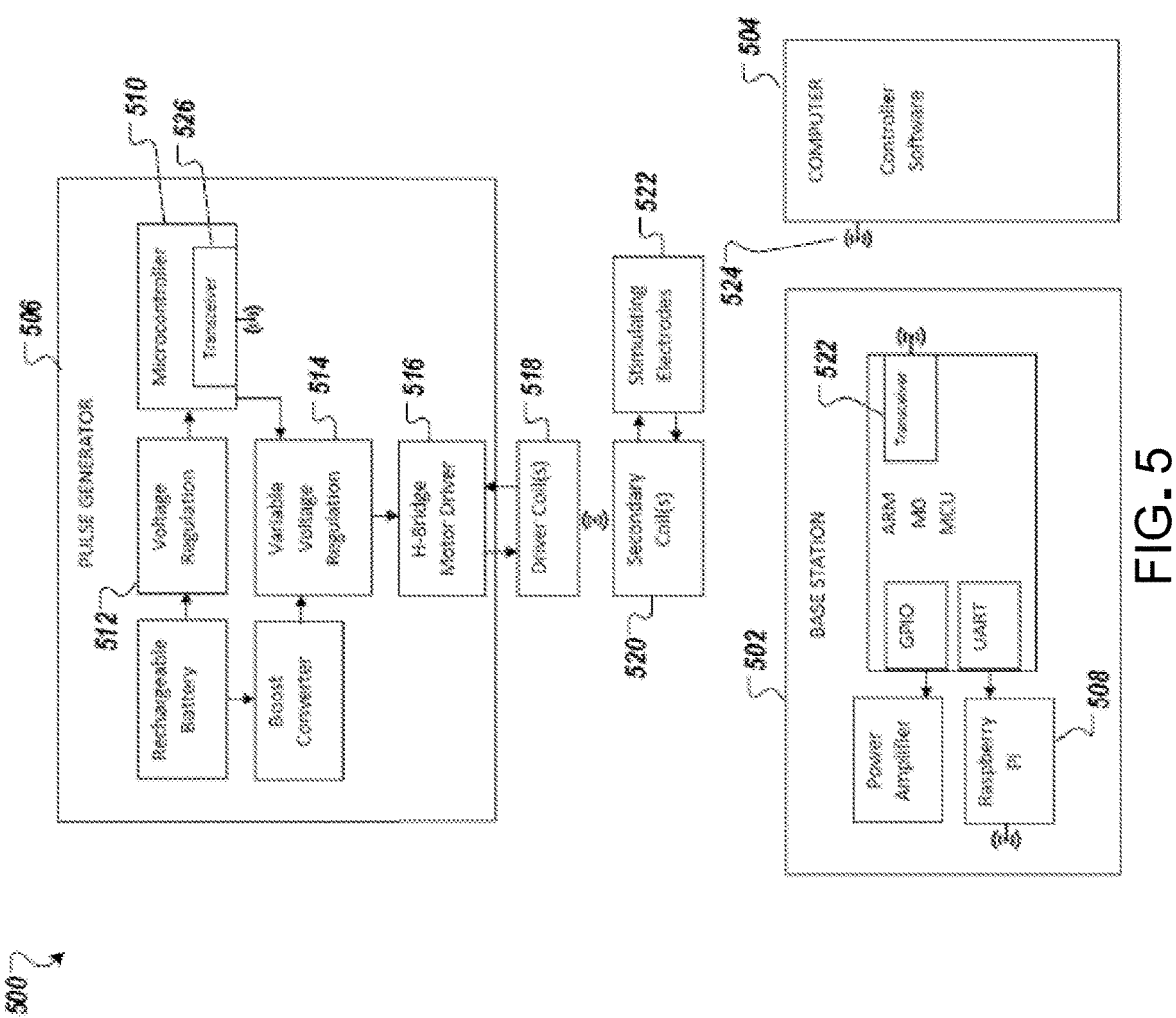
FIG. 5 shows an example of the wireless power transfer (WPT) system of the wireless glaucoma therapy system, including base station and signal generator.

FIG. 5 shows an example of an open-loop wireless glaucoma therapy system 500, including various components. The wireless glaucoma therapy system 500 includes a base station 502, a computer 504, and a pulse generator 506. The base station 502 and computer 504 cooperate to wirelessly transmit control signals to the pulse generator 506 to effectuate control programming set forth in software being executed by the computer 504. The base station 502 may be wirelessly connected to the pulse generator 506 via any suitable wireless communication technology or system (e.g. Raspberry Pi 508) capable of wirelessly communicating with a microcontroller 510 of the pulse generator 506. The base station 502 may also be wirelessly connected to the computer 504, using transceiver 522 and its associated antenna along with another transceiver and associated antenna 524 provided with the computer 504. It will be appreciated that, although shown with wireless communication between the base station 502 and the computer 504, as well as between the base station 502 and the pulse generator 506, any or all of these wireless communications pathways may be replaced via physical communications links (e.g. computer cable).

The pulse generator 506 receives the wireless control communications from the base station 502 via a transceiver 526 in communication with (or forming part of) the microcontroller 510. The microcontroller 510 cooperates with circuitry (e.g. voltage regulation 512, variable voltage regulation 514) to drive an H-bridge driver 516 coupled to one or more drive (WPT) coils 518 to transmit a time-varying electromagnetic field. This electromagnetic field may be administered to the eye via drive (WPT) coil(s) 518 positioned in proximity to the eye and optionally via one or more secondary coils 520 located on or within the eye. Through the principles of wireless electromagnetic energy (e.g. inductive, far-field RF, optical, etc.) coupling, the secondary coils 520 may be adapted to receive the time-varying electromagnetic field from the drive (WPT) coils 518 and transmit that energy into ocular structures of the eye via one or more stimulating electrodes 522 disposed on or within the eye, as discussed in detail below. Whether WPT-only (that is, drive/WPT coils 518 alone) or WPT in combination with secondary (stimulus) coils 520, the wireless glaucoma therapy system 500 is capable of administering a therapeutically effective amount of energy to achieve the desired reduction in aqueous humor inflow into and outflow from, respectively, the anterior segment of the eye.

Figure 6:
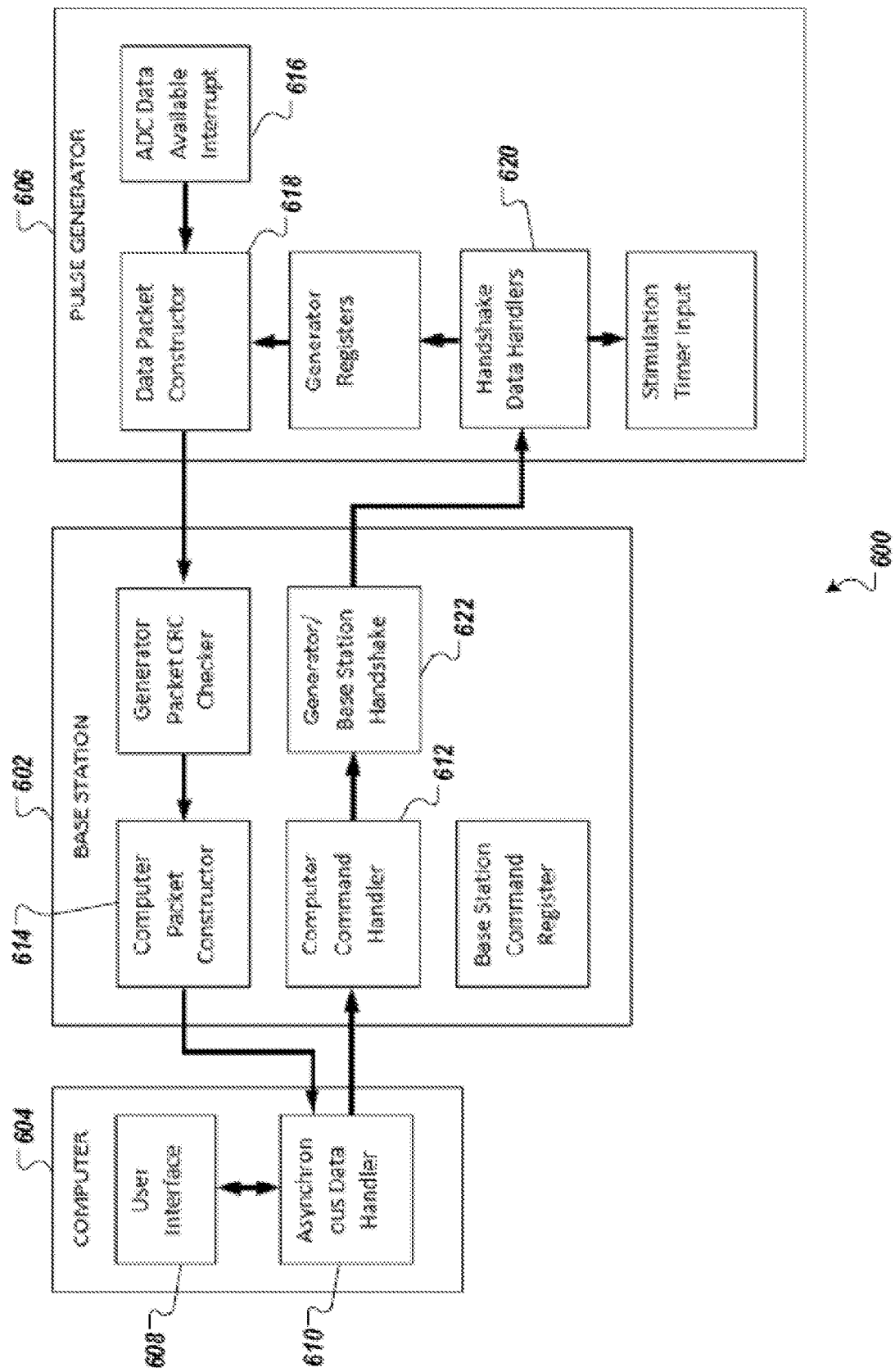
FIG. 6 shows a diagram of depicting an example of the communication pathway of the wireless glaucoma therapy system.

FIG. 6 shows a diagram of depicting an example of the communication pathway between the components of a wireless glaucoma therapy system 600 of the type shown in FIG. 5, with base station 602, computer 604, and pulse generator 606. The communication within wireless glaucoma therapy system 600 starts on the left, with a user interfacing with the computer 604 such as inputting instructions or the like via User Interface 608 (e.g. keyboard, GUI, etc. . . . ). The computer 604 is communicatively linked with the base station 602 via an asynchronous data handler 610 that sends output signals to a computer command handler 612 and receives input signals from a computer packet constructor 614.

Bidirectional communication during use of the system can greatly increase the flexibility and possible application use of an implantable device such as the wireless IOP sensor described herein, which would be coupled to the analog-to-digital converter (ADC) Data Available Interrupt module 616. The ability to transmit data potentially removes the burden of on-board data storage from the implantable device, but it also allows the implantable device to communicate its current status and settings in real time, allowing for increased confidence in implant performance over time. Furthermore, the ability to receive data allows the implantable device to be configured, calibrated, and instructed before, during, and after implantation; increasing its adaptability to varying circumstances. An implantable device that can both receive and transmit data (such as the wireless IOP sensor) has the added benefit of allowing an external user or system to reactively send instructions to the implantable device based off of recorded data obtained by the implantable device; effectively creating a closed-loop system.

Bidirectional communication can be performed, as illustrated in FIG. 6, by enforcing a coordinated handshake protocol with a custom designed external base station 602 which facilitates all communications with any outside user. After the pulse generator 606 acquires a specific number of samples, for example 40 data samples, from its analog-to-digital converter (ADC) Data Available Interrupt 616, a microcontroller with the pulse generator 606 initiates a data-packet transmission to the base station 602 using an on-board radio. Data packets can be constructed, for instance using conventional packetization techniques, to include recoded data, and subsequently communicated via transmission signal from a data packet constructor 618.

After a successively transmitting multiple packets, for instance the 100th data packet, the pulse generator 606 initiates a hand-shake with the base station 602. The handshake can be performed between respective handshake units (620, 622). After transmitting a specified data packet, or a data packet otherwise deemed as the end of communication (e.g., 100th data packet), the pulse generator 606 sets its radio to receive mode, and listens for a data packet from the base station 602 for a time, typically not exceeding 10 milliseconds. This gives the base station 602 an opportunity to send a single data packet to the pulse generator 606. The data packet can contain a 45-byte long payload, which is used to set firmware registers in the microcontroller of the pulse generator 606 that stores data acquisition, stimulation, and communication settings.

In some cases, the handshake driven communication scheme allows the pulse generator 606 to transmit acquired data rapidly, while maintaining the ability to receive data from an outside source with minimal radio activation time. For example, given a total data acquisition sample frequency of 5 kHz, the radio of the pulse generator 606 will transmit 125 data packets per second and initiate a handshake once every 800 milliseconds. Given the radio on-time described above, bidirectional communication is achieved with the radio being deactivated at least 86.7% of the time.

Another challenge in a wireless communication scheme is increasing data robustness. In order to properly analyze any data recorded by the pulse generator 606, the ability to identify when data has been corrupted or lost may be desired. Data can be corrupted or lost during wireless transmission in various conditions, including: if it is obstructed by a blockage that can absorb RF energy; if a nearby device communicating on the same frequency creates interference; and if the distance between the pulse generator 606 and the base station 602 exceeds the transmission range of the pulse generator 606. Furthermore, data can be lost in the scenario if the pulse generator 606 suddenly loses power during data acquisition or transmission.

Figure 7:
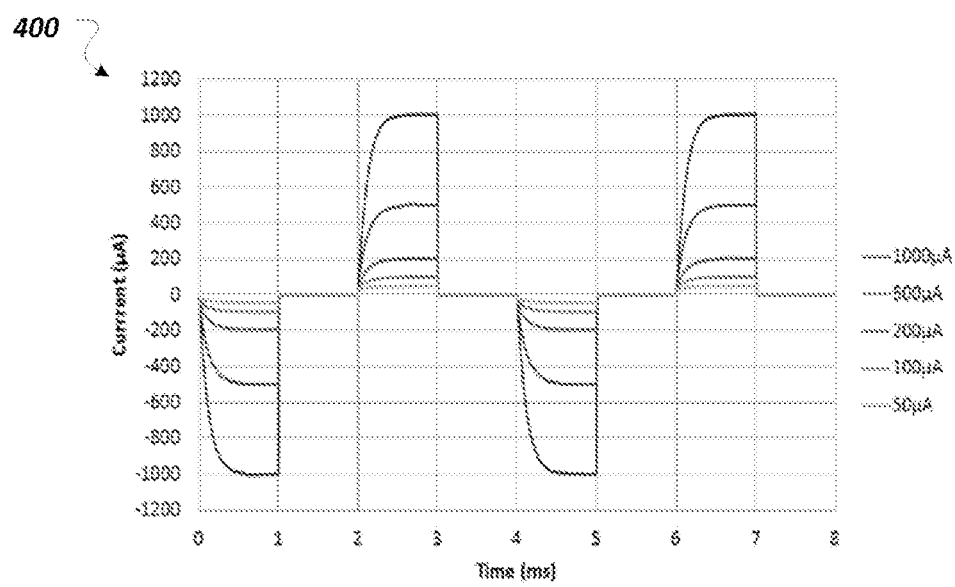
FIG. 7 shows an example graph displaying current-controlled, biphasic output measured from the stimulator outputs aspect of the wireless power transfer system.

FIG. 7 shows an example graph 700 displaying current-controlled, biphasic output measured from the stimulator outputs aspect of the wireless power transfer system. In this example, the stimulator output is measured on a benchtop using a 10 kΩ load across the stimulator outputs. The graph 700 displays the output signal as a relationship between time (ms), along the X-axis, versus current (µA) along the Y-axis. Pulse width, current amplitude, and duty cycle can be selectable parameters in real-time through reverse telemetry from the base station to the WPT coil or other suitable wirelessly powered device. A pulse width of 1 ms and a 50% duty cycle are used here to illustrate the current output for a range of amplitude settings.

FIGS. 8-11 illustrate several manners of positioning a WPT coil (e.g., coil 130 shown in FIG. 1) near the eye to enable the administration of wireless glaucoma therapy according to the principles set forth herein. These include, but are not necessarily limited to, glasses with WPT coil(s) for administering wireless glaucoma during normal activities of daily living (e.g. FIG. 8), WPT coil(s) on an optical frame used by ophthalmologists and/or optometrists in a clinical setting (e.g. FIG. 9), and devices to enable the administration of wireless glaucoma therapy while the subject is sleeping (e.g. WPT 130 as part of a sleep mask, pillow, etc.). In each case, the WPT coil delivers the time-varying electromagnetic field to the eye in a therapeutically effective amount to reduce the IOP within the eye by decreasing the inflow and/or increasing the outflow of aqueous humor into and out of, respectively, the anterior segment of the eye.

Whether disclosed below for "WPT-Only" usage or with stimulus coils as well, it will be appreciated that the embodiments shown and described herein may be provided in combination with a host of additional features. For example, a wireless IOP sensor (described herein) may be provided to monitor the IOP and regulate or modify the delivery of therapy in a closed-loop manner. A Fresnel lens may also be employed on the glass lenses to focus incoming light rays onto the retina of the eye for the purpose of vision correction. The Fresnel lens (described in detail below) is constructed with a series of metallic traces (in order to achieve vision correction) which makes the Fresnel lens capable of receiving the time-varying electromagnetic fields. The Fresnel lens may be employed with the WPT system (including WPT coil) in order to deliver glaucoma therapy in addition to vision correction.

Figure 8A:
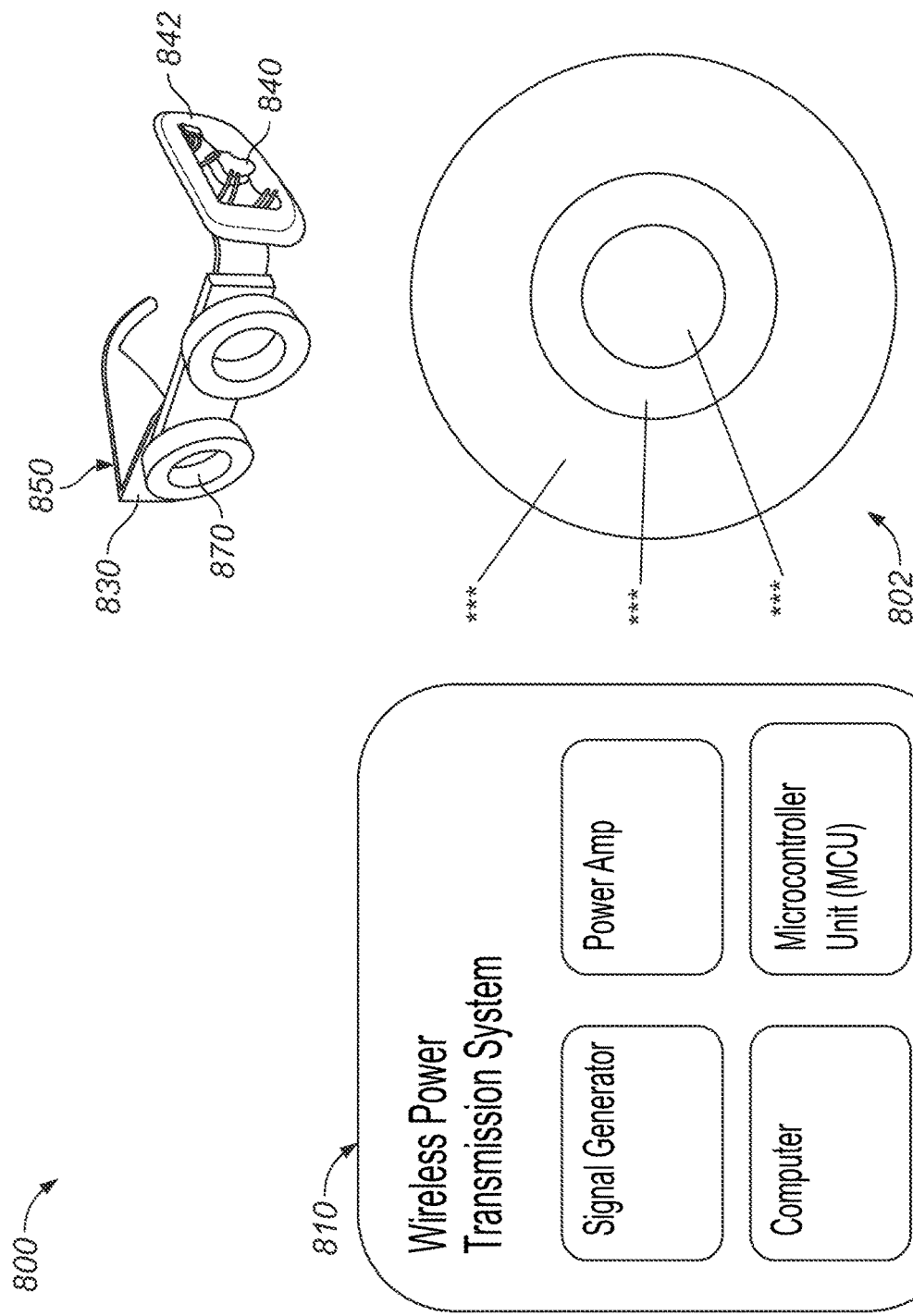
FIGS. 8A-8E show an example wireless glaucoma therapy system involving the use of a wireless power transfer (WPT) coil associated with glasses for implementing the disclosed techniques.
Figure 8E:
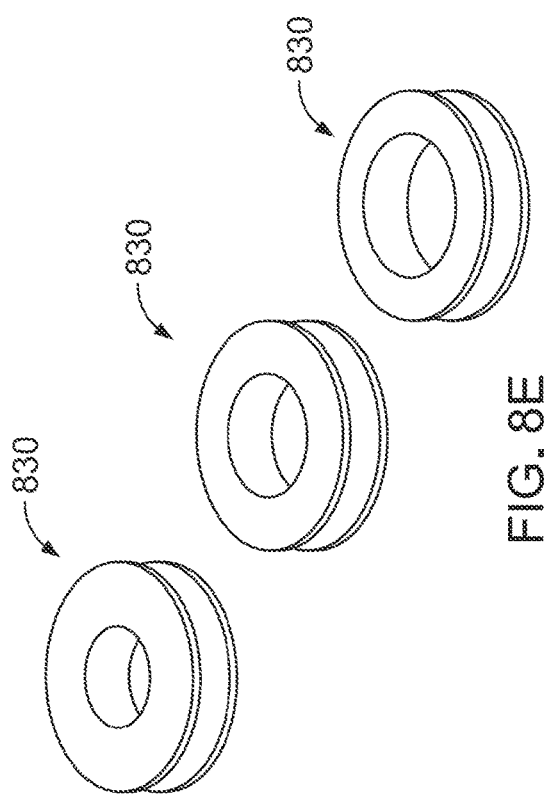

FIG. 8A shows an example wireless glaucoma therapy system 800 includes a wireless power transfer (WPT) system 810 for generating time-varying electromagnetic fields and transmitting them to wireless power transfer (WPT) coils 830. Each WPT coil 830 is disposed on a frame of the glasses 850 and configured to deliver the time-varying electromagnetic fields to the eye 802 of a mammalian subject. The coils 830 are disposed on the frame of the glasses 850 at a fixed distance above the eye 802 and are aligned coaxially about an axis passing through the approximate center of the viewing aperture of the glasses. This serves to increase efficiency and consistency of the electromagnetic field exposure to the ocular structures within the eye 802 of the mammalian subject. The WPT coils 830 include viewing apertures to coincide with the viewing apertures of the glasses, such that a wearer of the glasses can still see while receiving wireless glaucoma therapy according to the disclosed techniques.

In this embodiment, the glasses 850 are equipped with a pulse generator 840 (e.g., of the type shown and described with reference to FIG. 5) disposed within a housing 842 formed on one leg of the glasses 850. The WPT system 810 may include circuitry and components similar to the base station 506 of the type shown and described with reference to FIG. 5. Instead, such base station circuitry and components could form part of an "app" for a mobile device (e.g. iPhone by Apple, Inc., Galaxy by Samsung, etc. . . . ), including the ability to communicate with the pulse generator 840 via any suitable Bluetooth communication technology (e.g. Raspberry Pi).

Figure 8C:
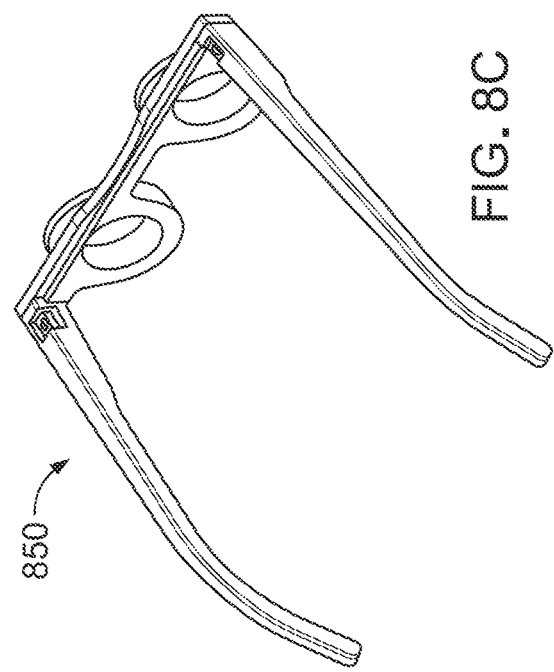
Figure 8D:
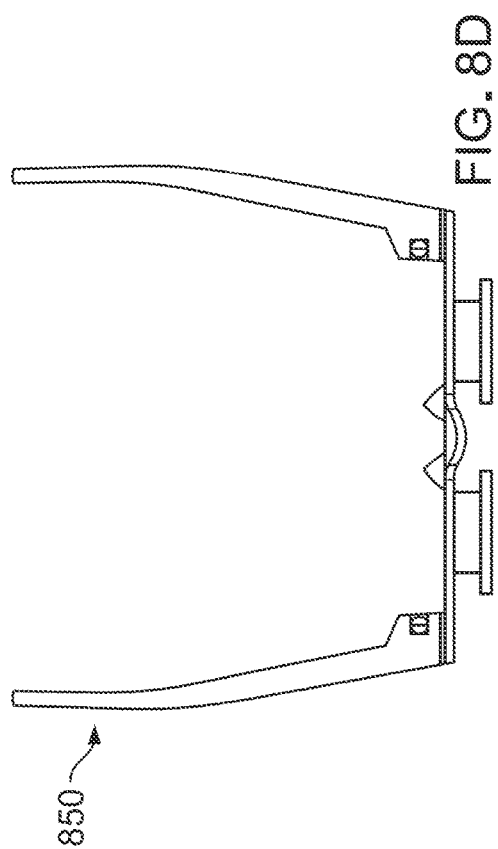
Figure 8B:
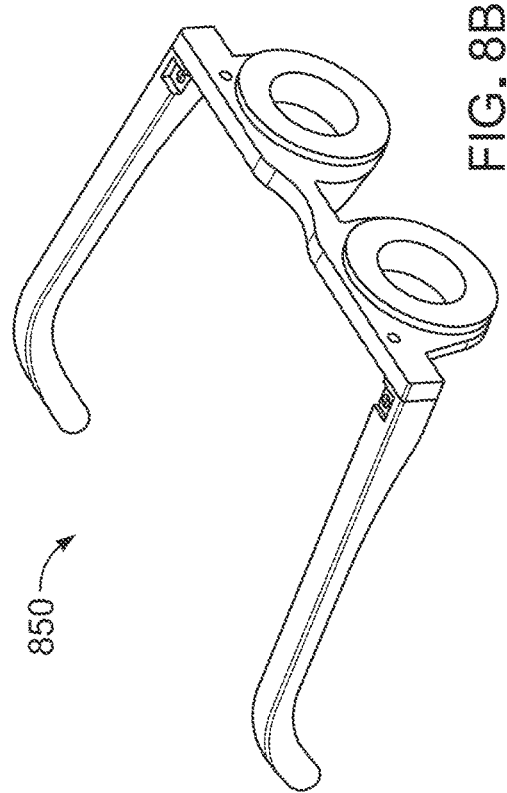

FIGS. 8B-8D show an alternate embodiment with the main difference that the glasses 850 do not include the on-board pulse generator 840 and the WPT coils 830 (FIGS. 8D and 8E) may be removably attached to the glasses 850. This allows the user and/or healthcare professional to increase or decrease the range of electromagnetic fields by simply changing the existing WPT coil 830 to one with a more suitable size or number of turns (larger and higher for increased magnetic field, and smaller and lower for lower magnetic field). It also decreases the weight of the glasses 850 (by removing the pulse generator, batteries, etc.).

FIGS. 9A-9E show an alternate embodiment for positioning WPT coils in proximity to the eye of a mammalian subject, this time involving the use of an optical frame 930 rather than the glasses 850 of FIG. 8. Other than this change, in most respects the wireless glaucoma therapy system 900 is similar to wireless glaucoma therapy system 800 of FIG. 8 such that a full description need not be repeated. The depicted wireless glaucoma therapy system 900 of FIG. 9A includes a wireless power transfer (WPT) system 910 (depicted in a block diagram), for generating time-varying electromagnetic fields and transmitting them to one or more WPT coils 920. The one or more WPT coils 920 are disposed on the optical frame 930 and configured to deliver the time-varying electromagnetic fields to the eye 902 at a desired distance away from the eye 902. In one embodiment, the WPT system 910 and WPT coils 920 are capable of transmitting time-varying electromagnetic fields to the eye 902 at a sufficient level and manner to result in a decrease in the IOP. This decrease in IOP is based on a fluid outflow increase and possibly also a fluid inflow decrease.

A stimulus driver connector 932 can be coupled to WPT coils 920 mounted on or otherwise carried by the optical frame 930 such that the WPT coil 920 may be hard-wire connected to the WPT system 910. A direct connection to the stimulus driver 934 may provide a higher level of energy transmission into the eye 902, which can result in IOP reduction in a shorter time period or to a greater extent than that accomplished by the WPT system 910 and WPT coil 920 alone. In some embodiments, a stimulus coil (not shown) may be disposed and configured in one or more components of the optical frame 930 such that the stimulus coil is positioned near the eye 902.

Figure 9A:
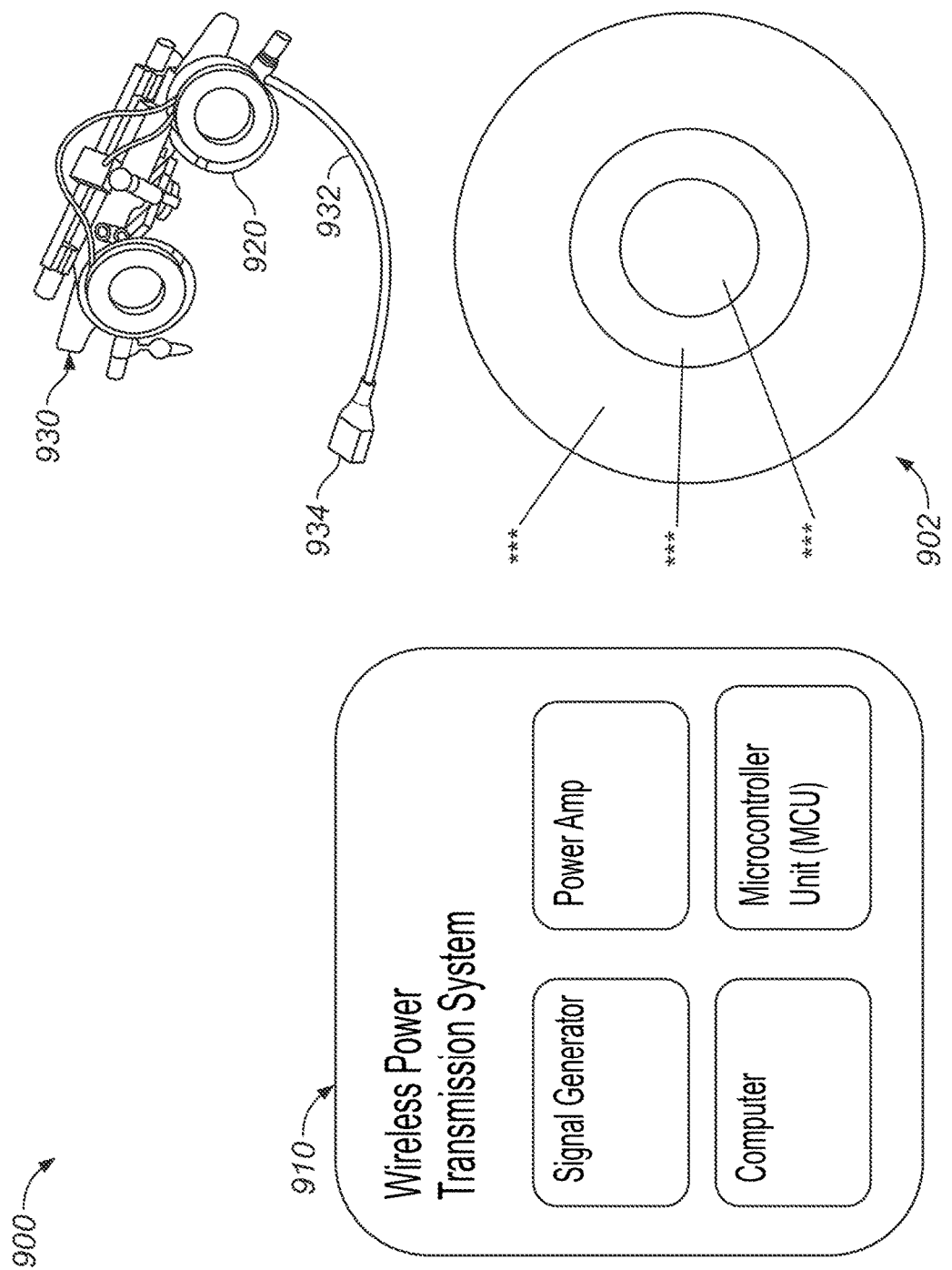
FIGS. 9A-9E shows an example wireless glaucoma therapy system involving the use of a wireless power transfer (WPT) coil associated with optical frames for implementing the disclosed techniques.
Figure 9D:
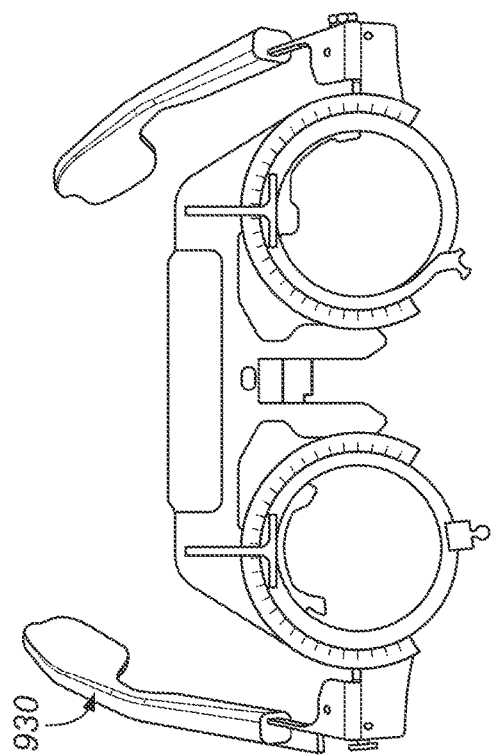
Figure 9E:
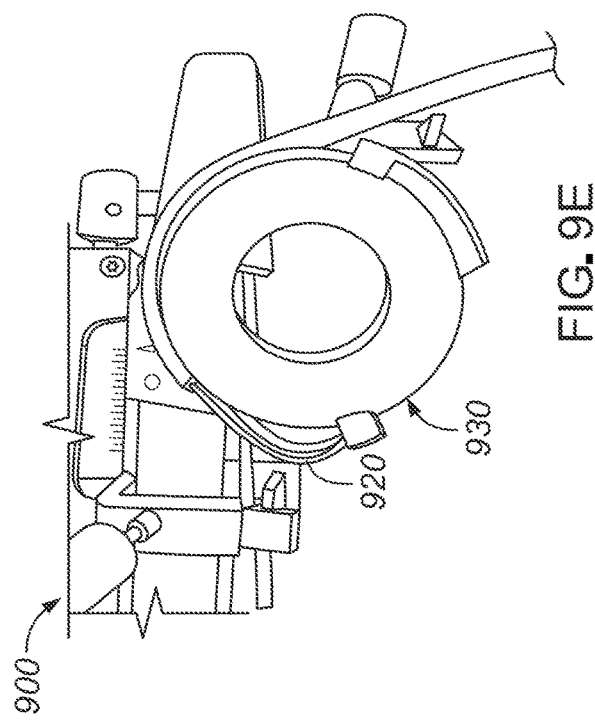
Figure 9B:
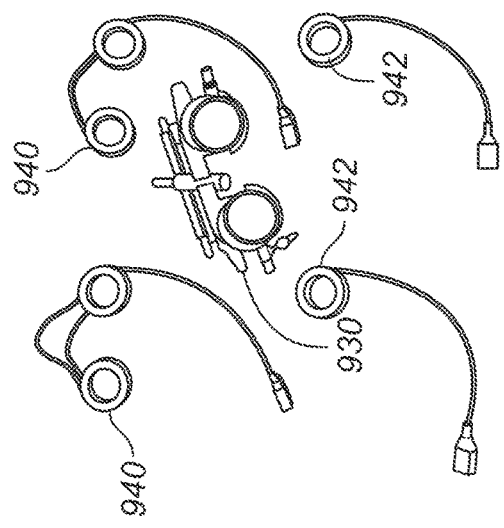

FIG. 9B shows a magnified image of the wireless glaucoma therapy system 900, showing the optical frames 930 carrying a single WPT coil 920. This may be useful when providing wireless glaucoma therapy to a patient in a clinic setting, such as the office of an ophthalmologist and/or optometrist, to administer the wireless glaucoma therapy to a single eye rather than both (e.g. to isolate and assess or deliver therapy in a targeted manner).

In some embodiments, the wireless glaucoma therapy system 910 does not obstruct vision and is wearable, comfortable, and discrete. The operation of the system 910 occurs based on a phenomena of induced electrical currents on conductors in the presence of time-varying magnetic fields. The coils 920 fitted to the frames 930 are constructed of wound, enamel-covered copper wire. The coils 920 may be constructed to have any number of suitable characteristics, including (by way of example only) a weight in the range of 15-25 grams, a resistance in the range of 0.5 Q to 1.5 Q, and an inductance in the range of 150 uH to 450 uH. The coils 1120 are connected to an external circuit board equipped with one or more battery, a microcontroller, and circuitry for the generation of pulsed magnetic fields to excite specifically-tailored electrical currents on the passive circuitry of the frames.

The optical frame can comprise commercially available optical frames, for example, the "Optometry Optician Fully Adjustable Frame" offered by Vktech, Inc. The frames can be equipped with fitted coils 920 (as shown in the photo image shown in FIG. 9A) to provide the wireless power.

The optical frame 930 can include a range of desired frame specification and dimensions. One or more of the following non-limiting frame specifications and dimensions can be applied in certain embodiments: (1) range of PD adjustments (e.g., PD of both eyes ranging from about 48 to 80 mm, left or right PD ranging from about 24 to about 40 mm minimum (2) a graduated value of about 1 mm; (3) a dividing disc axial graduation; (4) a left dividing disc of 120°~0°~135°; (5) right dividing disc of 45°~180°~60°; (6) axial graduation increases along the lens frame axis counterclockwise, and the graduated distance being about 5°; (7) an inner diameter of lens frame of about 32.5 mm; (8) the number of lens that can be inserted into left or right lens frame simultaneously can be 4 pieces; (9) the degree of lens rotating around optical axis in the lens frame can be 360°; (10) non-parallelism between lens' optical axis and lens frame's geometric axis can be less than or equal to 2.5°; (11) non-concentricity between lens' optical center and lens frame geometric center can be less than or equal to 0.5 mm; (12) displacement of lens in relation to position of lens frame geometric center can be less than or equal to 0.3 mm; (13) a range of nose rest adjustment can include a length of about 0 to about 14 mm and an angle of about 0° to about 30°; (14) a range of left or right lens frame leg's length adjustment can range from about 98 mm to about 135 mm; (15) a maximum interval between left and right lens frame legs can be about 200 mm; (16) the material can be a lightweight metal or plastic; (16) any desirable color or mix of colors can be used (e.g., black and silver); and (17) the size can be 15.50*6.00*3.50 cm.

Figure 9C:
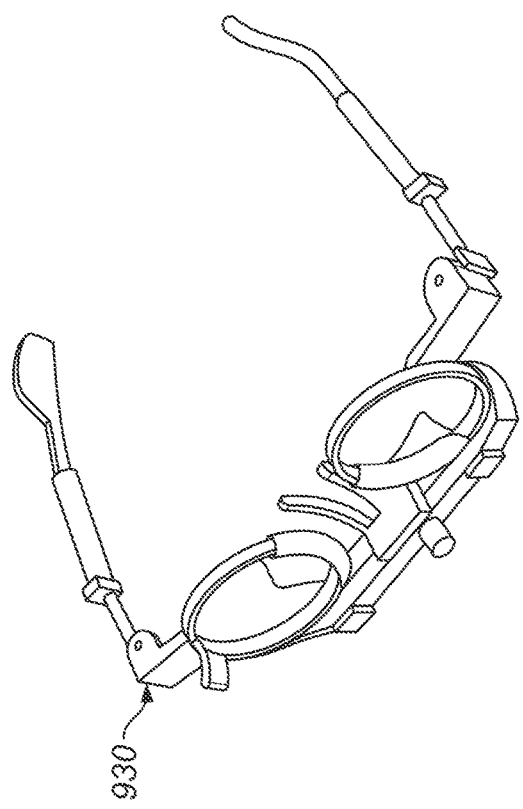

FIGS. 9C and 9D show different views of an example optical frame 930 (without the coils 920) that can be used with the wireless glaucoma therapy system 900. FIG. 9E shows an example optical frame 930 along aside with two dual-coil assemblies 940 and two single-coil assemblies 942. In some embodiments, the optical frame 930 can use one dual coil assembly 940, or one or two single-coil assemblies 942.

FIGS. 10A-B show an illustration of a coil assembly 950 for use with the optical frame 930 that can include at least two pairs of electrical coils, wherein a first pair of electrical coils is used to deliver wireless energy into the eye of the patient based on a stimulation signal having a first phase, and wherein a second pair of electrical coils is used to deliver wireless energy into the eye of the patient based on a stimulation signal having a second phase that is opposite from the first phase of the stimulation signal employed with the first pair of electrical coils.

The first pair of coils may be positioned approximately 90 degrees from the second pair of coils. In this configuration, within the context of a 12-hour clock, the first coil (of the first pair of coils) will be disposed at the 12 o'clock position, the third coil (from the second pair of coils) will be disposed at the 3 o'clock position, the second coil (of the first pair of coils) will be disposed at the 6 o'clock position, and the fourth coil (of the second pair of coils) will be disposed at the 9 o'clock position.

The first pair of coils includes a first electrical coil capable of being positioned at a first location over the patient's eye and a second electrical coil capable of being positioned at a second location over the patient's eye which is opposite (180 degrees) from the first location of the first electrical coil. The second pair of coils includes a third electrical coil capable of being positioned at a third location over the patient's eye and a fourth electrical coil capable of being positioned at a fourth location over the patient's eye which is opposite (180 degrees) from the third location of the third electrical coil.

The first location, second location, third location and/or fourth location may be such that the respective electrical coil may be disposed entirely over a part of the iris, disposed in an overlapping fashion over part of the iris and part of the pupil, and/or disposed entirely over a part of the pupil. These locations may be pre-determined (that is, manufactured at pre-established locations and without any adjustability) and prescribed or otherwise administered to the patient depending upon the professional judgment of the ophthalmologist and/or optometrist (or other medical professional) treating or otherwise caring for the patient as to the optimal locations. In another aspect, the optical frame may be manufactured such that the locations of the first and second pair of electrical coils may be adjustable, which would allow the ophthalmologists and/or optometrist (or other medical professional) adjust the location of the first and second pair of electrical coils of the optical frame over the eye of the patient according to their professional judgment.

FIG. 10B shows an example coil assembly 960 (configured to be mounted to an optical frame) with coils 1-4 disposed on extensions extending from coil assembly. The extensions are configured to position the coils 1-4 at a location that is adjacent to the eye. The distance between the electrical coils of the optical frame and the surface of the eye may vary depending upon whether: (a) the coils of the optical frame are being used in conjunction with passive coils and electrodes positioned on (e.g. via contact lenses with such passive circuitry) or within the patient's eye (e.g. via surgical implantation of such passive circuitry); or (b) the coils of the optical frame are being used alone to deliver the wireless energy into the patient's eye for the treatment of glaucoma (that is, without the use of contact lenses with passive circuitry and/or the surgical implantation of passive circuitry within the patient's eye). More specifically, the coils of the optical frame may be positioned further away from the patient's eye under scenario (a) and closer to the patient's eye under scenario (b). By way of example only, under scenario (a) the first and second pair of electrical coils may be positioned within or adjacent to the periphery of the frames (e.g. which form the aperture of the glasses), while under scenario (b) the first and second pair of electrical coils may be positioned adjacent to the surface of the eye such as through the use of one or more extensions that extend from the optical frame towards the eye of the patient when the optical frames are worn.

The electrical coils of the optical frame are provided as pairs (e.g. the first pair comprising the first coil and the second coil, and the second pair comprising the third coil and the fourth coil) so that the stimulation signals administered into the eye through each pair are out of phase with one another. In so doing, the amount of energy being administered into the eye will be effectively balanced when the stimulation signals administered through the first pair of coils and second pair of coils are the same or effectively so. In so desired, the signal characteristics of the first stimulation signal (that is, administered through the first pair of coils) and the second stimulation signal (that is, administered through the second pair of coils) may be different so as to modulate the impact of the stimulation on the eye (e.g. increase or decrease the stimulation imbalance to modulate IOP, etc.).

FIG. 11 shows an example wireless glaucoma therapy system 1100 involving the use of a wireless power transfer (WPT) coil associated with a sleep mask for implementing the disclosed techniques. The sleep mask can include a soft fabric cover 1120, glasses 1150 contained within the cover, and an elastic band 1122 coupled to the glasses 1150 to secure the sleep mask over a user's eyes. The wireless glaucoma therapy system 1100 is similar in all respects to the prior versions disclosed and described with reference to FIG. 8-10, with the exception that the WPT coils 1130 are dimensioned to be disposed within the sleep mask 1120 (versus part of a pair of glasses or an optical frame). By placing the WPT coils 1130 within the fabric cover 1120, a patient may place the WPT coils 1130 adjacent to their eyes over night or during periods of rest where the patient wants to have their eyes closed or light blocked out. This, in turn, allows the patient to continue to receive wireless glaucoma therapy during periods such as overnight, when it wearing glasses is not desirable or comfortable for the patient. Depending upon the amount of wireless glaucoma therapy that needs to be administered over time in order to stave off blindness or the onset of glaucoma, allowing a user to obtain wireless glaucoma therapy night may be an easy way to increase adoption of wireless glaucoma therapy.

FIG. 12 shows an example wireless glaucoma therapy system 1200 involving the use of a wireless power transfer (WPT) coil associated with a pillow 1220 for implementing the disclosed techniques. The pillow 1220 can include a soft cover 1222, cushion 1224 disposed within the pillow cover 1222, and WPT coils 1250 contained within or adjacent to the cushion 1224. The wireless glaucoma therapy system 1200 is similar in all respects to the prior versions disclosed and described with reference to FIG. 8-10, with the exception that the WPT coils 1230 are dimensioned to be disposed within the pillow 1220 (vs. part of a pair of glasses or an optical frame). By placing the WPT coils 1230 within the pillow 1220, a patient may position their head on the pillow 1220 so as to receive wireless glaucoma therapy during periods such as overnight, when it wearing glasses is not desirable or comfortable for the patient. Depending upon the amount of wireless glaucoma therapy that needs to be administered over time in order to stave off blindness or the onset of glaucoma, allowing a user to obtain wireless glaucoma therapy night may be an easy way to increase adoption of wireless glaucoma therapy.

Any of the features disclosed and discussed with respect to the manners of positioning WPT coils in proximity to the eye of FIGS. 8-12 may be combined amongst those shown in the drawings, e.g., features associated with the glasses 850 of FIG. 8 and optical frames 920 of FIG. 9.

Stimulus Coils and Fresnel Lens

The WPT system and technology described above may be used with any of the various stimulus coil embodiments disclosed herein and optionally in combination with the various Fresnel lens embodiments disclosed herein. The various Fresnel lens embodiments may be used alone or in combination with any of the various stimulus coil embodiments to administer wireless glaucoma therapy according to the disclosed techniques. The various stimulus coil embodiments and Fresnel lens embodiments set forth herein may use different reference numerals throughout the drawings and specification when referring to the same or similar components, features and functionality in other or prior embodiments. Notwithstanding those differences in numbering, it will be appreciated that the disclosures of the various embodiments may be incorporated into the disclosures of the same or similar embodiments so as to facilitate the understanding and appreciation of the many features, functions and inventive aspects within this disclosure.

FIG. 13 is a front view of an eye 1350 of a mammalian subject configured with a contact lens 1300 equipped with a stimulus coil 1305 for implementing the disclosed techniques. In FIG. 13, boundaries of eye structures are shown in dashed lines, whereas contact lens structures are shown in solid lines. The stimulus coil 1305 is shown generally with a first circular electrode 1310 and a second circular electrode 1315 located outside the first circular electrode 1310, with the two electrodes 1310, 1315 being disposed on opposite sides of the limbus (that is, the region adjacent the junction 1355 of the iris 1360 and sclera 1365). The first electrode 1310 and second electrode 1315 form part of a coil structure 1305 having one or more turns, wherein the entire coil structure is designed to receive the time-varying electromagnetic fields from a WPT coil (the WPT coil not shown in FIG. 13) and to transmit that as a stimulation signal to ocular tissue through the first electrode 1310 and second electrode 1315. As will be described below, the positioning of the first electrode 1310 and second electrode 1315 along either side of the limbus 1355 allows the stimulation signal to activate certain ocular structures (e.g. ciliary body, Canal of Schlemm, etc.) to increase aqueous humor outflow from the anterior chamber, as well as activate ion pumps in the targeted ocular structure(s) sufficient to result in a decrease in the aqueous humor inflow into the anterior segment of the eye. The current-controlled biphasic stimulation signal of FIG. 7 causes the current flowing between the first electrode 1310 and second electrode 1315 to reverse when the signal switches phases. This advantageously presents a balanced influx of energy into the eye and prevents the premature deterioration of the metallic traces that comprise the electrodes that may otherwise occur due to electrolysis if the current were to flow continuously in a single direction overtime. First electrode 1310 and second electrode 1315 may take a variety of suitable forms, including (but not limited to) the circular embodiment shown in FIGS. 15-16 and the serpentine embodiments shown in FIGS. 17-19.

FIG. 14 shows a diagram of the relevant anatomy of a mammalian eye configured with a contact lens (the lens not shown for clarity) equipped with a stimulus coil comprising first electrode 1410 and second electrode 1415 for implementing the disclosed techniques. The first electrode 1410 is disposed over the iris 1460 adjacent the border with the sclera 1465 and the second electrode 1415 is disposed over the sclera 1465 adjacent to the border with the iris 1460. This has the effect of positioning the first electrode 1410 and second electrode 1415 on either side of the limbus 1455 and in physical proximity to the ciliary body 1470 and canal of Schlemm 1475. By positioning the first electrode 1410 and second electrode 1415 in that manner, the stimulus coil comprising first and second electrodes 1410, 1415 is advantageously positioned to deliver the stimulus signal (time-varying electromagnetic field) to ocular structures (including but not necessarily limited to the ciliary body 1470 and canal of Schlemm 1475) in order to effectuate the desired reduction in aqueous humor inflow and/or increase in aqueous humor outflow in order to reduce elevated IOP within the eye 1450 according to the disclosed techniques.

The stimulus coil 1305, 1405 represented in FIGS. 13 and 14 may take any number of suitable forms, including but not limited to a circular stimulus coil shown in FIGS. 15-16 and a serpentine stimulus coil shown in FIGS. 17-19.

With reference to FIG. 15, the circular stimulus coil 1505 includes a single metallic trace 1506 (in dashed lines) formed into two (2) turns disposed in a generally circular manner within an insulation element 1508. The insulation element 1508 is a thin insulative coating that covers all aspects of the metallic trace 1506 except for two (2) regions that define an outer electrode 1510 and an inner electrode 1512. The metallic trace 1506 may comprise any number of suitable conductive materials, including but not limited to gold. The insulation element 1508 may comprise any number of suitable insulative materials, including but not limited to any commercially available dielectric barriers such as paraleyne-C. Fabrication of the circular stimulus coil 1505, including the metallic trace 1506 and insulation member 1508 will be described in detail below with reference to FIGS. 20 and 21. The outer electrode 1510 and inner electrode 1512 are disposed on opposite sides of the circular stimulation coil 1505 and are spaced radially apart from one another (that is, with the radius of the outer electrode 1510 being larger than the radius of the inner electrode 1512) such that in use the outer electrode 1510 and inner electrode 1512 are disposed on either side of the limbus to accomplish the therapeutic effects described above. The stimulation coil 1505 may form part of a contact lens 1520 (inset illustration in FIG. 15) or may be implanted into eye (e.g. in the sub-conjunctival region of an eye of a mammalian subject).

FIG. 16 is an exploded view of a metallic trace 1606 of similar construction as metallic trace 1506 of FIG. 15, with the main difference that metallic trace 1606 includes four (4) turns, denoted first turn 1606*a*, second turn 1606*b*, third turn 1606*c* and fourth turn 1606*d*. First turn 1606*a* is the innermost and fourth turn 1606*d* is the outermost. Each turn of the metallic trace 1606 is radially coupled together via a series of insulative links 1620 extending between the adjacent turns. When initially manufactured, the insulative links 1620 have the shape and appearance of "puzzle pieces" as denoted 1620*p*. During use and/or the process of manufacturing a contact lens with the metallic trace 1606, stretching will cause the insulative links 1620 to take the shape and appearance of an "S" as denoted 1620*s*. The radial coupling of the turns of metallic trace 1606 is a feature that facilitates the resulting stimulus coil (e.g. stimulus coil 1505 of FIG. 15) to stretch to accommodate the curvature of the eye when disposed within a contact lens (e.g. contact lens 1520 of FIG. 15).

Although the stimulus coil 1505 of FIG. 15 is shown with a single outer electrode 1510 and a single inner electrode 1512 disposed on opposite sides of the stimulus coil 1505 (which provides the current flow shown in FIGS. 13 and 14), it will be appreciated that the circular stimulus coil 1505 may be provided in other arrangements. For example, the stimulus coil 1505 may be provided such that the outer electrode 1510 and inner electrode 1512 are disposed in radially spaced relation from one another along the same side and location of the stimulus coil 1505. In this manner, the resulting current flow will be more focused in that region of ocular anatomy (e.g. a point or region of the overall limbus). It is also contemplated that the circular stimulation coil 1505 may be provided with multiple outer electrodes 1510 and multiple inner electrodes 1512, forming multiple pairs of radially spaced inner and outer electrodes positioned at multiple locations about the periphery of the stimulus coil 1505. In this manner, there will be multiple regions or locations of focused current flow along the ocular anatomy (e.g. multiple points along the limbus).

With reference to FIG. 17, the stimulus coil takes the form of a serpentine stimulus coil 1705 (shown without any insulation layer for clarity) with a single metallic trace 1706 formed into multiple turns disposed in a generally serpentine manner (as compared to the circular shape of stimulus coil 1505 of FIG. 15). Although not shown within an insulation element (like insulation element 1508 of FIG. 15), it will be appreciated that an insulation element is provided which covers all aspects of the metallic trace 1706) except for the outermost turn 1706*a* and the innermost turn 1706*b* that respectively define an outer electrode 1710 and an inner electrode 1712. The outer electrode 1710 and inner electrode 1712 may be of any desired length. By way of example only, the outer electrode 1710 extends between peaks P1 and P1 along the outermost turn of the metallic trace 1706, while the inner electrode 1712 extends between valleys V1 and V2 along the innermost turn of the metallic trace 1706. The metallic trace 1706 and insulation layer (not shown) may be manufactured according to the fabrication methods set forth in FIGS. 20-21, which will be described below. The outer electrode 1710 and inner electrode 1712 are designed to be disposed on opposite sides of the serpentine stimulus coil 1705 and are spaced radially apart from one another (that is, with the radius of the outer electrode 1710 being larger than the radius of the inner electrode 1712) such that in use the outer electrode 1710 and inner electrode 1712 are disposed on either side of the limbus to accomplish the therapeutic effects described above. The serpentine structure advantageously allows the stimulus coil 1705 to accommodate the curvature of the eye, as augmented by the insulative links 1720 that allow stretching between the adjacent turns in the same manner as the insulative links 1620 described above with reference to FIG. 16.

Any number of alternate constructions of the serpentine stimulus coil may be practiced, including but not limited to the alternate construction shown in FIG. 19. FIG. 18 shows a serpentine stimulus coil 1805 of one alternate construction (shown without an insulation layer for clarity, in the same manner as the stimulation coil 1705 of FIG. 17). The serpentine coil 1805 includes a metallic trace structure 1806 including an outer trace 1806*a*, an inner trace 1806*b*, a plurality of intermediate traces 1806*c*, a plurality of outer linking traces 1806*d*, and a plurality of inner linking traces 1806*e*. The outer trace 1806*a* includes an outer electrode 1810 defined (by way of example only) between peaks P1 and P2. The inner trace 1806*b* includes an inner electrode 1812 defined (by way of example only) between valleys V1 and V2. With combined reference to FIGS. 17 and 18, the intermediate traces 1806*c* are of similar construction as the intermediate turns between outer trace 1706*a* and inner trace 1706*b* for the stimulus coil 1705 of FIG. 17, coupled together via the same type of links 1720 (which may be of similar construction as the links 1620 of FIG. 16). The outer linking traces 1806*d* extend between the intermediate traces 1806*c* and the outer trace 1806*a*. The inner linking traces 1806*e* extend between the inner trace 1806*b* and the intermediate traces 1806*c*. The outer linking traces 1806*d* position the outer trace 1806*a* (and the outer electrode 1810) a distance from the intermediate traces 1806*c*, while the inner linking traces 1806*e* position the inner trace 1806*b* a distance from the intermediate traces 1806*c*. Collectively, the outer and inner linking traces 1806*d*, 1806*e* provide a wider overall footprint for the stimulus coil 1805 (relative to stimulus coil 1705 of FIG. 17). This design is particularly dimensioned to accommodate an enlarged cornea, which is the case when the mammalian subject is a rabbit based on their cornea being larger than that of humans.

FIG. 19 shows a serpentine stimulus coil 1905 of another alternate construction (shown without an insulation layer for clarity, in the same manner as the stimulation coil 1705 of FIG. 17). The serpentine coil 1905 includes a metallic trace structure 1906 including an outer trace 1906*a*, an inner trace 1906*b*, a plurality of intermediate traces 1906*c*, and a plurality of connecting links 1920 (akin to connecting links 1620 of FIG. 16 and connecting links 1720 of FIG. 17). The outer trace 1906*a* includes an outer electrode 1910 defined (by way of example only) between points P1 and P2 along the outer trace 1906*a*. The inner trace 1906*b* includes an inner electrode 1912 defined (by way of example only) between points P3 and P4 along the inner trace 1906*b*. The main difference from the serpentine stimulus coil 1705 of FIG. 17 resides in the shape and construction of the metallic trace structure 1906. In particular, the metallic trace structure 1906 is constructed such that the inner trace 1906*b* has a generally circular shape. The outer trace 1906*a* is constructed to include a series of thick block elements 1915 and a series of thin block elements 1916 connected via a series of curved connecting links 1917. The intermediate traces 1906*c* are constructed to include a series of thin block elements 1916 connected of curved connecting elements 1917. Each region within the overall trace structure 1906 is coupled together via connecting links 1920 (in the same manner as links 1620 of FIG. 16 and links 1720 of FIG. 17). Like the serpentine design of FIGS. 17 and 18, this structure advantageously allows the serpentine stimulus coil 1905 to expand radially to accommodate the curvature of the eye.

FIGS. 20 and 21 illustrate an exemplary fabrication method for manufacturing the round stimulus coil of FIGS. 15 and 16 and the serpentine stimulation coils of FIGS. 17-19.

Step 1: Passive Coil Fabrication

In this exemplary fabrication method, fabrication of the passive coil starts by the deposition of a dielectric barrier (e.g. Parylene-C) as a substrate and a photoresist material (as sacrificial layer) on a Si wafer (FIG. 20a). A metal conductive layer (e.g. gold with exemplary thickness of 1000 nm) is sputter (FIG. 20b) on the Parylene substrate. The gold layer is patterned with positive photoresist and etched via gold etchant to generate electrode trace (FIG. 20c). A second Parylene-C layer is deposited covering the whole wafer (FIG. 20d). The second parylene layer is patterned with another photoresist and etched via O$_2$ plasma to open a window for electrical contacting (FIGS. 20e and 20f). Afterwards, the photoresist layer on top of the second parylene layer for creating the window opening is removed completely after etching (FIG. 20f). A third layer of photoresist is deposited and patterned similarly but slightly larger than the first etching mask. The third etching step will etch through the two parylene layers entirely and expose the outline of device (FIG. 20g). Finally, the underlying structure is released by immersing the wafer in ACETONE such that the parylene encapsulated coil with opening contact pad has been fabricated (FIG. 20h.

The fabrication steps described above may be employed to manufacture any of the coil designs set forth in this disclosure, including but not limited to the large circular stimulus coils of FIGS. 15-16, the serpentine stimulus coils of FIGS. 17-19, the small circular stimulus coils described below with reference to FIGS. 24-26 (whether tethered or non-tethered), and the Fresnel lens arrangements described below with reference to FIGS. 30-33. For any coils that require application to a substrate (e.g., a contact lens, an intraocular lens, etc.), the coils must be equipped with an adhesive coating to enable the metallic traces to be adhered to the substrate material, as will be described in Step 2 below.

Step 2: Selectively Adhesive Coating

For any coils that need to be adhered to or disposed within a substrate (e.g. a contact lens, intraocular lens), the coils as manufactured via the fabrication method of FIG. 20 need to have an adhesive coating added to establish a connection between the substrate and the coil. By way of example only, the adhesive coating may be Titanium (Ti) with an exemplary thickness of 100 nm. An exemplary fabrication method for adding the adhesive coating is set forth in FIG. 21. Contact lenses can be obtained from any commercially available contact lens or fabricated via injection molding technology with poly-hydroxyethyl methacrylate (poly-HEMA) hydrogel. PolyHEMA possesses a good biocompatibility, a high air/water permeability, and a similar flexibility as human tissue. Thus, it is a proper material for a contact lens.

Since the electrode of the passive stimulus coil is covered with parylene, depositing an effective adhesion material for binding the parylene and polyHEMA (contact lens) is utilized. A specific coating of adhesion material is provided, namely titanium (Ti) with an exemplary thickness of 100 nm. In this further exemplary fabrication method, the fabricated parylene encapsulated passive coil (from step 1) is flipped over and attached on Si wafer (FIG. 21a,b). A photoresist is then coated and patterned on the coil surface as a mask to realize the deposition of adhesion material on a specific area (FIG. 21c). The adhesion material is then evaporated/spray coated on the entire wafer (FIG. 21d). The passive coil along with adhesion material can be released from the silicon wafer and photoresist material by soaking in photoresist stripper (FIG. 21e).

All the optional materials for each step of fabrications have been list in TABLE 1.

|  | Encapsulate substrate | Electrode | Sacrificial material | Adhesion material | Solution for releasing |
|---|---|---|---|---|---|
| Name | Parylene C/N Polyimide 2525 | Gold Platinum | SiO2 photoresist(AZ9260) | Saline A-174 APTES Medical epoxy | BOE ACETONE Stripper |

Step 3: Compressible/Stretchable Electrode Pattern Design

According to Euclidean geometry law, the spherical surface is unholdable. The area mismatching from planar pattern to spherical pattern is unavoidable. The electrode trace fabricated on a two-dimensional (2D) flat platform will be either wrinkled or cracked during the transferring process on a three-dimensional (3D) spherical concave contact lens. The wrinkled electrode will generate discomfort to patient for wearing, and the cracked electrode will disconnect the electric signal and nullify the device. To solve this problem, a coplanar compressible electrode routing is designed and fabricated on Si wafer (2D platform). FIGS. 18-19 show two designs that involve a serpentine routing pattern during the manufacture of the underlying metallic trace structure within the stimulus coil 1805 of FIG. 18 and the stimulus coil 1905 of FIG. 19. The metallic trace structure 1906 of the stimulus coil 1805 of FIG. 18 includes a serpentine routing pattern for both the outer trace 1806a and inner trace 1806b (and hence outer electrode 1810 and inner electrode 1812). The metallic trace structure 1906 of the stimulus coil 1905 of FIG. 19 includes a serpentine routing pattern for the outer trace 1906a (and hence the outer electrode 1910) and a circular routing pattern for the inner trace 1906b (resulting in the inner electrode 1912 formed as an arc or radius).

The serpentine features of the stimulus coils 1805 and 1905 provide a number of advantages, including (but not limited to) an increased ability to expand and contract to accommodate the curvature of the eye when the respective stimulus coil is as part of a contact lens or implanted within the eye (e.g. in the sub-conjunctival region). The serpentine features include those of the radial connecting links (1620 of FIG. 16, 1720 of FIG. 17, 1920 of FIG. 19) between the radial trace elements or regions (e.g. outer traces 1706a, 1806a, 1906a, inner traces 1706b, 1806b, 1906b, and any intermediate traces such as 1706c, 1806c, 1906c). These radial connecting links are serpentine connection "bridges" that not only hold the entire metallic trace structure of the stimulus coil together, but also advantageously imparts a stretchable/compressible functionality by lengthening or shortening the distance between the respective radial trace element or region. The radial connecting links may be constructed from any suitable materials, including but not limited to insulative materials (e.g. paraleyne C) and/or conductive material (e.g. gold). In either event, the radial connecting links add to the expandable/compressible characteristics of the associated stimulus coil 1805, 1905, which helps when transferring the coil onto a spherical contact lens as shown and described below with reference to FIGS. 22-23. This process of two-dimensional (2D) to three-dimensional (3D) deformation of the serpentine stimulus coils 1705, 1805, 1905 will be described below. When the substrate with 2D planar structure turns to 3D spherical structure, the total area and perimeter of outer edge of contact lens will be reduced. The expandability/compressibility makes the metallic trace structures helps optimize the shape of the concave surface to diminish or minimize any wrinkling and/or cracking of the underlying metallic trace, which advantageously reduces the likelihood of discomfort of patient.

Step 4: Converting of 2D Planar Coil to 3D Spherical Lens

Any coils in the present disclosure that need to be placed on a curved substrate (e.g. contact lens, intraocular lens, Fresnel lens), one of two strategies may be employed to transfer the 2D flat coils on the 3D spherical/curved lens.

Strategy I:

FIG. 22 illustrates the first 2D-to-3D strategy as shown with a serpentine stimulus coil selected (by way of example only) from those shown and described above with reference to FIGS. 17-19. FIG. 22 illustrates the main steps of the fabrication. Due to the property of stretchability and compressibility of the PHEMA polymer, a 3D spherical concave PHEMA lens can be compressed on a carrier substrate formed to a round flat or 'drumhead' shape. A jig ring, which is specially designed for holding the lens, uniformly squeezes the lens onto the flat carrier. The radial tension provided by the jig ring outwardly expands the spherical lens. The jig ring will be removed once the lenses are deformed completely to a round flat shape, and the shear force (friction) between the lens and carrier substrate will hold the lens continually in its current flat shape and not come back to its original spherical shape. With this kind of 'drumhead' shape, all the points of the PHEMA lens are in biaxial tension. The overall area and circumstance of the lens will be increased during this process. The extent of expansion and the underlying mechanics determine the overall magnitude of this tension.

The parylene encapsulated passive coil (from step 1) pre-coated with adhesive (from step 2) is directly transferred on this tensioned, planar 'drumhead' shape lens. Followed by 90 seconds UV-curing process with 350 nm UV light at 10 mW light intensity, the coils are stuck and firmly attached to the soft surface of the elastomer through a strong specific chemical crosslink binding effect. Afterwards by merging the entire device into de-ionized water, the compressed planar lens will relax back to its initial spherical shape but with a slightly larger radius of curvature. During this releasing process, compressive strain forces act on the serpentine connection wire will bring the active components of coil (open window area) closer, which means the circumstance of coil is reduced. The narrow, thin connecting serpentine electrode trace will accommodate these strains by their coplanar deforming to adopt arc shapes. This process allows the planar-to-spherical geometrical transformation to be accomplished without creating substantial strains in any of active components (opening window area) of the coil. The deformation of coil appears during the process of the pre-stretched lens relaxing back to its original shape.

Strategy II:

Instead of applying force on the spherical lens, the second "2D-to-3D" strategy applies the radical force uniformly on the stretchable coil via the surface tension of water. As shown in FIG. 23, the PHEMA contact lens are flipped over and attached on a spherical substrate (14 mm ball bearing to mimic human eye). After selectively coated with adhesive via a shadow mask, the coils are carefully dropped on the surface of water. The entire ball bearing substrate with contact lens on top are emerged in the water and located beneath the floating coil. With lifting up the ball bearing substrate out of water, the coils and lens are combined together. The surface tension of water extracts the electrode trace radially (arrows in FIG. 22), and the gap between two electrodes trace will expand and thus accommodate the planar coils onto the spherical lens. For a better centralization effect, during the lifting up process, an alignment between coils and lens is required.

Similar to strategy I, the serpentine connection bridges accommodate the strain force by elongating the distance between the electrode traces to adopt the arc shape. The stretched coil on the lens with spherical shape is then exposed under UV light to cure the adhesive. The entire coil embedded lens can be released from the ball bearing after emerging in the water for 10 minutes. Finally, the lens flipped over to its original state with coil attached on its concave side. The deformation of coil appears during the process of lifting up the ball bear out of the water due to the water surface tension.

FIGS. 24 and 25 show front and side views, respectively, of an eye of a mammalian subject configured with a stimulus coil structure 2400 implanted within a sub-conjunctival region for implementing the disclosed techniques. The sub-conjunctival stimulus coil structure 2400 includes a plurality of small circular stimulus coils 2402 coupled together physically but not electrically. As will be described below, each small circular stimulus coil 2402 is of the same general construction as the large circular stimulus coil 1505 shown and described with reference to FIGS. 15-16, with the exception that the diameter of the small circular stimulus coils 2400 of FIGS. 24-25 are substantially smaller. This tethered arrangement (with the small circular stimulus coils 2402 physically connected) allows the overall stimulus coil structure 2400 to be surgically implanted in the sub-conjunctival region of the eye of a mammalian subject. As with the large circular stimulus coil 1505 of FIG. 15, each small circular stimulus coil 2400 includes an outer electrode 2410 and an inner electrode 2412.

The outer electrode 2410 and inner electrode 2412 are disposed on either side of the limbus (the region adjacent the junction of the iris and sclera). The outer electrode 2410 and inner electrode 2412 form part of a coil structure having one or more turns, wherein the entire coil structure 2400 is designed to receive the time-varying electromagnetic fields from a WPT coil (as described above) and transmit that as a stimulation signal to ocular tissue through the outer electrode 2410 and inner electrode 2412 of each small circular stimulus coil 2402. Positioning the sub-conjunctival stimulus coil structure 2400 such that the outer electrode 2410 and inner electrode 2412 of each small circular stimulus coil 2402 are disposed along either side of the limbus has the effect of positioning these electrodes in physical proximity to the ciliary body and canal of Schlemm. By positioning the inner electrode 2412 and outer electrode 2410 in that manner, each stimulus coil 2402 is advantageously positioned to deliver the stimulus signal (time-varying electromagnetic field) to ocular structures (including but not necessarily limited to the ciliary body and canal of Schlemm) in order to effectuate the desired reduction in aqueous humor inflow and/or increase in aqueous humor outflow in order to reduce elevated IOP within the eye according to the disclosed techniques. The current-controlled biphasic stimulation signal of FIG. 7 causes the current flowing between the outer electrode 2410 and inner electrode 2412 of each small circular stimulus coil 2402 to reverse when the signal switches phases. This advantageously presents a balanced influx of energy into the eye and prevents the premature deterioration of the metallic traces that comprise the electrodes that would otherwise occur due to electrolysis if the current were to flow continuously in a single direction overtime.

The stimulus coil structure 2400 represented generally in FIGS. 24 and 25 may take any number of suitable forms, including but not limited to providing the stimulus coil structure 2400 and each small circular stimulus coil 2402 as shown in FIG. 26. As explained above, each small circular stimulus coil 2402 is constructed in a similar manner as the large circular stimulus coil 1505 of FIGS. 15-16, with the main difference being that of diameter. Another difference is the that a plurality of small circular stimulus coils 2402 are physically connected (aka "tethered") so as to form a single structure via a connecting structure 2430, with individual small circular stimulus coils 2402 forming a generally circular perimeter about the connecting structure 2430. The connecting structure 2430 includes a central ring 2432 with a spoke 2434 extending therefrom for connection to each of the small circular stimulus coils 2402. As will be described below, coupling the plurality of small circular stimulus coils is advantageous in that it provides consistency of placement (e.g. sub-conjunctival implantation) to ensure the inner electrode 2412 and outer electrode 2410 of each small circular stimulus coil 2402 is positioned on either side of the limbus to effect the glaucoma therapy of the disclosed techniques.

Each small circular stimulus coil 2402 also includes an arrow A (preferably constructed from the same material as the underlying metallic trace forming the stimulus coil 2402) to help identify the location of the outer electrode 2410 in order to ensure proper surgical placement (if implanted) or orientation (if disposed within a contact lens). The outer electrodes 2410 and inner electrodes 2412 of each small circular stimulus coil 2402 are shown in FIG. 16 with arrows at the general location of each electrode 2410, 2410. It will be appreciated that the specific length of the electrodes 2410 and 2412 may vary depending upon the degree to which the outer trace and inner trace, respectively, are exposed by removing a region of insulation layer during the fabrication process described with reference to FIG. 21. By identifying the outer electrode, by process of elimination a user (surgeon or patient) will be able to deduce the location of the inner electrode 2412, given that it's known (at least in this basic embodiment) that the inner electrode 2412 is located 180 degrees from the outer electrode 2410. The metallic traces forming the small circular stimulus coil 2402 are radially coupled together using the series of connecting links 1620 as shown and described above with reference to FIG. 16.

FIGS. 27 and 28 show front and side views, respectively, of an eye of a mammalian subject configured with a stimulus coil pair 2700 implanted within an intraocular lens (IOL) for implementing the disclosed techniques. The pair of stimulus coils 2700 includes an anterior stimulus coil 2700a and a posterior stimulus coil 2700p which each comprise a single small circular stimulus coil as described above with reference to FIG. 26. The anterior stimulus coil 2700a and posterior stimulus coil 2700p need not be physically connected to one another but are oriented in a juxtaposed arrangement such that the arrow A of the anterior stimulus coil 2700a is facing one direction (e.g. at the top facing left) and the arrow A of the posterior stimulus coil 2700p is facing the opposite direction (e.g. at the bottom facing right). In this position, the outer electrode 2710 of the anterior stimulus coil 2700a is positioned adjacent to but radially spaced from the inner electrode 2712 of the posterior stimulus coil 2700p, while the inner electrode 2712 of the anterior stimulus coil 2700a is positioned adjacent to but radially spaced from the outer electrode 2710 of the posterior stimulus coil 2700p. In this manner, two (2) regions of current flow are created along the perimeter of the ocular tissue of interest (e.g. limbus) to accomplish the desired reduction in elevated IOP. The current flow is denoted with an arcuate dashed line with arrows on either end to demonstrate the bi-phasic nature of the current flow based on the stimulation pulse of FIG. 7.

The anterior stimulus coil 2700a and posterior stimulus coil 2700p may be surgically implanted within a native intraocular lens (IOL) of the mammalian subject or comprise part of a prosthetic IOL. When configured to be surgically implanted into the native IOL, the anterior stimulus coil 2700a and posterior stimulus coil 2700p may be manufactured with shape-memory properties (such as by the use of Nitinol shape memory material) for aspects of the coil structures. When configured as a prosthetic IOL, the anterior stimulus coil 2700a and posterior stimulus coil 2700p may be disposed within a substrate suitable for use as an intraocular lens. In this instance, the anterior stimulus coil 2700a and posterior stimulus coil 2700p may include an adhesive coating as described above with reference to FIGS. 20-21 and, if curved or spherical, may employ the 2D-to-3D techniques described above with reference to FIGS. 22-23.

The electrode pairs (the first formed by the outer electrode 2710 of the anterior stimulus coil 2700a and the inner electrode 2712 of the posterior stimulus coil 2700p, and the second formed by the inner electrode 2712 of the anterior stimulus coil 2700a and the outer electrode 2710 of the posterior stimulus coil 2700p) are disposed on either side of the limbus (the region adjacent the junction of the iris and sclera). Through this positioning, allows the resulting stimulation signal from each electrode pair to activate certain ocular structures (e.g. ciliary body, Canal of Schlemm, etc. . . . ) to increase aqueous humor outflow from the anterior chamber, as well as activate ion pumps in the ocular structures sufficient to result in a decrease in the aqueous humor inflow into the anterior segment of the eye. The current-controlled biphasic stimulation signal of FIG. 7 causes the current flowing between the outer electrode 2710 and inner electrode 2712 of each small circular stimulus coil 2700a, 2700p to reverse when the signal switches phases. This advantageously presents a balanced influx of energy into the eye and prevents the premature deterioration of the metallic traces that comprise the electrodes that would otherwise occur due to electrolysis if the current were to flow continuously in a single direction overtime.

FIG. 28 shows a diagram of the relevant anatomy of a mammalian eye configured with the pair of IOL stimulus coils, namely anterior stimulus coil 2700a and posterior stimulus coil 2700p for implementing the disclosed techniques. For each of the anterior stimulus coil 2700a and posterior stimulus coil 2700p, the inner electrode 2712 is disposed over the iris adjacent the border with the sclera and the outer electrode 2710 is disposed over the sclera adjacent to the border with the iris. This has the effect of positioning the inner electrode 2712 and outer electrode 2710 of each small circular stimulus coil 2700a, 2700p on either side of the limbus and in physical proximity to the ciliary body and canal of Schlemm. By positioning the inner electrode 2712 and outer electrode 2710 in that manner, each electrode pair 2700 formed by the juxtapositioned and spaced apart anterior stimulus coil 2700a and posterior stimulus coil 2700p is advantageously positioned to deliver the stimulus signal (time-varying electromagnetic field) to ocular structures (including but not necessarily limited to the ciliary body and canal of Schlemm) in order to effectuate the desired reduction in aqueous humor inflow and/or increase in aqueous humor outflow in order to reduce elevated IOP within the eye according to the disclosed techniques. The anterior stimulus coil 2700a and posterior stimulus coil 2700p are configured and dimensioned such that, during use, the most medially located aspect of each stimulation coil extends far enough into the pupil to effectuate the desired therapeutic effect for glaucoma without blocking or otherwise covering the pupil aperture to impede vision.

The anterior stimulus coil 2700a and posterior stimulus coil 2700p represented generally in FIGS. 27 and 28 may take any number of suitable forms, including but not limited to providing each small circular stimulus coil 2700a, 2700p as shown in FIG. 26. As explained above, each small circular stimulus coil 2402 of FIG. 26 is constructed in a similar manner as the large round stimulus coil of FIGS. 15-16, with the main difference being that of diameter. Another difference is the inclusion of an arrow A (preferably constructed from the same material as the underlying metallic trace) to help identify the location of the outer electrode 2710 in order to ensure proper surgical placement (if implanted as part of a pair of stimulus coils 2700a, 2700p) or orientation (if disposed within a prosthetic IOL). By identifying the outer electrode, by process of elimination a user (surgeon or patient) will be able to deduce the location of the inner electrode 2712, given that it's known (at least in this basic embodiment) that the inner electrode 2712 is located 180 degrees from the outer electrode 2710. The metallic traces forming the small circular stimulus coil 2700a, 2700p are radially coupled together using the series of connecting links 1620 as shown and described above with reference to FIG. 16.

FIGS. 29 and 30 show a front view and side view, respectively, of an eye of a mammalian subject configured with a Fresnel lens 2900 for implementing vision correction according to disclosed techniques. As will be described below, the Fresnel lens 2900 may be used alone or in combination with the glaucoma therapy techniques disclosed herein without departing from the scope of the disclosure. The Fresnel lens 2900 is configured to focus incoming light rays on the retina to achieve vision correction. Typically, there are two ways for vision correction: eyeglasses and contact lens. Eyeglasses is the most common and traditional way to correct vision, however, due to its bulky size, heavy weight and inconvenience to carry (especially for sports) people prefer using contacts lens instead of eyeglasses. Compared with eyeglasses, contact lens demonstrates many benefits, such as easy to carry, light, and very convenient to use, however, dry-eye syndrome can arise for contact lens wearers and currently there are limited treatment options.

The Fresnel lens 2900 may be employed in any number of suitable manners, including but not necessarily limited to, surgical implantation in any number of suitable locations (e.g. the exterior of the eye and/or within the eye), as part of a contact lens, and/or as part of a prosthetic intraocular lens (IOL), as will be described herein. The diameter of the implantable intraocular Fresnel lens 2900 may be in the range of around 2 mm to 4 mm to satisfy the sizing requirements for a wide range of patients. In one aspect, the Fresnel lens 2900 is dimensioned to only cover the center area of pupil as shown in FIG. 30. By way of comparison, a standard contact lens has an average diameter of 14-16 mm. Due to the drastic reduction in size (2-4 mm vs. 14-16 mm), the proposed Fresnel lens 2900 only covers a small area of the eye and thus will minimize if not eliminate dry eye syndrome. Moreover, the Fresnel lens 2900 is ultra-thin (ranging from around 1 µm-2 µm in thickness) which allows more water and oxygen penetrate easily to the eye.

The Fresnel lens 2900 may be implanted in or on any suitable structure or location of the eye. In one aspect, the Fresnel lens 2900 may be implanted on the peripheral cornea and thus cause no damage to the actual eye. A fully biocompatible and flexible material is used as the main substrate to fabricate the Fresnel lens 2900. The optional material has been listed in the table in the fabrication section to be described below with reference to FIG. 32. The Fresnel lens 2900 may include any number of additional features, including but not limited to the addition of multiple tiny holes or apertures (by way of example only, 1 µm in diameter) to facilitate the transmission of water and oxygen to the eye during use.

Mechanism

The light rays through the Fresnel lens 2900 can be converged and focused on the specific point due to refraction. This may be accomplished in any number of suitable manners, including but not limited to that shown in FIG. 31a, which employs the use of alternating opaque zones (dark) and transparent zones (white). The focal length f of the lens is related to the zone number n (n=1, 2, ... ), zone radius m and the wavelength λ of the light. The focal length can be expressed via the equation of $f=r_{(n)}^2/n\lambda$. Within the context of a human subject (by way of example only), the average diameter of human eye in the light incident direction is fixed at 22 mm. The pattern of the Fresnel lens 2900 will be decided via the wavelength of light rays. Typically, the wavelength of visible light varies from 380 nm to 700 nm. The different wavelength of light will cause multiple focusing points. Considering that all colors can be produced via primary color blue (475 nm), Green (510 nm) and Red (700 nm), two strategies have been devised to solve the chromatic abbreviation problem.

As shown in FIG. 31b, Strategy 1 (the so-called "3 segments" approach) trisects the entire disk area with specific pattern for each color, denoted green segment 2902, blue segment 2904, and red segment 2906. One third (⅓) of each primary light (passing through each segment 2902, 2904, 2906) will be focused on the retia with 22 mm focal length. The sharpness of image and resolution for each color will be improved. Similar to the Strategy I ("3 segments approach"), Strategy 2 (so-called "3 centric-ring" approach) combines all Fresnel lens patterns using three primary colors together with same center but at different locations or zones. In order to achieve a uniform light distribution, the various locations or zones may involve varying characteristics for each primary color, such as (but not limited to) providing the implantable intraocular Fresnel lens such that the active blue light, green light and red light have an effective area of 11%, 38% and 51%, respectively, represented as blue light section 2922, green light section 2924 and red light section 2926.

Fabrication Process

Figures 32A, 32B, 32C, 32D, 32E, 32F, 32G:
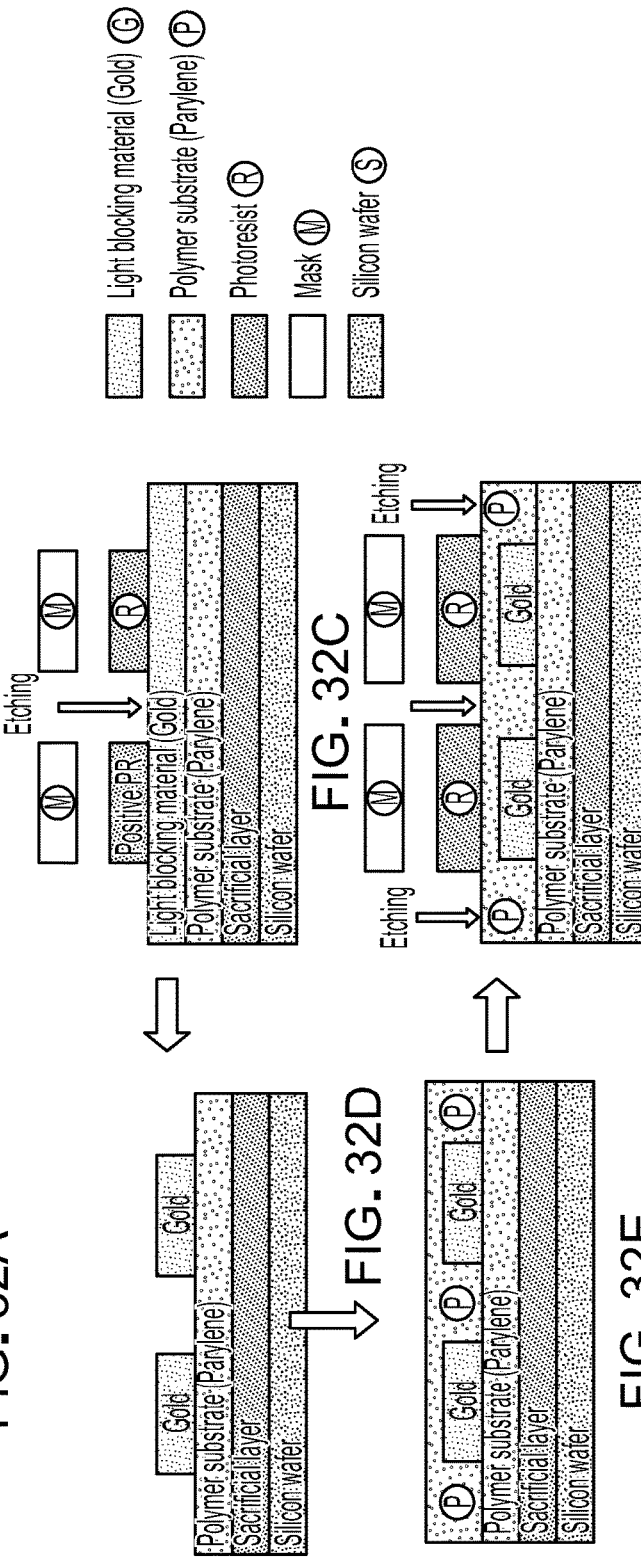

The Fresnel lens 2900 may be fabricated in any suitable manner, including but not limited to the fabrication method set forth in FIG. 32. In one aspect, it may be fabricated using parylene as the polymer substrate and gold as light blocking material, however, it will be appreciated that multiple optional materials might be available to fabricate the Fresnel lens 2900 as well. The fabrication of the Fresnel lens 2900 starts by the deposition of Parylene-C (as substrate) and photoresist (as sacrificial layer) on a Si wafer (FIG. 32a). Two ultra-thin metal layers Ti(5 nm)/Gold(50 nm) are sputtered (FIG. 32b) on the Parylene substrate. The gold layer and Ti layer are patterned with positive photoresist and etched via gold etchant and hydrofluoric acid respectively to generate an opaque trace (FIG. 32c,d). At this point, a second Parylene-C layer may be deposited covering the whole wafer (FIG. 32e). Next, another layer of photoresist may be deposit and patterned with asterisk or other shapes to produce the final substrate pattern. The third etching step will etch through the two parylene layers entirely and expose the outline of device (FIG. 32f). Finally, the device may be released by immersing the wafer in ACETONE such that the polymer based binary Fresnel lens 2900 has been fabricated (FIG. 32g).

The material used in the fabrication process includes but is not limited to parylene, gold, photoresist, etc. . . . . . All the optional materials haven demonstrated in the table below for the purpose of fully biocompatible, flexible, oxygen and air permeable:

|  | Encapsulate substrate | Opaque area | Sacrificial material | Adhesion material | Solution for releasing |
|---|---|---|---|---|---|
| Name | Poly-HEMA PDMS Collamer PMMA Parylene C/N Polyimide 2525 PET | Light blocking Poly-HEMA PMMA Liquid crystal polymer Gold Platinum Carbon nanotube | SiO2 photoresist(AZ series) | Saline A-174 APTES Medical epoxy, etc Water soluble polymer | BOE ACETONE |

Substrate Pattern for Eye Accommodation

Since the Fresnel lens 2900 is fabricated based on a flat 2D structure, the potential exists for an area mismatch to occur during process of transferring the design from two-dimensional (2D) to a curved three-dimensional (3D) spherical surface. This potential is minimized if not eliminated altogether due to the small size (exemplary diameter of 2 mm-4 mm), which advantageously enables an optimal curved accommodation size of the Fresnel lens 2900 of the present disclosure. The Fresnel lens 2900 may be provided with any number of additional features to further reduce or mitigate any mismatching issues. Such features include, but are not necessarily limited to, providing the Fresnel lens 2900 with an asterisk pattern for the substrate holding layer, as shown in FIG. 33a-c. The shape of the asterisk pattern reduces the strain tension during the process of converting from 2D to 3D and thus lead to a better accommodation with the eye. The fabricated polymer-based binary Fresnel lens 2900 is shown in FIG. 33d (within contact lens receptacles).

The Fresnel lens 2900 may be employed separately (solely for vision correction) or in combination with any suitable glaucoma therapy systems or techniques. These may include, but are not necessarily limited to those set forth herein, for example, large diameter stimulation coils such as those described with reference to FIGS. 13-19 (whether implanted in the sub-conjunctival region or as part of a contact lens), small diameter stimulation coils such as those described with reference to FIGS. 24-28 (whether part of a contact lens, implanted in the sub-conjunctival region (see FIGS. 24-26), or implanted in the intraocular lens (native or part of a prosthetic IOL, see FIGS. 27-28)). It will also be appreciated that the Fresnel lens 2900 with or without the glaucoma therapy system and disclosed techniques may be employed with any of a variety of intraocular implants, including but not limited to intraocular implants for sensing glucose levels or performing any other desirable ocular function or therapy.

FIGS. 34 and 35 show front and side views, respectively, of an eye of a mammalian subject configured with a Fresnel lens 3400 and a contact lens 3440 equipped with a stimulus coil 3450 for implementing the disclosed techniques. The stimulus coil 3450 may be any suitable stimulus coil, including but not limited to that the large diameter stimulation coils described herein with reference to FIGS. 13-23 and the underlying contact lens 3440 may be of any suitable construction, shape and size. The Fresnel lens 3400 may be part of the contact lens 3440 or implanted separately from the contact lens 3440 (e.g. on the cornea, within the sub-conjunctival region, within the IOL, etc. . . . ).

The Fresnel lens 3400 includes an electrode 3402 disposed along the outer periphery which cooperates with an electrode 3452 on the outer periphery of the large stimulation coil 3450. The electrode 3402 of the Fresnel lens 3400 and the electrode 3452 of the stimulation coil 3450 are radially spaced apart from one another such that the electrode 3402 of the Fresnel lens 3400 is located adjacent to but radially outside of the pupil, while the electrode 3452 of the large stimulation coil 3450 is located adjacent to but radially outside the iris. In this manner, the current flow between the electrode 3402 of the Fresnel lens 3400 and the electrode 3452 of the large stimulation coil 3450 will activate certain ocular structures (e.g. ciliary body, Canal of Schlemm, etc. . . . ) to increase aqueous humor outflow from the anterior chamber, as well as activate ion pumps in the targeted ocular structures sufficient to result in a decrease in the aqueous humor inflow into the anterior segment of the eye. The current-controlled biphasic stimulation signal of FIG. 7 causes the current flowing between the electrode 3402 of the Fresnel lens 3402 and electrode 3452 of the large stimulation coil 3450 to reverse when the signal switches phases. This advantageously presents a balanced influx of energy into the eye and prevents the premature deterioration of the metallic traces that comprise the electrodes that would otherwise occur due to electrolysis if the current were to flow continuously in a single direction overtime.

FIG. 36 shows a front view of an eye of a mammalian subject configured with a Fresnel lens 3600 for vision correction and a serpentine stimulus coil 3660 for glaucoma therapy according to the disclosed techniques. The stimulus coil 3660 is, by way of example only, of the type shown and described with reference to FIGS. 17-19, but may also comprise any other large diameter stimulus coil such as the large round stimulus coil 1505 shown and described with reference to FIG. 15. The construction and operation of the stimulus coil 3660 may be similar, and in some instances identical, to the serpentine stimulus coils 1605, 1705, and 1805 and, accordingly, that description is hereby incorporated into this section of the disclosure such that all details need not be repeated here. The Fresnel lens 3600 may comprise part of the same structure as the serpentine stimulus coil 3660 or a separate structure. If part of the same structure, the combined Fresnel lens 3600 and the serpentine stimulus coil 3660 (though not electrically connected to one another) may comprise part of a contact lens or be implanted as a single structure into the sub-conjunctival region of the eye. If separate structures, the Fresnel lens 3600 may be formed on or within a suitable substrate (e.g. intraocular lens (IOL) prosthetic, a contact lens, etc. . . . ) or be implanted separately from the serpentine stimulus coil 3660 (e.g. within a native IOL, within a sub-conjunctival region, etc. . . . ), while the serpentine stimulus coil 3660 may be formed on or within a suitable substrate (e.g. a contact lens, etc. . . . ) or be implanted separately from the Fresnel lens 3600 (e.g. within a sub-conjunctival region, etc. . . . ). In this embodiment, the Fresnel lens 3600 is used solely for vision correction and does not participate in the glaucoma therapy according to disclosed techniques.

In one embodiment, the serpentine stimulus coil 3600 includes a single metallic trace formed into multiple turns disposed in a generally serpentine manner with a serpentine outer electrode 3610 and a serpentine inner electrode 3612. The outer electrode 3610 and inner electrode 3612 are the outermost and innermost, respectively, turns of the serpentine stimulus coil 3600. The serpentine outer electrode 3610 includes a plurality of outer peaks OP and outer valleys OV. The outer peaks OP of serpentine outer electrode 3610 are disposed in proximity to but radially outward from the limbus, while the outer valleys OV are disposed at a location near or slightly outside the limbus. The serpentine inner electrode 3612 includes a plurality of inner peaks IP and inner valleys IV. The inner peaks IP of serpentine inner electrode 3612 are disposed in proximity to but radially inward from the limbus, while the inner valleys IV are disposed at a location near or slightly outside the limbus.

In alternative embodiment, the stimulation coil 3600 may be constructed with such that the insulation layer (described above with reference to FIG. 21) creates exposed areas along the trace to define the outer electrode 3610 and inner electrode 3612 in any number of different locations on the stimulus coil 3600. For example, the underlying metallic trace may be equipped with exposed regions to define outer electrode 3610 and inner electrode 3612 as single or multiple electrodes along the respective outer and inner regions along the outer and inner periphery of the stimulus coil 3600, including but not limited to: along the entire length of the outer electrode 3610, the entire length of the inner electrode 3612, at single locations along the length of the outer electrode 3610 (e.g. at single points along the outer peaks OP and/or outer valleys OV), at single locations along the length of the inner electrode 3612 (e.g. at single points along the inner peaks IP and/or inner valleys IV), at multiple points along the length of the inner electrode 3612 (e.g. at some or all of the inner peaks IP and/or inner valleys IV), and/or multiple points along the length of the inner electrode 3612 (e.g. at some or all of the inner peaks IP and/or inner valleys IV) and/or along the length of the outer electrode 3610 (e.g. at some or all of the outer peaks OP and/or outer valleys OV).

Configured in this manner, in use the electrically conductive length(s) and/or point(s) along the inner electrode 3612 and outer electrode 3610 of the stimulus coil 3600 are disposed on either side of the limbus, which has the effect of positioning these electrically conductive length(s) and/or points(s) in physical proximity to the ciliary body and canal of Schlemm. In so doing, the stimulus coil 3600 is advantageously positioned to deliver the stimulus signal (time-varying electromagnetic field) to ocular structures (including but not necessarily limited to the ciliary body and canal of Schlemm) in order to effectuate the desired reduction in aqueous humor inflow and/or increase in aqueous humor outflow in order to reduce elevated IOP within the eye according to the disclosed techniques. The current-controlled biphasic stimulation signal of FIG. 7 causes the current flowing between the electrical length(s) and/or point(s) along the outer electrode 3610 and the inner electrode 3612 of the stimulation coil 3600 to reverse when the signal switches phases. This advantageously presents a balanced influx of energy into the eye and prevents the premature deterioration of the metallic traces that comprise the electrodes that would otherwise occur due to electrolysis if the current were to flow continuously in a single direction overtime.

FIG. 37 shows a front view of an eye of a mammalian subject configured with a Fresnel lens 3700 and a large diameter stimulus coil 3760 for implementing the disclosed techniques. In this embodiment, the Fresnel lens 3700 actively participates in the glaucoma therapy in addition to aiding in vision correction according to disclosed techniques. The Fresnel lens 3700 and stimulus coil 3760 are electrically connected to one another via a wire 3765. Based on this physical and electrically connection, the Fresnel lens 3700 and stimulation coil 3760 are formed as a single structure, which may be included as part of a substrate (e.g. on or within a contact lens, etc. . . . ) or provided separate from any substrate (e.g. for sub-conjunctival implantation, etc. . . . ).

The stimulus coil 3760 is, by way of example only, of the type shown and described with reference to FIGS. 15-16, but may also comprise any other large diameter stimulus coil such as the serpentine stimulus coils shown and described with reference to FIGS. 17-19 (and described above in combination with reference to FIG. 36). As described above, the circular stimulus coil 3660 may include two (2) or more electrodes which, in use, are disposed on either side of the limbus to accomplish the therapeutic effects described herein. For example, as shown in FIG. 17-19, the stimulus coil 3760 may be provided with a single outer electrode 3710 and a single inner electrode 3712 disposed on opposite sides of the stimulus coil 3760 (which provides the current flow similar to that shown in FIGS. 13 and 14). The circular stimulus coil 3760 may be provided in other arrangements, including such that the outer electrode 3710 and inner electrode 3712 are disposed in radially spaced relation from one another along the same side and location of the stimulus coil 3760. In this manner, the resulting current flow will be more focused in that region of ocular anatomy (e.g. a point or region of the overall limbus). It is also contemplated that the circular stimulation coil 3760 may be provided with multiple outer electrodes 3710 and multiple inner electrodes 3712, forming multiple pairs of radially spaced inner and outer electrodes positioned at multiple locations about the periphery of the stimulus coil 3760. In this manner, there will be multiple regions or locations of focused current flow along the ocular anatomy (e.g. multiple points along the limbus).

Configured in this manner, in use the electrically conductive length(s) and/or point(s) along the inner electrode 3712 and outer electrode 3710 of the stimulus coil 3760 are disposed on either side of the limbus, which has the effect of positioning these electrically conductive length(s) and/or points(s) in physical proximity to the ciliary body and canal of Schlemm. In so doing, the stimulus coil 3760 is advantageously positioned to deliver the stimulus signal (time-varying electromagnetic field) to ocular structures (including but not necessarily limited to the ciliary body and canal of Schlemm) in order to effectuate the desired reduction in aqueous humor inflow and/or increase in aqueous humor outflow in order to reduce elevated IOP within the eye according to the disclosed techniques. The current-controlled biphasic stimulation signal of FIG. 7 causes the current flowing between the electrical length(s) and/or point(s) along the outer electrode 3710 and the inner electrode 3712 of the stimulation coil 3760 to reverse when the signal switches phases. This advantageously presents a balanced influx of energy into the eye and prevents the premature deterioration of the metallic traces that comprise the electrodes that would otherwise occur due to electrolysis if the current were to flow continuously in a single direction overtime.

FIGS. 38-39 show front and side views, respectively, of an eye of a mammalian subject configured with a Fresnel lens 3800 implanted in the intraocular lens (IOL) and a stimulus coil structure 3860 implanted in a sub-conjunctival region for implementing the disclosed techniques. The Fresnel lens 3800 may be any suitable Fresnel lens, including but not limited to the Fresnel lens 2900 described above with reference to FIGS. 29-33 (the contents of which are hereby incorporated into this section such that a full discussion need not be repeated here). The stimulus coil structure 3860 may be any suitable stimulus coil, including but not limited to that stimulation coil structure described herein with reference to FIGS. 24-26 (the contents of which are hereby incorporated into this section such that a full discussion need not be repeated here). In use, the Fresnel lens 3800 is used solely for vision correction according to disclosed techniques, while the stimulus coil 3860 is used solely for the glaucoma therapy according to disclosed techniques. The stimulus coil 3860 includes an outer electrode 3862 and an inner electrode 3864, which in use are positioned about the limbus to effectuate the disclosed wireless glaucoma therapy techniques.

Although shown implanted in the intraocular lens (IOL), it will be appreciated that the Fresnel lens 3800 may be implanted in other regions of the eye (e.g. on the surface of the cornea, within the sub-conjunctival region so long as disposed over the pupil). Although shown separately in FIG. 39 (and thus implanted separately), it will be appreciated that the Fresnel lens 3800 may be formed as part of the stimulus coil structure such that the combined structure may be disposed on or in a substrate for use with the eye (e.g. a contact lens) or implanted as a single structure (e.g. within the sub-conjunctival region of eye). In each of these proposed embodiments, the combination of the Fresnel lens 3800 and the stimulus coil 3860 advantageously combines the vision correction capabilities of the Fresnel lens 3800 with the glaucoma therapy capabilities of the stimulus coil 3860 described and explained throughout this disclosure.

FIG. 40-41 show front and side views, respectively, of an eye of a mammalian subject configured with a Fresnel lens 4000 and a pair of intraocular stimulus coils 4060 (namely, anterior stimulation coil 4060a and posterior stimulation coil 4060b) implanted in an intraocular lens (IOL) for implementing the disclosed techniques. The Fresnel lens 4000 may be any suitable Fresnel lens, including but not limited to the Fresnel lens 2900 described above with reference to FIGS. 29-33 (the contents of which are hereby incorporated into this section such that a full discussion need not be repeated here). The stimulus coil structure 4060 may be any suitable stimulus coil, including but not limited to that stimulation coil structure described herein with reference to FIGS. 27-28 (the contents of which are hereby incorporated into this section such that a full discussion need not be repeated here). In use, the Fresnel lens 4000 is used solely for vision correction according to disclosed techniques, while the stimulus coils 4060a, 4060p are used solely for the glaucoma therapy according to disclosed techniques.

As shown in FIG. 41, the Fresnel lens 4000 and pair of stimulus coils (namely, anterior stimulus coil 4060a and posterior stimulus coil 4060p) are implanted in an intraocular lens (IOL) in the eye of the mammalian subject. The Fresnel lens 4000 may be constructed as separate structures or part of the same structure with one or both of the anterior stimulus coil 4060a and posterior stimulus coil 4060p. In either event, the Fresnel lens 4000 is disposed within the circular aperture of the anterior stimulus coil 4060a (see, e.g. the opening defined with the small circular stimulus coil 2402 of FIG. 26, which is the same as the anterior stimulus coil 4060a and posterior stimulus coil 4060p). The Fresnel lens 4000 is dimensioned to consume the bulk of the pupil so as to facilitate the focusing of incoming light on the retina. The anterior stimulus coil 4060a and posterior stimulus coil 4060p are configured and dimensioned such that, during use, the most medially located aspect of each stimulation coil extends far enough into the pupil to effectuate the desired therapeutic effect for glaucoma without blocking or otherwise covering the pupil aperture to impede vision. The Fresnel lens 4000 may be any suitable shape and configuration, including but not limited to generally planar and/or curved.

The anterior stimulus coil 4060a and posterior stimulus coil 4060p need not be physically connected to one another but are oriented in a juxtaposed arrangement such that the arrow A of the anterior stimulus coil 4060a is facing one direction (e.g. at the top facing left) and the arrow A of the posterior stimulus coil 4060p is facing the opposite direction (e.g. at the bottom facing right). In this position, the outer electrodes of the anterior and posterior stimulus coils 4060a, 4060p will be positioned adjacent to but radially spaced from the respective inner electrodes, while the inner electrodes of the anterior and posterior stimulus coils 4060a, 4060p will be positioned adjacent to but radially spaced from the respective outer electrodes. In this manner, two (2) regions of current flow are created along the perimeter of the ocular tissue of interest (e.g. limbus) to accomplish the desired reduction in elevated IOP.

Although shown where both are implanted in the intraocular lens (IOL), it will be appreciated that the Fresnel lens 4000 (if a separate structure from the stimulus coils 4060a, 4060p) may be implanted in other regions of the eye (e.g. on the surface of the cornea, within the sub-conjunctival region so long as disposed over the pupil). It will also be appreciated that the Fresnel lens 4000 and stimulus coils 4060a, 4060p may be formed as a combined structure that may be implanted directly into a native IOL (with or without being applied to an underlying substrate to form a prosthetic IOL implant). Lastly, the Fresnel lens 4000 and stimulus coils 4060a, 4060p (whether a single structure or combined structure) may be applied to a substrate to form a prosthetic IOL for implantation in a native IOL or replacement of a native IOL.

The various stimulation coils (including the Fresnel lens) represent significant advancements over the prior art and have the capacity and potential to revolutionize glaucoma therapy and vision correction according to the systems and techniques disclosed herein. The systems and techniques present a host of advantages, including but not limited to the ability to employ the stimulus coils in a wide variety of physical locations, including against or near the eye (e.g. via contact lens) and/or within the eye (e.g. sub-conjunctival, IOL) and at or near the target ocular structures in order to achieve the desired therapeutic effects (that is, reduction of IOP below elevated levels and preferably within the range of standard IOP levels). The ability to implant the various coils near the target ocular structures is a function of the fact the coils are passive and thus capable of being manufactured with a small physical profile.

Wireless Pressuring Sensing

FIG. 42A-B show diagrams of a wireless pressure sensing system for measuring intraocular pressure (IOP) within an eye of a mammalian subject as part of a wireless glaucoma therapy system, including: (A) IOP monitor system and (B) Readout full system implant comprises a readout ASIC, an antenna and a powering coil.

FIG. 42B is a conceptual diagram of a microsystem implant that comprises a pressure sensor, a readout IC, a powering coil and an antenna. The use of a pressure sensor for measuring IOP may be employed with any mammalian patient, including humans and animals (e.g. rodents).

The design of uninterrupted pressure sensing monitors presents a number of design challenges, with size constraint and power consumption being the most important ones. As depicted in FIGS. 42A-B, due to the small implant site, the diameter and thickness of the receive coil for energy harvesting should preferably not exceed more than 2.6 mm and 100 µm, respectively. This area restriction limits the energy efficiency of the WPT and thus the instantaneous power consumption of the chip. The size constraint for the implant also limits the combined dimensions of the pressure sensor and readout IC to 750 µm×750 µm×300 µm. Table 1 illustrates the size specifications for pressure sensing microsystems.

| Specifications for pressure monitoring microsystem | |
| --- | --- |
| Parameters | Specifications |
| ASIC dimensions | <750 µm × 750 µm × 250 µm |
| Sensor dimensions | <700 µm × 500 µm × 50 µm |
| Telemetry antenna diameter | <2.4 mm |
| Powering coil size | <2.6 mm; <100 µm thick |
| ASIC peak power consumption | <500 µW |

State-of-the-art commercial capacitive pressure sensors (E1.3N, microFAB Bremen) are often employed in pressure sensing applications in humans, however, it cannot be used for animal studies due to its large size. A push forward in piezo resistive pressure sensor fabrication technology yields micro-scale sensors (700 µm×100 µm×50 µm) and thus make them ideal candidates for this application. Apart from its smaller size, the piezo resistive pressure sensor also offers better linearity than capacitive sensors.

This disclosure presents a sub-cubic millimeter (sub-mm3) sized continuous pressure monitoring microsystem that includes a piezo resistive differential pressure sensor, a fully wireless CMOS read-out ASIC, a loop antenna for data transmission, and a receiver powering coil. The readout ASIC is highly integrated and senses the change in differential resistance with applied pressure and provides a resistance-to-digital (R-D) conversion. The chip also includes a 2.45 GHz ISM band active transmitter (TX) to wirelessly transmit the raw sensing data. The system is battery-less thereby increasing the life span of the implant and is wirelessly powered by exciting a cavity resonator at 700 MHz.

The main goal for the system is to provide all the necessary functionality to the implant by designing a highly integrated system-on-chip (SoC), without using any external components, in the given size limit. Having features such as, on-chip first order calibration, data processing, active transmission and signal conditioning remove the need for a constant nearby external device to perform these tasks, which is essential in a scenario where the experiments are done on a freely moving animal. A simple base station, such as a smartphone, kept a few tens of centimeters away, is all we need to demodulate and display the pressure data in real time.

FIG. 43 is a block diagram of a wireless IOP sensing system on a chip (SoC) for implementing the disclosed techniques. The depicted wireless IOP sensing SoC includes four major blocks: energy harvesting (EH) and power management, resistance-to-frequency converter (R-F) front-end circuit, a digital core that finally provides a resistance-to-digital (R-D) conversion, and a 2.45 GHz ISM band TX. Also shown in the figure is a three-terminal differential piezo resistive pressure sensor, consisting of two resistive elements $R_{S1}$ and $R_{S2}$, which senses the applied pressure P by increasing the resistance of $R_{S1}$ and decreasing the resistance of $R_{S2}$ by the same amount $\Delta RS$ (for $R_{S2} > R_{S1}$). The change in differential resistance $R_{DIFF}$ is given by:

$$R_{DIFF} = [R_{S2} - \Delta R_S] - [R_{S1} + \Delta R_S]$$

$$R_{DIFF} = (R_{S2} - R_{S1}) - 2\Delta R_S; (R_{S2} > R_{S1})$$

where, $2\Delta RS$ is the change in the differential sense resistance with the applied pressure P. The resistance of both the elements increases with the temperature, thereby canceling out the temperature variation in a differential measurement. The R-F front-end circuit measures the change $2\Delta RS$ and hence the applied pressure.

For WPT for rodents, 700 MHz RF energy is utilized to excite the resonance cavity. The use of a high value of frequency allows the implant to harvest the energy with a very small, two-turn receive coil (100 µm thickness, and 2.6 mm diameter) and the on-chip adaptive matching network. The EH section of the SoC utilizes two capacitors for the matching network, as can be seen in the Figure _. The drop-in power transfer efficiency (PTE) due to the coil misalignment and other factors is addressed by an efficiency tracking loop that maximizes PTE under various operating conditions by automatically tuning the capacitor bank in the matching network. In addition, a sub-1V bandgap reference (BGR) circuit is designed to provide the pseudo-differential reference and common mode voltages for the R-F front-end circuit. The BGR also generates bias currents for the entire chip. Two on-chip n+ diffusion base resistances (RB1 and RB2) were implemented with the values close to the sensor resistances for calibration purposes.

A binary-counter based digital core logic provides the frequency to digital conversion and packetizes the data for wireless transmission. Finally, the data packets are transmitted by an On-Off-Key (OOK) modulated ISM band TX at 2.45 GHz. The TX consists of a voltage controlled power oscillator (VCPO) utilizing a LC resonant circuit to generate its carrier frequency in the 2.45 GHz ISM band. An off-chip loop antenna (2.4 mm diameter) is employed for the TX that also acts as a high-Q inductive element L for the LC resonator thereby minimizing both power consumption and the overall size of the system by eliminating the matching network between the TX and the antenna. The use of an active TX also eliminates the "self-jamming" problem associated with the passive backscattering based transmitters.

FIG. 44 is a block diagram of energy harvesting (EH) and power management subsystems. In this work, the WPT leverages the cavity resonance based near field method due to its high PTE and ability to deliver large amounts of power to the implant. The cavity is excited by a 700-MHz RF source. An on-chip 4-stage rectifier provides an AC-DC conversion by multiplying the voltage induced on the receive coil. High efficiency and low leakage Schottky diodes with forward voltage drop of <200 mV are used to implement the rectifier. The unregulated voltage $V_{RECT}$ at the output of the rectifier acts as a supply voltage for the rest of the power management circuits. Although the orientation of the coil remains fixed once the device is implanted, an ultra-low power energy efficiency loop is employed that tracks the $V_{RECT}$ and tunes the capacitor bank in the on-chip matching network.

FIG. 45 is a schematic diagram of the bandgap reference to generate pseudo-differential reference voltages and bias currents for the SoC chip. This figure shows the sub-1V and sub-1 µW BGR, which generates the pseudo differential voltages for the R-F circuit, and reference voltages and the 100 nA bias currents for the entire chip. The BGR generates a total of seven precise reference voltages from 100 mV to 700 mV in steps of 100 mV. The pseudo differential voltage of 100 mV is ensured by using three reference voltages (VR7=700 mV, VR6=600 mV, and VR5=500 mV) and using VR6 as a common mode voltage. The difference value of a precise 100 mV voltage (i.e., (VR7−VR6) and (VR6−VR5) is provided by the R-F circuit (section 5). The output reference voltage for the BGR is given by:

$$V_{RN} = \frac{R_N}{R_X} V_{R,Conv}$$

where, N is from 1 to 7 in the output resistor ladder, and $V_{R,Conv}$ is the conventional bandgap voltage of 1.25 V. As shown in the equation above, the generation of multiple reference voltages with a precise step of 100 mV, in the presence of process variations, requires the multiple degrees of matching between the resistors in the BGR circuit. In order to accomplish the task, first, we match the resistors R5, R6 and R7 with each other by treating R6 as a "common-mode" resistor. Second, we match the combination of (R5+R6+R7) with the resistors R1, R2, R3, and R4. Finally, we match all the resistors RX, RZ and (RO=R1+ . . . +R7) in the BGR with each other. The matching is achieved by utilizing common centroid and symmetrical layout techniques. We used high density but well-matched poly resistors to implement all the resistors in the BGR circuit. A power-on-reset (POR) circuit pulls the gate of the PMOS current sources (M1-M4) down during startup. As a result, the PMOS current sources inject a finite amount of current into the BGR core during startup to ensure a stable operating point for the BGR.

FIG. 46 is a schematic diagram of one of the four voltage regulators and their supply domains. The linear voltage regulators are implemented to provide a clean supply voltage to various blocks of the chip by regulating the unstable output voltage of the rectifier $V_{RECT}$. In order to decouple the supply domains of various circuit blocks, four separate linear voltage regulators are employed. FIG. 46 depicts the schematic diagram of the voltage regulator and the supply voltage domains of the circuit blocks. Since an external capacitor is not available, the regulator is internally compensated with a minimum phase margin of 57 degrees. An NMOS pass transistor is utilized to ensure the stability across the variable load conditions with a good power supply rejection ratio (PSRR). The reference voltage divider in the regulators consists of two identical PMOS transistors operating in the weak threshold region. These transistors provide extremely high on-chip resistance (~22 MΩ each) and thus consume a negligible amount of quiescent current.

FIG. 47 is a concept diagram of the implemented R-F converter. A differential resistance-to-frequency (R-F) conversion is performed in two steps: first, resistance-to-current (R-I) conversion, and second, current-to-frequency (I-F) conversion. Two separate R-F converters were implemented in this work for the comparison purposes. FIG. 37 shows a concept diagram for an R-F converter, where an R-I circuit senses the differential change in the sensor resistance and provides an output current $I_{OUT}$. The current $I_{OUT}$ is then fed to the I-F converter consisting of a current control oscillator (CCO). The CCO changes its frequency by sensing the current IOUT and thereby providing an I-F and hence R-F conversion.

FIG. 48 is a schematic diagram of a conventional R-I converter. There are two major challenges in the design of an R-I converter: linearity, and low power operation. FIG. 48 illustrates the schematic diagram of a conventional linear R-I converter. A negative feedback loop consisting of an op-amp, an NMOS transistor, and a sensing resistor element, forces the voltage drop across the sense resistor to be equal to the constant reference voltage from BGR. The current generated in this manner is highly linear and inversely proportional to the sense resistance ($I_R = V_{REF}/R_S$). This current is then copied to the subsequent CCO through current mirrors (M2-M3). The power consumption of the circuit is dependent on the absolute values of $R_S$ and $V_{REF}$. Since the absolute base value of $R_S$ is fixed, a low value of $V_{REF}$ can be generated by the BGR to minimize power consumption. However, the minimum value of $V_{REF}$ is limited by the dynamic range of the circuit. Thus, the power consumption of the R-I converter is mainly limited by the absolute value of the sense resistor and the required sensitivity.

FIG. 49 is a schematic diagram of first differential R-I (R-I1) converter. The principle of an R-I converter depicted in FIG. 45 can also be extended to differential measurements. FIG. 39 shows the schematic diagram of the first differential R-I converter (R-I1). The difference in current $I_{RS1}(=V_{REF}/R_{S1})$ and $I_{RS2}(=V_{REF}/R_{S2})$ is given by:

$$I_D = I_{RS1} - I_{RS2} = \frac{V_{REF}}{R_{S1}} - \frac{V_{REF}}{R_{S2}}; (R_{S2} > R_{S1})$$

where, $R_{S1}$ and $R_{S2}$ are the base values of the sensor resistors at atmospheric pressure and their values are known a priori. If ΔRS is the change in the sensor resistance with applied pressure P, then the equation 4.3 can be rearranged in accordance with equation 4.1 as:

$$I_D = \frac{V_{REF}}{R_{S1} + \Delta R_S} - \frac{V_{REF}}{R_{S2} - \Delta R_S}$$

$$I_D = V_{REF} \left[ \frac{(R_{S2} - R_{S1}) - 2\Delta R_S}{(R_{S1} + \Delta R_S)(R_{S2} - \Delta R_S)} \right]$$

The term ($R_{S2}-R_{S1}$) is a constant difference between the base values of the sensor resistances, when the pressure is not applied. The change in resistance $\Delta R_S$ with applied pressure is small compared to the absolute base values of the sense resistors (i.e. $\Delta R_S \ll R_{S1,2}$). Moreover, the absolute values of the sense resistances are close to each other and are of the same order. For instance, the approximate values of the Volcano pressure sensor used in this work has $R_{S2} \approx 3.6$ K$\Omega$ and $R_{S1} \approx 3.3$ K$\Omega$ at atmospheric pressure. The maximum change in differential resistance $\Delta R_S$ is 12$\Omega$ across the IOP range (0-60 mmHg). Therefore, the equation can be written as:

$$I_D = V_{REF}\left[\frac{(R_{S2} - R_{S1}) - 2\Delta R_S}{R_{S1}R_{S2}}\right]$$

$$I_D = I_{DS,Const} - \Delta I_{DS}$$

Here, the difference current ID has two parts: a constant current $I_{D,Const}$ and the change in the current $\Delta I_{DS}$ with the change in sensor resistance with applied pressure. These two parts are given as: $I_{DS,const} = V_{REF}[(R_{S2}-R_{S1})/R_{S2}/R_{S1}]$, and $\Delta I_{DS} = V_{REF}[2\Delta R_S/R_{S2}R_{S1}]$.

Both of the operational transconductance amplifiers (OTA) in the R-I1 converter were identical with a high open loop gain of 100 dB. A two-stage miller-compensated OTA was designed for very low power, noise, and offset. Both of the OTAs were matched together to further reduce the effect of an off set between two current branches. A 100-mV reference voltage $V_{REF}$ is chosen as a tradeoff between minimum power consumption and maximum dynamic range across the pressure range. A full scale dynamic range of 70 nA is achieved in the $\Delta I_D$.

FIG. 50 is a schematic diagram of second differential R-I (R-I2) converter. Since an R-I$_1$ converter uses two current branches to sense differential resistance, high power consumption is inevitable with such a structure. A 50% power saving can be achieved with the use of only one sensing current branch to measure the differential current. To accomplish the task, a second R-I$_2$ converter is proposed in this work. The schematic of the R-I2 converter is depicted in FIG. 50.

Three negative feedback loops are introduced in the R-I2 converter. A pseudo-differential reference voltage $V_{REF}$ of 100 mV is generated by the BGR as explained earlier ($V_{REF} = VR_7 - VR_6 = VR_6 - VR_5$). The first and second feedback loop (depicted as 1 and 2 in the FIG. 47) set the reference voltages of VR7=700 mV and VR5=500 mV at the nodes "X" and "Y", respectively, and are designed with a high loop gain (>95 dB). The third feedback loop sets the common-mode reference voltage of VR6=600 mV at node "N". As a result, each resistor in the sensor sees a voltage drop of 100 mV across it. The difference current $\Delta$ID flows through the transistors M3 and M4, which is copied via current mirrors M4-M5. Since the third feedback loop sees both first and second loops as a load, it has a lower loop gain (>70 dB) compared to the other two feedbacks. The first and second feedback loops are designed with lower settling time than the third feedback loop, to ensure accurate startup and stability. All of the OTAs are matched with each other in a single block to reduce the effect of off set voltages. In the calibration mode, the on-chip base resistors (RB1,2) are switched to the feedback loop via the analog multiplexers and the sensor resistor elements are switched to the ground.

FIG. 51 is a schematic diagram of the ring oscillator, providing I-F conversion. The I-F converter consists of a wide tuning range ring oscillator as depicted in FIG. 41. A current starved inverter and a transmission gate constitute a single-stage of the ring oscillator. The bias voltage (VBP and VBN) generated by the R-I converter controls the oscillation frequency of the ring oscillator by regulating the resistance of the transmission gate (RT). The oscillation frequency $f_{osc}$, for the wide tuning range N-stage ring oscillator is given by:

$$f_{osc} = \frac{g_m}{2NC_P(1 + g_m R_T)}$$

where, $g_m$ is the total effective transconductance of a single stage inverter, N is the total number of stages, and $C_P$ is the total parasitic capacitance at the gate of a single stage inverter that consists of the total gate capacitance of the PMOS and NMOS transistors and the wiring capacitance.

For $g_m R_T \gg 1$, the prior equation can be rearranged as:

$$f_{osc} = \frac{1}{2NC_P R_T}$$

The average value of Vds/$I_T$ provides the effective resistance of the transmission gate $R_T$, where $V_{ds}$ and $I_T$ are the voltage drop and current across the transmission gate, respectively. For $V_{dsat} < V_{DD}/2$, $I_T$ remains constant when a step-input rises from $V_{DD}/2$ to $V_{DD}$ and $R_T$ can be approximated as:

$$R_T = \frac{2\ln 2}{V_{DD}} \int_{V_{DD}/2}^{V_{DD}} \frac{V}{I_T} dV = \frac{3\ln 2}{4} \frac{V_{DD}}{I_T} \approx \frac{V_{DD}}{2I_T}$$

By combining equations, the oscillation frequency $f_{osc}$ of the I-F converter is given by:

$$f_{osc} = \frac{I_T}{NC_P V_{DD}}$$

Since the current through the transmission gate $I_T$ is controlled by the bias volt-ages $V_{BP}$ and $V_{BN}$, generated by the R-I converter, $f_{osc}$ is a linear function of the difference current $I_D$ ($I_T = I_D$). In order to make this function extremely linear, the inverters in the conventional wide tuning ring oscillators are made current starved with the current $I_D$. This also minimizes the crowbar current of the inverters, and hence reduces the voltage droop in the output of a capacitor-less voltage regulator, which provides a clean supply to the oscillator. High-VTH transistors were used for the inverters, which further reduces its crowbar current.

Although the temperature effect is canceled out in the differential current due to the sensor properties, it can change the absolute base value of the oscillation frequency. Similarly, the supply variation in the regulated output can alter the oscillation frequency and therefore the accuracy of the measurement. Temperature variation for the IOP monitor system may be taken into account, as well.

If implanted in a physical environment with varying temperature, the impact can be combatted or mitigated by using two on-chip base resistors ($R_{B1}$ and $R_{B2}$ with values close to the absolute base values of the sense resistors and with the same initial resistance difference, are implemented with n+ diffusion resistors. The n+ diffusion resistor has a positive temperature coefficient very close to the sense resistor in the temperature range of interest. Since both the resistors values are close to each other, a near perfect matching is achieved by laying them out in a common centroid fashion. The difference current in the base resistance sensing mode depends only on the temperature and supply variations and is utilized to calibrate the variations in the pressure sensing mode. Since the resistances of both the sensor resistors change by the same amount with a temperature change, a difference current is given by setting $\Delta R_S$ equal to zero in equation:

$$I_D = I_{DS,Const} = V_{REF}\left[\frac{R_{S2} - R_{S1}}{R_{S2}R_{S1}}\right]$$

Similarly, a difference currant in the base sensing mode is given by:

$$I_D = I_{DB,Const} = V_{REF}\left[\frac{R_{B2} - R_{B1}}{R_{B2}R_{B1}}\right]$$

By dividing equation 4.12 by equation 4.13, we get:

$$\frac{I_{DS,Const}}{I_{DB,Const}} = \left(\frac{R_{S2} - R_{S1}}{R_{B2} - R_{B1}}\right)\frac{R_{B2}R_{B1}}{R_{S2}R_{S1}} = \frac{f_{osc,S}}{f_{osc,B}}$$

The resistances in the above equations are absolute base values and their values are known a priori. Since the sensor and base resistors share the same oscillator for R-F conversion, the ratio of their frequencies $f_{osc,S}/f_{osc,B}$ is independent of $V_{DD}$, as suggested by equation 11. Therefore, an initial calibration for temperature and supply voltage variation can be easily achieved by having a separate time slot for the on-chip differential base resistance sensing mode. A differential sensing and an on-chip base resistor calibration method in this work enable accurate pressure measurements without having an extra temperature, voltage and current sensing mode.

The values of the sensor and base resistors frequencies are calculated by the counter-based digital core logic, operating at a constant reference frequency $f_{REF}$. A similar oscillator to the one being used in the I-F conversion but with more stages, is employed to generate a much lower reference frequency ($f_{REF}$=1.5 KHz). A temperature independent constant bias current is utilized for the reference oscillator. The much lower clock speed ($f_{REF}$) for the digital core minimizes its dynamic power consumption and reduces the OOK data rate for the TX.

FIG. 52 is a digital Core: (a) Block diagram. (b) F-D converter. (c) Block diagram of encoder (ENC). (d) State diagram of ENC. FIG. 42(a) shows the block diagram of the digital core which provides frequency-to-digital (F-D) conversion and encodes the resulting data for a burst transmission. The F-D converter in FIG. 49(b) consists of two counters $CNT_{SEN}$ and $CNT_{REF}$. When receiving the Start signal from the timer, both counters are reset and start counting upward. Once $CNT_{REF}$ reaches 350 cycles, the conversion is completed with an end-of conversion (EoC) pulse stopping both counters and the value of $CNT_{SEN}$ (Data) is read out, which guarantees a minimum frequency resolution of (1 bit)/(5 Hz) at a reference clock ($CLK_{REF}$) frequency of 1.5 KHz. The $CNT_{REF}$ and $CNT_{SEN}$ are designed for 10 and 18 bits, respectively, to avoid overflow in both the counters at maximum input clock ($CLK_{IN}$) frequency.

FIGS. 52 (c) and (d) show the block and state diagram of the encoder (ENC), respectively. Initially in the SLEEP state, the output of the encoder PKTO is fixed at logic "0" to turn off the TX. When receiving an EoC pulse, the encoder latches data from the F-D converter and proceeds to the next state based on the input signals DIFRS and SELRS, as indicated in FIG. 49 (d). In the SAMP RB and SAMP RS state, in which the digital outputs generated from the reference base resistor (RB) and sensing resistor (RS), respectively are recorded, the data from the F-D converter is directly stored into the sampling parallel-to-serial register (P 2SR SAMP) with 18-bit precision. While in the DIF F RS state, where only the RS difference is stored, the P 2SR SAMP is disabled from writing to hold the value stored in SAMP RS states. Meanwhile, the RS difference is calculated by subtracting the data with the previously recorded RS and stored into the differential parallel-to-serial register (P 2SR DIFF). Considering a 10-kHz dynamic range of CLKIN, the precision of the P 2SR DIFF is set to 12 bits. The flip-bit generator (FB Gen) counts the number of logic "1" in all the three states via bitwise summing of the parallel data DatP. If the summed value is greater than a threshold value, set at 9 for 18-bit digital data and 6 for 12-bit difference, each bit of DatP is reversed and the flip-bit register (FB) is updated to logic "1". In the next cycles, the encoder enters either the SRL PKSAMP state where the data stored in P 2SR SAMP is serially outputted in sample packets (PKSAMP), or the SRL PKSAMP state where the RS difference stored in P 2SR DIFF is serially outputted in differential packets (PKSAMP). At the same time, a 3-bit cyclic redundant check (CRC) code is also derived from the DatS. The encoder returns to the SLEEP state after the formation of the data packet and waits for the next Each pulse.

FIG. 53 is a timing diagram of digital core and the packet structure. In particular, FIG. 53 illustrates the timing diagram of the digital core and structures for both the sample packet (PKSAMP) and the differential packet (PKDIFF). The PKSAMP consists of a 4-bit header (HB) indicating the starting of a specific packet, a flip bit (FB), 18-bit data, a 3-bit CRC code, and a 4-bit tail (T B) indicating the ending of a packet transmission. The structure of the PKDIF F is similar to that of the PKSAMP except having a 12-bit RS difference data instead of 18-bits. The headers of PKSAMP transmitting the data from RB and RS are set as "1001" and "1010", respectively, and that of PKDIF F is set as "1100". The timer of the digital core is implemented with a packet counter, which, upon receiving an EoC pulse, is incremented by 1 and reset when its value is equal to (NPKC-1), where NPKC is the number of packets per cycle and is set to be equal to 10. As shown in FIG. 50, the Start pulse for the F-D launches two CLKREF cycles after both EoC and reset-digital-core (RSTDC) pulses, allowing CLKIN of the F-D converter to stabilize before the conversion starts. Both the SELRS and the DIFRS signals are disabled when the packet counter is reset, and become active high when the value of the packet counter is greater than 0 and 1, respectively. As a result, among the NPKC packet outputs (PKTO), the 1st and 2nd ones are PKSAMP recording the digital data converted from RB and RS, and the rest of the 8 packets are PKDIF F recording RS differences, each of which is separated by 352 CLKREF cycles. At the receiver, the exact values of RS can be recovered at 18-bit precision by summing RS differences with the Data obtained from the 2nd PKSAMP. Therefore, by applying differential encoding and bit-flipping strategies to data from the slow-varying IOP signals, the number of bit "1" in data packets and hence the switching-ON rate of OOK TX can be minimized without degrading the sampling rate and data precision, saving overall power dissipation dominated by the TX during the data transmission phase.

FIG. 54 is a schematic diagram of the 2.45 GHz ISM band transmitter, comprising a voltage-controlled power oscillator (VCPO) and an off-chip loop antenna. Real-time pressure monitoring with a limited amount of harvested wireless energy requires a very low, both instantaneous and average, power consumption for the transmitter. In this work, an OOK modulated, 2.45 GHz ISM band, transmitter was designed for wireless transmission of the data packets. FIG. 54 shows the schematic of the transmitter that comprises a LC voltage controlled power oscillator (VCPO). The TX was aggressively optimized for extremely low data rate (~1 bps) applications, where the minimization of the leakage current and the supply voltage scaling are the two major design criteria. In this work, the design of the TX was mainly aimed towards the reduction of both instantaneous and average power consumption. A 2.45 GHz ISM band was chosen for the carrier frequency as a trade-off between power dissipation, antenna efficiency, and tissue losses. An off-chip loop antenna, with a diameter of 2.4 mm, is fabricated on the printed circuit board (PCB) that connects directly to the VCPO at nodes X and Y. Since the circumference of the loop antenna is much smaller than its transmitting wavelength at 2.45 GHz, it considered an electrically small antenna. The equivalent lumped circuit model of an electrically small loop can be represented as a series combination of an inductor (LA) and a small resistor (RA) as can be seen in FIG. 55. Therefore, an off-chip electrically small loop can be effectively utilized as the inductive element for the LC tank circuit of the VCPO. The self-resonance frequency of the loop antenna is typically much higher than the resonance frequency of the LC tank and can be modeled by adding a parallel capacitor CSRF.

The design of the antenna is optimized to maximize its radiation efficiency and minimize the tissue losses in an implantable environment for the given size constraints (Table 1). It is a well-known fact that the radiation efficiency of an antenna increases with its physical size or carrier frequency (since the carrier wavelength approaches the physical dimension of the antenna). However, tissue conductivity also increases with frequency, resulting in higher tissue losses. In order to efficiently utilize the space available for the implant, a diameter of 2.4 mm was chosen for the loop antenna. A carrier frequency of 2.45 GHz offers a good balance between the radiation efficiency and tissue losses. The antenna was designed and optimized using the full-wave 3-D electromagnetic simulation software ANSYS High Frequency Structural Simulator (HFSS). The antenna parameters with HFSS simulations are listed in Table 4.2.

TABLE 4.2

HFSS simulation and calculation results for the loop antenna

| Simulations @ 2.45 GHz | L (nH) | L with wirebond (nH) | Antenna Gain (dB) | Calculated Efficiency (%) | Q |
|---|---|---|---|---|---|
| 20 μm thick Parylene substrate with 20 μm Parylene coating layer | 4.87 | 6.4 | −21.57 | 1.47 | 121 |
| Gold trace on 20 μm Parylene substrate with a coating layer | 4.88 | 6.41 | −22.86 | 1.27 | 91 |
| FR-4 board (Air) | 4.75 | 6.27 | −19.9 | 1.47 | 172 |

FIGS. 56 (a) and (b) show the simulated radiation pattern for the loop antenna, designed on a FR-4 PCB and a parylene substrate, respectively.

FIG. 54 shows the schematic diagram of the VCPO. The core of the oscillator consists of the NMOS (M1-M2) and PMOS (M3-M4) cross-connected transistor pairs, an LC tank circuit, and a tail current source NMOS transistor M5. Having both the PMOS and NMOS cross-couple pairs increases the effective transconductance of the VCPO, thereby reducing the startup current required for the VCPO to ensure oscillations. This configuration also discards a need for center tapping the loop antenna to bias the VCPO, thereby simplifying final device packaging which is essential in the IOP monitor system. The sizes of the transistors M1-M4 are designed carefully to minimize the phase noise, while ensuring an acceptable start-up condition for the VCPO [152]. Additional power saving during startup is achieved by using a high-Q inductive element for the LC tank circuit, which is implemented by an off-chip loop antenna.

The data packets from the digital core directly OOK modulate the TX by dynamically switching the tail current source transistor M5. The size of the transistor M5 is chosen such that the VCPO delivers 80 μW (−11 dBm) of instantaneous power to the loop antenna. The TX is operated at a regulated supply voltage of 1.2 V. The TX was simulated with extracted layout parasitics and extracted s-parameters of the antenna from HFSS simulations. With no on-chip tuning capacitor, the maximum frequency of the VCPO is limited by the parasitic capacitances at node X and Y (mainly due to the bond-pad and device capacitances). The extracted simulations in the Cadence R Spectre R RF result in the maximum VCPO oscillation frequency of 3.4 GHz without the tuning capacitors. Thus, a Metal-Insulator-Metal (MIM) capacitor was introduced in the LC tank circuit to obtain a carrier frequency at 2.45 GHz ISM Band (2.4 GHZ-2.5 GHz).

Since the TX design is extremely power efficient, it can be useful in various other short-range biomedical communication applications, such as a wireless body area network (WBAN). Therefore, the design of this TX is also optimized as a separate stand-alone structure. A 5-bit capacitive MIM DAC is implemented to provide a tuning range from 2.3 GHz-2.7 GHz, as depicted in FIG. 57. This tuning range would also cover a 2360 MHz-2400 MHz frequency band allocated for WBAN (IEEE 802.15.6) [153]. Unlike the digital switch implemented in [151], this work utilizes a resistor based switch biasing scheme [154] that provides a definite off-state negative gate-to-source voltage Vgs for the NMOS switch depicted in FIG. 47. A frequency-shift-keying (FSK) modulation with variable bandwidth is also possible by dynamically switching the DAC tuning capacitors via data packets. In order to reconfigure the output power delivered, seven tail current sources M5<6:0> with binary weighted sizes are employed.

The pressure sensing readout ASIC is implemented and fabricated in a standard 0.18 μm CMOS process. The chip occupies 750 μm×750 μm of silicon area, including bond pads. The microphotograph of the chip is illustrated in FIG. 48. Since the full system SoC has a limited number of testing bond pads due to the size restriction, separate test structure dies were fabricated to characterize the individual circuit blocks. First, the DC testing of the individual circuit blocks was performed. The pressure sensor resistor is placed in the pressure chamber to carry out the measurements. The pressure in the chamber is varied from 0 mmHg to 60 mmHg and the variation in difference current ID is measured for both R-I1 and R-I2 circuit blocks (FIG. 59). The dynamic range of ID was measured to be 105 nA across the pressure range of 0-60 mmHg, which is very close to the simulated value. FIG. 50 (a) illustrates the pseudo-differential reference voltage across the sensor resistor terminals for the R-I2 converter. The voltage drop across both the sensing elements was precise and measured to be 100 mV, as can be seen in Figure. Similarly, the voltage drop across the sensing elements in R-I1 converter was accurately measured to be 100 mV (FIG. 60 (b)).

The output voltages of the all four voltage regulators are measured to be within ±3% of the designed values across multiple dies. The measured bias current of the chip is 97 nA, which is very close to the designed value of 100 nA.

A TX test structure allowing frequency and current tuning is used to characterize its performance. A loop antenna with 2.4 mm diameter is fabricated on a FR4 printed circuit board (PCB). The TX die is directly wire-bonded to the antenna trace in order to minimize the effect of parasitics. Since the loop antenna is directly connected to the nodes X and Y of the VCPO (FIG. 54) and no buffers or PA were implemented, a direct probing of the TX output was not possible. Therefore, all the measurements for the TX are done in a wireless test setup. A horn antenna with a gain 8 dBi is placed approximately 20 cm away from the TX chip. The horn antenna is connected to the Agilent E4404B spectrum analyzer, which receives the transmitted data. A value −52 dBm of the peak power was received with this setup. With the help of the well-known Friis transmission formula for the received power, the peak output power of the TX is calculated to be −33.76 dBm. The VCPO power consumption for this setup was measured to be 69.8 µW (=−11.56 dBm), providing loop antenna gain of −22.2 dB.

FIG. 61 depicts the output spectrum of the TX, OOK modulated by a pseudo-random-binary-sequence (PRBS) at 1 Mbps, 5 Mbps and 10 Mbps data rates. Although the TX is not designed to provide a FSK modulation, the future revision of this design can easily accommodate a sub-DAC capacitive array to enable FSK modulation along with the course tuning array which is already implemented in this chip. To demonstrate the possibility of FSK modulation, the minimum capacitor of 43 fF in the tuning DAC array is switched with a 1 Mbps PRBS data, resulting in a wide-band FSK spectrum depicted in FIG. 52. The transmitter consumes 140 µW in this mode. The VCPO achieves a phase noise of −115 dBc/Hz at an offset of 1 MHz from the carrier frequency.

Next, full system testing is carried out by placing the sensing element in a pressure chamber. The sensing element is connected to the R-I converter of the chip. The full system SoC employs the R-I2 converter due to its low power feature. The digital core sends the Sel RS signal to the R-I2 converter to select either the sensing element or the on-chip base resistor (Sel RS=0 selects the sensing element and Sel RS=1 selects base resistance). The measured output frequency of the R-F circuit corresponding to the on-chip base resistance was 360 KHz. FIG. 53 shows the measured periodic Sel RS signal, R-F converter output, reference oscillator clock, and digital data packets at a constant pressure. The measured data packets for the base frequency (30 bits), sensing element frequency (30 bits), and difference frequency (24 bits) are illustrated in FIG. 64. The header bits (HB) are different for all three types of packets for decoding purposes, as can be seen in the figure.

FIG. 65 depicts the measured sensor and base frequencies within the pressure range of interest. The sensor frequency ranges from 390.7 KHz to 379.9 KHz, resulting in the resolution of 0.024 mmHg/LSB with the digital core counter conversion time of 350 reference clock cycles at 1.5 KHz. However, the actual sensor resolution is limited by the thermal-noise. The thermal noise of the op-amps in the R-I converter circuit is the dominant noise source in the readout chip due to their low power dissipation. The noise simulation of the R-I converter suggests an rms error of 0.31 (mmHg)rms in the pressure readout. The measured value of the average base resistor frequency remains constant at 360 KHz.

A sensing resistance dynamic range of 12Ω was measured with the Agilent 4284A Precision LCR meter for the pressure range of 0-60 mmHg. Maximum non-linearity is measured to be 87 mΩ with the two-point calibration, resulting in the readout sensitivity of 0.44 mmHg. The measured sensing resistance linearity is depicted in FIG. 56 for the nominal difference in sensor resistances (RS1−RS2) of 312Ω. This sensitivity is enough to accommodate both the IOP pressure range. The rms error can be reduced by either increasing the conversion time or averaging the multiple data samples taken at each pressure point. FIG. 67 shows the improvement in the measured sensitivity when the number of data samples to be averaged are increased.

Next, the SoC was measured in a wireless setup. A 2-turn, 100 µm thick, receive powering coil of 2.6 mm diameter is connected in front of the on-chip matching network. The sensor is placed in the pressure chamber and the system is kept in a cavity resonator which is excited by a 700 MHz RF source. The data is received by a spectrum analyzer and demodulated by the base-station comprises of commercial-off-the-shelf (COTS) components. FIG. 68 depicts the output power spectrum of the received data packets. Demodulated data packets are then fed to a FPGA board which has an UART interface to a computer. The received data packets are decoded real-time in the matlab software. FIG. 69 shows the received data by a spectrum analyzer and corresponding digital packets, demonstrating correct packet reception.

Since the sensitivity of the pressure sensing chip is mainly limited by noise, it is important to characterize it in a wireless setup. FIG. 70 shows deviation due to noise in the wirelessly measured data at a constant pressure. A total of 60 data packets were averaged for each noise measurement. FIG. 71 depicts the resulting histogram for wirelessly measured noise. The standard deviation (1 σ) is measured to be 429.12 ppm, or 133.9 mΩ for a nominal difference in sensor resistances of 312Ω, resulting in a pressure sensitivity of 0.67 mmHg. FIG. 72 depicts the wirelessly measured pressure with time and compares it with a reference sensor. After the 2-point calibration, the maximum measured error in the pressure reading was 0.81 mmHg with a standard deviation of 0.63 mmHg.

Temperature effects on the sensing and base frequencies were also characterized and the results are depicted in FIG. 73. The maximum error in the recorded pressure due to temperature variation was measured to be 0.54 mmHg, after performing a 2-point calibration in the temperature range of 30° C. to 38° C. With a 3-point calibration, the error in the pressure measurement due to temperature is further reduced to 0.39 mmHg.

Thanks to the burst data transmission, the chip consumes 61.4 µW from the harvested energy. Table 4.3 illustrates the measured performance summary of the ASIC.

TABLE 4.3

Performance Summary

| | |
|---|---|
| Process node | 0.18 μm |
| Unregulated supply | 1.35 V |
| Power consumption | 61.4 μW |
| Rectifier Efficiency | 15.35% |
| Power Transfer Efficiency (PTE) | 4.3% |
| Difference resistance resolution | 133.9 mΩ (1σ) |
| Pressure resolution | 0.67 mmHg (1σ) |

The performance comparison of the ASIC with the previously published pressure monitor systems is presented in Table 4.4.

TABLE 4.4

Comparison with previous work

| | | This Work | [127] JSSC'11 | [42] TbioCAS'10 | [108] TCAS1'13 | [41] JSSC'01 |
|---|---|---|---|---|---|---|
| | Unregulated Supply Voltage | 1.35 V | 1.5 V | >1.5 V | — | >3 V |
| | Regulated Supply Voltage | 1.2 V, 1 V | | 1.5 V | 3.6 V | 3 V |
| | Energy Harvesting Source | MRC/Cavity | RF Resonator | RF | Battery | Inductive |
| | Energy Harvesting Frequency | 340 MHz-434 MHz | 2.4 GHz | 3.65 GHz | — | 13.56 MHz |
| | Sensor | Resistive (differential) | Capacitive | Capacitive | Capacitive | Capacitive |
| | Full System (Wireless) | ✓ | ✓ | ✓ | x | ✓ |
| | TX Frequency | 2.45 GHz | 2.4 GHz | 2.4 GHz | — | 13.56 MHz |
| | TX $P_{out}$ | −33.8 dBm | N/A | −45 dBm | — | N/A |
| | TX Data Rate | 1.5 kbps/ 103 bps (Burst) | 21-25 kbps | 8 Mbps | — | 26.5 kbps |
| | Modulation | OOK | Backscatter | OOK | FSK | Backscatter |
| | Pressure Resolution | 0.67 mmHg | 0.9 mmHg | 1.27 mmHg | 0.5 mmHg‡ | 0.73 mmHg* (9-bit) |
| Power | Power Management | 2.1 μA | 1.041 μW | 39.38 μW | 116.9 nW | N/A |
| | Readout Front End | 39.37 μA | 1.19 μW | 158.91 μW | 7 μW | N/A |
| | TX | 5.4 μW (6.86%) | — | 1.1506 mW | 47 mW | — |
| | Total Power | 61.4 μW | 2.3 μW | 1.3533 mW | N/A | 210 μW† |
| | CMOS Technology | 0.18 μm | 0.13 μm | 0.13 μm | 0.18 μm | 1.2 μm |
| | Chip Area | 0.75 × 0.75 mm² | 1 × 0.7 mm² | 0.7 × 0.7 mm² | 1.8 mm² | 6.76 mm² |
| | Micro-system Volume | 0.78 mm³†† | N/A | N/A | 1.5 mm³ | N/A |

‡Resolution is not measured for fully wireless system,
*Converted to mmHg from given pressure range and resolution of 9-bits,
†power consumption from regulated supply,
††After the chip back-lapping process.

Finally, the ASIC performance was evaluated in the in-vivo rabbit experiment. The intraocular pressure was recorded from an anesthetized rabbit. The pressure sensor was implanted inside the eye and connected to the ASIC microsystem that is kept outside the animal. FIG. 74 illustrates the experimental setup. The pressure response of the eye of the rabbit to infusion of saline into the eye, at a constant rate of 4 ml/Hour, was recorded and depicted in the graph at the bottom of FIG. 74.

Through the aspects described herein, a low-power, sub-mm3 IOP pressure monitoring microsystem is presented in this disclosure. The microsystem can be implanted in any suitable area within an eye of a mammalian subject to wirelessly measure and monitor IOP in a mammalian eye. The microsystem integrates a pressure sensor, a powering coil, a loop antenna and a low-power wireless pressure readout ASIC in a given space of 2.6 mm diameter. Thanks to the low power pressure sensing front-end, power management, and transmitter circuitry, the power consumption of the chip is only 61.4 μW, while harvesting the energy wirelessly form a 700 MHz RF source through a cavity resonator.

FIG. 74 shows a histogram corresponding to the wireless noise measurements in FIG. 70, providing 429 ppm (133.9 mΩ) 1σ deviation for 312Ω nominal ΔRS that results in the IOP sensitivity of 0.67 mmHg.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented using one or more modules of computer program instructions encoded on a computer-readable medium for execution by, or to control the operation of, data processing apparatus. The computer-readable medium can be a manufactured product, such as hard drive in a computer system or an optical disc sold through retail channels, or an embedded system. The computer-readable medium can be acquired separately and later encoded with the one or more modules of computer program instructions, such as by delivery of the one or more modules of computer program instructions over a wired or wireless network. The computer-readable medium can be a machine-readable storage device, a machine-readable storage substrate, a memory device, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a runtime environment, or a combination of one or more of them. In addition, the apparatus can employ various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM (Erasable Programmable Read-Only Memory), EEPROM (Electrically Erasable Programmable Read-Only Memory), and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., LCD (liquid crystal display), OLED (organic light emitting diode) or other monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The computing system can include clients and servers. A client and server are generally remote from each other and typically interact through a communication network. The relationship of client and server arises by virtue of computer programs running on the respective computers and having a client-server relationship to each other. Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described is this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

While this specification contains many implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. In addition, the actions recited in the claims can be performed in a different order and still achieve desirable results.

What is claimed is:

1. A system for wirelessly reducing intraocular pressure in an eye of a mammalian subject, comprising:
   a coil constructed from an elongated conductor formed into a plurality of windings, wherein said coil is adapted to be positioned in proximity to an eye of a mammalian subject at a location that is external to an external surface of the eye;
   a signal generator in electrical communication with said coil, wherein said signal generator is configured to generate a signal to produce an electromagnetic field transmitted wirelessly from said coil to said eye of said mammalian subject in a therapeutically effective amount to reduce an intraocular pressure within said eye of said mammalian subject;
   a base station in wireless communication with said signal generator, wherein the base station is configured to generate one or more control signals for modulating generation of said signal by said signal generator to produce said electromagnetic field transmitted wirelessly from said coil to said eye of said mammalian subject; and
   a computing device in wireless communication with said base station, wherein the computing device is configured to receive one or more inputs indicating user-defined adjustments to said electromagnetic field transmitted wirelessly from said coil to said eye of said mammalian subject.

2. The system of claim 1, wherein said intraocular pressure within said eye of said mammalian subject is reduced by at least one of (i) decreasing aqueous humor inflow into an anterior segment of said eye and (ii) increasing aqueous humor outflow from said anterior segment of said eye.

3. The system of claim 2, wherein said decrease in aqueous humor inflow into said segment of said eye occurs as a result of said electromagnetic field being configured to cause a ciliary epithelium pump within a ciliary body within said eye to reverse or slow the generation of intraocular fluid into said anterior segment of said eye.

4. The system of claim 2, wherein said increase in aqueous humor outflow from said anterior segment of said eye occurs as a result of said electromagnetic field being configured to cause at least one fluid pathway out of said anterior segment to open, dilate, or otherwise increase in fluid outflow facility.

5. The system of claim 4, wherein said at least one fluid pathway within said eye includes a drainage pathway through at least a portion of the Canal of Schlemm of said eye and a uveoscleral outflow mechanism from the anterior segment of said eye.

6. The system of claim 1, wherein said therapeutically effective amount of said electromagnetic field is in the range of $10^{-6}$ Tesla to $10^{-1}$ Tesla.

7. The system of claim 1, wherein said signal is a biphasic rectangular waveform with a frequency in the range of 0.1 Hz to 1 KHz, a pulse duration in the range of 0.1 milliseconds to 1000 microseconds, and a pulse amplitude in the range of 0.01 milli-Amps to 100 milli-Amps.

8. The system of claim 1, wherein said coil is part of at least one of a pair of glasses to be worn by said mammalian subject, an optical frame to be worn by said mammalian subject, a sleep mask adapted to be worn by said mammalian subject, and a pillow adapted to be used by said mammalian subject.

9. The system of claim 1, comprising:
   a passive stimulation electrode assembly adapted to be positioned at least one of on, within and near said eye of said mammalian subject, wherein said passive stimulation electrode assembly is adapted to wirelessly receive said electromagnetic field from said coil and stimulate at least one intraocular structure to reduce said intraocular pressure within said mammalian eye.

10. The system of claim 9, wherein said stimulation of said at least one intraocular structure by said passive stimulation electrode assembly being configured to reduce said intraocular pressure by at least one of (i) decreasing aqueous humor inflow into said anterior segment of said eye, and (ii) increasing aqueous humor outflow from said anterior segment of said eye.

11. The system of claim 10, wherein said decrease in aqueous humor inflow into said anterior segment of said eye by said passive stimulation electrode assembly occurs as a result of said stimulation by said passive stimulation electrode assembly being adapted to cause a ciliary epithelium pump within a ciliary body within said eye to reverse or slow the generation of aqueous humor into said anterior segment of said eye.

12. The system of claim 10, wherein said increase in aqueous humor outflow from said anterior segment of said eye by said passive stimulation electrode assembly occurs as a result of said stimulation by said passive stimulation electrode assembly being adapted to cause at least one fluid pathway out of said anterior segment to open, dilate, or otherwise increase in fluid outflow facility.

13. The system of claim 12, wherein said at least one fluid pathway within said eye includes a drainage pathway through at least a portion of the Canal of Schlemm of said eye and a uveoscleral outflow mechanism from the anterior segment of said eye.

14. The system of claim 9, wherein said passive stimulation electrode assembly is part of a contact lens adapted to be positioned on said eye of said mammalian subject.

15. The system of claim 14, wherein said passive stimulation electrode assembly is positioned at least one of within said contact lens and on an eye-contacting surface of said contact lens.

16. The system of claim 14, wherein said passive stimulation electrode assembly includes at least one serpentine trace to enable said passive stimulation electrode assembly to assume a 3-dimensional shape to facilitate placement over said eye of said mammalian subject as part of said contact lens.

17. The system of claim 9, wherein said passive stimulation electrode assembly is adapted to be implanted within said eye of said mammalian subject.

18. The system of claim 1, further comprising a wireless pressure sensor adapted to be disposed within said eye of said mammalian subject to enable closed-loop feedback for the delivery of said stimulation signal.

* * * * *

UNITED STATES PATENT AND TRADEMARK OFFICE
CERTIFICATE OF CORRECTION

PATENT NO. : 11,191,961 B2  
APPLICATION NO. : 16/312720  
DATED : December 7, 2021  
INVENTOR(S) : Pedro Irazoqui et al.

Page 1 of 1

It is certified that error appears in the above-identified patent and that said Letters Patent is hereby corrected as shown below:

On the Title Page

Item (57) at Line 9 of the Abstract, delete "Frensel" and insert -- Fresnel --.

Signed and Sealed this
Second Day of August, 2022

Katherine Kelly Vidal
*Director of the United States Patent and Trademark Office*